(12) United States Patent
Papadakis

(10) Patent No.: US 12,286,658 B2
(45) Date of Patent: Apr. 29, 2025

(54) ENHANCING FORMATION OF MILK OLIGOSACCHARIDES (HMOS) BY MODIFYING LACTOSE IMPORT IN THE CELL

(71) Applicant: DSM IP Assets B.V., Heerlen (DK)

(72) Inventor: Manos Papadakis, Hørsholm (DK)

(73) Assignee: DSM IP Assets B.V., Heerlen (DK)

( * ) Notice: Subject to any disclaimer, the term of this patent is extended or adjusted under 35 U.S.C. 154(b) by 0 days.

(21) Appl. No.: 18/561,258

(22) PCT Filed: May 17, 2022

(86) PCT No.: PCT/EP2022/063311
§ 371 (c)(1),
(2) Date: Nov. 15, 2023

(87) PCT Pub. No.: WO2022/243308
PCT Pub. Date: Nov. 24, 2022

(65) Prior Publication Data
US 2024/0279697 A1     Aug. 22, 2024

(30) Foreign Application Priority Data

May 17, 2021   (DK) .............................. PA202170249

(51) Int. Cl.
| C12P 19/18 | (2006.01) |
| C12N 9/10 | (2006.01) |
| C12N 15/52 | (2006.01) |
| C12P 19/00 | (2006.01) |

(52) U.S. Cl.
CPC ............ *C12P 19/00* (2013.01); *C12N 9/1051* (2013.01); *C12N 15/52* (2013.01); *C12Y 204/01038* (2013.01); *C12Y 204/01122* (2013.01); *C12Y 204/01147* (2013.01)

(58) Field of Classification Search
CPC ......... C12P 19/18; C12P 19/04; C12P 21/005; C12N 15/70; C12N 9/1081; C12N 1/20; C12N 15/63; C12N 9/2471; C12Y 204/01; C12Y 204/99004; C12Y 204/01038; C12Y 204/99001; C12Y 402/01047; C12Y 204/01065
USPC .......................................................... 435/74
See application file for complete search history.

(56) References Cited

U.S. PATENT DOCUMENTS

| 2018/0305724 A1 | 10/2018 | Jennewein et al. |
| 2019/0119314 A1 | 4/2019 | Chassagne et al. |

FOREIGN PATENT DOCUMENTS

| DK | 202170249 A1 | 11/2022 |
| EP | 1054062 | 6/2009 |
| EP | 2927316 | 10/2015 |
| EP | 3494805 | 6/2019 |
| EP | 3569713 | 11/2019 |
| WO | WO 2010142305 | 12/2010 |
| WO | WO 2012112777 | 8/2012 |
| WO | WO 2014018596 | 1/2014 |
| WO | WO 2015188834 | 12/2015 |
| WO | WO 2015197082 | 12/2015 |
| WO | WO 2016040531 | 3/2016 |
| WO | WO 2016095924 | 6/2016 |
| WO | WO 2017042382 | 3/2017 |
| WO | WO 2017101958 | 6/2017 |
| WO | WO 2017152918 | 9/2017 |
| WO | WO 2017182965 | 10/2017 |
| WO | WO 2019123324 | 6/2019 |
| WO | WO 2020178178 | 9/2020 |
| WO | WO 2020255054 | 12/2020 |
| WO | WO 2021148610 | 7/2021 |
| WO | WO 2021148611 | 7/2021 |
| WO | WO 2021148615 | 7/2021 |
| WO | WO 2022157280 | 7/2022 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Altschul et al. Nucl. Acids Res. 25, 3389 (1997).
Gebus et al. Carbohydrate Research (2012) 363, 83-90.
GenBank, "acylneuraminate cytidylyltransferase family protein [Vibrio brasiliensis]", Accession No. WP_006881452.1, Mar. 26, 2023.
GenBank, "alpha-2,3-sialyltransferase [Neisseria meningitidis]", Accession No. AAC44541.1, Nov. 7, 1996.
GenBank, "CMP-Neu5Ac synthetase [Campylobacter jejuni]", Accession No. AAK91728.1, Jul. 23, 2016.
GenBank, "*E. coli* gene lacZ coding for beta-galactosidase (EC 3.2.1.23)", Accession No. V00296.1 (GI:41901), Jul. 26, 2016.
GenBank, "*Escherichia coli* nanA gene for N-acetylneuraminate lyase, complete cds", Accession No. D00067.1 (GL216588), Jun. 15, 2010.
GenBank, "Helicobacter pylori 26695, complete genome", Accession No. CP003904, Jan. 31, 2014.
GenBank, "Major facilitator superfamily MFS_1 [Yersinia bercovieri ATCC 43970]" ,Accession No. EEQ08298.1., Jun. 1, 2009.
GenBank, "MFS transporter [Rosenbergiella nectarea]", Accession No. WP_092672081.1., Aug. 26, 2023.

(Continued)

Primary Examiner — Robert B Mondesi
Assistant Examiner — Mohammad Y Meah
(74) Attorney, Agent, or Firm — Neal, Gerber & Eisenberg LLP

(57) ABSTRACT

This invention relates to a method of producing one or more human milk oligosaccharides (HMOs), in particular LNT and/or LNnT, in a genetically engineered cell comprising an enhanced oligosaccharide transport capability. The genetically modified cell comprises a series of genetic modification which enable the production of one or more HMO(s), and a series of genetic modification that enhances the transport of lactose and produced HMO(s).

20 Claims, 11 Drawing Sheets

Specification includes a Sequence Listing.

(56) References Cited

OTHER PUBLICATIONS

GenBank, "MFS transporter [Rouxiella badensis]", Accession No. WP_017489914.1., Aug. 30, 2023.
GenBank, "Multispecies: Mfs transporter [Pantoea]", Accession No. WP_048785139.1, Aug. 31, 2023.
GenBank, "Multispecies: sugar efflux transporter [Serratia]", Accession No. WP_060448169.1., Feb. 28, 2022.
GenBank, "N-acetylneuraminate synthase [Flavobacterium limnosediminis]", Accession No. WP 023580510.1, Jun. 1, 2019.
GenBank, "predicted N-acetylmannosamine kinase [Escherichia coli str. K-12 substr. W3110]", Accession No. BAE77265.1 (GL85676015), Sep. 29, 2018.
GenBank, "putative N-acetylmannosamine-6-phosphate 2-epimerase [Escherichia coli str. K-12 substr. MG1655]", Gene ID: 947745.
GenBank, "putative sialic acid synthase [Campylobacter jejuni]", Accession No. AAK91726.1, Jul. 23, 2016.
GenBank, "sugar efflux transporter [Yersinia alsatica]", Accession No. WP 087817556.1, Aug. 9, 2023.
GenBank, "UDP-N-acetylglucosamine 2-epimerase [Escherichia coli S88]", Accession No. CAR04561.1, Feb. 27, 2015.
GenBank, beta-fructofuranosidase protein [Arthrobacter globiformis], Accession No. BAD18121.1, Aug. 3, 2004.
GenBank, putative N-acetylglucosamine-6-phosphate 2-epimerase [Campylobacter jejuni], Accession No. AAK91727.1, Jul. 23, 2016.
GenBank, "glycoside hydrolase family 32 protein [Avibacterium gallinarum]", Accession No. WP_103853210.1, Feb. 10, 2018.
Guan and Kaback, Annu Rev Biophys Biomol Struct. 2006, 35:67-91.
Herring and Blattner. J. Bacteriol., 2004, 186: 2673-81.
Murphy, J Bacteriol. (1998);180(8):2063-7.
Muyrers et al., EMBO Rep. (2000) 1(3): 239-243.
Needleman and Wunsch, 1970, J. Mol. Biol. 48: 443-453.
Penumetcha, et al., BIOS, (2010), 81(1):7-15.
Rice, et al. EMBOSS: The European Molecular Biology Open Software Suite, 2000, Trends Genet. 16: 276-277.
Vetcher et al., Appl Environ Microbiol. (2005);71(4):1829-35.
Waddell C.S. and Craig N.L., Genes Dev. Feb. 1988;2(2):137-49.
Warming et al. Nucleic Acids Res. 2005, 33(4): e36.
Wenzel et al., Chem Biol. (2005), 12(3):349-56.
Wilson K. and Walker J., Principles and Techniques of Biochemistry and Molecular Biology (2010), Cambridge University Press.
Zhang, et al. Nature Genetics (1998) 20: 123-128.
First Technical Examination Report for DK Application No. PA202170249, mailed Nov. 25, 2021, 7 pages.
Second Technical Examination Report for DK Application No. PA202170249, mailed Aug. 29, 2022, 5 pages.
Isono, N. et al.: "Cloning and heterologous expression of a β-fructofuranosidase gene from Arthrobacter globiformis IFO 3062, and site-directed mutagenesis of the essential aspartic acid and glutamic acid of the active site." Journal of Bioscience and Bioengineering, 2004, vol. 97, No. 4, pp. 244-249.
Third Technical Examination Report for DK Application No. PA202170249, mailed Mar. 2, 2023, 4 pages.
Intention to Grant for DK Application No. PA202170249, mailed Jul. 7, 2023, 2 pages.
Granted claims of DK Application No. PA202170249.
International Search Report and Written Opinion for PCT/EP2022/063311, mailed Mar. 2, 2023.
De Rossi, Edda et al, "The Multidrug Transporters Belonging to Major Facilitator Superfamily (MFS) in *Mycobacterium tuberculosis*", Washington, DC Nov. 1, 2002 (Nov. 1, 2002), vol. 8, No. 11, pp. 714-724, Retrieved from the Internet: URL:http://link.springer.com/article/10.1007/BF03402035/fulltext.html.

* cited by examiner

SEQUENCE LISTING

```
<160> NUMBER OF SEQ ID NOS: 103

<210> SEQ ID NO 1
<211> LENGTH: 417
<212> TYPE: PRT
<213> ORGANISM: Escherichia coli
<220> FEATURE:
<221> NAME/KEY: MISC_FEATURE
<222> LOCATION: (1)..(417)
<223> OTHER INFORMATION: Lactose permease LacY GenBank ID: NP_414877.1

<400> SEQUENCE: 1

Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
                20                  25                  30

Trp Leu His Asp Ile Asn His Ile Ser Lys Ser Asp Thr Gly Ile Ile
            35                  40                  45

Phe Ala Ala Ile Ser Leu Phe Ser Leu Leu Phe Gln Pro Leu Phe Gly
        50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Phe Ile Phe Ile Phe Gly
```

```
                    85                  90                  95
Pro Leu Gln Tyr Asn Ile Leu Val Gly Ser Ile Val Gly Gly Ile
            100                 105                 110
Tyr Leu Gly Phe Cys Phe Asn Ala Gly Ala Pro Ala Val Glu Ala Phe
            115                 120                 125
Ile Glu Lys Val Ser Arg Arg Ser Asn Phe Glu Phe Gly Arg Ala Arg
    130                 135                 140
Met Phe Gly Cys Val Gly Trp Ala Leu Cys Ala Ser Ile Val Gly Ile
145                 150                 155                 160
Met Phe Thr Ile Asn Asn Gln Phe Val Phe Trp Leu Gly Ser Gly Cys
                165                 170                 175
Ala Leu Ile Leu Ala Val Leu Leu Phe Phe Ala Lys Thr Asp Ala Pro
            180                 185                 190
Ser Ser Ala Thr Val Ala Asn Ala Val Gly Ala Asn His Ser Ala Phe
            195                 200                 205
Ser Leu Lys Leu Ala Leu Glu Leu Phe Arg Gln Pro Lys Leu Trp Phe
    210                 215                 220
Leu Ser Leu Tyr Val Ile Gly Val Ser Cys Thr Tyr Asp Val Phe Asp
225                 230                 235                 240
Gln Gln Phe Ala Asn Phe Phe Thr Ser Phe Phe Ala Thr Gly Glu Gln
                245                 250                 255
Gly Thr Arg Val Phe Gly Tyr Val Thr Thr Met Gly Glu Leu Leu Asn
            260                 265                 270
Ala Ser Ile Met Phe Phe Ala Pro Leu Ile Ile Asn Arg Ile Gly Gly
            275                 280                 285
Lys Asn Ala Leu Leu Leu Ala Gly Thr Ile Met Ser Val Arg Ile Ile
    290                 295                 300
Gly Ser Ser Phe Ala Thr Ser Ala Leu Glu Val Val Ile Leu Lys Thr
305                 310                 315                 320
Leu His Met Phe Glu Val Pro Phe Leu Leu Val Gly Cys Phe Lys Tyr
                325                 330                 335
Ile Thr Ser Gln Phe Glu Val Arg Phe Ser Ala Thr Ile Tyr Leu Val
            340                 345                 350
Cys Phe Cys Phe Phe Lys Gln Leu Ala Met Ile Phe Met Ser Val Leu
    355                 360                 365
Ala Gly Asn Met Tyr Glu Ser Ile Gly Phe Gln Gly Ala Tyr Leu Val
            370                 375                 380
Leu Gly Leu Val Ala Leu Gly Phe Thr Leu Ile Ser Val Phe Thr Leu
385                 390                 395                 400
Ser Gly Pro Gly Pro Leu Ser Leu Leu Arg Arg Gln Val Asn Glu Val
                405                 410                 415
Ala

<210> SEQ ID NO 2
<211> LENGTH: 1254
<212> TYPE: DNA
<213> ORGANISM: Escherichia coli K-12
<220> FEATURE:
<221> NAME/KEY: misc_feature
<222> LOCATION: (1)..(1254)
<223> OTHER INFORMATION: Nucleic acid sequence encoding LacY, GenBank
      ID: NC_000913.3

<400> SEQUENCE: 2
atgtactatt taaaaaacac aaactttttgg atgttcggtt tattcttttt ctttactttt     60
```

-continued

| | |
|---|---|
| tttatcatgg gagcctactt cccgttttc ccgatttggc tacatgacat caaccatatc | 120 |
| agcaaaagtg atacgggtat tatttttgcc gctatttctc tgttctcgct attattccaa | 180 |
| ccgctgtttg gtctgctttc tgacaaactc gggctgcgca atacctgct gtggattatt | 240 |
| accggcatgt tagtgatgtt tgcgccgttc tttatttta tcttcgggcc actgttacaa | 300 |
| tacaacattt tagtaggatc gattgttggt ggtatttatc taggcttttg ttttaacgcc | 360 |
| ggtgcgccag cagtagaggc atttattgag aaagtcagcc gtcgcagtaa tttcgaattt | 420 |
| ggtcgcgcgc ggatgtttgg ctgtgttggc tgggcgctgt gtgcctcgat tgtcggcatc | 480 |
| atgttcacca tcaataatca gtttgttttc tggctgggct ctggctgtgc actcatcctc | 540 |
| gccgttttac tctttttcgc caaaacggat gcgccctctt ctgccacggt tgccaatgcg | 600 |
| gtaggtgcca accattcggc atttagcctt aagctggcac tggaactgtt cagacagcca | 660 |
| aaactgtggt ttttgtcact gtatgttatt ggcgtttcct gcacctacga tgttttgac | 720 |
| caacagtttg ctaatttctt tacttcgttc tttgctaccg gtgaacaggg tacgcgggta | 780 |
| tttggctacg taacgacaat gggcgaatta cttaacgcct cgattatgtt ctttgcgcca | 840 |
| ctgatcatta atcgcatcgg tgggaaaaac gccctgctgc tggctggcac tattatgtct | 900 |
| gtacgtatta ttggctcatc gttcgccacc tcagcgctgg aagtggttat tctgaaaacg | 960 |
| ctgcatatgt ttgaagtacc gttcctgctg gtgggctgct taaatatat taccagccag | 1020 |
| tttgaagtgc gttttcagc gacgattat ctggtctgtt tctgcttctt taagcaactg | 1080 |
| gcgatgattt ttatgtctgt actggcgggc aatatgtatg aaagcatcgg tttccagggc | 1140 |
| gcttatctgg tgctgggtct ggtggcgctg ggcttcacct taatttccgt gttcacgctt | 1200 |
| agcggccccg gcccgctttc cctgctgcgt cgtcaggtga atgaagtcgc ttaa | 1254 |

<210> SEQ ID NO 3
<211> LENGTH: 433
<212> TYPE: PRT
<213> ORGANISM: Escherichia coli
<220> FEATURE:
<221> NAME/KEY: MISC_FEATURE
<222> LOCATION: (1)..(433)
<223> OTHER INFORMATION: Lactose permease, GenBank ID: WP_042094275.1

<400> SEQUENCE: 3

```
Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
                20                  25                  30

Trp Leu His Asp Ile Asn His Ile Ser Lys Ser Asp Thr Gly Ile Ile
            35                  40                  45

Phe Ala Ala Ile Ser Leu Phe Ser Leu Leu Phe Gln Pro Leu Phe Gly
        50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Ile Phe Ile Phe Phe Gly
                85                  90                  95

Pro Leu Leu Gln Tyr Asn Ile Leu Val Gly Ser Ile Val Gly Gly Ile
                100                 105                 110

Tyr Leu Gly Phe Cys Phe Asn Ala Gly Ala Pro Ala Val Glu Ala Phe
            115                 120                 125

Ile Glu Lys Val Ser Arg Arg Ser Asn Phe Glu Phe Gly Arg Ala Arg
        130                 135                 140
```

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
            165                 170                 175

Ala Leu Ile Leu Ala Val Leu Leu Phe Phe Ala Lys Thr Asp Ala Pro
        180                 185                 190

Ser Ser Ala Thr Val Ala Asn Ala Val Gly Ala Asn His Ser Ala Phe
    195                 200                 205

Ser Leu Lys Leu Ala Leu Glu Leu Phe Arg Gln Pro Lys Leu Trp Phe
210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
            245                 250                 255

Gly Thr Arg Val Phe Gly Tyr Val Thr Thr Met Gly Glu Leu Leu Asn
        260                 265                 270

Ala Ser Ile Met Phe Phe Ala Pro Leu Ile Ile Asn Arg Ile Gly Gly
    275                 280                 285

Lys Asn Ala Leu Leu Leu Ala Gly Thr Ile Met Ser Val Arg Ile Ile
290                 295                 300

Gly Ser Ser Phe Ala Thr Ser Ala Leu Glu Val Val Ile Leu Lys Thr
305                 310                 315                 320

Leu His Met Phe Glu Val Pro Phe Leu Leu Val Gly Cys Phe Lys Tyr
            325                 330                 335

Ile Thr Ser Gln Phe Glu Val Arg Phe Ser Ala Thr Ile Tyr Leu Val
        340                 345                 350

Cys Phe Cys Phe Phe Lys Gln Leu Ala Met Ile Phe Met Ser Val Leu
    355                 360                 365

Ala Gly Asn Met Tyr Glu Ser Ile Gly Phe Gln Gly Ala Tyr Leu Val
370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
            405                 410                 415

Ala Tyr Gly Cys Gly Ala Ser Ala Leu Ser Asp Gln His Ile Arg Ala
        420                 425                 430

Glu

<210> SEQ ID NO 4
<211> LENGTH: 417
<212> TYPE: PRT
<213> ORGANISM: Proteobacteria
<220> FEATURE:
<221> NAME/KEY: MISC_FEATURE
<222> LOCATION: (1)..(417)
<223> OTHER INFORMATION: Lactose permease, GenBank ID: WP_000291549.1

<400> SEQUENCE: 4

Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
            20                  25                  30

Trp Leu His Asp Ile Asn His Ile Ser Lys Ser Asp Thr Gly Ile Ile
        35                  40                  45

Phe Ala Ala Ile Ser Leu Phe Ser Leu Leu Phe Gln Pro Leu Phe Gly
    50                  55                  60

Leu Leu Ser Asp Lys Leu Gly Leu Arg Lys Tyr Leu Leu Trp Ile Ile
 65                  70                  75                  80

Thr Gly Met Leu Val Met Phe Ala Pro Phe Ile Phe Ile Phe Ile Gly
                 85                  90                  95

Pro Leu Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
        115                 120                 125

Ile Glu Lys Val Ser Arg Arg Ser Asn Phe Glu Phe Gly Arg Ala Arg
130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
                165                 170                 175

Ala Leu Ile Leu Ala Val Leu Leu Phe Phe Ala Lys Thr Asp Ala Pro
            180                 185                 190

Ser Ser Ala Thr Val Ala Asn Ala Val Gly Ala Asn His Ser Ala Phe
        195                 200                 205

Ser Leu Lys Leu Ala Leu Glu Leu Phe Arg Gln Pro Lys Leu Trp Phe
210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
                245                 250                 255

Gly Thr Arg Val Phe Gly Tyr Val Thr Thr Met Gly Glu Leu Leu Asn
            260                 265                 270

Ala Ser Ile Met Phe Phe Ala Pro Leu Ile Ile Asn Arg Ile Gly Gly
        275                 280                 285

Lys Asn Ala Leu Leu Leu Ala Gly Thr Ile Met Ser Val Arg Ile Ile
290                 295                 300

Gly Ser Ser Phe Ala Thr Ser Ala Leu Glu Val Val Ile Leu Lys Thr
305                 310                 315                 320

Leu His Met Phe Glu Val Pro Phe Leu Leu Val Gly Cys Phe Lys Tyr
                325                 330                 335

Ile Thr Ser Gln Phe Glu Val Arg Phe Ser Ala Thr Ile Tyr Leu Val
            340                 345                 350

Cys Phe Cys Phe Phe Lys Gln Leu Ala Met Ile Phe Met Ser Val Leu
        355                 360                 365

Ala Gly Asn Met Tyr Glu Ser Ile Gly Phe Gln Gly Ala Tyr Leu Val
370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
                405                 410                 415

Ala

<210> SEQ ID NO 5
<211> LENGTH: 417
<212> TYPE: PRT
<213> ORGANISM: Campylobacter jejuni
<220> FEATURE:
<221> NAME/KEY: MISC_FEATURE
<222> LOCATION: (1)..(417)
<223> OTHER INFORMATION: Lactose permease GenBank ID: WP_089607162.1

```
<400> SEQUENCE: 5

Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
            20                  25                  30

Trp Leu His Asp Ile Asn His Ile Ser Lys Ser Asp Thr Gly Ile Ile
                35                  40                  45

Phe Ala Ala Ile Ser Leu Phe Ser Leu Leu Phe Gln Pro Leu Phe Gly
            50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Phe Ile Phe Ile Phe Gly
                85                  90                  95

Pro Leu Gln Tyr Asn Ile Leu Val Gly Ser Ile Val Gly Gly Ile
                100                 105                 110

Tyr Leu Gly Phe Cys Phe Asn Ala Gly Ala Pro Ala Val Glu Ala Phe
            115                 120                 125

Ile Glu Lys Val Ser Arg Arg Ser Asn Phe Glu Phe Gly Arg Ala Arg
130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
                165                 170                 175

Cys Leu Ile Leu Ala Val Leu Leu Phe Phe Ala Lys Thr Asp Ala Pro
            180                 185                 190

Ser Ser Ala Thr Val Ala Asn Ala Val Gly Ala Asn His Ser Ala Phe
            195                 200                 205

Ser Leu Lys Leu Ala Leu Glu Leu Phe Arg Gln Pro Lys Leu Trp Phe
            210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
                245                 250                 255

Gly Thr Arg Val Phe Gly Tyr Val Thr Thr Met Gly Glu Leu Leu Asn
                260                 265                 270

Ala Ser Ile Met Phe Phe Ala Pro Leu Ile Ile Asn Arg Ile Gly Gly
            275                 280                 285

Lys Asn Ala Leu Leu Leu Ala Gly Thr Ile Met Ser Val Arg Ile Ile
290                 295                 300

Gly Ser Ser Phe Ala Thr Ser Ala Leu Glu Val Val Ile Leu Lys Thr
305                 310                 315                 320

Leu His Met Phe Glu Val Pro Phe Leu Leu Val Gly Cys Phe Lys Tyr
                325                 330                 335

Ile Thr Ser Gln Phe Glu Val Arg Phe Ser Ala Thr Ile Tyr Leu Val
                340                 345                 350

Cys Phe Cys Phe Phe Lys Gln Leu Ala Met Ile Phe Met Ser Val Leu
            355                 360                 365

Ala Gly Asn Met Tyr Glu Ser Ile Gly Phe Gln Gly Ala Tyr Leu Val
            370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
                405                 410                 415
```

Ala

<210> SEQ ID NO 6
<211> LENGTH: 417
<212> TYPE: PRT
<213> ORGANISM: Klebsiella pneumoniae
<220> FEATURE:
<221> NAME/KEY: MISC_FEATURE
<222> LOCATION: (1)..(417)
<223> OTHER INFORMATION: Lactose permease, GenBank ID: WP_152280604.1

<400> SEQUENCE: 6

```
Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
            20                  25                  30

Trp Leu His Asp Ile Asn His Ile Ser Lys Ser Asp Thr Gly Ile Ile
        35                  40                  45

Phe Ala Ala Ile Ser Leu Phe Ser Leu Leu Phe Gln Pro Leu Phe Gly
    50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Phe Ile Phe Ile Phe Gly
                85                  90                  95

Pro Leu Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
        115                 120                 125

Ile Glu Lys Val Ser Arg Arg Ser Asn Phe Glu Phe Gly Arg Ala Arg
    130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
                165                 170                 175

Ala Leu Ile Leu Ala Val Leu Leu Phe Phe Ala Lys Thr Asp Ala Pro
            180                 185                 190

Ser Ser Ala Thr Val Ala Asn Ala Val Gly Ala Asn His Ser Ala Phe
        195                 200                 205

Ser Leu Lys Leu Ala Leu Glu Leu Phe Arg Gln Pro Lys Leu Trp Phe
    210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
                245                 250                 255

Gly Thr Arg Val Phe Gly Tyr Val Thr Thr Met Gly Glu Leu Leu Asn
            260                 265                 270

Ala Ser Ile Met Phe Phe Ala Pro Leu Ile Ile Asn Arg Ile Gly Gly
        275                 280                 285

Lys Asn Ala Leu Leu Leu Ala Gly Thr Ile Met Ser Val Arg Ile Ile
    290                 295                 300

Gly Ser Ser Phe Ala Thr Ser Ala Leu Glu Val Ile Leu Lys Thr
305                 310                 315                 320

Leu His Met Phe Glu Val Pro Phe Leu Leu Val Gly Cys Phe Lys Tyr
                325                 330                 335

Ile Thr Ser Gln Phe Glu Val Arg Phe Ser Ala Thr Ile Tyr Leu Val
```

```
                    340                 345                 350
Cys Phe Cys Phe Phe Lys Gln Leu Ala Met Ile Phe Met Ser Ile Leu
            355                 360                 365

Ala Gly Asn Met Tyr Glu Ser Ile Gly Phe Gln Gly Ala Tyr Leu Val
            370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Lys Val Asn Glu Val
            405                 410                 415

Ala

<210> SEQ ID NO 7
<211> LENGTH: 417
<212> TYPE: PRT
<213> ORGANISM: Cronobacter sakazakii
<220> FEATURE:
<221> NAME/KEY: MISC_FEATURE
<222> LOCATION: (1)..(417)
<223> OTHER INFORMATION: Lactose permease, GenBank ID: EGT4952364.1

<400> SEQUENCE: 7

Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
                20                  25                  30

Trp Leu His Asp Ile Asn His Ile Ser Lys Ser Asp Thr Gly Ile Ile
            35                  40                  45

Phe Ala Ala Ile Ser Leu Phe Ser Leu Leu Phe Gln Pro Leu Phe Gly
        50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Ile Phe Ile Phe Ile Gly
                85                  90                  95

Pro Leu Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
        115                 120                 125

Ile Glu Lys Val Ser Arg Arg Ser Asn Phe Glu Tyr Gly Arg Ala Arg
130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
                165                 170                 175

Ala Phe Ile Leu Ala Val Leu Leu Phe Phe Ala Lys Thr Asp Ala Pro
            180                 185                 190

Ser Ser Ala Thr Val Ala Asn Ala Val Gly Ala Asn His Ser Ala Phe
        195                 200                 205

Ser Leu Lys Leu Ala Leu Glu Leu Phe Arg Gln Pro Lys Leu Trp Phe
    210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
                245                 250                 255

Gly Thr Arg Val Phe Gly Tyr Val Thr Thr Met Gly Glu Leu Leu Asn
            260                 265                 270
```

```
Ala Ser Ile Met Phe Phe Ala Pro Leu Ile Ile Asn Arg Ile Gly Gly
            275                 280                 285

Lys Asn Ala Leu Leu Leu Ala Gly Thr Ile Met Ser Val Arg Ile Ile
290                 295                 300

Gly Ser Ser Phe Ala Thr Ser Ala Leu Glu Val Val Ile Leu Lys Thr
305                 310                 315                 320

Leu His Met Leu Glu Val Pro Phe Leu Leu Val Gly Cys Phe Lys Tyr
                325                 330                 335

Ile Thr Ser Gln Phe Glu Val Arg Phe Ser Ala Thr Ile Tyr Leu Val
                340                 345                 350

Cys Phe Cys Phe Phe Lys Gln Leu Ala Met Ile Phe Met Ser Ile Leu
                355                 360                 365

Ala Gly Asn Met Tyr Glu Ser Ile Gly Phe Gln Gly Ala Tyr Leu Val
            370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
                405                 410                 415

Ala
```

<210> SEQ ID NO 8
<211> LENGTH: 417
<212> TYPE: PRT
<213> ORGANISM: Citrobacter freundii
<220> FEATURE:
<221> NAME/KEY: MISC_FEATURE
<222> LOCATION: (1)..(417)
<223> OTHER INFORMATION: Lactose permease, GenBank ID NO: WP_134216118.1

<400> SEQUENCE: 8

```
Met Tyr Tyr Leu Lys Asn Thr Asn Phe Trp Met Phe Gly Phe Phe Phe
1               5                   10                  15

Phe Phe Tyr Phe Phe Ile Met Gly Ala Tyr Phe Pro Phe Pro Ile
            20                  25                  30

Trp Leu His Glu Val Asn His Ile Ser Lys Gly Asp Thr Gly Ile Ile
            35                  40                  45

Phe Ala Cys Ile Ser Leu Phe Ser Leu Leu Phe Gln Pro Ile Phe Gly
50                  55                  60

Leu Leu Ser Asp Lys Leu Gly Leu Arg Lys His Leu Leu Trp Val Ile
65                  70                  75                  80

Thr Gly Met Leu Val Met Phe Ala Pro Phe Phe Ile Tyr Val Phe Gly
                85                  90                  95

Pro Leu Leu Gln Val Asn Ile Leu Leu Gly Ser Ile Val Gly Gly Ile
                100                 105                 110

Tyr Leu Gly Phe Ile Tyr Asn Ala Gly Ala Pro Ala Ile Glu Ala Tyr
            115                 120                 125

Ile Glu Lys Ala Ser Arg Arg Ser Asn Phe Glu Phe Gly Arg Ala Arg
130                 135                 140

Met Phe Gly Cys Val Gly Trp Ala Leu Cys Ala Ser Ile Ala Gly Ile
145                 150                 155                 160

Met Phe Thr Ile Asn Asn Gln Phe Val Phe Trp Leu Gly Ser Gly Cys
                165                 170                 175

Ala Val Ile Leu Ala Leu Leu Leu Phe Ser Lys Thr Asp Ala Pro
                180                 185                 190

Ser Ser Ala Lys Val Ala Asp Ala Val Gly Ala Asn Asn Ser Ala Phe
                195                 200                 205
```

Ser Leu Lys Leu Ala Leu Glu Leu Phe Lys Gln Pro Lys Leu Trp Phe
    210                 215                 220

Leu Ser Leu Tyr Val Val Gly Val Ser Cys Thr Tyr Asp Val Phe Asp
225                 230                 235                 240

Gln Gln Phe Ala Asn Phe Phe Thr Ser Leu Phe Ala Thr Gly Glu Gln
                245                 250                 255

Gly Thr Arg Val Phe Gly Tyr Val Thr Thr Met Gly Glu Leu Leu Asn
            260                 265                 270

Ala Ser Ile Met Phe Phe Ala Pro Leu Ile Val Asn Arg Ile Gly Gly
        275                 280                 285

Lys Asn Ala Leu Leu Leu Ala Gly Thr Ile Met Ser Val Arg Ile Ile
    290                 295                 300

Gly Ser Ser Phe Ala Thr Thr Ala Leu Glu Val Val Ile Leu Lys Thr
305                 310                 315                 320

Leu His Met Phe Glu Ile Pro Phe Leu Ile Val Gly Cys Phe Lys Tyr
                325                 330                 335

Ile Thr Ser Gln Phe Glu Val Arg Phe Ser Ala Thr Ile Tyr Leu Val
            340                 345                 350

Cys Phe Cys Phe Lys Gln Leu Ala Met Ile Phe Met Ser Val Leu
        355                 360                 365

Ala Gly Lys Met Tyr Glu Ser Ile Gly Phe Gln Gly Ala Tyr Leu Val
    370                 375                 380

Leu Gly Ile Ile Ala Leu Ser Phe Thr Leu Ile Ser Val Phe Thr Leu
385                 390                 395                 400

Ser Gly Pro Gly Pro Phe Ser Leu Leu Arg Arg Arg Glu Ser Val Ala
                405                 410                 415

Leu

<210> SEQ ID NO 9
<211> LENGTH: 418
<212> TYPE: PRT
<213> ORGANISM: Citrobacter freundii
<220> FEATURE:
<221> NAME/KEY: MISC_FEATURE
<222> LOCATION: (1)..(418)
<223> OTHER INFORMATION: Lactose permease, GenBank ID: EDI1749185.1

<400> SEQUENCE: 9

Met Tyr Tyr Leu Lys Asn Thr Asn Phe Trp Met Leu Gly Phe Phe Phe
1                   5                   10                  15

Phe Phe Tyr Phe Phe Ile Met Gly Ala Tyr Phe Pro Phe Phe Pro Ile
                20                  25                  30

Trp Leu His Asp Ile Asn His Ile Ser Lys Gly Asp Thr Gly Ile Ile
            35                  40                  45

Phe Ala Cys Ile Ser Leu Phe Ser Leu Leu Phe Gln Pro Val Phe Gly
        50                  55                  60

Leu Met Ser Asp Lys Leu Gly Leu Arg Lys Asn Leu Leu Trp Ile Ile
65                  70                  75                  80

Thr Gly Met Leu Val Met Phe Ala Pro Phe Phe Ile Tyr Val Phe Gly
                85                  90                  95

Pro Leu Leu His Phe Asn Ile Leu Leu Gly Ser Ile Val Gly Gly Ile
            100                 105                 110

Tyr Leu Gly Phe Ile Tyr Asn Ala Gly Ala Pro Ala Ile Glu Ala Tyr
        115                 120                 125

Ile Glu Lys Ala Ser Arg Arg Ser His Phe Glu Phe Gly Arg Ala Arg

```
                130               135               140
Met Phe Gly Cys Val Gly Trp Ala Leu Cys Ala Ser Ile Val Gly Val
145                 150                 155                 160

Met Phe Thr Ile Asn Asn Glu Phe Val Phe Trp Leu Gly Ser Gly Cys
                165                 170                 175

Ala Val Ile Leu Ala Leu Leu Leu Phe Phe Ser Arg Thr Asp Ser Gly
                180                 185                 190

Ser Ser Ala Val Val Ala Asp Ala Val Gly Ala Asn Ser Ser Pro Phe
            195                 200                 205

Ser Leu Lys Leu Ala Leu Glu Leu Phe Lys Gln Pro Lys Leu Trp Phe
        210                 215                 220

Leu Ser Leu Tyr Val Val Gly Val Ser Cys Thr Tyr Asp Val Phe Asp
225                 230                 235                 240

Gln Gln Phe Ala Asn Phe Phe Thr Ser Phe Phe Ala Ser Gly Glu Gln
                245                 250                 255

Gly Thr Arg Val Phe Gly Tyr Val Thr Thr Met Gly Glu Leu Leu Asn
                260                 265                 270

Ala Cys Ile Met Phe Phe Ala Pro Phe Ile Val Asn Arg Ile Gly Gly
                275                 280                 285

Lys Asn Ala Leu Leu Met Ala Gly Ile Ile Met Ser Val Arg Ile Ile
290                 295                 300

Gly Ser Ser Phe Ala Thr Thr Ala Gly Glu Val Val Ile Leu Lys Thr
305                 310                 315                 320

Leu His Met Phe Glu Ile Pro Phe Leu Ile Val Gly Cys Phe Lys Tyr
                325                 330                 335

Ile Thr Ser Gln Phe Glu Val Arg Phe Ser Ala Thr Ile Tyr Leu Val
                340                 345                 350

Cys Phe Cys Phe Phe Lys Gln Leu Ala Met Ile Phe Met Ser Val Leu
                355                 360                 365

Ala Gly Asn Met Tyr Glu Lys Ile Gly Phe Gln Gly Ala Tyr Leu Val
                370                 375                 380

Leu Gly Leu Ile Ala Leu Val Phe Thr Leu Ile Ser Val Ala Thr Leu
385                 390                 395                 400

Ser Gly Ala Gly Pro Leu Ala Val Met Arg Val Ser Gln Gln Lys Ser
                405                 410                 415

Ala Ser

<210> SEQ ID NO 10
<211> LENGTH: 423
<212> TYPE: PRT
<213> ORGANISM: Rouxiella badensis
<220> FEATURE:
<221> NAME/KEY: MISC_FEATURE
<222> LOCATION: (1)..(423)
<223> OTHER INFORMATION: Lactose permease, GenBank ID: WP_084912833.1

<400> SEQUENCE: 10

Met Tyr Tyr Ile Lys Asn Thr Asn Phe Trp Thr Phe Gly Leu Phe Phe
1               5                   10                  15

Phe Phe Tyr Phe Phe Ile Met Gly Ala Tyr Phe Pro Phe Phe Pro Ile
                20                  25                  30

Trp Leu His Asp Ile Asn His Ile Asn Gln Ser Asp Thr Gly Ile Ile
                35                  40                  45

Phe Ala Ser Ile Ser Phe Phe Ser Leu Val Phe Gln Pro Leu Phe Gly
            50                  55                  60
```

```
Leu Leu Ser Asp Lys Leu Gly Leu Lys Lys His Leu Leu Trp Ile Ile
 65                  70                  75                  80

Thr Gly Met Leu Val Met Phe Ala Pro Phe Phe Ile Tyr Val Phe Gly
                 85                  90                  95

Pro Leu Lys Thr Asn Ile Leu Leu Gly Ser Ile Val Gly Gly Val
            100                 105                 110

Tyr Leu Gly Phe Ile Tyr Asn Gly Gly Ala Pro Ala Ile Glu Ala Tyr
            115                 120                 125

Ile Glu Lys Val Ser Arg Arg Ser Ser Phe Glu Phe Gly Arg Ala Arg
            130                 135                 140

Met Phe Gly Cys Val Gly Trp Ala Ile Cys Ala Ser Val Val Gly Ile
145                 150                 155                 160

Met Phe Thr Ile Asn Ser Gln Phe Val Phe Trp Leu Gly Ser Gly Cys
                165                 170                 175

Ala Val Ile Leu Ala Val Leu Leu Val Ala Lys Pro Ala Val Gly
            180                 185                 190

Ala Thr Ala Lys Val Ala Asn Glu Leu Gly Ala Asn Ser Lys Pro Phe
            195                 200                 205

Ser Leu Arg Leu Ala Ala Glu Leu Leu Lys Asp Lys Lys Leu Trp Phe
210                 215                 220

Leu Gly Leu Tyr Val Val Gly Val Ser Cys Thr Tyr Glu Val Phe Asp
225                 230                 235                 240

Gln Gln Phe Ala Asn Phe Phe Thr Ser Phe Ser Ala Asp Glu
                245                 250                 255

Gly Thr Arg Val Phe Gly Tyr Ile Thr Thr Met Gly Glu Leu Leu Asn
                260                 265                 270

Ala Leu Val Met Phe Phe Ala Pro Leu Ile Val Asn Arg Ile Gly Gly
            275                 280                 285

Lys Asn Ala Leu Leu Leu Ala Gly Ile Ile Met Ser Val Arg Ile Ile
        290                 295                 300

Gly Ser Ser Phe Ala Ser Thr Pro Val Glu Val Val Leu Lys Thr
305                 310                 315                 320

Leu His Met Phe Glu Val Pro Phe Leu Ile Val Gly Cys Phe Lys Tyr
                325                 330                 335

Ile Thr Ser Val Phe Glu Val Arg Phe Ser Ala Thr Ile Tyr Leu Val
            340                 345                 350

Cys Phe Cys Phe Phe Lys Gln Ile Ala Met Ile Phe Met Ser Val Phe
            355                 360                 365

Ala Gly Asp Met Tyr Gly Lys Ile Gly Phe His Gly Thr Tyr Leu Ile
            370                 375                 380

Leu Gly Leu Ile Ala Leu Ala Phe Thr Leu Leu Ser Val Phe Thr Leu
385                 390                 395                 400

Ser Gly Arg Gly Pro Leu Gln Ala Phe Lys Pro Val Ala Arg Thr Val
                405                 410                 415

Glu Lys Pro Val Ser Asn Val
            420
```

<210> SEQ ID NO 11
<211> LENGTH: 417
<212> TYPE: PRT
<213> ORGANISM: Serratia marcescens
<220> FEATURE:
<221> NAME/KEY: MISC_FEATURE
<222> LOCATION: (1)..(417)
<223> OTHER INFORMATION: Lactose permease, GenBank ID: WP_103826752.1

```
<400> SEQUENCE: 11

Met Tyr Tyr Leu Lys Asn Thr Asn Phe Trp Met Phe Gly Leu Phe Phe
1               5                   10                  15

Phe Phe Tyr Phe Phe Met Gly Ala Tyr Phe Pro Phe Phe Pro Ile
            20                  25                  30

Trp Leu His Asp Ile Asn His Ile Ser Lys Ser Asp Thr Gly Ile Ile
                35                  40                  45

Phe Ala Ala Ile Ser Leu Phe Ser Leu Leu Phe Gln Pro Leu Phe Gly
        50                  55                  60

Leu Leu Ser Asp Lys Leu Gly Leu Arg Lys Tyr Leu Leu Trp Ile Ile
65                  70                  75                  80

Thr Gly Met Leu Val Met Phe Ala Pro Phe Phe Ile Phe Ile Phe Gly
                85                  90                  95

Pro Leu Gln Tyr Asn Ile Leu Val Gly Ser Ile Val Gly Gly Ile
            100                 105                 110

Tyr Leu Gly Phe Cys Phe Asn Ala Gly Ala Pro Ala Val Glu Ala Phe
            115                 120                 125

Ile Glu Lys Val Ser Arg Arg Ser Asn Phe Glu Tyr Gly Arg Ala Arg
130                 135                 140

Met Phe Gly Cys Val Gly Trp Ala Leu Cys Ala Ser Ile Val Gly Ile
145                 150                 155                 160

Met Phe Thr Ile Asn Asn Gln Phe Val Phe Trp Leu Gly Ser Gly Cys
                165                 170                 175

Ala Phe Ile Leu Ala Val Leu Leu Phe Phe Ala Lys Thr Asp Ala Pro
            180                 185                 190

Ser Ser Ala Thr Val Ala Asn Ala Val Gly Ala Asn His Ser Ala Phe
            195                 200                 205

Ser Leu Lys Leu Ala Leu Glu Leu Phe Arg Gln Pro Lys Leu Trp Phe
            210                 215                 220

Leu Ser Leu Tyr Val Ile Gly Val Ser Cys Thr Tyr Asp Val Phe Asp
225                 230                 235                 240

Gln Gln Phe Ala Asn Phe Phe Thr Ser Phe Phe Ala Thr Gly Glu Gln
            245                 250                 255

Gly Thr Arg Val Phe Gly Tyr Val Thr Thr Met Gly Glu Leu Leu Asn
            260                 265                 270

Ala Ser Ile Met Phe Phe Ala Pro Leu Ile Ile Asn Arg Ile Gly Gly
            275                 280                 285

Lys Asn Ala Leu Leu Leu Ala Gly Thr Ile Met Ser Val Arg Ile Ile
            290                 295                 300

Gly Ser Ser Phe Ala Thr Ser Ala Leu Glu Val Val Ile Leu Lys Thr
305                 310                 315                 320

Leu His Met Phe Glu Val Pro Phe Leu Leu Val Gly Cys Phe Lys Tyr
                325                 330                 335

Ile Thr Ser Gln Phe Glu Val Arg Phe Ser Ala Thr Ile Tyr Leu Val
            340                 345                 350

Cys Phe Cys Phe Phe Lys Gln Leu Ala Met Ile Phe Met Ser Ile Leu
            355                 360                 365

Ala Gly Asn Met Tyr Glu Ser Ile Gly Phe Gln Gly Ala Tyr Leu Val
            370                 375                 380

Leu Gly Leu Val Ala Leu Gly Phe Thr Leu Ile Ser Val Phe Thr Leu
385                 390                 395                 400

Ser Gly Pro Gly Pro Leu Ser Leu Leu Arg Arg Gln Val Asn Glu Val
            405                 410                 415
```

Ala

<210> SEQ ID NO 12
<211> LENGTH: 420
<212> TYPE: PRT
<213> ORGANISM: Serratia fonticola
<220> FEATURE:
<221> NAME/KEY: MISC_FEATURE
<222> LOCATION: (1)..(420)
<223> OTHER INFORMATION: Lactose permease, GenBank ID: WP_021804673.1

<400> SEQUENCE: 12

Met Tyr Tyr Leu Lys Asn Thr Asn Phe Trp Met Phe Gly Leu Phe Phe
1               5                   10                  15

Phe Phe Tyr Phe Phe Ile Met Gly Ala Tyr Phe Pro Phe Phe Pro Ile
            20                  25                  30

Trp Leu His Asp Ile Asn Gln Val Ser Lys Ser Asp Thr Gly Ile Ile
        35                  40                  45

Phe Ala Ser Ile Ser Phe Ser Leu Leu Phe Gln Pro Ile Phe Gly
    50                  55                  60

Leu Leu Ser Asp Lys Leu Gly Leu Arg Lys His Leu Leu Trp Ile Ile
65                  70                  75                  80

Thr Gly Met Leu Ile Leu Phe Ala Pro Phe Phe Ile Tyr Val Phe Gly
                85                  90                  95

Pro Leu Leu Arg Thr Asn Ile Val Leu Gly Ser Ile Ala Gly Gly Ile
            100                 105                 110

Tyr Leu Gly Phe Ile Tyr Asn Gly Gly Ala Pro Ala Ile Glu Ala Tyr
        115                 120                 125

Ile Glu Lys Val Ser Arg Arg Ser Ser Phe Glu Phe Gly Arg Ala Arg
    130                 135                 140

Leu Phe Gly Cys Val Gly Trp Ala Leu Cys Ala Ser Val Val Gly Ile
145                 150                 155                 160

Met Phe Thr Ile Asn Asn Glu Phe Val Phe Trp Leu Gly Ser Gly Cys
                165                 170                 175

Ala Val Ile Leu Ala Ile Leu Leu Ile Ala Lys Pro Glu Ala Gly
            180                 185                 190

Ser Thr Ala Gln Val Ala Asp Lys Leu Gly Ala Asn Ser Lys Pro Phe
        195                 200                 205

Asn Leu Arg Leu Ala Phe Glu Leu Leu Lys Asp Ser Lys Leu Trp Phe
    210                 215                 220

Leu Ala Leu Tyr Val Val Gly Val Ser Cys Thr Tyr Asp Val Phe Asp
225                 230                 235                 240

Gln Gln Phe Ala Asn Phe Phe Thr Ser Phe Ser Ser Glu Gln
                245                 250                 255

Gly Thr Arg Val Phe Gly Tyr Val Thr Thr Met Gly Glu Leu Leu Asn
            260                 265                 270

Ala Ser Ile Met Phe Phe Ala Pro Leu Ile Val Asn Arg Ile Gly Gly
        275                 280                 285

Lys Asn Ala Leu Leu Leu Ala Gly Leu Ile Met Ser Ile Arg Ile Ile
    290                 295                 300

Gly Ser Ser Phe Ala Ser Thr Pro Val Glu Val Ile Leu Lys Thr
305                 310                 315                 320

Leu His Met Phe Glu Ile Pro Phe Leu Ile Val Gly Cys Phe Lys Tyr
                325                 330                 335

Ile Thr Ser Val Phe Glu Val Arg Phe Ser Ala Thr Ile Tyr Leu Val

```
            340             345             350
Cys Phe Cys Phe Phe Lys Gln Leu Ala Ile Met Phe Met Ser Val Phe
            355             360             365

Ala Gly Asn Met Tyr Glu Lys Val Gly Phe His Gly Thr Tyr Leu Ile
        370             375             380

Leu Gly Leu Ile Ala Leu Ser Phe Thr Leu Ile Ser Val Phe Thr Leu
385             390             395             400

Ser Gly Arg Gly Pro Leu Ser Ala Phe Lys Pro Glu Pro Glu Ala Val
            405             410             415

Arg Asn Met Ala
            420

<210> SEQ ID NO 13
<211> LENGTH: 423
<212> TYPE: PRT
<213> ORGANISM: Rouxiella silvae
<220> FEATURE:
<221> NAME/KEY: MISC_FEATURE
<222> LOCATION: (1)..(423)
<223> OTHER INFORMATION: Lactose permease, GenBank ID: WP_084984472.1

<400> SEQUENCE: 13

Met Asn Tyr Met Arg Asn Thr Asn Phe Trp Thr Phe Gly Leu Phe Phe
1               5                   10                  15

Phe Phe Tyr Phe Phe Ile Met Gly Ala Tyr Phe Pro Phe Phe Pro Ile
            20                  25                  30

Trp Leu His Asp Ile Asn His Ile Asn Gln Ser Asp Thr Gly Ile Ile
        35                  40                  45

Phe Ala Cys Ile Ser Phe Phe Ser Leu Val Phe Gln Pro Leu Phe Gly
    50                  55                  60

Leu Leu Ser Asp Lys Leu Gly Leu Lys Lys His Leu Leu Trp Ile Ile
65                  70                  75                  80

Thr Gly Met Leu Val Leu Phe Ala Pro Phe Phe Ile Tyr Val Phe Gly
                85                  90                  95

Pro Leu Leu Gln Thr Asn Ile Leu Leu Gly Ser Ile Val Gly Gly Ile
            100                 105                 110

Tyr Leu Gly Phe Ile Tyr Asn Gly Gly Ala Pro Ala Ile Glu Ala Tyr
        115                 120                 125

Ile Glu Lys Val Ser Arg Arg Ser Ser Phe Glu Phe Gly Arg Ala Arg
    130                 135                 140

Met Phe Gly Cys Val Gly Trp Ala Ile Cys Ala Ser Val Val Gly Ile
145                 150                 155                 160

Met Phe Thr Ile Asn Asn Gln Phe Val Phe Trp Leu Gly Ser Gly Cys
                165                 170                 175

Ala Val Ile Leu Ala Ile Leu Leu Ile Ala Lys Pro Ala Val Gly
            180                 185                 190

Ala Ser Ala Lys Val Ala Asn Glu Leu Gly Ala Asn Ser Lys Pro Phe
        195                 200                 205

Asn Leu Arg Leu Ala Ala Glu Leu Leu Lys Asp Lys Lys Leu Trp Phe
    210                 215                 220

Leu Gly Leu Tyr Val Val Gly Val Ser Cys Thr Tyr Glu Val Phe Asp
225                 230                 235                 240

Gln Gln Phe Ala Asn Phe Phe Thr Ser Phe Phe Ser Ser Ala Asp Gln
                245                 250                 255

Gly Thr Arg Val Phe Gly Tyr Ile Thr Thr Leu Gly Glu Leu Leu Asn
            260                 265                 270
```

```
Ala Phe Ile Met Phe Phe Ala Pro Ala Ile Val Asn Arg Ile Gly Gly
            275                 280                 285

Lys Asn Ala Leu Leu Leu Ala Gly Ala Ile Met Ser Val Arg Ile Ile
            290                 295                 300

Gly Ser Ser Phe Ala Ser Thr Pro Val Glu Val Val Leu Leu Lys Thr
305                 310                 315                 320

Leu His Met Phe Glu Ile Pro Phe Leu Ile Val Gly Cys Phe Lys Tyr
                325                 330                 335

Ile Thr Ser Val Phe Glu Val Arg Phe Ser Ala Thr Ile Tyr Leu Val
                340                 345                 350

Cys Phe Cys Phe Phe Lys Gln Ile Ala Met Ile Phe Met Ser Ile Phe
                355                 360                 365

Ala Gly Glu Met Tyr Gly Lys Val Gly Phe His Gly Thr Tyr Leu Ile
            370                 375                 380

Leu Gly Leu Ile Ala Leu Ala Phe Thr Leu Val Ser Ile Phe Thr Leu
385                 390                 395                 400

Thr Gly Arg Gly Pro Leu Gln Ala Phe Lys Pro Ser Gln Arg Val Ser
                405                 410                 415

Glu Thr Arg Pro Val Ser Pro
            420

<210> SEQ ID NO 14
<211> LENGTH: 412
<212> TYPE: PRT
<213> ORGANISM: Aeromonas
<220> FEATURE:
<221> NAME/KEY: MISC_FEATURE
<222> LOCATION: (1)..(412)
<223> OTHER INFORMATION: Lactose permease, GenBank ID: WP_199428647.1

<400> SEQUENCE: 14

Met Phe Gly Ala Ile Phe Phe Leu Tyr Phe Phe Ile Met Gly Ala Tyr
1               5                   10                  15

Phe Pro Phe Phe Pro Ile Trp Leu His Asp Val Asn Gly Ile Ser Lys
            20                  25                  30

Ala Glu Thr Gly Ile Val Phe Gly Thr Ile Ser Leu Phe Ala Leu Leu
        35                  40                  45

Phe Gln Pro Val Phe Gly Leu Val Ser Asp Lys Leu Gly Leu Lys Lys
    50                  55                  60

His Leu Leu Trp Ile Ile Ile Gly Leu Leu Val Phe Phe Ala Pro Phe
65                  70                  75                  80

Phe Leu Tyr Val Leu Ala Pro Leu Leu Lys Leu Asn Ile Tyr Leu Gly
                85                  90                  95

Ser Ile Val Gly Gly Met Tyr Ile Gly Phe Val Phe Ala Gly Gly Ala
            100                 105                 110

Pro Ala Ile Glu Ala Tyr Val Glu Lys Val Ser Arg Ser Ser Gln Phe
        115                 120                 125

Glu Phe Gly Arg Ala Arg Met Phe Gly Ala Ile Gly Trp Ala Leu Cys
    130                 135                 140

Ala Ser Ile Val Gly Ile Met Phe Thr Ile Asn Asn Glu Phe Val Phe
145                 150                 155                 160

Trp Met Gly Ser Ala Phe Ala Val Val Met Ala Val Leu Phe Tyr Phe
                165                 170                 175

Ile Asn Pro Gly Arg Gly Ser Thr Ser Glu Val Leu Asp Ser Ile Gly
            180                 185                 190
```

```
Ala Asn Gln Lys Gly Phe Ser Ile Lys Leu Ala Met Arg Leu Leu Lys
            195                 200                 205

Gln Ala Lys Phe Trp Phe Phe Thr Leu Tyr Val Ile Gly Val Ala Cys
    210                 215                 220

Thr Tyr Asp Val Phe Asp Gln Gln Phe Ala Asn Phe Thr Ala Phe
225                 230                 235                 240

Phe Asp Thr Lys Glu Glu Gly Thr Arg Tyr Phe Gly Tyr Val Thr Thr
                245                 250                 255

Met Gly Glu Leu Leu Asn Ala Ser Ile Met Phe Phe Ala Pro Leu Ile
            260                 265                 270

Val Asn Arg Ile Gly Gly Lys Asn Ala Leu Leu Ile Ala Gly Thr Ile
    275                 280                 285

Met Ser Ile Arg Ile Ile Gly Ser Ser Phe Ala Glu Thr Val Ser His
    290                 295                 300

Val Ile Leu Leu Lys Thr Leu His Met Leu Glu Val Pro Phe Leu Leu
305                 310                 315                 320

Val Gly Thr Phe Lys Tyr Ile Thr Ser Glu Phe Asp Val Arg Phe Ser
                325                 330                 335

Ala Thr Ile Trp Leu Ile Gly Tyr Gln Phe Phe Lys Gln Leu Ala Thr
            340                 345                 350

Met Phe Met Ser Val Trp Ala Gly Ser Met Tyr Glu Val Met Gly Phe
    355                 360                 365

Arg Glu Thr Tyr Leu Val Leu Gly Ile Ile Ala Ala Thr Phe Thr Phe
    370                 375                 380

Ile Ser Ile Phe Thr Leu Ser Gly Met Gly Pro Leu Gly Leu Leu Lys
385                 390                 395                 400

Gly Arg Thr Met Val Ser Lys Lys Thr Ala Ser Tyr
                405                 410

<210> SEQ ID NO 15
<211> LENGTH: 425
<212> TYPE: PRT
<213> ORGANISM: Yersinia pestis
<220> FEATURE:
<221> NAME/KEY: MISC_FEATURE
<222> LOCATION: (1)..(425)
<223> OTHER INFORMATION: Lactose permease, GenBank ID: WP_046596210.1

<400> SEQUENCE: 15

Met Lys Ile Ser Lys Thr Gly Asn Tyr Thr Ile Leu Phe Thr Val Ser
1               5                   10                  15

Phe Phe Ile Met Ala Ser Tyr Tyr Pro Phe Phe Pro Ile Trp Leu His
            20                  25                  30

Asp Ile Asn Asn Leu Ser Lys Thr Asp Thr Gly Ile Val Phe Gly Ser
        35                  40                  45

Ile Ser Leu Phe Ala Leu Ala Phe Gln Pro Ile Met Gly Pro Leu Ser
    50                  55                  60

Asp Lys Leu Gly Leu Arg Lys Thr Leu Met Trp Ile Ile Val Gly Leu
65                  70                  75                  80

Leu Val Leu Phe Ala Pro Phe Phe Ile Tyr Val Phe Ser Pro Leu Leu
                85                  90                  95

Lys Tyr Asn Ile Phe Ile Gly Ala Ile Val Gly Gly Cys Tyr Leu Gly
            100                 105                 110

Phe Val Phe Thr Gly Gly Ser His Ala Ile Glu Ala Tyr Ile Glu Lys
    115                 120                 125

Val Ser Arg His Ser Asn Phe Glu Tyr Gly Arg Val Arg Met Phe Gly
```

```
            130                 135                 140
Cys Ile Gly Trp Ala Leu Cys Ala Thr Val Val Gly Ile Leu Tyr Thr
145                 150                 155                 160

Val Asn Asn Gln Leu Ile Phe Trp Met Ala Ser Gly Cys Ala Leu Ile
            165                 170                 175

Leu Ala Val Leu Leu Phe Phe Ala Arg Pro Asp Arg Gln Ser Thr Ala
            180                 185                 190

Phe Val Val Asp Thr Leu Gly Ala Asn Lys Ala Val Phe Asn Leu Lys
            195                 200                 205

Asn Ala Leu Ala Leu Leu Arg Lys Arg Glu Leu Trp Phe Phe Val Met
210                 215                 220

Tyr Ile Val Gly Val Ala Cys Ile Tyr Asp Val Phe Asp Gln Gln Phe
225                 230                 235                 240

Ala Asn Phe Phe Thr Ser Phe Phe Ala Thr Lys Gln Gln Gly Thr Glu
            245                 250                 255

Ile Phe Gly Phe Val Thr Thr Gly Gly Glu Ile Leu Asn Ala Thr Val
            260                 265                 270

Met Phe Phe Ala Pro Val Ile Ile Ala Arg Ile Gly Ser Lys Asn Ala
            275                 280                 285

Leu Leu Leu Ala Gly Thr Ile Met Ser Val Arg Ile Leu Gly Ser Ala
290                 295                 300

Phe Ala Thr Thr Ala Thr Gln Val Val Phe Leu Lys Met Leu His Met
305                 310                 315                 320

Phe Glu Val Pro Phe Leu Leu Val Gly Ser Phe Lys Tyr Ile Thr Gln
            325                 330                 335

Val Phe Glu Val Arg Phe Ser Ala Thr Val Tyr Leu Ile Gly Phe Cys
            340                 345                 350

Phe Ser Lys Gln Leu Ser Met Met Phe Met Ser Val Phe Ala Gly Arg
            355                 360                 365

Met Tyr Gly Ser Met Gly Tyr Gln Asp Thr Tyr Met Val Leu Gly Val
            370                 375                 380

Ile Val Leu Ser Phe Thr Leu Ile Ser Ala Phe Thr Leu Ser Gly Arg
385                 390                 395                 400

Ser Ala Val Ala Asn Leu Ala Ser Arg Leu Lys Glu Asp Pro Ser Val
            405                 410                 415

Thr Pro Pro Val Ser Gln Pro Gln Ser
            420                 425

<210> SEQ ID NO 16
<211> LENGTH: 587
<212> TYPE: PRT
<213> ORGANISM: Kluyveromyces lactis
<220> FEATURE:
<221> NAME/KEY: MISC_FEATURE
<222> LOCATION: (1)..(587)
<223> OTHER INFORMATION: Lactose permease, GenBank ID: XP_452193.1

<400> SEQUENCE: 16

Met Ala Asp His Ser Ser Ser Ser Ser Leu Gln Lys Lys Pro Ile
1               5                   10                  15

Asn Thr Ile Glu His Lys Asp Thr Leu Gly Asn Asp Arg Asp His Lys
            20                  25                  30

Glu Ala Leu Asn Ser Asp Asn Asp Asn Thr Ser Gly Leu Lys Ile Asn
        35                  40                  45

Gly Val Pro Ile Glu Asp Ala Arg Glu Glu Val Leu Leu Pro Gly Tyr
    50                  55                  60
```

```
Leu Ser Lys Gln Tyr Tyr Lys Leu Tyr Gly Leu Cys Phe Ile Thr Tyr
 65                  70                  75                  80

Leu Cys Ala Thr Met Gln Gly Tyr Asp Gly Ala Leu Met Gly Ser Ile
                 85                  90                  95

Tyr Thr Glu Asp Ala Tyr Leu Lys Tyr Tyr His Leu Asp Ile Asn Ser
            100                 105                 110

Ser Ser Gly Thr Gly Leu Val Phe Ser Ile Phe Asn Val Gly Gln Ile
        115                 120                 125

Cys Gly Ala Phe Phe Val Pro Leu Met Asp Trp Lys Gly Arg Lys Pro
    130                 135                 140

Ala Ile Leu Ile Gly Cys Leu Gly Val Val Ile Gly Ala Ile Ile Ser
145                 150                 155                 160

Ser Leu Thr Thr Thr Lys Ser Ala Leu Ile Gly Gly Arg Trp Phe Val
                165                 170                 175

Ala Phe Phe Ala Thr Ile Ala Asn Ala Ala Pro Thr Tyr Cys Ala
            180                 185                 190

Glu Val Ala Pro Ala His Leu Arg Gly Lys Val Ala Gly Leu Tyr Asn
        195                 200                 205

Thr Leu Trp Ser Val Gly Ser Ile Val Ala Ala Phe Ser Thr Tyr Gly
    210                 215                 220

Thr Asn Lys Asn Phe Pro Asn Ser Ser Lys Ala Phe Lys Ile Pro Leu
225                 230                 235                 240

Tyr Leu Gln Met Met Phe Pro Gly Leu Val Cys Ile Phe Gly Trp Leu
                245                 250                 255

Ile Pro Glu Ser Pro Arg Trp Leu Val Gly Val Gly Arg Glu Glu Glu
            260                 265                 270

Ala Arg Glu Phe Ile Ile Lys Tyr His Leu Asn Gly Asp Arg Thr His
        275                 280                 285

Pro Leu Leu Asp Met Glu Met Ala Glu Ile Ile Glu Ser Phe His Gly
    290                 295                 300

Thr Asp Leu Ser Asn Pro Leu Glu Met Leu Asp Val Arg Ser Leu Phe
305                 310                 315                 320

Arg Thr Arg Ser Asp Arg Tyr Arg Ala Met Leu Val Ile Leu Met Ala
                325                 330                 335

Trp Phe Gly Gln Phe Ser Gly Asn Asn Val Cys Ser Tyr Tyr Leu Pro
            340                 345                 350

Thr Met Leu Arg Asn Val Gly Met Lys Ser Val Ser Leu Asn Val Leu
        355                 360                 365

Met Asn Gly Val Tyr Ser Ile Val Thr Trp Ile Ser Ser Ile Cys Gly
    370                 375                 380

Ala Phe Phe Ile Asp Lys Ile Gly Arg Arg Glu Gly Phe Leu Gly Ser
385                 390                 395                 400

Ile Ser Gly Ala Ala Leu Ala Leu Thr Gly Leu Ser Ile Cys Thr Ala
                405                 410                 415

Arg Tyr Glu Lys Thr Lys Lys Ser Ala Ser Asn Gly Ala Leu Val
            420                 425                 430

Phe Ile Tyr Leu Phe Gly Gly Ile Phe Ser Phe Ala Phe Thr Pro Met
        435                 440                 445

Gln Ser Met Tyr Ser Thr Glu Val Ser Thr Asn Leu Thr Arg Ser Lys
    450                 455                 460

Ala Gln Leu Leu Asn Phe Val Val Ser Gly Val Ala Gln Phe Val Asn
465                 470                 475                 480
```

```
Gln Phe Ala Thr Pro Lys Ala Met Lys Asn Ile Lys Tyr Trp Phe Tyr
                485                 490                 495

Val Phe Tyr Val Phe Phe Asp Ile Phe Glu Phe Ile Val Ile Tyr Phe
            500                 505                 510

Phe Phe Val Glu Thr Lys Gly Arg Ser Leu Glu Glu Leu Glu Val Val
            515                 520                 525

Phe Glu Ala Pro Asn Pro Arg Lys Ala Ser Val Asp Gln Ala Phe Leu
            530                 535                 540

Ala Gln Val Arg Ala Thr Leu Val Gln Arg Asn Asp Val Arg Val Ala
545                 550                 555                 560

Asn Ala Gln Asn Leu Lys Glu Gln Glu Pro Leu Lys Ser Asp Ala Asp
            565                 570                 575

His Val Glu Lys Leu Ser Glu Ala Glu Ser Val
            580                 585

<210> SEQ ID NO 17
<211> LENGTH: 262
<212> TYPE: PRT
<213> ORGANISM: Chromobacterium violaceum
<220> FEATURE:
<221> NAME/KEY: MISC_FEATURE
<222> LOCATION: (1)..(262)
<223> OTHER INFORMATION: cvb3galT, -1,3-galactosyltransferase, GeneBank
      ID:: WP_080969100.1

<400> SEQUENCE: 17

Met Asp Thr Ile Met Ile Lys Arg Pro Leu Val Ser Val Ile Leu Pro
1               5                   10                  15

Val Asn Lys Asn Asn Pro His Leu Glu Ala Ile Gln Ser Ile Lys
            20                  25                  30

Asn Gln Thr Tyr Lys Glu Leu Glu Leu Ile Ile Ala Asn Asn Cys
            35                  40                  45

Glu Asp Asn Phe Tyr Ser Leu Leu Lys Tyr Gln Asp Gln Lys Thr
50                  55                  60

Lys Ile Ile Arg Thr Ser Ile Lys Tyr Leu Pro Phe Ser Leu Asn Leu
65                  70                  75                  80

Gly Val His Leu Ser Gln Gly Leu Tyr Ile Ala Arg Met Asp Ser Asp
                85                  90                  95

Asp Ile Ser Val Leu Asp Arg Ile Glu Lys Gln Val Lys Arg Phe Leu
            100                 105                 110

Asn Thr Pro Glu Leu Ser Ile Leu Gly Ser Asn Val Glu Tyr Ile Asn
            115                 120                 125

Glu Ala Ser Glu Ser Ile Gly Tyr Ser Asn Tyr Pro Leu Asp His Ser
            130                 135                 140

Ser Ile Val Asn Ser Phe Pro Phe Arg Cys Asn Leu Ala His Pro Thr
145                 150                 155                 160

Ile Met Val Lys Lys Glu Val Ile Thr Thr Leu Gly Gly Tyr Met Tyr
                165                 170                 175

Gly Ser Leu Ser Glu Asp Tyr Asp Leu Trp Ile Arg Ala Ser Arg His
            180                 185                 190

Gly Asn Phe Lys Phe Ser Asn Ile Asp Glu Pro Leu Leu Lys Tyr Arg
            195                 200                 205

Ile His Lys Gly Gln Ala Thr Asn Lys Ser Asn Ala Tyr Asn Ile Phe
            210                 215                 220

Ala Phe Asp Ser Ser Leu Lys Ile Arg Glu Phe Leu Leu Asn Gly Asn
225                 230                 235                 240
```

```
Val Gln Tyr Leu Leu Gly Ala Ala Arg Gly Phe Phe Ala Phe Leu Tyr
                245                 250                 255

Val Arg Phe Ile Lys Lys
            260

<210> SEQ ID NO 18
<211> LENGTH: 439
<212> TYPE: PRT
<213> ORGANISM: Artificial Sequence
<220> FEATURE:
<223> OTHER INFORMATION: galTK, -1,3-galactosyltransferase, homologous
      to GeneBank ID: BD182026.1

<400> SEQUENCE: 18

Met Ile Ser Val Tyr Ile Ile Ser Leu Lys Glu Ser Gln Arg Arg Leu
1               5                   10                  15

Asp Thr Glu Lys Leu Val Leu Glu Ser Asn Glu Lys Phe Lys Gly Arg
            20                  25                  30

Cys Val Phe Gln Ile Phe Asp Ala Ile Ser Pro Lys His Glu Asp Phe
        35                  40                  45

Glu Lys Phe Val Gln Glu Leu Tyr Asp Ser Ser Leu Leu Lys Ser
    50                  55                  60

Asp Trp Phe His Ser Asp Tyr Cys Tyr Gln Glu Leu Leu Pro Gln Glu
65                  70                  75                  80

Phe Gly Cys Tyr Leu Ser His Tyr Leu Leu Trp Lys Glu Cys Val Lys
                85                  90                  95

Leu Asn Gln Pro Val Val Ile Leu Glu Asp Asp Val Ala Leu Glu Ser
            100                 105                 110

Asn Phe Met Gln Ala Leu Glu Asp Cys Leu Lys Ser Pro Phe Asp Phe
        115                 120                 125

Val Arg Leu Tyr Gly His Tyr Trp Gly Gly His Lys Thr Asn Leu Cys
    130                 135                 140

Ala Leu Pro Val Tyr Thr Glu Thr Glu Ala Glu Ala Ser Ile Glu
145                 150                 155                 160

Lys Thr Pro Ile Glu Asn Tyr Glu Val Thr Ser Pro Pro Pro Asn
                165                 170                 175

Pro Thr Arg Asp Thr Gln Gln Asp Phe Ile Thr Glu Thr Gln Gln Asp
            180                 185                 190

Pro Lys Glu Leu Ser Glu Pro Cys Lys Ile Ala Pro Gln Lys Ile Ser
        195                 200                 205

Phe Asn Gln Val Val Phe Lys Lys Ile Lys Arg Lys Leu Asn Arg Phe
    210                 215                 220

Ile Gly Ser Ile Leu Ala Arg Thr Glu Val Tyr Lys Asn Ile Val Ala
225                 230                 235                 240

Lys Tyr Asp Asp Leu Thr Thr Lys Tyr Asp Asp Leu Thr Thr Lys Tyr
                245                 250                 255

Asp Asp Leu Thr Thr Lys Tyr Asp Asp Leu Thr Thr Lys Tyr Asp Asp
            260                 265                 270

Leu Asn Lys Asn Ile Ala Glu Lys Tyr Asp Glu Leu Met Gly Lys Tyr
        275                 280                 285

Glu Ser Leu Leu Ala Lys Glu Val Asn Ile Lys Glu Thr Phe Trp Glu
    290                 295                 300

Ser Arg Ala Asp Ser Glu Lys Glu Ala Leu Phe Leu Asp His Phe Tyr
305                 310                 315                 320

Leu Thr Ser Val Tyr Val Ala Thr Ala Gly Tyr Tyr Leu Thr Pro
                325                 330                 335
```

-continued

```
Lys Gly Ala Lys Thr Phe Ile Glu Ala Thr Glu Arg Phe Lys Ile Ile
            340                 345                 350

Glu Pro Val Asp Met Phe Ile Asn Asn Pro Thr Tyr His Asp Ile Ala
            355                 360                 365

Asn Phe Thr Tyr Val Pro Cys Pro Val Ser Leu Asn Lys His Ala Phe
        370                 375                 380

Asn Ser Thr Ile Gln Asn Ala Lys Lys Pro Asp Ile Ser Leu Lys Pro
385                 390                 395                 400

Pro Lys Lys Ser Tyr Phe Asp Asn Leu Phe Tyr His Lys Phe Asn Ala
                405                 410                 415

Arg Lys Cys Leu Lys Ala Phe Asn Lys Tyr Ser Lys Gln Tyr Ala Pro
            420                 425                 430

Leu Lys Thr Pro Lys Glu Val
            435

<210> SEQ ID NO 19
<211> LENGTH: 273
<212> TYPE: PRT
<213> ORGANISM: Helicobacter pylori
<220> FEATURE:
<221> NAME/KEY: MISC_FEATURE
<222> LOCATION: (1)..(273)
<223> OTHER INFORMATION: -1,4-gal-transferase, GalT, GenBank ID:
      WP_001262061.1

<400> SEQUENCE: 19

Met Arg Val Phe Ala Ile Ser Leu Asn Gln Lys Val Cys Asp Thr Phe
1               5                   10                  15

Gly Leu Val Phe Arg Asp Thr Thr Leu Leu Asn Ser Ile Asn Ala
            20                  25                  30

Thr His His Gln Ala Gln Ile Phe Asp Ala Ile Tyr Ser Lys Thr Phe
        35                  40                  45

Glu Gly Gly Leu His Pro Leu Val Lys Lys His Leu His Pro Tyr Phe
    50                  55                  60

Ile Thr Gln Asn Ile Lys Asp Met Gly Ile Thr Thr Asn Leu Ile Ser
65                  70                  75                  80

Glu Val Ser Lys Phe Tyr Tyr Ala Leu Lys Tyr His Ala Lys Phe Met
                85                  90                  95

Ser Leu Gly Glu Leu Gly Cys Tyr Ala Ser His Tyr Ser Leu Trp Glu
            100                 105                 110

Lys Cys Ile Glu Leu Asn Glu Ala Ile Cys Ile Leu Glu Asp Asp Ile
        115                 120                 125

Thr Leu Lys Glu Asp Phe Lys Glu Gly Leu Asp Phe Leu Glu Lys His
    130                 135                 140

Ile Gln Glu Leu Gly Tyr Ile Arg Leu Met His Leu Leu Tyr Asp Ala
145                 150                 155                 160

Ser Val Lys Ser Glu Pro Leu Ser His Lys Asn His Glu Ile Gln Glu
                165                 170                 175

Arg Val Gly Ile Ile Lys Ala Tyr Ser Glu Gly Val Gly Thr Gln Gly
            180                 185                 190

Tyr Val Ile Thr Pro Lys Ile Ala Lys Val Phe Leu Lys Cys Ser Arg
        195                 200                 205

Lys Trp Val Val Pro Val Asp Thr Ile Met Asp Ala Thr Phe Ile His
    210                 215                 220

Gly Val Lys Asn Leu Val Leu Gln Pro Phe Val Ile Ala Asp Asp Glu
225                 230                 235                 240
```

```
Gln Ile Ser Thr Ile Ala Arg Lys Glu Glu Pro Tyr Ser Pro Lys Ile
                245                 250                 255

Ala Leu Met Arg Glu Leu His Phe Lys Tyr Leu Lys Tyr Trp Gln Phe
            260                 265                 270

Val

<210> SEQ ID NO 20
<211> LENGTH: 332
<212> TYPE: PRT
<213> ORGANISM: Neisseria meningitidis
<220> FEATURE:
<221> NAME/KEY: MISC_FEATURE
<222> LOCATION: (1)..(332)
<223> OTHER INFORMATION: lgtA, -1,3-N-acetyl-glucosaminyltransferase,
      GeneBank ID: WP_033911473.1

<400> SEQUENCE: 20

Met Gln Pro Leu Val Ser Val Leu Ile Cys Ala Tyr Asn Val Glu Lys
1               5                   10                  15

Tyr Phe Ala Gln Ser Leu Ala Ala Val Val Asn Gln Thr Trp Arg Asn
                20                  25                  30

Leu Glu Ile Leu Ile Val Asp Asp Gly Ser Thr Asp Gly Thr Leu Ala
            35                  40                  45

Ile Ala Lys Asp Phe Gln Lys Arg Asp Ser Arg Ile Lys Ile Leu Ala
        50                  55                  60

Gln Ala Gln Asn Ser Gly Leu Ile Pro Ser Leu Asn Ile Gly Leu Asp
65                  70                  75                  80

Glu Leu Ala Lys Ser Gly Met Gly Glu Tyr Ile Ala Arg Thr Asp Ala
                85                  90                  95

Asp Asp Ile Ala Ala Pro Asp Trp Ile Glu Lys Ile Val Gly Glu Met
            100                 105                 110

Glu Lys Asp Arg Ser Ile Ile Ala Met Gly Ala Trp Leu Glu Val Leu
        115                 120                 125

Ser Glu Glu Lys Asp Gly Asn Arg Leu Ala Arg His His Arg His Gly
130                 135                 140

Lys Ile Trp Lys Lys Pro Thr Arg Pro Glu Asp Ile Ala Asp Phe Phe
145                 150                 155                 160

Pro Phe Gly Asn Pro Ile His Asn Asn Thr Met Ile Met Arg Arg Ser
                165                 170                 175

Val Ile Asp Gly Gly Leu Arg Tyr Asn Thr Glu Arg Asp Trp Ala Glu
            180                 185                 190

Asp Tyr Gln Phe Trp Tyr Asp Val Ser Lys Leu Gly Arg Leu Ala Tyr
        195                 200                 205

Tyr Pro Glu Ala Leu Val Lys Tyr Arg Leu His Ala Asn Gln Val Ser
210                 215                 220

Ser Lys Tyr Ser Ile Arg Gln His Glu Ile Ala Gln Gly Ile Gln Lys
225                 230                 235                 240

Thr Ala Arg Asn Asp Phe Leu Gln Ser Met Gly Phe Lys Thr Arg Phe
                245                 250                 255

Asp Ser Leu Glu Tyr Arg Gln Ile Lys Ala Val Ala Tyr Glu Leu Leu
            260                 265                 270

Glu Lys His Leu Pro Glu Glu Asp Phe Glu Arg Ala Arg Arg Phe Leu
        275                 280                 285

Tyr Gln Cys Phe Lys Arg Thr Asp Thr Leu Pro Ala Gly Ala Trp Leu
290                 295                 300
```

```
Asp Phe Ala Ala Asp Gly Arg Met Arg Arg Leu Phe Thr Leu Arg Gln
305                 310                 315                 320

Tyr Phe Gly Ile Leu His Arg Leu Leu Lys Asn Arg
                325                 330

<210> SEQ ID NO 21
<211> LENGTH: 334
<212> TYPE: PRT
<213> ORGANISM: Pasteurella multocida
<220> FEATURE:
<221> NAME/KEY: MISC_FEATURE
<222> LOCATION: (1)..(334)
<223> OTHER INFORMATION: pmnagT, -1,3-N-acetylglucosaminyl-transferase,
      GeneBankID: WP_014390683.1

<400> SEQUENCE: 21

Met Glu Asn Lys Pro Leu Val Ser Val Leu Ile Cys Ala Tyr Asn Val
1               5                   10                  15

Glu Lys Tyr Ile Glu Glu Cys Ile Asn Ala Val Ile Asn Gln Thr Tyr
            20                  25                  30

Lys Asn Leu Glu Ile Ile Ile Val Asn Asp Gly Ser Ser Asp Asn Thr
        35                  40                  45

Tyr Phe Leu Leu Lys Lys Leu Ala Glu Lys Asp Asn Arg Ile Lys Ile
    50                  55                  60

Leu Asn Phe Asn Asn His Ile Gly Ile Ile Ser Ala Leu Asn Glu Gly
65                  70                  75                  80

Leu Lys Glu Ile Ala Gly Glu Tyr Ile Ala Arg Thr Asp Ser Asp Asp
                85                  90                  95

Ile Thr Lys Pro Asp Trp Ile Glu Lys Ile Leu Thr Cys Met Gln Asn
            100                 105                 110

Asp Pro Lys Ile Ile Ala Met Gly Ser Tyr Leu Thr Val Leu Ser Glu
        115                 120                 125

Glu Asn Asn Gly Ser Val Leu Ala Asn His His Lys Asn Lys Val Glu
    130                 135                 140

Trp Lys Asn Pro Leu Glu His Lys Asp Ile Val Glu Lys Met Leu Phe
145                 150                 155                 160

Gly Asn Pro Ile His Asn Asn Ser Met Val Met Arg Ser Glu Ile Tyr
                165                 170                 175

Thr Lys Tyr His Leu Ile Tyr Asp Pro Asp Tyr His Tyr Ala Glu Asp
            180                 185                 190

Tyr Lys Phe Trp Leu Glu Val Ser Arg Ile Gly Lys Leu Ala Asn Tyr
        195                 200                 205

Pro Glu Ser Leu Val Tyr Tyr Arg Leu His Arg Asn Gln Thr Ser Ser
    210                 215                 220

Ile His Asn Ser Gln Gln Glu Ile Asn Gly Lys Lys Leu Arg Leu Gln
225                 230                 235                 240

Ala Leu Asn Tyr Tyr Leu Lys Asp Leu Gly Ile Asp Tyr Gln Leu Pro
                245                 250                 255

Glu Lys Phe Leu Phe Lys Asp Ile Ala Leu Leu Gln Glu Ile Phe Tyr
            260                 265                 270

Glu Arg Gly Met Phe Arg Glu Asn Ile Ile Arg Arg Ile Ile Tyr Glu
        275                 280                 285

Cys Tyr Leu Ser Leu Gly Glu Tyr Asn Tyr Lys Asp Ile Tyr Tyr Phe
    290                 295                 300

Leu Ile Asn Lys Asn Asn Phe Leu Ser Ile Lys Asp Lys Phe Lys Ile
305                 310                 315                 320
```

```
Ile Lys Lys Tyr Leu Arg Pro Asp Lys Tyr Ser Ser Thr Tyr
            325                 330
```

<210> SEQ ID NO 22
<211> LENGTH: 330
<212> TYPE: PRT
<213> ORGANISM: Haemophilus ducreyi
<220> FEATURE:
<221> NAME/KEY: MISC_FEATURE
<222> LOCATION: (1)..(330)
<223> OTHER INFORMATION: HD0466, glycosyltransferase family 2 protein, GeneBank ID: WP_010944479.1

<400> SEQUENCE: 22

```
Met Thr Thr Leu Val Ser Val Leu Ile Cys Ala Tyr Asn Val Glu Lys
1               5                   10                  15

Tyr Ile Asp Glu Cys Leu Asn Ala Val Ile Ala Gln Thr Tyr Lys Asn
            20                  25                  30

Leu Glu Ile Ile Val Val Asn Asp Gly Ser Thr Asp Gly Thr Leu Ala
        35                  40                  45

Lys Leu Arg Gln Phe Glu Ala Lys Asp Pro Arg Val Lys Ile Ile Asp
    50                  55                  60

Asn Ile Val Asn Gln Gly Thr Ser Lys Ser Leu Asn Ile Gly Ile Gln
65                  70                  75                  80

Tyr Cys Gln Gly Glu Ile Ile Ala Arg Thr Asp Ser Asp Asp Ile Val
                85                  90                  95

Asp Ile His Trp Ile Glu Thr Leu Met Arg Glu Leu Asp Asn Ser Pro
            100                 105                 110

Glu Thr Ile Ala Ile Ser Ala Tyr Leu Glu Phe Leu Ala Glu Lys Gly
        115                 120                 125

Asn Gly Ser Lys Leu Ser Arg Ser Arg Lys His Gly Lys Asn Ala Glu
130                 135                 140

Asn Pro Ile Ser Ser Glu Ala Ile Ser Gln Arg Met Leu Phe Gly Asn
145                 150                 155                 160

Pro Val His Asn Asn Val Ala Leu Val Arg Arg Lys Val Phe Ser Glu
                165                 170                 175

Tyr Gly Leu Arg Phe Asp Pro Asp Tyr Ile His Ala Glu Asp Tyr Lys
            180                 185                 190

Phe Trp Phe Glu Val Ser Lys Leu Gly Lys Met Arg Thr Tyr Pro Lys
        195                 200                 205

Ala Leu Val Lys Tyr Arg Leu His Ala Thr Gln Val Ser Ser Ala Tyr
    210                 215                 220

Asn Gln Lys Gln Arg Ser Ile Ala Lys Lys Ile Lys Arg Glu Ala Ile
225                 230                 235                 240

Ser His Tyr Leu Gln Gln Tyr Gly Ile Gln Leu Pro Glu Lys Leu Thr
                245                 250                 255

Ile His Asp Leu Phe Ser Ile Phe Ser Pro Gln Ile Glu Leu Ser Leu
            260                 265                 270

Thr Val Ala Asn Lys Gln Glu Leu Phe Trp Ser Leu Ala Thr Ser Leu
        275                 280                 285

Ser Glu Tyr His Phe Arg Asp Leu Leu Lys Ile Tyr Ser Leu Asp Ile
    290                 295                 300

Phe His Gln Leu Ser Phe Lys Tyr Lys Lys Arg Ile Phe Arg Lys Phe
305                 310                 315                 320

Leu Leu Pro Asn Arg Tyr Pro Ser Val Ile
                325                 330
```

<210> SEQ ID NO 23
<211> LENGTH: 302
<212> TYPE: PRT
<213> ORGANISM: Artificial Sequence
<220> FEATURE:
<223> OTHER INFORMATION: FutC (-1,2-fucosyl-transferase)

<400> SEQUENCE: 23

```
Met Ala Phe Lys Val Val Gln Ile Cys Gly Gly Leu Gly Asn Gln Met
1               5                   10                  15

Phe Gln Tyr Ala Phe Ala Lys Ser Leu Gln Lys His Ser Asn Thr Pro
            20                  25                  30

Val Leu Leu Asp Ile Thr Ser Phe Asp Trp Ser Asp Arg Lys Met Gln
        35                  40                  45

Leu Glu Leu Phe Pro Ile Asp Leu Pro Tyr Ala Ser Ala Lys Glu Ile
    50                  55                  60

Ala Ile Ala Lys Met Gln His Leu Pro Lys Leu Val Arg Asp Ala Leu
65                  70                  75                  80

Lys Cys Met Gly Phe Asp Arg Val Ser Gln Glu Ile Val Phe Glu Tyr
                85                  90                  95

Glu Pro Lys Leu Leu Lys Pro Ser Arg Leu Thr Tyr Phe Phe Gly Tyr
            100                 105                 110

Phe Gln Asp Pro Arg Tyr Phe Asp Ala Ile Ser Pro Leu Ile Lys Gln
        115                 120                 125

Thr Phe Thr Leu Pro Pro Pro Glu Asn Asn Lys Asn Asn Asn Lys
    130                 135                 140

Lys Glu Glu Glu Tyr Gln Cys Lys Leu Ser Leu Ile Leu Ala Ala Lys
145                 150                 155                 160

Asn Ser Val Phe Val His Ile Arg Arg Gly Asp Tyr Val Gly Ile Gly
                165                 170                 175

Cys Gln Leu Gly Ile Asp Tyr Gln Lys Lys Ala Leu Glu Tyr Met Ala
            180                 185                 190

Lys Arg Val Pro Asn Met Glu Leu Phe Val Phe Cys Glu Asp Leu Glu
        195                 200                 205

Phe Thr Gln Asn Leu Asp Leu Gly Tyr Pro Phe Met Asp Met Thr Thr
    210                 215                 220

Arg Asp Lys Glu Glu Ala Tyr Trp Asp Met Leu Leu Met Gln Ser
225                 230                 235                 240

Cys Gln His Gly Ile Ile Ala Asn Ser Thr Tyr Ser Trp Trp Ala Ala
                245                 250                 255

Tyr Leu Ile Glu Asn Pro Glu Lys Ile Ile Gly Pro Lys His Trp
            260                 265                 270

Leu Phe Gly His Glu Asn Ile Leu Cys Lys Gly Trp Val Lys Ile Glu
        275                 280                 285

Ser His Phe Glu Val Lys Ser Gln Lys Tyr Asn Ala Leu Gly
    290                 295                 300
```

<210> SEQ ID NO 24
<211> LENGTH: 292
<212> TYPE: PRT
<213> ORGANISM: Sulfuriflexus mobilis
<220> FEATURE:
<221> NAME/KEY: MISC_FEATURE
<222> LOCATION: (1)..(292)
<223> OTHER INFORMATION: Smob, -1,2-fucosyltransferase, GeneBank ID:
      WP_126455392.1

<400> SEQUENCE: 24

```
Met Ile Ile Ser Gln Ile Ile Gly Gly Leu Gly Asn Gln Met Phe Gln
1               5                   10                  15

Tyr Ala Ala Gly Arg Ala Leu Ser Leu Val Arg Gly Gln Pro Leu Leu
            20                  25                  30

Leu Asp Val Thr Gly Phe Ala Gly Tyr Gly Leu His Gln Gly Phe Glu
        35                  40                  45

Leu Gln Arg Val Phe Asp Cys Pro Ile Gly Ile Ala Thr Glu Glu Asp
    50                  55                  60

Val Arg Gly Ile Leu Gly Trp Gln Phe Ser Ala Gly Ile Arg Arg Ile
65                  70                  75                  80

Val Ala Arg Pro Gly Met Ala Ala Phe Arg Arg Lys Gly Phe Ile Val
            85                  90                  95

Glu Pro His Phe His Tyr Trp Pro Glu Ile Lys Asn Val Pro Arg Asp
            100                 105                 110

Cys Tyr Leu Leu Gly Tyr Trp Gln Ser Glu Arg Tyr Phe Arg Ala Ala
            115                 120                 125

Thr Ala Asp Ile Arg Ala Asp Phe Ser Phe Lys Ser Pro Leu Val Asn
        130                 135                 140

Arg Asn Ala Glu Thr Ala Ala Gln Ile Asp Gln Val Asn Ala Ile Ser
145                 150                 155                 160

Leu His Met Arg Arg Gly Asp Tyr Val Asn Asn Pro Lys Thr Ser Ala
                165                 170                 175

Thr His Gly Leu Cys Ser Leu Asp Tyr Tyr Gln Ala Ala Ile Lys Phe
            180                 185                 190

Val Ser Glu Arg Val Glu Glu Pro Phe Phe Ile Phe Ser Asp Asp
            195                 200                 205

Ile Ala Trp Val Lys Ala Asn Leu Lys Leu Asp Phe Pro Cys Gln Tyr
    210                 215                 220

Val Asp His Asn His Gly Ala Glu Ser Phe Asn Asp Met His Leu Met
225                 230                 235                 240

Ser Leu Cys Gln His His Ile Ile Ala Asn Ser Ser Phe Ser Trp Trp
                245                 250                 255

Gly Ala Trp Leu Asn Ser Asp Pro Lys Lys Ile Val Leu Ala Pro Lys
            260                 265                 270

Lys Trp Phe Ala Asn Lys Asn Asn Ile Lys Asp Leu Phe Pro Pro Gly
            275                 280                 285

Trp Val Ser Leu
    290

<210> SEQ ID NO 25
<211> LENGTH: 292
<212> TYPE: PRT
<213> ORGANISM: Methylobacter tundripaludum
<220> FEATURE:
<221> NAME/KEY: MISC_FEATURE
<222> LOCATION: (1)..(292)
<223> OTHER INFORMATION: Mtun, -1,2-fucosyltransferase, GeneBank ID:
      WP_031437198.1

<400> SEQUENCE: 25

Met Val Ile Thr His Leu Ile Gly Gly Leu Gly Asn Gln Met Phe Gln
1               5                   10                  15

Tyr Ala Ala Gly Arg Ala Val Ser Leu Glu Arg Gly Val Ser Leu Ser
            20                  25                  30

Leu Asp Ile Ser Gly Phe Ala Asn Tyr Gly Leu His Gln Gly Phe Glu
        35                  40                  45
```

-continued

Leu Gln Arg Ile Phe Asn Cys Thr Ala Glu Ile Ala Asn Glu Ala Asp
        50                  55                  60

Val Arg Gly Ile Leu Gly Trp Gln Ser Ser Pro Arg Ile Arg Gln Leu
65                  70                  75                  80

Leu Ser Arg Gln Asn Met Ala Ile Phe Arg Arg Glu Gly Phe Val Val
                85                  90                  95

Glu Pro His Phe His Tyr Trp Gln Gly Ile Lys Ser Val Pro Arg Asp
                100                 105                 110

Cys Tyr Leu Thr Gly Tyr Trp Gln Ser Glu Gln Tyr Phe Leu Glu Ala
            115                 120                 125

Ala Ala Gln Ile Arg Ala Asp Phe Thr Phe Lys Leu Pro Leu Asp Asn
        130                 135                 140

Gln Asn Ile Glu Leu Ala Lys Gln Ile Asn Ala Val Asn Ala Val Ser
145                 150                 155                 160

Leu His Val Arg Arg Gly Asp Tyr Ala Asn Thr Pro Glu Thr Thr Ala
                165                 170                 175

Thr His Gly Leu Cys Ser Leu Asp Tyr Tyr Arg Val Ala Ile Arg His
            180                 185                 190

Ile Ala Glu Gln Val Gln Pro His Phe Val Phe Ser Asp Asp
        195                 200                 205

Ile Ala Trp Val Lys Asn Asn Leu Ser Ile Asp Phe Pro Cys Gln Tyr
        210                 215                 220

Val Asp His Asn Gln Gly Ala Glu Ser Tyr Asn Asp Met Arg Leu Met
225                 230                 235                 240

Ser Met Cys Arg His His Ile Ile Ala Asn Ser Ser Phe Ser Trp Trp
                245                 250                 255

Gly Ala Trp Leu Asn Pro Asn Val Asn Lys Ile Val Val Ala Pro Ser
            260                 265                 270

Arg Trp Phe Ala Lys Gln Thr Asp Val Arg Asp Leu Leu Pro Gln Gly
                275                 280                 285

Trp Ile Lys Gln
        290

<210> SEQ ID NO 26
<211> LENGTH: 425
<212> TYPE: PRT
<213> ORGANISM: Helicobacter pylori
<220> FEATURE:
<221> NAME/KEY: MISC_FEATURE
<222> LOCATION: (1)..(425)
<223> OTHER INFORMATION: FutA, -1,3-fucosyl-transferase, GenBank ID:
      NP_207177.1

<400> SEQUENCE: 26

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
                20                  25                  30

Asn Trp Trp Gly Asp Glu Glu Ile Lys Glu Phe Lys Lys Ser Val Leu
            35                  40                  45

Tyr Phe Ile Leu Ser Gln Arg Tyr Ala Ile Thr Leu His Gln Asn Pro
        50                  55                  60

Asn Glu Phe Ser Asp Leu Val Phe Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
            115                 120                 125

His Leu His Tyr Lys Ala Glu Leu Val Asn Asp Thr Thr Ala Pro Tyr
        130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
        355                 360                 365

Leu Arg Val Asn Tyr Asp Asp Leu Arg Val Asn Tyr Asp Arg Leu Leu
    370                 375                 380

Gln Asn Ala Ser Pro Leu Leu Glu Leu Ser Gln Asn Thr Thr Phe Lys
385                 390                 395                 400

Ile Tyr Arg Lys Ala Tyr Gln Lys Ser Leu Pro Leu Leu Arg Ala Val
                405                 410                 415

Arg Lys Leu Val Lys Lys Leu Gly Leu
            420                 425

<210> SEQ ID NO 27
<211> LENGTH: 478
<212> TYPE: PRT
<213> ORGANISM: Helicobacter pylori NCTC 11639
<220> FEATURE:
<221> NAME/KEY: MISC_FEATURE
<222> LOCATION: (1)..(478)
<223> OTHER INFORMATION: FucT, alpha1,3-fucosyltransferase, GenBank ID
      NO: AAB81031.1

<400> SEQUENCE: 27

Met Phe Gln Pro Leu Leu Asp Ala Tyr Val Glu Ser Ala Ser Ile Glu
1               5                   10                  15

```
Lys Met Ala Ser Lys Ser Pro Pro Leu Lys Ile Ala Val Ala Asn
             20              25              30

Trp Trp Gly Asp Glu Ile Lys Glu Phe Lys Asn Ser Val Leu Tyr
             35              40              45

Phe Ile Leu Ser Gln Arg Tyr Thr Ile Thr Leu His Gln Asn Pro Asn
 50              55              60

Glu Phe Ser Asp Leu Val Phe Gly Asn Pro Leu Gly Ser Ala Arg Lys
 65               70              75              80

Ile Leu Ser Tyr Gln Asn Ala Lys Arg Val Phe Tyr Thr Gly Glu Asn
             85              90              95

Glu Ser Pro Asn Phe Asn Leu Phe Asp Tyr Ala Ile Gly Phe Asp Glu
             100             105             110

Leu Asp Phe Asn Asp Arg Tyr Leu Arg Met Pro Leu Tyr Tyr Asp Arg
             115             120             125

Leu His His Lys Ala Glu Ser Val Asn Asp Thr Thr Ala Pro Tyr Lys
 130             135             140

Leu Lys Asp Asn Ser Leu Tyr Ala Leu Lys Lys Pro Ser His Cys Phe
 145             150             155             160

Lys Glu Lys His Pro Asn Leu Cys Ala Val Val Asn Asp Glu Ser Asp
             165             170             175

Pro Leu Lys Arg Gly Phe Ala Ser Phe Val Ala Ser Asn Pro Asn Ala
             180             185             190

Pro Ile Arg Asn Ala Phe Tyr Asp Ala Leu Asn Ser Ile Glu Pro Val
             195             200             205

Thr Gly Gly Gly Ser Val Arg Asn Thr Leu Gly Tyr Asn Val Lys Asn
 210             215             220

Lys Asn Glu Phe Leu Ser Gln Tyr Lys Phe Asn Leu Cys Phe Glu Asn
225             230             235             240

Thr Gln Gly Tyr Gly Tyr Val Thr Glu Lys Ile Ile Asp Ala Tyr Phe
             245             250             255

Ser His Thr Ile Pro Ile Tyr Trp Gly Ser Pro Ser Val Ala Lys Asp
             260             265             270

Phe Asn Pro Lys Ser Phe Val Asn Val His Asp Phe Lys Asn Phe Asp
             275             280             285

Glu Ala Ile Asp Tyr Ile Lys Tyr Leu His Thr His Lys Asn Ala Tyr
 290             295             300

Leu Asp Met Leu Tyr Glu Asn Pro Leu Asn Thr Leu Asp Gly Lys Ala
305             310             315             320

Tyr Phe Tyr Gln Asn Leu Ser Phe Lys Lys Ile Leu Ala Phe Phe Lys
             325             330             335

Thr Ile Leu Glu Asn Asp Thr Ile Tyr His Asp Asn Pro Phe Ile Phe
             340             345             350

Cys Arg Asp Leu Asn Glu Pro Leu Val Thr Ile Asp Leu Arg Val
             355             360             365

Asn Tyr Asp Asp Leu Arg Val Asn Tyr Asp Asp Leu Arg Ile Asn Tyr
             370             375             380

Asp Asp Leu Arg Val Asn Tyr Asp Asp Leu Arg Ile Asn Tyr Asp Asp
385             390             395             400

Leu Arg Val Asn Tyr Asp Asp Leu Arg Val Asn Tyr Asp Asp Leu Arg
             405             410             415

Ile Asn Tyr Asp Asp Leu Arg Val Asn Tyr Asp Asp Leu Arg Val Asn
             420             425             430
```

```
Tyr Glu Arg Leu Leu Ser Lys Ala Thr Pro Leu Leu Glu Leu Ser Gln
            435                 440                 445

Asn Thr Thr Ser Lys Ile Tyr Arg Lys Ala Tyr Gln Lys Ser Leu Pro
    450                 455                 460

Leu Leu Arg Ala Ile Arg Arg Trp Val Lys Lys Leu Gly Leu
465                 470                 475

<210> SEQ ID NO 28
<211> LENGTH: 432
<212> TYPE: PRT
<213> ORGANISM: Helicobacter pylori
<220> FEATURE:
<221> NAME/KEY: MISC_FEATURE
<222> LOCATION: (1)..(432)
<223> OTHER INFORMATION: FucTIII, alpha-1,4 fucosyltransferase, GenBank
      ID: AAR88243.1

<400> SEQUENCE: 28

Met Phe Gln Pro Leu Leu Asp Ala Tyr Ile Asp Ser Thr Arg Leu Asp
1               5                   10                  15

Glu Thr Asp Tyr Lys Pro Pro Leu Lys Ile Ala Val Ala Asn Trp Trp
                20                  25                  30

Gly Gly Val Glu Glu Phe Lys Lys Ser Thr Leu Tyr Phe Ile Leu Ser
            35                  40                  45

Gln Arg Tyr Thr Ile Thr Leu His Arg Asn Pro Asp Lys Pro Ala Asp
    50                  55                  60

Ile Val Phe Gly Asn Pro Leu Gly Ser Ala Arg Lys Ile Leu Ser Tyr
65                  70                  75                  80

Gln Asn Ala Lys Arg Val Phe Tyr Thr Gly Glu Asn Glu Val Pro Asn
                85                  90                  95

Phe Asn Leu Phe Asp Tyr Ala Ile Gly Phe Asp Glu Leu Asp Phe Asn
            100                 105                 110

Asp Arg Tyr Leu Arg Met Pro Leu Tyr Tyr Ala His Leu His Tyr Glu
        115                 120                 125

Ala Glu Leu Val Asn Asp Thr Thr Ser Pro Tyr Lys Ile Lys Asp Asn
    130                 135                 140

Ser Leu Tyr Ala Leu Lys Lys Pro Ser His His Phe Lys Glu Asn His
145                 150                 155                 160

Pro Asn Leu Cys Ala Val Val Asn Asn Glu Ser Asp Pro Leu Lys Arg
                165                 170                 175

Gly Phe Ala Ser Phe Val Ala Ser Asn Pro Asn Ala Pro Lys Arg Asn
            180                 185                 190

Ala Phe Tyr Asp Ala Leu Asn Ser Ile Glu Pro Val Thr Gly Gly Gly
        195                 200                 205

Ser Val Lys Asn Thr Leu Gly Tyr Asn Val Lys Asn Lys Asn Glu Phe
    210                 215                 220

Leu Ser Gln Tyr Lys Phe Asn Leu Cys Phe Glu Asn Ser Gln Gly Tyr
225                 230                 235                 240

Gly Tyr Val Thr Glu Lys Ile Leu Asp Ala Tyr Phe Ser His Thr Ile
                245                 250                 255

Pro Ile Tyr Trp Gly Ser Pro Ser Val Ala Lys Asp Phe Asn Pro Lys
            260                 265                 270

Ser Phe Val Asn Val His Asp Phe Asn Asn Phe Asp Glu Ala Ile Asp
        275                 280                 285

His Val Arg Tyr Leu His Thr His Pro Asn Ala Tyr Leu Asp Met Leu
    290                 295                 300
```

```
Tyr Glu Asn Pro Leu Asn Thr Leu Asp Gly Lys Ala Tyr Phe Tyr Gln
305                 310                 315                 320

Asn Leu Ser Phe Lys Lys Ile Leu Asp Phe Phe Lys Thr Ile Leu Glu
            325                 330                 335

Asn Asp Thr Ile Tyr His Cys Asp Ala His Asn Tyr Ser Ala Leu His
                340                 345                 350

Arg Asp Leu Asn Glu Pro Leu Val Ser Ile Asp Asp Leu Arg Ile Asn
            355                 360                 365

Tyr Asp Asp Leu Arg Ile Asn Tyr Asp Leu Arg Ile Asn Tyr Asp
    370                 375                 380

Asp Leu Arg Ile Asn Tyr Glu Arg Leu Leu Gln Asn Ala Ser Pro Leu
385             390                 395                 400

Leu Glu Leu Ser Gln Asn Thr Ser Phe Lys Ile Tyr Arg Lys Ala Tyr
                405                 410                 415

Gln Lys Ser Leu Pro Leu Leu Arg Ala Ile Arg Arg Trp Val Lys Lys
            420                 425                 430
```

<210> SEQ ID NO 29
<211> LENGTH: 483
<212> TYPE: PRT
<213> ORGANISM: Artificial Sequence
<220> FEATURE:
<223> OTHER INFORMATION: Pd2 (-1,3-sialyl-transferase)

<400> SEQUENCE: 29

```
Met Cys Asn Ser Asp Asn Thr Ser Leu Lys Glu Thr Val Ser Ser Asn
1               5                   10                  15

Ser Ala Asp Val Val Glu Thr Glu Tyr Gln Leu Thr Pro Ile Asp
            20                  25                  30

Ala Pro Ser Ser Phe Leu Ser His Ser Trp Glu Gln Thr Cys Gly Thr
        35                  40                  45

Pro Ile Leu Asn Glu Ser Asp Lys Gln Ala Ile Ser Phe Asp Phe Val
    50                  55                  60

Ala Pro Glu Leu Lys Gln Asp Glu Lys Tyr Cys Phe Thr Phe Lys Gly
65                  70                  75                  80

Ile Thr Gly Asp His Arg Tyr Ile Thr Asn Thr Thr Leu Thr Val Val
                85                  90                  95

Ala Pro Thr Leu Glu Val Tyr Ile Asp His Ala Ser Leu Pro Ser Leu
            100                 105                 110

Gln Gln Leu Ile His Ile Ile Gln Ala Lys Asp Glu Tyr Pro Ser Asn
        115                 120                 125

Gln Arg Phe Val Ser Trp Lys Arg Val Thr Val Asp Ala Asp Asn Ala
    130                 135                 140

Asn Lys Leu Asn Ile His Thr Tyr Pro Leu Lys Gly Asn Asn Thr Ser
145                 150                 155                 160

Pro Glu Met Val Ala Ala Ile Asp Glu Tyr Ala Gln Ser Lys Asn Arg
                165                 170                 175

Leu Asn Ile Glu Phe Tyr Thr Asn Thr Ala His Val Phe Asn Asn Leu
            180                 185                 190

Pro Pro Ile Ile Gln Pro Leu Tyr Asn Asn Glu Lys Val Lys Ile Ser
        195                 200                 205

His Ile Ser Leu Tyr Asp Asp Gly Ser Ser Gly Tyr Val Ser Leu Tyr
    210                 215                 220

Gln Trp Lys Asp Thr Pro Asn Lys Ile Glu Thr Leu Glu Gly Glu Val
225                 230                 235                 240
```

```
Ser Leu Leu Ala Asn Tyr Leu Ala Gly Thr Ser Pro Asp Ala Pro Lys
                245                 250                 255

Gly Met Gly Asn Arg Tyr Asn Trp His Lys Leu Tyr Asp Thr Asp Tyr
            260                 265                 270

Tyr Phe Leu Arg Glu Asp Tyr Leu Asp Val Glu Ala Asn Leu His Asp
        275                 280                 285

Leu Arg Asp Tyr Leu Gly Ser Ser Ala Lys Gln Met Pro Trp Asp Glu
    290                 295                 300

Phe Ala Lys Leu Ser Asp Ser Gln Gln Thr Leu Phe Leu Asp Ile Val
305                 310                 315                 320

Gly Phe Asp Lys Glu Gln Leu Gln Gln Tyr Ser Gln Ser Pro Leu
                325                 330                 335

Pro Asn Phe Ile Phe Thr Gly Thr Thr Thr Trp Ala Gly Gly Glu Thr
                340                 345                 350

Lys Glu Tyr Tyr Ala Gln Gln Gln Val Asn Val Ile Asn Asn Ala Ile
                355                 360                 365

Asn Glu Thr Ser Pro Tyr Tyr Leu Gly Lys Asp Tyr Asp Leu Phe Phe
            370                 375                 380

Lys Gly His Pro Ala Gly Gly Val Ile Asn Asp Ile Ile Leu Gly Ser
385                 390                 395                 400

Phe Pro Asp Met Ile Asn Ile Pro Ala Lys Ile Ser Phe Glu Val Leu
                405                 410                 415

Met Met Thr Asp Met Leu Pro Asp Thr Val Ala Gly Ile Ala Ser Ser
                420                 425                 430

Leu Tyr Phe Thr Ile Pro Ala Asp Lys Val Asn Phe Ile Val Phe Thr
                435                 440                 445

Ser Ser Asp Thr Ile Thr Asp Arg Glu Glu Ala Leu Lys Ser Pro Leu
            450                 455                 460

Val Gln Val Met Leu Thr Leu Gly Ile Val Lys Glu Lys Asp Val Leu
465                 470                 475                 480

Phe Trp Ala

<210> SEQ ID NO 30
<211> LENGTH: 342
<212> TYPE: PRT
<213> ORGANISM: Artificial Sequence
<220> FEATURE:
<223> OTHER INFORMATION: Nst (-1,3-sialyl-transferase)

<400> SEQUENCE: 30

Met Glu Arg Asn Ala Val Ser Leu Leu Lys Glu Lys Leu Phe Asn Glu
1               5                   10                  15

Glu Gly Glu Pro Val Asn Leu Ile Phe Cys Tyr Thr Ile Leu Gln Met
                20                  25                  30

Lys Val Ala Glu Arg Ile Met Ala Gln His Pro Gly Glu Arg Phe Tyr
            35                  40                  45

Val Val Leu Met Ser Glu Asn Arg Asn Glu Lys Tyr Asp Tyr Tyr Phe
        50                  55                  60

Asn Gln Ile Lys Asp Lys Ala Glu Arg Ala Tyr Phe Phe His Leu Pro
65                  70                  75                  80

Tyr Gly Leu Asn Lys Ser Phe Asn Phe Ile Pro Thr Met Ala Glu Leu
                85                  90                  95

Lys Val Lys Ser Met Leu Leu Pro Lys Val Lys Arg Ile Tyr Leu Ala
                100                 105                 110

Ser Leu Glu Lys Val Ser Ile Ala Ala Phe Leu Ser Thr Tyr Pro Asp
```

```
                115                 120                 125
Ala Glu Ile Lys Thr Phe Asp Asp Gly Thr Gly Asn Leu Ile Gln Ser
        130                 135                 140

Ser Ser Tyr Leu Gly Asp Glu Phe Ser Val Asn Gly Thr Ile Lys Arg
145                 150                 155                 160

Asn Phe Ala Arg Met Met Ile Gly Asp Trp Ser Ile Ala Lys Thr Arg
                165                 170                 175

Asn Ala Ser Asp Glu His Tyr Thr Ile Phe Lys Gly Leu Lys Asn Ile
            180                 185                 190

Met Asp Asp Gly Arg Arg Lys Met Thr Tyr Leu Pro Leu Phe Asp Ala
        195                 200                 205

Ser Glu Leu Lys Thr Gly Asp Glu Thr Gly Gly Thr Val Arg Ile Leu
    210                 215                 220

Leu Gly Ser Pro Asp Lys Glu Met Lys Glu Ile Ser Glu Lys Ala Ala
225                 230                 235                 240

Lys Asn Phe Lys Ile Gln Tyr Val Ala Pro His Pro Arg Gln Thr Tyr
                245                 250                 255

Gly Leu Ser Gly Val Thr Thr Leu Asn Ser Pro Tyr Val Ile Glu Asp
            260                 265                 270

Tyr Ile Leu Arg Glu Ile Lys Lys Asn Pro His Thr Arg Tyr Glu Ile
        275                 280                 285

Tyr Thr Phe Phe Ser Gly Ala Ala Leu Thr Met Lys Asp Phe Pro Asn
    290                 295                 300

Val His Val Tyr Ala Leu Lys Pro Ala Ser Leu Pro Glu Asp Tyr Trp
305                 310                 315                 320

Leu Lys Pro Val Tyr Ala Leu Phe Thr Gln Ser Gly Ile Pro Ile Leu
                325                 330                 335

Thr Phe Asp Asp Lys Asn
            340

<210> SEQ ID NO 31
<211> LENGTH: 373
<212> TYPE: PRT
<213> ORGANISM: Escherichia coli K-12
<220> FEATURE:
<221> NAME/KEY: MISC_FEATURE
<222> LOCATION: (1)..(373)
<223> OTHER INFORMATION: gmd, GDP-mannose 4,6-dehydratas, GenBank ID:
      NP_416557.1

<400> SEQUENCE: 31

Met Ser Lys Val Ala Leu Ile Thr Gly Val Thr Gly Gln Asp Gly Ser
1               5                   10                  15

Tyr Leu Ala Glu Phe Leu Leu Glu Lys Gly Tyr Glu Val His Gly Ile
            20                  25                  30

Lys Arg Arg Ala Ser Ser Phe Asn Thr Glu Arg Val Asp His Ile Tyr
        35                  40                  45

Gln Asp Pro His Thr Cys Asn Pro Lys Phe His Leu His Tyr Gly Asp
    50                  55                  60

Leu Ser Asp Thr Ser Asn Leu Thr Arg Ile Leu Arg Glu Val Gln Pro
65                  70                  75                  80

Asp Glu Val Tyr Asn Leu Gly Ala Met Ser His Val Ala Val Ser Phe
                85                  90                  95

Glu Ser Pro Glu Tyr Thr Ala Asp Val Asp Ala Met Gly Thr Leu Arg
            100                 105                 110

Leu Leu Glu Ala Ile Arg Phe Leu Gly Leu Glu Lys Lys Thr Arg Phe
```

```
            115                 120                 125
Tyr Gln Ala Ser Thr Ser Glu Leu Tyr Gly Leu Val Gln Glu Ile Pro
    130                 135                 140

Gln Lys Glu Thr Thr Pro Phe Tyr Pro Arg Ser Pro Tyr Ala Val Ala
145                 150                 155                 160

Lys Leu Tyr Ala Tyr Trp Ile Thr Val Asn Tyr Arg Glu Ser Tyr Gly
                165                 170                 175

Met Tyr Ala Cys Asn Gly Ile Leu Phe Asn His Glu Ser Pro Arg Arg
            180                 185                 190

Gly Glu Thr Phe Val Thr Arg Lys Ile Thr Arg Ala Ile Ala Asn Ile
        195                 200                 205

Ala Gln Gly Leu Glu Ser Cys Leu Tyr Leu Gly Asn Met Asp Ser Leu
    210                 215                 220

Arg Asp Trp Gly His Ala Lys Asp Tyr Val Lys Met Gln Trp Met Met
225                 230                 235                 240

Leu Gln Gln Glu Gln Pro Glu Asp Phe Val Ile Ala Thr Gly Val Gln
                245                 250                 255

Tyr Ser Val Arg Gln Phe Val Glu Met Ala Ala Ala Gln Leu Gly Ile
            260                 265                 270

Lys Leu Arg Phe Glu Gly Thr Gly Val Glu Glu Lys Gly Ile Val Val
        275                 280                 285

Ser Val Thr Gly His Asp Ala Pro Gly Val Lys Pro Gly Asp Val Ile
    290                 295                 300

Ile Ala Val Asp Pro Arg Tyr Phe Arg Pro Ala Glu Val Glu Thr Leu
305                 310                 315                 320

Leu Gly Asp Pro Thr Lys Ala His Glu Lys Leu Gly Trp Lys Pro Glu
                325                 330                 335

Ile Thr Leu Arg Glu Met Val Ser Glu Met Val Ala Asn Asp Leu Glu
            340                 345                 350

Ala Ala Lys Lys His Ser Leu Leu Lys Ser His Gly Tyr Asp Val Ala
        355                 360                 365

Ile Ala Leu Glu Ser
    370

<210> SEQ ID NO 32
<211> LENGTH: 373
<212> TYPE: PRT
<213> ORGANISM: Enterobacteriaceae
<220> FEATURE:
<221> NAME/KEY: MISC_FEATURE
<222> LOCATION: (1)..(373)
<223> OTHER INFORMATION: gmd, GDP-mannose 4,6-dehydratas, GenBank ID:
      WP_000048190.1

<400> SEQUENCE: 32

Met Ser Lys Val Ala Leu Ile Thr Gly Val Thr Gly Gln Asp Gly Ser
1               5                   10                  15

Tyr Leu Ala Glu Phe Leu Leu Glu Lys Gly Tyr Glu Val His Gly Ile
            20                  25                  30

Lys Arg Arg Ala Ser Ser Phe Asn Thr Glu Arg Val Asp His Ile Tyr
        35                  40                  45

Gln Asp Pro His Thr Cys Asn Pro Lys Phe His Leu His Tyr Gly Asp
    50                  55                  60

Leu Ser Asp Thr Ser Asn Leu Thr Arg Ile Leu Arg Glu Val Gln Pro
65                  70                  75                  80

Asp Glu Val Tyr Asn Leu Gly Ala Met Ser His Val Ala Val Ser Phe
```

85                  90                  95
Glu Ser Pro Glu Tyr Thr Ala Asp Val Asp Ala Met Gly Thr Leu Arg
                100                 105                 110

Leu Leu Glu Ala Ile Arg Phe Leu Gly Leu Glu Lys Lys Thr Arg Phe
            115                 120                 125

Tyr Gln Ala Ser Thr Ser Glu Leu Tyr Gly Leu Val Gln Glu Ile Pro
        130                 135                 140

Gln Lys Glu Thr Thr Pro Phe Tyr Pro Arg Ser Pro Tyr Ala Val Ala
145                 150                 155                 160

Lys Leu Tyr Ala Tyr Trp Ile Thr Val Asn Tyr Arg Glu Ser Tyr Gly
                165                 170                 175

Met Tyr Ala Cys Asn Gly Ile Leu Phe Asn His Glu Ser Pro Arg Arg
                180                 185                 190

Gly Glu Thr Phe Val Thr Arg Lys Ile Thr Arg Ala Ile Ala Asn Ile
            195                 200                 205

Ala Gln Gly Leu Glu Ser Cys Leu Tyr Leu Gly Asn Met Asp Ser Leu
        210                 215                 220

Arg Asp Trp Gly His Ala Lys Asp Tyr Val Lys Met Gln Trp Met Met
225                 230                 235                 240

Leu Gln Gln Glu Gln Pro Glu Asp Phe Val Ile Ala Thr Gly Val Gln
                245                 250                 255

Tyr Ser Val Arg Gln Phe Val Glu Met Ala Ala Gln Leu Gly Ile
                260                 265                 270

Lys Leu Arg Phe Glu Gly Thr Gly Val Glu Glu Lys Gly Ile Val Val
            275                 280                 285

Ser Val Thr Gly His Asp Ala Pro Gly Val Lys Pro Gly Asp Val Ile
        290                 295                 300

Ile Ala Val Asp Pro Arg Tyr Phe Arg Pro Ala Glu Val Glu Thr Leu
305                 310                 315                 320

Leu Gly Asp Pro Thr Lys Ala His Glu Lys Leu Gly Trp Lys Pro Glu
                325                 330                 335

Ile Thr Leu Arg Glu Met Val Ser Glu Met Val Ala Asn Asp Leu Glu
            340                 345                 350

Ala Ala Lys Lys His Ser Leu Leu Lys Ser His Gly Tyr Asp Val Ala
        355                 360                 365

Ile Ala Leu Glu Ser
        370

<210> SEQ ID NO 33
<211> LENGTH: 321
<212> TYPE: PRT
<213> ORGANISM: Escherichia coli K-12
<220> FEATURE:
<221> NAME/KEY: MISC_FEATURE
<222> LOCATION: (1)..(321)
<223> OTHER INFORMATION: WcaG, GDP-L-fucose synthase

<400> SEQUENCE: 33

Met Ser Lys Gln Arg Val Phe Ile Ala Gly His Arg Gly Met Val Gly
1               5                   10                  15

Ser Ala Ile Arg Arg Gln Leu Glu Gln Arg Gly Asp Val Glu Leu Val
            20                  25                  30

Leu Arg Thr Arg Asp Glu Leu Asn Leu Leu Asp Ser Arg Ala Val His
        35                  40                  45

Asp Phe Phe Ala Ser Glu Arg Ile Asp Gln Val Tyr Leu Ala Ala Ala
    50                  55                  60

Lys Val Gly Gly Ile Val Ala Asn Asn Thr Tyr Pro Ala Asp Phe Ile
65                  70                  75                  80

Tyr Gln Asn Met Met Ile Glu Ser Asn Ile His Ala Ala His Gln
            85                  90                  95

Asn Asp Val Asn Lys Leu Leu Phe Leu Gly Ser Ser Cys Ile Tyr Pro
                100                 105                 110

Lys Leu Ala Lys Gln Pro Met Ala Glu Ser Glu Leu Leu Gln Gly Thr
            115                 120                 125

Leu Glu Pro Thr Asn Glu Pro Tyr Ala Ile Ala Lys Ile Ala Gly Ile
130                 135                 140

Lys Leu Cys Glu Ser Tyr Asn Arg Gln Tyr Gly Arg Asp Tyr Arg Ser
145                 150                 155                 160

Val Met Pro Thr Asn Leu Tyr Gly Pro His Asp Asn Phe His Pro Ser
                165                 170                 175

Asn Ser His Val Ile Pro Ala Leu Leu Arg Arg Phe His Glu Ala Thr
            180                 185                 190

Ala Gln Asn Ala Pro Asp Val Val Trp Gly Ser Gly Thr Pro Met
            195                 200                 205

Arg Glu Phe Leu His Val Asp Asp Met Ala Ala Ser Ile His Val
210                 215                 220

Met Glu Leu Ala His Glu Val Trp Leu Glu Asn Thr Gln Pro Met Leu
225                 230                 235                 240

Ser His Ile Asn Val Gly Thr Gly Val Asp Cys Thr Ile Arg Glu Leu
                245                 250                 255

Ala Gln Thr Ile Ala Lys Val Val Gly Tyr Lys Gly Arg Val Phe
            260                 265                 270

Asp Ala Ser Lys Pro Asp Gly Thr Pro Arg Lys Leu Leu Asp Val Thr
            275                 280                 285

Arg Leu His Gln Leu Gly Trp Tyr His Glu Ile Ser Leu Glu Ala Gly
            290                 295                 300

Leu Ala Ser Thr Tyr Gln Trp Phe Leu Glu Asn Gln Asp Arg Phe Arg
305                 310                 315                 320

Gly

<210> SEQ ID NO 34
<211> LENGTH: 321
<212> TYPE: PRT
<213> ORGANISM: Enterobacteriaceae
<220> FEATURE:
<221> NAME/KEY: MISC_FEATURE
<222> LOCATION: (1)..(321)
<223> OTHER INFORMATION: WcaG, GDP-L-fucose synthase, GenBank ID:
      WP_000043654.1

<400> SEQUENCE: 34

Met Ser Lys Gln Arg Val Phe Ile Ala Gly His Arg Gly Met Val Gly
1               5                   10                  15

Ser Ala Ile Arg Arg Gln Leu Glu Gln Arg Gly Asp Val Glu Leu Val
            20                  25                  30

Leu Arg Thr Arg Asp Glu Leu Asn Leu Leu Asp Ser Arg Ala Val His
        35                  40                  45

Asp Phe Phe Ala Ser Glu Arg Ile Asp Gln Val Tyr Leu Ala Ala Ala
    50                  55                  60

Lys Val Gly Gly Ile Val Ala Asn Asn Thr Tyr Pro Ala Asp Phe Ile
65                  70                  75                  80

Tyr Gln Asn Met Met Ile Glu Ser Asn Ile Ile His Ala Ala His Gln
                85                  90                  95

Asn Asp Val Asn Lys Leu Leu Phe Leu Gly Ser Ser Cys Ile Tyr Pro
            100                 105                 110

Lys Leu Ala Lys Gln Pro Met Ala Glu Ser Glu Leu Leu Gln Gly Thr
            115                 120                 125

Leu Glu Pro Thr Asn Glu Pro Tyr Ala Ile Ala Lys Ile Ala Gly Ile
            130                 135                 140

Lys Leu Cys Glu Ser Tyr Asn Arg Gln Tyr Gly Arg Asp Tyr Arg Ser
145                 150                 155                 160

Val Met Pro Thr Asn Leu Tyr Gly Pro His Asp Asn Phe His Pro Ser
                165                 170                 175

Asn Ser His Val Ile Pro Ala Leu Leu Arg Arg Phe His Glu Ala Thr
            180                 185                 190

Ala Gln Asn Ala Pro Asp Val Val Trp Gly Ser Gly Thr Pro Met
            195                 200                 205

Arg Glu Phe Leu His Val Asp Asp Met Ala Ala Ser Ile His Val
            210                 215                 220

Met Glu Leu Ala His Glu Val Trp Leu Glu Asn Thr Gln Pro Met Leu
225                 230                 235                 240

Ser His Ile Asn Val Gly Thr Gly Val Asp Cys Thr Ile Arg Glu Leu
                245                 250                 255

Ala Gln Thr Ile Ala Lys Val Val Gly Tyr Lys Gly Arg Val Val Phe
            260                 265                 270

Asp Ala Ser Lys Pro Asp Gly Thr Pro Arg Lys Leu Leu Asp Val Thr
            275                 280                 285

Arg Leu His Gln Leu Gly Trp Tyr His Glu Ile Ser Leu Glu Ala Gly
            290                 295                 300

Leu Ala Ser Thr Tyr Gln Trp Phe Leu Glu Asn Gln Asp Arg Phe Arg
305                 310                 315                 320

Gly

<210> SEQ ID NO 35
<211> LENGTH: 159
<212> TYPE: PRT
<213> ORGANISM: Escherichia coli
<220> FEATURE:
<221> NAME/KEY: MISC_FEATURE
<222> LOCATION: (1)..(159)
<223> OTHER INFORMATION: WcaH, GDP-mannose mannosyl hydrolase,
      GenBank ID: NP_416555.2

<400> SEQUENCE: 35

Met Phe Leu Arg Gln Glu Asp Phe Ala Thr Val Val Arg Ser Thr Pro
1               5                   10                  15

Leu Val Ser Leu Asp Phe Ile Val Glu Asn Ser Arg Gly Glu Phe Leu
            20                  25                  30

Leu Gly Lys Arg Thr Asn Arg Pro Ala Gln Gly Tyr Trp Phe Val Pro
            35                  40                  45

Gly Gly Arg Val Gln Lys Asp Glu Thr Leu Glu Ala Ala Phe Glu Arg
        50                  55                  60

Leu Thr Met Ala Glu Leu Gly Leu Arg Leu Pro Ile Thr Ala Gly Gln
65                  70                  75                  80

Phe Tyr Gly Val Trp Gln His Phe Tyr Asp Asp Asn Phe Ser Gly Thr
                85                  90                  95

Asp Phe Thr Thr His Tyr Val Val Leu Gly Phe Arg Phe Arg Val Ser

```
                    100                 105                 110
Glu Glu Glu Leu Leu Leu Pro Asp Glu Gln His Asp Asp Tyr Arg Trp
                    115                 120                 125

Leu Thr Ser Asp Ala Leu Leu Ala Ser Asp Asn Val His Ala Asn Ser
            130                 135                 140

Arg Ala Tyr Phe Leu Ala Glu Lys Arg Thr Gly Val Pro Gly Leu
145                 150                 155

<210> SEQ ID NO 36
<211> LENGTH: 159
<212> TYPE: PRT
<213> ORGANISM: Escherichia
<220> FEATURE:
<221> NAME/KEY: MISC_FEATURE
<222> LOCATION: (1)..(159)
<223> OTHER INFORMATION: WcaH, GDP-mannose mannosyl hydrolase, GenBank
      ID: WP_001393539.1

<400> SEQUENCE: 36

Met Phe Leu Arg Gln Glu Asp Phe Ala Thr Val Val Arg Ser Thr Pro
1               5                   10                  15

Leu Val Ser Leu Asp Phe Ile Val Glu Asn Ser Arg Gly Glu Phe Leu
            20                  25                  30

Leu Gly Lys Arg Thr Asn Arg Pro Ala Gln Gly Tyr Trp Phe Val Pro
        35                  40                  45

Gly Gly Arg Val Gln Lys Asp Glu Thr Leu Glu Ala Ala Phe Glu Arg
    50                  55                  60

Leu Thr Met Ala Glu Leu Gly Leu Arg Leu Pro Ile Thr Ala Gly Gln
65                  70                  75                  80

Phe Tyr Gly Val Trp Gln His Phe Tyr Asp Asp Asn Phe Ser Gly Thr
                85                  90                  95

Asp Phe Thr Thr His Tyr Val Val Leu Gly Phe Arg Phe Arg Val Ser
                    100                 105                 110

Glu Glu Glu Leu Leu Leu Pro Asp Glu Gln His Asp Asp Tyr Arg Trp
                    115                 120                 125

Leu Thr Ser Asp Ala Leu Leu Ala Ser Asp Asn Val His Ala Asn Ser
            130                 135                 140

Arg Ala Tyr Phe Leu Ala Glu Lys Arg Thr Gly Val Pro Gly Leu
145                 150                 155

<210> SEQ ID NO 37
<211> LENGTH: 407
<212> TYPE: PRT
<213> ORGANISM: Escherichia coli
<220> FEATURE:
<221> NAME/KEY: MISC_FEATURE
<222> LOCATION: (1)..(407)
<223> OTHER INFORMATION: WcaI, colanic acid biosynthesis
      fucosyltransferase, GenBank ID: NP_416554.1

<400> SEQUENCE: 37

Met Lys Ile Leu Val Tyr Gly Ile Asn Tyr Ser Pro Glu Leu Thr Gly
1               5                   10                  15

Ile Gly Lys Tyr Thr Gly Glu Met Val Glu Trp Leu Ala Ala Gln Gly
            20                  25                  30

His Glu Val Arg Val Ile Thr Ala Pro Pro Tyr Tyr Pro Gln Trp Gln
        35                  40                  45

Val Gly Glu Asn Tyr Ser Ala Trp Arg Tyr Lys Arg Glu Glu Gly Ala
    50                  55                  60
```

Ala Thr Val Trp Arg Cys Pro Leu Tyr Val Pro Lys Gln Pro Ser Thr
 65                  70                  75                  80

Leu Lys Arg Leu Leu His Leu Gly Ser Phe Ala Val Ser Ser Phe Phe
             85                  90                  95

Pro Leu Met Ala Gln Arg Arg Trp Lys Pro Asp Arg Ile Ile Gly Val
            100                 105                 110

Val Pro Thr Leu Phe Cys Ala Pro Gly Met Arg Leu Leu Ala Lys Leu
        115                 120                 125

Ser Gly Ala Arg Thr Val Leu His Ile Gln Asp Tyr Glu Val Asp Ala
130                 135                 140

Met Leu Gly Leu Gly Leu Ala Gly Lys Gly Lys Gly Gly Lys Val Ala
145                 150                 155                 160

Gln Leu Ala Thr Ala Phe Glu Arg Ser Gly Leu His Asn Val Asp Asn
                165                 170                 175

Val Ser Thr Ile Ser Arg Ser Met Met Asn Lys Ala Ile Glu Lys Gly
            180                 185                 190

Val Ala Ala Glu Asn Val Ile Phe Pro Asn Trp Ser Glu Ile Ala
        195                 200                 205

Arg Phe Gln His Val Ala Asp Ala Asp Val Asp Ala Leu Arg Asn Gln
210                 215                 220

Leu Asp Leu Pro Asp Asn Lys Lys Ile Ile Leu Tyr Ser Gly Asn Ile
225                 230                 235                 240

Gly Glu Lys Gln Gly Leu Glu Asn Val Ile Glu Ala Ala Asp Arg Leu
                245                 250                 255

Arg Asp Glu Pro Leu Ile Phe Ala Ile Val Gly Gln Gly Gly Gly Lys
            260                 265                 270

Ala Arg Leu Glu Lys Met Ala Gln Gln Arg Gly Leu Arg Asn Met Gln
        275                 280                 285

Phe Phe Pro Leu Gln Ser Tyr Asp Ala Leu Pro Ala Leu Leu Lys Met
290                 295                 300

Gly Asp Cys His Leu Val Val Gln Lys Arg Gly Ala Ala Asp Ala Val
305                 310                 315                 320

Leu Pro Ser Lys Leu Thr Asn Ile Leu Ala Val Gly Gly Asn Ala Val
                325                 330                 335

Ile Thr Ala Glu Ala Tyr Thr Glu Leu Gly Gln Leu Cys Glu Thr Phe
            340                 345                 350

Pro Gly Ile Ala Val Cys Val Glu Pro Glu Ser Val Glu Ala Leu Val
        355                 360                 365

Ala Gly Ile Arg Gln Ala Leu Leu Leu Pro Lys His Asn Thr Val Ala
370                 375                 380

Arg Glu Tyr Ala Glu Arg Thr Leu Asp Lys Glu Asn Val Leu Arg Gln
385                 390                 395                 400

Phe Ile Asn Asp Ile Arg Gly
                405

<210> SEQ ID NO 38
<211> LENGTH: 407
<212> TYPE: PRT
<213> ORGANISM: Escherichia
<220> FEATURE:
<221> NAME/KEY: MISC_FEATURE
<222> LOCATION: (1)..(407)
<223> OTHER INFORMATION: WcaI, colanic acid biosynthesis
      fucosyltransferase , GenBank ID: WP_000699693.1

<400> SEQUENCE: 38

```
Met Lys Ile Leu Val Tyr Gly Ile Asn Tyr Ser Pro Glu Leu Thr Gly
1               5                   10                  15

Ile Gly Lys Tyr Thr Gly Glu Met Val Glu Trp Leu Ala Ala Gln Gly
                20                  25                  30

His Glu Val Arg Val Ile Thr Ala Pro Pro Tyr Tyr Pro Gln Trp Gln
                35                  40                  45

Val Gly Glu Asn Tyr Ser Ala Trp Arg Tyr Lys Arg Glu Glu Gly Ala
        50                  55                  60

Ala Thr Val Trp Arg Cys Pro Leu Tyr Val Pro Lys Gln Pro Ser Thr
65                  70                  75                  80

Leu Lys Arg Leu Leu His Leu Gly Ser Phe Ala Val Ser Ser Phe Phe
                85                  90                  95

Pro Leu Met Ala Gln Arg Arg Trp Lys Pro Asp Arg Ile Ile Gly Val
            100                 105                 110

Val Pro Thr Leu Phe Cys Ala Pro Gly Met Arg Leu Leu Ala Lys Leu
            115                 120                 125

Ser Gly Ala Arg Thr Val Leu His Ile Gln Asp Tyr Glu Val Asp Ala
        130                 135                 140

Met Leu Gly Leu Gly Leu Ala Gly Lys Gly Lys Gly Gly Lys Val Ala
145                 150                 155                 160

Gln Leu Ala Thr Ala Phe Glu Arg Ser Gly Leu His Asn Val Asp Asn
                165                 170                 175

Val Ser Thr Ile Ser Arg Ser Met Met Asn Lys Ala Ile Glu Lys Gly
            180                 185                 190

Val Ala Ala Glu Asn Val Ile Phe Phe Pro Asn Trp Ser Glu Ile Ala
        195                 200                 205

Arg Phe Gln His Val Ala Asp Ala Asp Val Asp Ala Leu Arg Asn Gln
    210                 215                 220

Leu Asp Leu Pro Asp Asn Lys Lys Ile Ile Leu Tyr Ser Gly Asn Ile
225                 230                 235                 240

Gly Glu Lys Gln Gly Leu Glu Asn Val Ile Glu Ala Ala Asp Arg Leu
                245                 250                 255

Arg Asp Glu Pro Leu Ile Phe Ala Ile Val Gly Gln Gly Gly Gly Lys
            260                 265                 270

Ala Arg Leu Glu Lys Met Ala Gln Gln Arg Gly Leu Arg Asn Met Gln
        275                 280                 285

Phe Phe Pro Leu Gln Ser Tyr Asp Ala Leu Pro Ala Leu Leu Lys Met
    290                 295                 300

Gly Asp Cys His Leu Val Val Gln Lys Arg Gly Ala Ala Asp Ala Val
305                 310                 315                 320

Leu Pro Ser Lys Leu Thr Asn Ile Leu Ala Val Gly Gly Asn Ala Val
                325                 330                 335

Ile Thr Ala Glu Ala Tyr Thr Glu Leu Gly Gln Leu Cys Glu Thr Phe
            340                 345                 350

Pro Gly Ile Ala Val Cys Val Glu Pro Glu Ser Val Glu Ala Leu Val
        355                 360                 365

Ala Gly Ile Arg Gln Ala Leu Leu Pro Lys His Asn Thr Val Ala
370                 375                 380

Arg Glu Tyr Ala Glu Arg Thr Leu Asp Lys Glu Asn Val Leu Arg Gln
385                 390                 395                 400

Phe Ile Asn Asp Ile Arg Gly
                405
```

```
<210> SEQ ID NO 39
<211> LENGTH: 478
<212> TYPE: PRT
<213> ORGANISM: Escherichia coli K-12
<220> FEATURE:
<221> NAME/KEY: MISC_FEATURE
<222> LOCATION: (1)..(478)
<223> OTHER INFORMATION: ManC, mannose-1-phosphate guanylyltransferase,
      GenBank ID: NP_416553.1

<400> SEQUENCE: 39

Met Ala Gln Ser Lys Leu Tyr Pro Val Val Met Ala Gly Gly Ser Gly
1               5                   10                  15

Ser Arg Leu Trp Pro Leu Ser Arg Val Leu Tyr Pro Lys Gln Phe Leu
            20                  25                  30

Cys Leu Lys Gly Asp Leu Thr Met Leu Gln Thr Thr Ile Cys Arg Leu
        35                  40                  45

Asn Gly Val Glu Cys Glu Ser Pro Val Val Ile Cys Asn Glu Gln His
    50                  55                  60

Arg Phe Ile Val Ala Glu Gln Leu Arg Gln Leu Asn Lys Leu Thr Glu
65                  70                  75                  80

Asn Ile Ile Leu Glu Pro Ala Gly Arg Asn Thr Ala Pro Ala Ile Ala
                85                  90                  95

Leu Ala Ala Leu Ala Ala Lys Arg His Ser Pro Glu Ser Asp Pro Leu
            100                 105                 110

Met Leu Val Leu Ala Ala Asp His Val Ile Ala Asp Glu Asp Ala Phe
        115                 120                 125

Arg Ala Ala Val Arg Asn Ala Met Pro Tyr Ala Glu Ala Gly Lys Leu
    130                 135                 140

Val Thr Phe Gly Ile Val Pro Asp Leu Pro Glu Thr Gly Tyr Gly Tyr
145                 150                 155                 160

Ile Arg Arg Gly Glu Val Ser Ala Gly Glu Gln Asp Met Val Ala Phe
                165                 170                 175

Glu Val Ala Gln Phe Val Glu Lys Pro Asn Leu Glu Thr Ala Gln Ala
            180                 185                 190

Tyr Val Ala Ser Gly Glu Tyr Tyr Trp Asn Ser Gly Met Phe Leu Phe
        195                 200                 205

Arg Ala Gly Arg Tyr Leu Glu Glu Leu Lys Lys Tyr Arg Pro Asp Ile
    210                 215                 220

Leu Asp Ala Cys Glu Lys Ala Met Ser Ala Val Asp Pro Asp Leu Asn
225                 230                 235                 240

Phe Ile Arg Val Asp Glu Glu Ala Phe Leu Ala Cys Pro Glu Glu Ser
                245                 250                 255

Val Asp Tyr Ala Val Met Glu Arg Thr Ala Asp Ala Val Val Val Pro
            260                 265                 270

Met Asp Ala Gly Trp Ser Asp Val Gly Ser Trp Ser Ser Leu Trp Glu
        275                 280                 285

Ile Ser Ala His Thr Ala Glu Gly Asn Val Cys His Gly Asp Val Ile
    290                 295                 300

Asn His Lys Thr Glu Asn Ser Tyr Val Tyr Ala Glu Ser Gly Leu Val
305                 310                 315                 320

Thr Thr Val Gly Val Lys Asp Leu Val Val Val Gln Thr Lys Asp Ala
                325                 330                 335

Val Leu Ile Ala Asp Arg Asn Ala Val Gln Asp Val Lys Lys Val Val
            340                 345                 350

Glu Gln Ile Lys Ala Asp Gly Arg His Glu His Arg Val His Arg Glu
```

```
                355                 360                 365
Val Tyr Arg Pro Trp Gly Lys Tyr Asp Ser Ile Asp Ala Gly Asp Arg
        370                 375                 380

Tyr Gln Val Lys Arg Ile Thr Val Lys Pro Gly Glu Gly Leu Ser Val
385                 390                 395                 400

Gln Met His His Arg Ala Glu His Trp Val Val Val Ala Gly Thr
                405                 410                 415

Ala Lys Val Thr Ile Asp Gly Asp Ile Lys Leu Leu Gly Glu Asn Glu
                420                 425                 430

Ser Ile Tyr Ile Pro Leu Gly Ala Thr His Cys Leu Glu Asn Pro Gly
                435                 440                 445

Lys Ile Pro Leu Asp Leu Ile Glu Val Arg Ser Gly Ser Tyr Leu Glu
                450                 455                 460

Glu Asp Asp Val Val Arg Phe Ala Asp Arg Tyr Gly Arg Val
465                 470                 475

<210> SEQ ID NO 40
<211> LENGTH: 478
<212> TYPE: PRT
<213> ORGANISM: Escherichia
<220> FEATURE:
<221> NAME/KEY: MISC_FEATURE
<222> LOCATION: (1)..(478)
<223> OTHER INFORMATION: ManC, mannose-1-phosphate guanyltransferase,
      GenBank ID: WP_000079274.1

<400> SEQUENCE: 40

Met Ala Gln Ser Lys Leu Tyr Pro Val Val Met Ala Gly Gly Ser Gly
1               5                   10                  15

Ser Arg Leu Trp Pro Leu Ser Arg Val Leu Tyr Pro Lys Gln Phe Leu
                20                  25                  30

Cys Leu Lys Gly Asp Leu Thr Met Leu Gln Thr Thr Ile Cys Arg Leu
            35                  40                  45

Asn Gly Val Glu Cys Glu Ser Pro Val Val Ile Cys Asn Glu Gln His
        50                  55                  60

Arg Phe Ile Val Ala Glu Gln Leu Arg Gln Leu Asn Lys Leu Thr Glu
65                  70                  75                  80

Asn Ile Ile Leu Glu Pro Ala Gly Arg Asn Thr Ala Pro Ala Ile Ala
                85                  90                  95

Leu Ala Ala Leu Ala Ala Lys Arg His Ser Pro Glu Ser Asp Pro Leu
                100                 105                 110

Met Leu Val Leu Ala Ala Asp His Val Ile Ala Asp Glu Asp Ala Phe
            115                 120                 125

Arg Ala Ala Val Arg Asn Ala Met Pro Tyr Ala Glu Ala Gly Lys Leu
        130                 135                 140

Val Thr Phe Gly Ile Val Pro Asp Leu Pro Glu Thr Gly Tyr Gly Tyr
145                 150                 155                 160

Ile Arg Arg Gly Glu Val Ser Ala Gly Glu Gln Asp Met Val Ala Phe
                165                 170                 175

Glu Val Ala Gln Phe Val Glu Lys Pro Asn Leu Glu Thr Ala Gln Ala
            180                 185                 190

Tyr Val Ala Ser Gly Glu Tyr Tyr Trp Asn Ser Gly Met Phe Leu Phe
        195                 200                 205

Arg Ala Gly Arg Tyr Leu Glu Glu Leu Lys Lys Tyr Arg Pro Asp Ile
    210                 215                 220

Leu Asp Ala Cys Glu Lys Ala Met Ser Ala Val Asp Pro Asp Leu Asn
```

```
                                225                 230                 235                 240

Phe Ile Arg Val Asp Glu Glu Ala Phe Leu Ala Cys Pro Glu Glu Ser
                            245                 250                 255

Val Asp Tyr Ala Val Met Glu Arg Thr Ala Asp Ala Val Val Val Pro
                            260                 265                 270

Met Asp Ala Gly Trp Ser Asp Val Gly Ser Trp Ser Ser Leu Trp Glu
                            275                 280                 285

Ile Ser Ala His Thr Ala Glu Gly Asn Val Cys His Gly Asp Val Ile
                            290                 295                 300

Asn His Lys Thr Glu Asn Ser Tyr Val Tyr Ala Glu Ser Gly Leu Val
        305                 310                 315                 320

Thr Thr Val Gly Val Lys Asp Leu Val Val Gln Thr Lys Asp Ala
                            325                 330                 335

Val Leu Ile Ala Asp Arg Asn Ala Val Gln Asp Val Lys Lys Val Val
                            340                 345                 350

Glu Gln Ile Lys Ala Asp Gly Arg His Glu His Arg Val His Arg Glu
                            355                 360                 365

Val Tyr Arg Pro Trp Gly Lys Tyr Asp Ser Ile Asp Ala Gly Asp Arg
        370                 375                 380

Tyr Gln Val Lys Arg Ile Thr Val Lys Pro Gly Glu Gly Leu Ser Val
        385                 390                 395                 400

Gln Met His His His Arg Ala Glu His Trp Val Val Ala Gly Thr
                            405                 410                 415

Ala Lys Val Thr Ile Asp Gly Asp Ile Lys Leu Leu Gly Glu Asn Glu
                            420                 425                 430

Ser Ile Tyr Ile Pro Leu Gly Ala Thr His Cys Leu Glu Asn Pro Gly
                            435                 440                 445

Lys Ile Pro Leu Asp Leu Ile Glu Val Arg Ser Gly Ser Tyr Leu Glu
                            450                 455                 460

Glu Asp Asp Val Val Arg Phe Ala Asp Arg Tyr Gly Arg Val
        465                 470                 475

<210> SEQ ID NO 41
<211> LENGTH: 456
<212> TYPE: PRT
<213> ORGANISM: Escherichia coli K-12
<220> FEATURE:
<221> NAME/KEY: MISC_FEATURE
<222> LOCATION: (1)..(456)
<223> OTHER INFORMATION: ManB, phosphomannomutase, GenBank ID:
      NP_416552.1

<400> SEQUENCE: 41

Met Lys Lys Leu Thr Cys Phe Lys Ala Tyr Asp Ile Arg Gly Lys Leu
1               5                   10                  15

Gly Glu Glu Leu Asn Glu Asp Ile Ala Trp Arg Ile Gly Arg Ala Tyr
                20                  25                  30

Gly Glu Phe Leu Lys Pro Lys Thr Ile Val Leu Gly Gly Asp Val Arg
            35                  40                  45

Leu Thr Ser Glu Thr Leu Lys Leu Ala Leu Ala Lys Gly Leu Gln Asp
        50                  55                  60

Ala Gly Val Asp Val Leu Asp Ile Gly Met Ser Gly Thr Glu Glu Ile
65                  70                  75                  80

Tyr Phe Ala Thr Phe His Leu Gly Val Asp Gly Gly Ile Glu Val Thr
                85                  90                  95

Ala Ser His Asn Pro Met Asp Tyr Asn Gly Met Lys Leu Val Arg Glu
```

```
            100                 105                 110
Gly Ala Arg Pro Ile Ser Gly Asp Thr Gly Leu Arg Asp Val Gln Arg
        115                 120                 125

Leu Ala Glu Ala Asn Asp Phe Pro Val Asp Glu Thr Lys Arg Gly
130                 135                 140

Arg Tyr Gln Gln Ile Asn Leu Arg Asp Ala Tyr Val Asp His Leu Phe
145                 150                 155                 160

Gly Tyr Ile Asn Val Lys Asn Leu Thr Pro Leu Lys Leu Val Ile Asn
                165                 170                 175

Ser Gly Asn Gly Ala Ala Gly Pro Val Val Asp Ala Ile Glu Ala Arg
            180                 185                 190

Phe Lys Ala Leu Gly Ala Pro Val Glu Leu Ile Lys Val His Asn Thr
        195                 200                 205

Pro Asp Gly Asn Phe Pro Asn Gly Ile Pro Asn Pro Leu Leu Pro Glu
210                 215                 220

Cys Arg Asp Asp Thr Arg Asn Ala Val Ile Lys His Gly Ala Asp Met
225                 230                 235                 240

Gly Ile Ala Phe Asp Gly Asp Phe Asp Arg Cys Phe Leu Phe Asp Glu
                245                 250                 255

Lys Gly Gln Phe Ile Glu Gly Tyr Tyr Ile Val Gly Leu Leu Ala Glu
            260                 265                 270

Ala Phe Leu Glu Lys Asn Pro Gly Ala Lys Ile His Asp Pro Arg
        275                 280                 285

Leu Ser Trp Asn Thr Val Asp Val Val Thr Ala Ala Gly Gly Thr Pro
290                 295                 300

Val Met Ser Lys Thr Gly His Ala Phe Ile Lys Glu Arg Met Arg Lys
305                 310                 315                 320

Glu Asp Ala Ile Tyr Gly Gly Glu Met Ser Ala His His Tyr Phe Arg
                325                 330                 335

Asp Phe Ala Tyr Cys Asp Ser Gly Met Ile Pro Trp Leu Leu Val Ala
            340                 345                 350

Glu Leu Val Cys Leu Lys Asp Lys Thr Leu Gly Glu Leu Val Arg Asp
        355                 360                 365

Arg Met Ala Ala Phe Pro Ala Ser Gly Glu Ile Asn Ser Lys Leu Ala
370                 375                 380

Gln Pro Val Glu Ala Ile Asn Arg Val Glu Gln His Phe Ser Arg Glu
385                 390                 395                 400

Ala Leu Ala Val Asp Arg Thr Asp Gly Ile Ser Met Thr Phe Ala Asp
                405                 410                 415

Trp Arg Phe Asn Leu Arg Thr Ser Asn Thr Glu Pro Val Val Arg Leu
            420                 425                 430

Asn Val Glu Ser Arg Gly Asp Val Pro Leu Met Glu Ala Arg Thr Arg
        435                 440                 445

Thr Leu Leu Thr Leu Leu Asn Glu
450                 455

<210> SEQ ID NO 42
<211> LENGTH: 456
<212> TYPE: PRT
<213> ORGANISM: Escherichia
<220> FEATURE:
<221> NAME/KEY: MISC_FEATURE
<222> LOCATION: (1)..(456)
<223> OTHER INFORMATION: ManB, phosphomannomutase, GenBank ID:
      WP_001350528.1
```

-continued

```
<400> SEQUENCE: 42

Met Lys Lys Leu Thr Cys Phe Lys Ala Tyr Asp Ile Arg Gly Lys Leu
1               5                   10                  15

Gly Glu Glu Leu Asn Glu Asp Ile Ala Trp Arg Ile Gly Arg Ala Tyr
                20                  25                  30

Gly Glu Phe Leu Lys Pro Lys Thr Ile Val Leu Gly Gly Asp Val Arg
            35                  40                  45

Leu Thr Ser Glu Thr Leu Lys Leu Ala Leu Ala Lys Gly Leu Gln Asp
        50                  55                  60

Ala Gly Val Asp Val Leu Asp Ile Gly Met Ser Gly Thr Glu Glu Ile
65                  70                  75                  80

Tyr Phe Ala Thr Phe His Leu Gly Val Asp Gly Gly Ile Glu Val Thr
                85                  90                  95

Ala Ser His Asn Pro Met Asp Tyr Asn Gly Met Lys Leu Val Arg Glu
            100                 105                 110

Gly Ala Arg Pro Ile Ser Gly Asp Thr Gly Leu Arg Asp Val Gln Arg
        115                 120                 125

Leu Ala Glu Ala Asn Asp Phe Pro Val Asp Glu Thr Lys Arg Gly
        130                 135                 140

Arg Tyr Gln Gln Ile Asn Leu Arg Asp Ala Tyr Val Asp His Leu Phe
145                 150                 155                 160

Gly Tyr Ile Asn Val Lys Asn Leu Thr Pro Leu Lys Leu Val Ile Asn
                165                 170                 175

Ser Gly Asn Gly Ala Ala Gly Pro Val Val Asp Ala Ile Glu Ala Arg
            180                 185                 190

Phe Lys Ala Leu Gly Ala Pro Val Glu Leu Ile Lys Val His Asn Thr
        195                 200                 205

Pro Asp Gly Asn Phe Pro Asn Gly Ile Pro Asn Pro Leu Leu Pro Glu
    210                 215                 220

Cys Arg Asp Asp Thr Arg Asn Ala Val Ile Lys His Gly Ala Asp Met
225                 230                 235                 240

Gly Ile Ala Phe Asp Gly Asp Phe Asp Arg Cys Phe Leu Phe Asp Glu
                245                 250                 255

Lys Gly Gln Phe Ile Glu Gly Tyr Tyr Ile Val Gly Leu Leu Ala Glu
            260                 265                 270

Ala Phe Leu Glu Lys Asn Pro Gly Ala Lys Ile Ile His Asp Pro Arg
        275                 280                 285

Leu Ser Trp Asn Thr Val Asp Val Val Thr Ala Ala Gly Gly Thr Pro
    290                 295                 300

Val Met Ser Lys Thr Gly His Ala Phe Ile Lys Glu Arg Met Arg Lys
305                 310                 315                 320

Glu Asp Ala Ile Tyr Gly Gly Glu Met Ser Ala His His Tyr Phe Arg
                325                 330                 335

Asp Phe Ala Tyr Cys Asp Ser Gly Met Ile Pro Trp Leu Leu Val Ala
            340                 345                 350

Glu Leu Val Cys Leu Lys Asp Lys Thr Leu Gly Glu Leu Val Arg Asp
        355                 360                 365

Arg Met Ala Ala Phe Pro Ala Ser Gly Glu Ile Asn Ser Lys Leu Ala
    370                 375                 380

Gln Pro Val Glu Ala Ile Asn Arg Val Glu Gln His Phe Ser Arg Glu
385                 390                 395                 400

Ala Leu Ala Val Asp Arg Thr Asp Gly Ile Ser Met Thr Phe Ala Asp
                405                 410                 415
```

```
Trp Arg Phe Asn Leu Arg Thr Ser Asn Thr Glu Pro Val Val Arg Leu
            420                 425                 430

Asn Val Glu Ser Arg Gly Asp Val Pro Leu Met Glu Ala Arg Thr Arg
            435                 440                 445

Thr Leu Leu Thr Leu Leu Asn Glu
        450                 455

<210> SEQ ID NO 43
<211> LENGTH: 546
<212> TYPE: PRT
<213> ORGANISM: Escherichia coli K-12
<220> FEATURE:
<221> NAME/KEY: MISC_FEATURE
<222> LOCATION: (1)..(546)
<223> OTHER INFORMATION: pgm, Phosphoglucomutase, GenBank ID:
      NP_415214.1

<400> SEQUENCE: 43

Met Ala Ile His Asn Arg Ala Gly Gln Pro Ala Gln Gln Ser Asp Leu
1               5                   10                  15

Ile Asn Val Ala Gln Leu Thr Ala Gln Tyr Tyr Val Leu Lys Pro Glu
            20                  25                  30

Ala Gly Asn Ala Glu His Ala Val Lys Phe Gly Thr Ser Gly His Arg
        35                  40                  45

Gly Ser Ala Ala Arg His Ser Phe Asn Glu Pro His Ile Leu Ala Ile
    50                  55                  60

Ala Gln Ala Ile Ala Glu Glu Arg Ala Lys Asn Gly Ile Thr Gly Pro
65                  70                  75                  80

Cys Tyr Val Gly Lys Asp Thr His Ala Leu Ser Glu Pro Ala Phe Ile
                85                  90                  95

Ser Val Leu Glu Val Leu Ala Ala Asn Gly Val Asp Val Ile Val Gln
            100                 105                 110

Glu Asn Asn Gly Phe Thr Pro Thr Pro Ala Val Ser Asn Ala Ile Leu
        115                 120                 125

Val His Asn Lys Lys Gly Gly Pro Leu Ala Asp Gly Ile Val Ile Thr
    130                 135                 140

Pro Ser His Asn Pro Pro Glu Asp Gly Gly Ile Lys Tyr Asn Pro Pro
145                 150                 155                 160

Asn Gly Gly Pro Ala Asp Thr Asn Val Thr Lys Val Val Glu Asp Arg
                165                 170                 175

Ala Asn Ala Leu Leu Ala Asp Gly Leu Lys Gly Val Lys Arg Ile Ser
            180                 185                 190

Leu Asp Glu Ala Met Ala Ser Gly His Val Lys Glu Gln Asp Leu Val
        195                 200                 205

Gln Pro Phe Val Glu Gly Leu Ala Asp Ile Val Asp Met Ala Ala Ile
    210                 215                 220

Gln Lys Ala Gly Leu Thr Leu Gly Val Asp Pro Leu Gly Gly Ser Gly
225                 230                 235                 240

Ile Glu Tyr Trp Lys Arg Ile Gly Glu Tyr Tyr Asn Leu Asn Leu Thr
                245                 250                 255

Ile Val Asn Asp Gln Val Asp Gln Thr Phe Arg Phe Met His Leu Asp
            260                 265                 270

Lys Asp Gly Ala Ile Arg Met Asp Cys Ser Ser Glu Cys Ala Met Ala
        275                 280                 285

Gly Leu Leu Ala Leu Arg Asp Lys Phe Asp Leu Ala Phe Ala Asn Asp
    290                 295                 300
```

```
Pro Asp Tyr Asp Arg His Gly Ile Val Thr Pro Ala Gly Leu Met Asn
305                 310                 315                 320

Pro Asn His Tyr Leu Ala Val Ala Ile Asn Tyr Leu Phe Gln His Arg
            325                 330                 335

Pro Gln Trp Gly Lys Asp Val Ala Val Gly Lys Thr Leu Val Ser Ser
        340                 345                 350

Ala Met Ile Asp Arg Val Val Asn Asp Leu Gly Arg Lys Leu Val Glu
            355                 360                 365

Val Pro Val Gly Phe Lys Trp Phe Val Asp Gly Leu Phe Asp Gly Ser
370                 375                 380

Phe Gly Phe Gly Gly Glu Glu Ser Ala Gly Ala Ser Phe Leu Arg Phe
385                 390                 395                 400

Asp Gly Thr Pro Trp Ser Thr Asp Lys Asp Gly Ile Ile Met Cys Leu
            405                 410                 415

Leu Ala Ala Glu Ile Thr Ala Val Thr Gly Lys Asn Pro Gln Glu His
            420                 425                 430

Tyr Asn Glu Leu Ala Lys Arg Phe Gly Ala Pro Ser Tyr Asn Arg Leu
        435                 440                 445

Gln Ala Ala Ala Thr Ser Ala Gln Lys Ala Ala Leu Ser Lys Leu Ser
450                 455                 460

Pro Glu Met Val Ser Ala Ser Thr Leu Ala Gly Asp Pro Ile Thr Ala
465                 470                 475                 480

Arg Leu Thr Ala Ala Pro Gly Asn Gly Ala Ser Ile Gly Gly Leu Lys
            485                 490                 495

Val Met Thr Asp Asn Gly Trp Phe Ala Ala Arg Pro Ser Gly Thr Glu
            500                 505                 510

Asp Ala Tyr Lys Ile Tyr Cys Glu Ser Phe Leu Gly Glu Glu His Arg
        515                 520                 525

Lys Gln Ile Glu Lys Glu Ala Val Glu Ile Val Ser Glu Val Leu Lys
530                 535                 540

Asn Ala
545

<210> SEQ ID NO 44
<211> LENGTH: 553
<212> TYPE: PRT
<213> ORGANISM: Escherichia coli
<220> FEATURE:
<221> NAME/KEY: MISC_FEATURE
<222> LOCATION: (1)..(553)
<223> OTHER INFORMATION: pgm, phosphoglucomutase, GenBank ID:
      WP_001396326.1

<400> SEQUENCE: 44

Met Gln Thr Lys Asp Lys Ala Met Ala Ile His Asn Arg Ala Gly Gln
1               5                   10                  15

Pro Ala Gln Gln Ser Asp Leu Ile Asn Val Ala Gln Leu Thr Ala Gln
            20                  25                  30

Tyr Tyr Val Leu Lys Pro Glu Ala Gly Asn Ala Glu His Ala Val Lys
        35                  40                  45

Phe Gly Thr Ser Gly His Arg Gly Ser Ala Ala Arg His Ser Phe Asn
    50                  55                  60

Glu Pro His Ile Leu Ala Ile Ala Gln Ala Ile Ala Glu Glu Arg Ala
65                  70                  75                  80

Lys Asn Gly Ile Thr Gly Pro Cys Tyr Val Gly Lys Asp Thr His Ala
                85                  90                  95
```

```
Leu Ser Glu Pro Ala Phe Ile Ser Val Leu Glu Val Leu Ala Ala Asn
                100                 105                 110

Gly Val Asp Val Ile Val Gln Glu Asn Asn Gly Phe Thr Pro Thr Pro
            115                 120                 125

Ala Val Ser Asn Ala Ile Leu Val His Asn Lys Lys Gly Gly Pro Leu
        130                 135                 140

Ala Asp Gly Ile Val Ile Thr Pro Ser His Asn Pro Pro Glu Asp Gly
145                 150                 155                 160

Gly Ile Lys Tyr Asn Pro Pro Asn Gly Gly Pro Ala Asp Thr Asn Val
                165                 170                 175

Thr Lys Val Val Glu Asp Arg Ala Asn Ala Leu Leu Ala Asp Gly Leu
            180                 185                 190

Lys Gly Val Lys Arg Ile Ser Leu Asp Glu Ala Met Ala Ser Gly His
        195                 200                 205

Val Lys Glu Gln Asp Leu Val Gln Pro Phe Val Glu Gly Leu Ala Asp
210                 215                 220

Ile Val Asp Met Ala Ala Ile Gln Lys Ala Gly Leu Thr Leu Gly Val
225                 230                 235                 240

Asp Pro Leu Gly Gly Ser Gly Ile Glu Tyr Trp Lys Arg Ile Gly Glu
                245                 250                 255

Tyr Tyr Asn Leu Asn Leu Thr Ile Val Asn Asp Gln Val Asp Gln Thr
            260                 265                 270

Phe Arg Phe Met His Leu Asp Lys Asp Gly Ala Ile Arg Met Asp Cys
        275                 280                 285

Ser Ser Glu Cys Ala Met Ala Gly Leu Leu Ala Leu Arg Asp Lys Phe
290                 295                 300

Asp Leu Ala Phe Ala Asn Asp Pro Asp Tyr Asp Arg His Gly Ile Val
305                 310                 315                 320

Thr Pro Ala Gly Leu Met Asn Pro Asn His Tyr Leu Ala Val Ala Ile
                325                 330                 335

Asn Tyr Leu Phe Gln His Arg Pro Gln Trp Gly Lys Asp Val Ala Val
            340                 345                 350

Gly Lys Thr Leu Val Ser Ser Ala Met Ile Asp Arg Val Val Asn Asp
        355                 360                 365

Leu Gly Arg Lys Leu Val Glu Val Pro Val Gly Phe Lys Trp Phe Val
370                 375                 380

Asp Gly Leu Phe Asp Gly Ser Phe Gly Phe Gly Gly Glu Glu Ser Ala
385                 390                 395                 400

Gly Ala Ser Phe Leu Arg Phe Asp Gly Thr Pro Trp Ser Thr Asp Lys
                405                 410                 415

Asp Gly Ile Ile Met Cys Leu Leu Ala Ala Glu Ile Thr Ala Val Thr
            420                 425                 430

Gly Lys Asn Pro Gln Glu His Tyr Asn Glu Leu Ala Lys Arg Phe Gly
        435                 440                 445

Ala Pro Ser Tyr Asn Arg Leu Gln Ala Ala Ala Thr Ser Ala Gln Lys
450                 455                 460

Ala Ala Leu Ser Lys Leu Ser Pro Glu Met Val Ser Ala Ser Thr Leu
465                 470                 475                 480

Ala Gly Asp Pro Ile Thr Ala Arg Leu Thr Ala Ala Pro Gly Asn Gly
                485                 490                 495

Ala Ser Ile Gly Gly Leu Lys Val Met Thr Asp Asn Gly Trp Phe Ala
            500                 505                 510
```

```
Ala Arg Pro Ser Gly Thr Glu Asp Ala Tyr Lys Ile Tyr Cys Glu Ser
        515                 520                 525

Phe Leu Gly Glu Glu His Arg Lys Gln Ile Glu Lys Glu Ala Val Glu
530                 535                 540

Ile Val Ser Glu Val Leu Lys Asn Ala
545                 550

<210> SEQ ID NO 45
<211> LENGTH: 302
<212> TYPE: PRT
<213> ORGANISM: Escherichia coli K-12
<220> FEATURE:
<221> NAME/KEY: MISC_FEATURE
<222> LOCATION: (1)..(302)
<223> OTHER INFORMATION: GalU, UTP-glucose-1-phosphate
      uridylyltransferase, GenBank: NP_415752.1

<400> SEQUENCE: 45

Met Ala Ala Ile Asn Thr Lys Val Lys Ala Val Ile Pro Val Ala
1               5                   10                  15

Gly Leu Gly Thr Arg Met Leu Pro Ala Thr Lys Ala Ile Pro Lys Glu
                20                  25                  30

Met Leu Pro Leu Val Asp Lys Pro Leu Ile Gln Tyr Val Val Asn Glu
            35                  40                  45

Cys Ile Ala Ala Gly Ile Thr Glu Ile Val Leu Val Thr His Ser Ser
        50                  55                  60

Lys Asn Ser Ile Glu Asn His Phe Asp Thr Ser Phe Glu Leu Glu Ala
65                  70                  75                  80

Met Leu Glu Lys Arg Val Lys Arg Gln Leu Leu Asp Glu Val Gln Ser
                85                  90                  95

Ile Cys Pro Pro His Val Thr Ile Met Gln Val Arg Gln Gly Leu Ala
            100                 105                 110

Lys Gly Leu Gly His Ala Val Leu Cys Ala His Pro Val Val Gly Asp
        115                 120                 125

Glu Pro Val Ala Val Ile Leu Pro Asp Val Ile Leu Asp Glu Tyr Glu
    130                 135                 140

Ser Asp Leu Ser Gln Asp Asn Leu Ala Glu Met Ile Arg Arg Phe Asp
145                 150                 155                 160

Glu Thr Gly His Ser Gln Ile Met Val Glu Pro Val Ala Asp Val Thr
                165                 170                 175

Ala Tyr Gly Val Val Asp Cys Lys Gly Val Glu Leu Ala Pro Gly Glu
            180                 185                 190

Ser Val Pro Met Val Gly Val Val Glu Lys Pro Lys Ala Asp Val Ala
        195                 200                 205

Pro Ser Asn Leu Ala Ile Val Gly Arg Tyr Val Leu Ser Ala Asp Ile
    210                 215                 220

Trp Pro Leu Leu Ala Lys Thr Pro Pro Gly Ala Gly Asp Glu Ile Gln
225                 230                 235                 240

Leu Thr Asp Ala Ile Asp Met Leu Ile Glu Lys Glu Thr Val Glu Ala
                245                 250                 255

Tyr His Met Lys Gly Lys Ser His Asp Cys Gly Asn Lys Leu Gly Tyr
            260                 265                 270

Met Gln Ala Phe Val Glu Tyr Gly Ile Arg His Asn Thr Leu Gly Thr
        275                 280                 285

Glu Phe Lys Ala Trp Leu Glu Glu Met Gly Ile Lys Lys
    290                 295                 300
```

-continued

```
<210> SEQ ID NO 46
<211> LENGTH: 302
<212> TYPE: PRT
<213> ORGANISM: Enterobacteriaceae
<220> FEATURE:
<221> NAME/KEY: MISC_FEATURE
<222> LOCATION: (1)..(302)
<223> OTHER INFORMATION: GalU, UTP-glucose-1-phosphate
      uridylyltransferase, WP_000718995.1

<400> SEQUENCE: 46

Met Ala Ala Ile Asn Thr Lys Val Lys Lys Ala Val Ile Pro Val Ala
1               5                   10                  15

Gly Leu Gly Thr Arg Met Leu Pro Ala Thr Lys Ala Ile Pro Lys Glu
            20                  25                  30

Met Leu Pro Leu Val Asp Lys Pro Leu Ile Gln Tyr Val Val Asn Glu
        35                  40                  45

Cys Ile Ala Ala Gly Ile Thr Glu Ile Val Leu Val Thr His Ser Ser
    50                  55                  60

Lys Asn Ser Ile Glu Asn His Phe Asp Thr Ser Phe Glu Leu Glu Ala
65                  70                  75                  80

Met Leu Glu Lys Arg Val Lys Arg Gln Leu Leu Asp Glu Val Gln Ser
                85                  90                  95

Ile Cys Pro Pro His Val Thr Ile Met Gln Val Arg Gln Gly Leu Ala
            100                 105                 110

Lys Gly Leu Gly His Ala Val Leu Cys Ala His Pro Val Val Gly Asp
        115                 120                 125

Glu Pro Val Ala Val Ile Leu Pro Asp Val Ile Leu Asp Glu Tyr Glu
    130                 135                 140

Ser Asp Leu Ser Gln Asp Asn Leu Ala Glu Met Ile Arg Arg Phe Asp
145                 150                 155                 160

Glu Thr Gly His Ser Gln Ile Met Val Glu Pro Val Ala Asp Val Thr
                165                 170                 175

Ala Tyr Gly Val Val Asp Cys Lys Gly Val Glu Leu Ala Pro Gly Glu
            180                 185                 190

Ser Val Pro Met Val Gly Val Val Glu Lys Pro Lys Ala Asp Val Ala
        195                 200                 205

Pro Ser Asn Leu Ala Ile Val Gly Arg Tyr Val Leu Ser Ala Asp Ile
    210                 215                 220

Trp Pro Leu Leu Ala Lys Thr Pro Pro Gly Ala Gly Asp Glu Ile Gln
225                 230                 235                 240

Leu Thr Asp Ala Ile Asp Met Leu Ile Glu Lys Glu Thr Val Glu Ala
                245                 250                 255

Tyr His Met Lys Gly Lys Ser His Asp Cys Gly Asn Lys Leu Gly Tyr
            260                 265                 270

Met Gln Ala Phe Val Glu Tyr Gly Ile Arg His Asn Thr Leu Gly Thr
        275                 280                 285

Glu Phe Lys Ala Trp Leu Glu Glu Glu Met Gly Ile Lys Lys
    290                 295                 300

<210> SEQ ID NO 47
<211> LENGTH: 338
<212> TYPE: PRT
<213> ORGANISM: Escherichia coli K-12
<220> FEATURE:
<221> NAME/KEY: MISC_FEATURE
<222> LOCATION: (1)..(338)
<223> OTHER INFORMATION: GalE, UDP-glucose 4-epimerase, GenBank ID:
```

NP_415280.3

<400> SEQUENCE: 47

Met Arg Val Leu Val Thr Gly Gly Ser Gly Tyr Ile Gly Ser His Thr
1               5                   10                  15

Cys Val Gln Leu Leu Gln Asn Gly His Asp Val Ile Ile Leu Asp Asn
            20                  25                  30

Leu Cys Asn Ser Lys Arg Ser Val Leu Pro Val Ile Glu Arg Leu Gly
        35                  40                  45

Gly Lys His Pro Thr Phe Val Glu Gly Asp Ile Arg Asn Glu Ala Leu
    50                  55                  60

Met Thr Glu Ile Leu His Asp His Ala Ile Asp Thr Val Ile His Phe
65                  70                  75                  80

Ala Gly Leu Lys Ala Val Gly Glu Ser Val Gln Lys Pro Leu Glu Tyr
                85                  90                  95

Tyr Asp Asn Asn Val Asn Gly Thr Leu Arg Leu Ile Ser Ala Met Arg
            100                 105                 110

Ala Ala Asn Val Lys Asn Phe Ile Phe Ser Ser Ser Ala Thr Val Tyr
        115                 120                 125

Gly Asp Gln Pro Lys Ile Pro Tyr Val Glu Ser Phe Pro Thr Gly Thr
    130                 135                 140

Pro Gln Ser Pro Tyr Gly Lys Ser Lys Leu Met Val Glu Gln Ile Leu
145                 150                 155                 160

Thr Asp Leu Gln Lys Ala Gln Pro Asp Trp Ser Ile Ala Leu Leu Arg
                165                 170                 175

Tyr Phe Asn Pro Val Gly Ala His Pro Ser Gly Asp Met Gly Glu Asp
            180                 185                 190

Pro Gln Gly Ile Pro Asn Asn Leu Met Pro Tyr Ile Ala Gln Val Ala
        195                 200                 205

Val Gly Arg Arg Asp Ser Leu Ala Ile Phe Gly Asn Asp Tyr Pro Thr
    210                 215                 220

Glu Asp Gly Thr Gly Val Arg Asp Tyr Ile His Val Met Asp Leu Ala
225                 230                 235                 240

Asp Gly His Val Val Ala Met Glu Lys Leu Ala Asn Lys Pro Gly Val
                245                 250                 255

His Ile Tyr Asn Leu Gly Ala Gly Val Gly Asn Ser Val Leu Asp Val
            260                 265                 270

Val Asn Ala Phe Ser Lys Ala Cys Gly Lys Pro Val Asn Tyr His Phe
        275                 280                 285

Ala Pro Arg Arg Glu Gly Asp Leu Pro Ala Tyr Trp Ala Asp Ala Ser
    290                 295                 300

Lys Ala Asp Arg Glu Leu Asn Trp Arg Val Thr Arg Thr Leu Asp Glu
305                 310                 315                 320

Met Ala Gln Asp Thr Trp His Trp Gln Ser Arg His Pro Gln Gly Tyr
                325                 330                 335

Pro Asp

<210> SEQ ID NO 48
<211> LENGTH: 338
<212> TYPE: PRT
<213> ORGANISM: Enterobacteriaceae
<220> FEATURE:
<221> NAME/KEY: MISC_FEATURE
<222> LOCATION: (1)..(338)
<223> OTHER INFORMATION: GalE, UDP-glucose 4-epimerase, GenBank ID:
    WP_001265438.1

```
<400> SEQUENCE: 48

Met Arg Val Leu Val Thr Gly Gly Ser Gly Tyr Ile Gly Ser His Thr
1               5                   10                  15

Cys Val Gln Leu Leu Gln Asn Gly His Asp Val Ile Ile Leu Asp Asn
            20                  25                  30

Leu Cys Asn Ser Lys Arg Ser Val Pro Val Ile Glu Arg Leu Gly
        35                  40                  45

Gly Lys His Pro Thr Phe Val Glu Gly Asp Ile Arg Asn Glu Ala Leu
50                  55                  60

Met Thr Glu Ile Leu His Asp His Ala Ile Asp Thr Val Ile His Phe
65                  70                  75                  80

Ala Gly Leu Lys Ala Val Gly Glu Ser Val Gln Lys Pro Leu Glu Tyr
                85                  90                  95

Tyr Asp Asn Asn Val Asn Gly Thr Leu Arg Leu Ile Ser Ala Met Arg
            100                 105                 110

Ala Ala Asn Val Lys Asn Phe Ile Phe Ser Ser Ser Ala Thr Val Tyr
        115                 120                 125

Gly Asp Gln Pro Lys Ile Pro Tyr Val Glu Ser Phe Pro Thr Gly Thr
130                 135                 140

Pro Gln Ser Pro Tyr Gly Lys Ser Lys Leu Met Val Glu Gln Ile Leu
145                 150                 155                 160

Thr Asp Leu Gln Lys Ala Gln Pro Asp Trp Ser Ile Ala Leu Leu Arg
                165                 170                 175

Tyr Phe Asn Pro Val Gly Ala His Pro Ser Gly Asp Met Gly Glu Asp
            180                 185                 190

Pro Gln Gly Ile Pro Asn Asn Leu Met Pro Tyr Ile Ala Gln Val Ala
        195                 200                 205

Val Gly Arg Arg Asp Ser Leu Ala Ile Phe Gly Asn Asp Tyr Pro Thr
210                 215                 220

Glu Asp Gly Thr Gly Val Arg Asp Tyr Ile His Val Met Asp Leu Ala
225                 230                 235                 240

Asp Gly His Val Val Ala Met Glu Lys Leu Ala Asn Lys Pro Gly Val
                245                 250                 255

His Ile Tyr Asn Leu Gly Ala Gly Val Gly Asn Ser Val Leu Asp Val
            260                 265                 270

Val Asn Ala Phe Ser Lys Ala Cys Gly Lys Pro Val Asn Tyr His Phe
        275                 280                 285

Ala Pro Arg Arg Glu Gly Asp Leu Pro Ala Tyr Trp Ala Asp Ala Ser
290                 295                 300

Lys Ala Asp Arg Glu Leu Asn Trp Arg Val Thr Arg Thr Leu Asp Glu
305                 310                 315                 320

Met Ala Gln Asp Thr Trp His Trp Gln Ser Arg His Pro Gln Gly Tyr
                325                 330                 335

Pro Asp

<210> SEQ ID NO 49
<211> LENGTH: 445
<212> TYPE: PRT
<213> ORGANISM: Escherichia coli K-12
<220> FEATURE:
<221> NAME/KEY: MISC_FEATURE
<222> LOCATION: (1)..(445)
<223> OTHER INFORMATION: GlmM, Phosphoglucosamine mutase, GenBank ID:
      NP_417643.1
```

```
<400> SEQUENCE: 49

Met Ser Asn Arg Lys Tyr Phe Gly Thr Asp Gly Ile Arg Gly Arg Val
1               5                   10                  15

Gly Asp Ala Pro Ile Thr Pro Asp Phe Val Leu Lys Leu Gly Trp Ala
            20                  25                  30

Ala Gly Lys Val Leu Ala Arg His Gly Ser Arg Lys Ile Ile Ile Gly
        35                  40                  45

Lys Asp Thr Arg Ile Ser Gly Tyr Met Leu Glu Ser Ala Leu Glu Ala
    50                  55                  60

Gly Leu Ala Ala Ala Gly Leu Ser Ala Leu Phe Thr Gly Pro Met Pro
65                  70                  75                  80

Thr Pro Ala Val Ala Tyr Leu Thr Arg Thr Phe Arg Ala Glu Ala Gly
                85                  90                  95

Ile Val Ile Ser Ala Ser His Asn Pro Phe Tyr Asp Asn Gly Ile Lys
            100                 105                 110

Phe Phe Ser Ile Asp Gly Thr Lys Leu Pro Asp Ala Val Glu Glu Ala
        115                 120                 125

Ile Glu Ala Glu Met Glu Lys Glu Ile Ser Cys Val Asp Ser Ala Glu
    130                 135                 140

Leu Gly Lys Ala Ser Arg Ile Val Asp Ala Ala Gly Arg Tyr Ile Glu
145                 150                 155                 160

Phe Cys Lys Ala Thr Phe Pro Asn Glu Leu Ser Leu Ser Glu Leu Lys
                165                 170                 175

Ile Val Val Asp Cys Ala Asn Gly Ala Thr Tyr His Ile Ala Pro Asn
            180                 185                 190

Val Leu Arg Glu Leu Gly Ala Asn Val Ile Ala Ile Gly Cys Glu Pro
        195                 200                 205

Asn Gly Val Asn Ile Asn Ala Glu Val Gly Ala Thr Asp Val Arg Ala
    210                 215                 220

Leu Gln Ala Arg Val Leu Ala Glu Lys Ala Asp Leu Gly Ile Ala Phe
225                 230                 235                 240

Asp Gly Asp Gly Asp Arg Val Ile Met Val Asp His Glu Gly Asn Lys
                245                 250                 255

Val Asp Gly Asp Gln Ile Met Tyr Ile Ile Ala Arg Glu Gly Leu Arg
            260                 265                 270

Gln Gly Gln Leu Arg Gly Gly Ala Val Gly Thr Leu Met Ser Asn Met
        275                 280                 285

Gly Leu Glu Leu Ala Leu Lys Gln Leu Gly Ile Pro Phe Ala Arg Ala
    290                 295                 300

Lys Val Gly Asp Arg Tyr Val Leu Glu Lys Met Gln Glu Lys Gly Trp
305                 310                 315                 320

Arg Ile Gly Ala Glu Asn Ser Gly His Val Ile Leu Leu Asp Lys Thr
                325                 330                 335

Thr Thr Gly Asp Gly Ile Val Ala Gly Leu Gln Val Leu Ala Ala Met
            340                 345                 350

Ala Arg Asn His Met Ser Leu His Asp Leu Cys Ser Gly Met Lys Met
        355                 360                 365

Phe Pro Gln Ile Leu Val Asn Val Arg Tyr Thr Ala Gly Ser Gly Asp
    370                 375                 380

Pro Leu Glu His Glu Ser Val Lys Ala Val Thr Ala Glu Val Glu Ala
385                 390                 395                 400

Ala Leu Gly Asn Arg Gly Arg Val Leu Leu Arg Lys Ser Gly Thr Glu
                405                 410                 415
```

```
Pro Leu Ile Arg Val Met Val Glu Gly Glu Asp Glu Ala Gln Val Thr
            420                 425                 430

Glu Phe Ala His Arg Ile Ala Asp Ala Val Lys Ala Val
            435                 440                 445

<210> SEQ ID NO 50
<211> LENGTH: 445
<212> TYPE: PRT
<213> ORGANISM: Enterobacteriaceae
<220> FEATURE:
<221> NAME/KEY: MISC_FEATURE
<222> LOCATION: (1)..(445)
<223> OTHER INFORMATION: GlmM, Phosphoglucosamine mutase, GenBank ID:
      WP_000071134.1

<400> SEQUENCE: 50

Met Ser Asn Arg Lys Tyr Phe Gly Thr Asp Gly Ile Arg Gly Arg Val
1               5                   10                  15

Gly Asp Ala Pro Ile Thr Pro Asp Phe Val Leu Lys Leu Gly Trp Ala
            20                  25                  30

Ala Gly Lys Val Leu Ala Arg His Gly Ser Arg Lys Ile Ile Ile Gly
        35                  40                  45

Lys Asp Thr Arg Ile Ser Gly Tyr Met Leu Glu Ser Ala Leu Glu Ala
    50                  55                  60

Gly Leu Ala Ala Ala Gly Leu Ser Ala Leu Phe Thr Gly Pro Met Pro
65                  70                  75                  80

Thr Pro Ala Val Ala Tyr Leu Thr Arg Thr Phe Arg Ala Glu Ala Gly
                85                  90                  95

Ile Val Ile Ser Ala Ser His Asn Pro Phe Tyr Asp Asn Gly Ile Lys
            100                 105                 110

Phe Phe Ser Ile Asp Gly Thr Lys Leu Pro Asp Ala Val Glu Glu Ala
        115                 120                 125

Ile Glu Ala Glu Met Glu Lys Glu Ile Ser Cys Val Asp Ser Ala Glu
    130                 135                 140

Leu Gly Lys Ala Ser Arg Ile Val Asp Ala Ala Gly Arg Tyr Ile Glu
145                 150                 155                 160

Phe Cys Lys Ala Thr Phe Pro Asn Glu Leu Ser Leu Ser Glu Leu Lys
                165                 170                 175

Ile Val Val Asp Cys Ala Asn Gly Ala Thr Tyr His Ile Ala Pro Asn
            180                 185                 190

Val Leu Arg Glu Leu Gly Ala Asn Val Ile Ala Ile Gly Cys Glu Pro
        195                 200                 205

Asn Gly Val Asn Ile Asn Ala Glu Val Gly Ala Thr Asp Val Arg Ala
    210                 215                 220

Leu Gln Ala Arg Val Leu Ala Glu Lys Ala Asp Leu Gly Ile Ala Phe
225                 230                 235                 240

Asp Gly Asp Gly Asp Arg Val Ile Met Val Asp His Glu Gly Asn Lys
                245                 250                 255

Val Asp Gly Asp Gln Ile Met Tyr Ile Ile Ala Arg Glu Gly Leu Arg
            260                 265                 270

Gln Gly Gln Leu Arg Gly Gly Ala Val Gly Thr Leu Met Ser Asn Met
        275                 280                 285

Gly Leu Glu Leu Ala Leu Lys Gln Leu Gly Ile Pro Phe Ala Arg Ala
    290                 295                 300

Lys Val Gly Asp Arg Tyr Val Leu Glu Lys Met Gln Glu Lys Gly Trp
305                 310                 315                 320
```

```
Arg Ile Gly Ala Glu Asn Ser Gly His Val Ile Leu Asp Lys Thr
                325                 330                 335

Thr Thr Gly Asp Gly Ile Val Ala Gly Leu Gln Val Leu Ala Ala Met
            340                 345                 350

Ala Arg Asn His Met Ser Leu His Asp Leu Cys Ser Gly Met Lys Met
        355                 360                 365

Phe Pro Gln Ile Leu Val Asn Val Arg Tyr Thr Ala Gly Ser Gly Asp
    370                 375                 380

Pro Leu Glu His Glu Ser Val Lys Ala Val Thr Ala Glu Val Glu Ala
385                 390                 395                 400

Ala Leu Gly Asn Arg Gly Arg Val Leu Leu Arg Lys Ser Gly Thr Glu
                405                 410                 415

Pro Leu Ile Arg Val Met Val Glu Gly Glu Asp Glu Ala Gln Val Thr
                420                 425                 430

Glu Phe Ala His Arg Ile Ala Asp Ala Val Lys Ala Val
                435                 440                 445

<210> SEQ ID NO 51
<211> LENGTH: 456
<212> TYPE: PRT
<213> ORGANISM: Escherichia coli K-12
<220> FEATURE:
<221> NAME/KEY: MISC_FEATURE
<222> LOCATION: (1)..(456)
<223> OTHER INFORMATION: GlmU, N-acetylglucosamine-1-phosphate
      uridyltransferase and glucosamine-1-phosphate acetyltransferase,
      GenBank ID: NP_418186.1

<400> SEQUENCE: 51

Met Leu Asn Asn Ala Met Ser Val Val Ile Leu Ala Ala Gly Lys Gly
1               5                   10                  15

Thr Arg Met Tyr Ser Asp Leu Pro Lys Val Leu His Thr Leu Ala Gly
                20                  25                  30

Lys Ala Met Val Gln His Val Ile Asp Ala Ala Asn Glu Leu Gly Ala
            35                  40                  45

Ala His Val His Leu Val Tyr Gly His Gly Gly Asp Leu Leu Lys Gln
        50                  55                  60

Ala Leu Lys Asp Asp Asn Leu Asn Trp Val Leu Gln Ala Glu Gln Leu
65                  70                  75                  80

Gly Thr Gly His Ala Met Gln Gln Ala Ala Pro Phe Phe Ala Asp Asp
                85                  90                  95

Glu Asp Ile Leu Met Leu Tyr Gly Asp Val Pro Leu Ile Ser Val Glu
                100                 105                 110

Thr Leu Gln Arg Leu Arg Asp Ala Lys Pro Gln Gly Gly Ile Gly Leu
            115                 120                 125

Leu Thr Val Lys Leu Asp Asp Pro Thr Gly Tyr Gly Arg Ile Thr Arg
130                 135                 140

Glu Asn Gly Lys Val Thr Gly Ile Val Glu His Lys Asp Ala Thr Asp
145                 150                 155                 160

Glu Gln Arg Gln Ile Gln Glu Ile Asn Thr Gly Ile Leu Ile Ala Asn
                165                 170                 175

Gly Ala Asp Met Lys Arg Trp Leu Ala Lys Leu Thr Asn Asn Asn Ala
            180                 185                 190

Gln Gly Glu Tyr Tyr Ile Thr Asp Ile Ile Ala Leu Ala Tyr Gln Glu
        195                 200                 205

Gly Arg Glu Ile Val Ala Val His Pro Gln Arg Leu Ser Glu Val Glu
```

```
               210                 215                 220

Gly Val Asn Asn Arg Leu Gln Leu Ser Arg Leu Glu Arg Val Tyr Gln
225                 230                 235                 240

Ser Glu Gln Ala Glu Lys Leu Leu Ala Gly Val Met Leu Arg Asp
                245                 250                 255

Pro Ala Arg Phe Asp Leu Arg Gly Thr Leu Thr His Gly Arg Asp Val
            260                 265                 270

Glu Ile Asp Thr Asn Val Ile Ile Glu Gly Asn Val Thr Leu Gly His
            275                 280                 285

Arg Val Lys Ile Gly Thr Gly Cys Val Ile Lys Asn Ser Val Ile Gly
            290                 295                 300

Asp Asp Cys Glu Ile Ser Pro Tyr Thr Val Val Glu Asp Ala Asn Leu
305                 310                 315                 320

Ala Ala Ala Cys Thr Ile Gly Pro Phe Ala Arg Leu Arg Pro Gly Ala
                325                 330                 335

Glu Leu Leu Glu Gly Ala His Val Gly Asn Phe Val Glu Met Lys Lys
                340                 345                 350

Ala Arg Leu Gly Lys Gly Ser Lys Ala Gly His Leu Thr Tyr Leu Gly
                355                 360                 365

Asp Ala Glu Ile Gly Asp Asn Val Asn Ile Gly Ala Gly Thr Ile Thr
            370                 375                 380

Cys Asn Tyr Asp Gly Ala Asn Lys Phe Lys Thr Ile Ile Gly Asp Asp
385                 390                 395                 400

Val Phe Val Gly Ser Asp Thr Gln Leu Val Ala Pro Val Thr Val Gly
                405                 410                 415

Lys Gly Ala Thr Ile Ala Ala Gly Thr Thr Val Thr Arg Asn Val Gly
                420                 425                 430

Glu Asn Ala Leu Ala Ile Ser Arg Val Pro Gln Thr Gln Lys Glu Gly
                435                 440                 445

Trp Arg Arg Pro Val Lys Lys Lys
    450                 455

<210> SEQ ID NO 52
<211> LENGTH: 456
<212> TYPE: PRT
<213> ORGANISM: Enterobacteriaceae
<220> FEATURE:
<221> NAME/KEY: MISC_FEATURE
<222> LOCATION: (1)..(456)
<223> OTHER INFORMATION: GlmU, N-acetylglucosamine-1-phosphate
      uridyltransferase and glucosamine-1-phosphate acetyltransferase,
      GenBank ID: WP_000933736.1

<400> SEQUENCE: 52

Met Leu Asn Asn Ala Met Ser Val Val Ile Leu Ala Ala Gly Lys Gly
1               5                   10                  15

Thr Arg Met Tyr Ser Asp Leu Pro Lys Val Leu His Thr Leu Ala Gly
            20                  25                  30

Lys Ala Met Val Gln His Val Ile Asp Ala Ala Asn Glu Leu Gly Ala
            35                  40                  45

Ala His Val His Leu Val Tyr Gly His Gly Gly Asp Leu Leu Lys Gln
            50                  55                  60

Ala Leu Lys Asp Asp Asn Leu Asn Trp Val Leu Gln Ala Glu Gln Leu
65                  70                  75                  80

Gly Thr Gly His Ala Met Gln Gln Ala Ala Pro Phe Phe Ala Asp Asp
                85                  90                  95
```

```
Glu Asp Ile Leu Met Leu Tyr Gly Asp Val Pro Leu Ile Ser Val Glu
            100                 105                 110

Thr Leu Gln Arg Leu Arg Asp Ala Lys Pro Gln Gly Gly Ile Gly Leu
        115                 120                 125

Leu Thr Val Lys Leu Asp Asp Pro Thr Gly Tyr Gly Arg Ile Thr Arg
    130                 135                 140

Glu Asn Gly Lys Val Thr Gly Ile Val Glu His Lys Asp Ala Thr Asp
145                 150                 155                 160

Glu Gln Arg Gln Ile Gln Glu Ile Asn Thr Gly Ile Leu Ile Ala Asn
                165                 170                 175

Gly Ala Asp Met Lys Arg Trp Leu Ala Lys Leu Thr Asn Asn Asn Ala
            180                 185                 190

Gln Gly Glu Tyr Tyr Ile Thr Asp Ile Ile Ala Leu Ala Tyr Gln Glu
        195                 200                 205

Gly Arg Glu Ile Val Ala Val His Pro Gln Arg Leu Ser Glu Val Glu
    210                 215                 220

Gly Val Asn Asn Arg Leu Gln Leu Ser Arg Leu Glu Arg Val Tyr Gln
225                 230                 235                 240

Ser Glu Gln Ala Glu Lys Leu Leu Leu Ala Gly Val Met Leu Arg Asp
                245                 250                 255

Pro Ala Arg Phe Asp Leu Arg Gly Thr Leu Thr His Gly Arg Asp Val
            260                 265                 270

Glu Ile Asp Thr Asn Val Ile Glu Gly Asn Val Thr Leu Gly His
        275                 280                 285

Arg Val Lys Ile Gly Thr Gly Cys Val Ile Lys Asn Ser Val Ile Gly
    290                 295                 300

Asp Asp Cys Glu Ile Ser Pro Tyr Thr Val Val Glu Asp Ala Asn Leu
305                 310                 315                 320

Ala Ala Ala Cys Thr Ile Gly Pro Phe Ala Arg Leu Arg Pro Gly Ala
                325                 330                 335

Glu Leu Leu Glu Gly Ala His Val Gly Asn Phe Val Glu Met Lys Lys
            340                 345                 350

Ala Arg Leu Gly Lys Gly Ser Lys Ala Gly His Leu Thr Tyr Leu Gly
        355                 360                 365

Asp Ala Glu Ile Gly Asp Asn Val Asn Ile Gly Ala Gly Thr Ile Thr
    370                 375                 380

Cys Asn Tyr Asp Gly Ala Asn Lys Phe Lys Thr Ile Ile Gly Asp Asp
385                 390                 395                 400

Val Phe Val Gly Ser Asp Thr Gln Leu Val Ala Pro Val Thr Val Gly
                405                 410                 415

Lys Gly Ala Thr Ile Ala Ala Gly Thr Thr Val Thr Arg Asn Val Gly
            420                 425                 430

Glu Asn Ala Leu Ala Ile Ser Arg Val Pro Gln Thr Gln Lys Glu Gly
        435                 440                 445

Trp Arg Arg Pro Val Lys Lys Lys
    450                 455

<210> SEQ ID NO 53
<211> LENGTH: 609
<212> TYPE: PRT
<213> ORGANISM: Escherichia coli K-12
<220> FEATURE:
<221> NAME/KEY: MISC_FEATURE
<222> LOCATION: (1)..(609)
<223> OTHER INFORMATION: GlmS, L-glutamine--D-fructose-6-phosphate
      aminotransferase, GenBank ID: NP_418185.1
```

<400> SEQUENCE: 53

```
Met Cys Gly Ile Val Gly Ala Ile Ala Gln Arg Asp Val Ala Glu Ile
1               5                   10                  15
Leu Leu Glu Gly Leu Arg Arg Leu Glu Tyr Arg Gly Tyr Asp Ser Ala
            20                  25                  30
Gly Leu Ala Val Val Asp Ala Glu Gly His Met Thr Arg Leu Arg Arg
        35                  40                  45
Leu Gly Lys Val Gln Met Leu Ala Gln Ala Ala Glu His Pro Leu
    50                  55                  60
His Gly Gly Thr Gly Ile Ala His Thr Arg Trp Ala Thr His Gly Glu
65                  70                  75                  80
Pro Ser Glu Val Asn Ala His Pro His Val Ser Glu His Ile Val Val
                85                  90                  95
Val His Asn Gly Ile Ile Glu Asn His Glu Pro Leu Arg Glu Glu Leu
            100                 105                 110
Lys Ala Arg Gly Tyr Thr Phe Val Ser Glu Thr Asp Thr Glu Val Ile
        115                 120                 125
Ala His Leu Val Asn Trp Glu Leu Lys Gln Gly Gly Thr Leu Arg Glu
130                 135                 140
Ala Val Leu Arg Ala Ile Pro Gln Leu Arg Gly Ala Tyr Gly Thr Val
145                 150                 155                 160
Ile Met Asp Ser Arg His Pro Asp Thr Leu Leu Ala Ala Arg Ser Gly
                165                 170                 175
Ser Pro Leu Val Ile Gly Leu Gly Met Gly Glu Asn Phe Ile Ala Ser
            180                 185                 190
Asp Gln Leu Ala Leu Leu Pro Val Thr Arg Arg Phe Ile Phe Leu Glu
        195                 200                 205
Glu Gly Asp Ile Ala Glu Ile Thr Arg Arg Ser Val Asn Ile Phe Asp
210                 215                 220
Lys Thr Gly Ala Glu Val Lys Arg Gln Asp Ile Glu Ser Asn Leu Gln
225                 230                 235                 240
Tyr Asp Ala Gly Asp Lys Gly Ile Tyr Arg His Tyr Met Gln Lys Glu
                245                 250                 255
Ile Tyr Glu Gln Pro Asn Ala Ile Lys Asn Thr Leu Thr Gly Arg Ile
            260                 265                 270
Ser His Gly Gln Val Asp Leu Ser Glu Leu Gly Pro Asn Ala Asp Glu
        275                 280                 285
Leu Leu Ser Lys Val Glu His Ile Gln Ile Leu Ala Cys Gly Thr Ser
290                 295                 300
Tyr Asn Ser Gly Met Val Ser Arg Tyr Trp Phe Glu Ser Leu Ala Gly
305                 310                 315                 320
Ile Pro Cys Asp Val Glu Ile Ala Ser Glu Phe Arg Tyr Arg Lys Ser
                325                 330                 335
Ala Val Arg Arg Asn Ser Leu Met Ile Thr Leu Ser Gln Ser Gly Glu
            340                 345                 350
Thr Ala Asp Thr Leu Ala Gly Leu Arg Leu Ser Lys Glu Leu Gly Tyr
        355                 360                 365
Leu Gly Ser Leu Ala Ile Cys Asn Val Pro Gly Ser Ser Leu Val Arg
370                 375                 380
Glu Ser Asp Leu Ala Leu Met Thr Asn Ala Gly Thr Glu Ile Gly Val
385                 390                 395                 400
Ala Ser Thr Lys Ala Phe Thr Thr Gln Leu Thr Val Leu Leu Met Leu
```

```
                        405                 410                 415
Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
    450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
            485                 490                 495

Ala Tyr Ala Ala Gly Glu Leu Lys His Gly Pro Leu Ala Leu Ile Asp
        500                 505                 510

Ala Asp Met Pro Val Ile Val Ala Pro Asn Asn Glu Leu Leu Glu
    515                 520                 525

Lys Leu Lys Ser Asn Ile Glu Glu Val Arg Ala Arg Gly Gly Gln Leu
530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
            565                 570                 575

Tyr Thr Val Pro Leu Gln Leu Leu Ala Tyr His Val Ala Leu Ile Lys
        580                 585                 590

Gly Thr Asp Val Asp Gln Pro Arg Asn Leu Ala Lys Ser Val Thr Val
            595                 600                 605

Glu

<210> SEQ ID NO 54
<211> LENGTH: 609
<212> TYPE: PRT
<213> ORGANISM: Enterobacteriaceae
<220> FEATURE:
<221> NAME/KEY: MISC_FEATURE
<222> LOCATION: (1)..(609)
<223> OTHER INFORMATION: GlmS, L-glutamine--D-fructose-6-phosphate
      aminotransferase, GenBank ID: WP_000334099.1

<400> SEQUENCE: 54

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
            85                  90                  95

Val His Asn Gly Ile Ile Glu Asn His Glu Pro Leu Arg Glu Glu Leu
        100                 105                 110

Lys Ala Arg Gly Tyr Thr Phe Val Ser Glu Thr Asp Thr Glu Val Ile
    115                 120                 125

Ala His Leu Val Asn Trp Glu Leu Lys Gln Gly Gly Thr Leu Arg Glu
    130                 135                 140
```

```
Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
530                 535                 540

Tyr Val Phe Ala Asp Gln Asp Ala Gly Phe Val Ser Ser Asp Asn Met
545                 550                 555                 560
```

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu

<210> SEQ ID NO 55
<211> LENGTH: 221
<212> TYPE: PRT
<213> ORGANISM: Campylobacter jejuni
<220> FEATURE:
<221> NAME/KEY: MISC_FEATURE
<222> LOCATION: (1)..(221)
<223> OTHER INFORMATION: NeuA, CMP-Neu5Ac synthetase, GenBank ID:
      AAK91728.1

<400> SEQUENCE: 55

Met Ser Leu Ala Ile Ile Pro Ala Arg Gly Gly Ser Lys Gly Ile Lys
1               5                   10                  15

Asn Lys Asn Leu Val Leu Leu Asn Asn Lys Pro Leu Ile Tyr Tyr Thr
            20                  25                  30

Ile Lys Ala Ala Leu Asn Ala Lys Ser Ile Ser Lys Val Val Val Ser
        35                  40                  45

Ser Asp Ser Asp Glu Ile Leu Asn Tyr Ala Lys Ser Gln Asn Val Asp
    50                  55                  60

Ile Leu Lys Arg Pro Ile Ser Leu Ala Gln Asp Asp Thr Thr Ser Asp
65                  70                  75                  80

Lys Val Leu Leu His Ala Leu Lys Phe Tyr Lys Asp Tyr Glu Asp Val
                85                  90                  95

Val Phe Leu Gln Pro Thr Ser Pro Leu Arg Thr Asn Ile His Ile Asn
            100                 105                 110

Glu Ala Phe Asn Leu Tyr Lys Asn Ser Asn Ala Asn Ala Leu Ile Ser
        115                 120                 125

Val Ser Glu Cys Asp Asn Lys Ile Leu Lys Ala Phe Val Cys Asn Asp
    130                 135                 140

Cys Gly Asp Leu Ala Gly Ile Cys Asn Asp Glu Tyr Pro Phe Met Pro
145                 150                 155                 160

Arg Gln Lys Leu Pro Lys Thr Tyr Met Ser Asn Gly Ala Ile Tyr Ile
                165                 170                 175

Leu Lys Ile Lys Glu Phe Leu Asn Asn Pro Ser Phe Leu Gln Ser Lys
            180                 185                 190

Thr Lys His Phe Leu Met Asp Glu Ser Ser Ser Leu Asp Ile Asp Cys
        195                 200                 205

Leu Glu Asp Leu Lys Lys Val Glu Gln Ile Trp Lys Lys
    210                 215                 220

<210> SEQ ID NO 56
<211> LENGTH: 231
<212> TYPE: PRT
<213> ORGANISM: Vibrio brasiliensis
<220> FEATURE:
<221> NAME/KEY: MISC_FEATURE
<222> LOCATION: (1)..(231)
<223> OTHER INFORMATION: NeuA, CMP-Neu5Ac synthetase, GenBank ID:
      WP_006881452.1

<400> SEQUENCE: 56

```
Met Arg Val Ala Leu Ile Thr Ala Arg Gly Gly Ser Lys Gly Leu Pro
1               5                   10                  15

Arg Lys Asn Val Leu Asn Val Asn Gly Leu Pro Leu Ile Gly Trp Thr
            20                  25                  30

Ile Asn Ala Ala Arg Glu Cys Ser Tyr Ile Asp Arg Val Phe Val Ser
        35                  40                  45

Thr Glu Asp Glu Glu Ile Ala Lys Ile Ser Leu Gly Met Gly Ala Glu
    50                  55                  60

Leu Ile Glu Arg Pro Cys Glu Leu Ala Gln Asp Asn Ser Thr Ser Asp
65                  70                  75                  80

Glu Val Ile Arg His Ala Ile Asp Trp Leu Asp Lys His Ser Ile Leu
                85                  90                  95

Ser Asp Leu Val Val Leu Leu Gln Pro Thr Ser Pro Leu Arg Thr Ser
            100                 105                 110

Ala His Ile Ser Glu Ala Ile Asp Leu Tyr Asp Ser Leu Asn Asn Pro
        115                 120                 125

Asn Ala Thr Ile Ile Ser Val Tyr Glu Pro Glu His Ser Pro Leu Lys
    130                 135                 140

Ala Phe Val Gln Leu Glu Asn Gly Thr Leu Lys Gly Ser Tyr Asn Glu
145                 150                 155                 160

Asp Ala Pro Tyr Thr Arg Arg Gln Glu Leu Pro Lys Ser Tyr Leu Ala
                165                 170                 175

Asn Gly Ala Ile Tyr Ile Phe Ser Pro Ser Ala Phe Met Ser Glu Ser
            180                 185                 190

Gln Ile Pro Arg Arg Asp Ile Tyr Pro Tyr Val Met Ser Thr Asn Glu
        195                 200                 205

Ser Glu Asp Ile Asp Ser Lys Ile Asp Leu Ile Arg Val Glu Lys Leu
    210                 215                 220

Leu Arg Gly Ser Phe Tyr Glu
225                 230
```

<210> SEQ ID NO 57
<211> LENGTH: 346
<212> TYPE: PRT
<213> ORGANISM: Campylobacter jejuni
<220> FEATURE:
<221> NAME/KEY: MISC_FEATURE
<222> LOCATION: (1)..(346)
<223> OTHER INFORMATION: NeuB, Neu5 Ac synthase, GenBank ID: AAK91726.1

<400> SEQUENCE: 57

```
Met Lys Glu Ile Lys Ile Gln Asn Ile Ile Ser Glu Glu Lys Ala
1               5                   10                  15

Pro Leu Val Val Pro Glu Ile Gly Ile Asn His Asn Gly Ser Leu Glu
            20                  25                  30

Leu Ala Lys Ile Met Val Asp Ala Ala Phe Ser Ala Gly Ala Lys Ile
        35                  40                  45

Ile Lys His Gln Thr His Ile Val Glu Asp Glu Met Ser Lys Ala Ala
    50                  55                  60

Lys Lys Val Ile Pro Gly Asn Ala Lys Ile Ser Ile Tyr Glu Ile Met
65                  70                  75                  80

Gln Lys Cys Ala Leu Asp Tyr Lys Asp Glu Leu Ala Leu Lys Glu Tyr
                85                  90                  95

Thr Glu Lys Leu Gly Leu Val Tyr Leu Ser Thr Pro Phe Ser Arg Ala
            100                 105                 110

Gly Ala Asn Arg Leu Glu Asp Met Gly Val Ser Ala Phe Lys Ile Gly
```

```
            115                 120                 125
Ser Gly Glu Cys Asn Asn Tyr Pro Leu Ile Lys His Ile Ala Ala Phe
130                 135                 140

Lys Lys Pro Met Ile Val Ser Thr Gly Met Asn Ser Ile Glu Ser Ile
145                 150                 155                 160

Lys Pro Thr Val Lys Ile Leu Leu Asp Asn Glu Ile Pro Phe Val Leu
                165                 170                 175

Met His Thr Thr Asn Leu Tyr Pro Thr Pro His Asn Leu Val Arg Leu
            180                 185                 190

Asn Ala Met Leu Glu Leu Lys Lys Glu Phe Ser Cys Met Val Gly Leu
        195                 200                 205

Ser Asp His Thr Thr Asp Asn Leu Ala Cys Leu Gly Ala Val Val Leu
    210                 215                 220

Gly Ala Cys Val Leu Glu Arg His Phe Thr Asp Ser Met His Arg Ser
225                 230                 235                 240

Gly Pro Asp Ile Val Cys Ser Met Asp Thr Lys Ala Leu Lys Glu Leu
                245                 250                 255

Ile Ile Gln Ser Glu Gln Met Ala Ile Ile Arg Gly Asn Asn Glu Ser
            260                 265                 270

Lys Lys Ala Ala Lys Gln Glu Gln Val Thr Ile Asp Phe Ala Phe Ala
        275                 280                 285

Ser Val Val Ser Ile Lys Asp Ile Lys Lys Gly Glu Val Leu Ser Met
    290                 295                 300

Asp Asn Ile Trp Val Lys Arg Pro Gly Leu Gly Ile Ser Ala Ala
305                 310                 315                 320

Glu Phe Glu Asn Ile Leu Gly Lys Lys Ala Leu Arg Asp Ile Glu Asn
                325                 330                 335

Asp Ala Gln Leu Ser Tyr Glu Asp Phe Ala
            340                 345

<210> SEQ ID NO 58
<211> LENGTH: 346
<212> TYPE: PRT
<213> ORGANISM: Flavobacterium limnosediminis
<220> FEATURE:
<221> NAME/KEY: MISC_FEATURE
<222> LOCATION: (1)..(346)
<223> OTHER INFORMATION: NeuB, Neu5 Ac synthase, GenBank ID:
      WP_023580510.1

<400> SEQUENCE: 58

Met Asn Pro Tyr Ile Glu Ile Ala Gly Arg Lys Ile Gly Leu Asp Tyr
1               5                   10                  15

Pro Pro Leu Val Ile Ala Glu Ile Gly Ile Asn His Glu Gly Ser Leu
            20                  25                  30

Gln Val Ala Lys Glu Ile Val Asp Ala Ala Phe Arg Ala Gly Val Glu
        35                  40                  45

Val Val Lys His Gln Thr His Ile Val Glu Asp Glu Met Ser Gly Ala
    50                  55                  60

Ala Lys Lys Val Ile Pro Gly Asn Ala Asp Val Ser Ile Tyr Glu Ile
65                  70                  75                  80

Met Glu Arg Cys Ala Leu Asp Glu Ser Glu Leu Glu Leu Lys Asn
                85                  90                  95

Tyr Val Glu Ser Lys Gly Met Ile Phe Ile Ser Thr Pro Phe Ser Arg
            100                 105                 110

Ala Ala Ala Glu Arg Leu Lys Lys Phe Asp Ile Pro Ala Tyr Lys Ile
```

```
                115                 120                 125
Gly Ser Gly Glu Cys Asn Asn Tyr Pro Leu Leu Glu His Ile Ala Ser
        130                 135                 140

Phe Gly Lys Pro Val Ile Leu Ser Thr Gly Met Asn Thr Val Asp Ser
145                 150                 155                 160

Ile Arg Lys Ala Val Ala Ile Phe Asp Lys His Asn Val Pro Val Ala
                165                 170                 175

Leu Leu His Thr Thr Asn Leu Tyr Pro Thr Pro Ile His Leu Val Arg
            180                 185                 190

Phe Gly Ala Met Met Glu Met His Asn Ala Phe Pro Asp Lys Val Phe
        195                 200                 205

Gly Leu Ser Asp His Thr Leu Asn Asn Asn Ala Cys Leu Gly Ala Val
    210                 215                 220

Ala Leu Gly Ala Ser Ile Leu Glu Arg His Phe Thr Asp His Met Ser
225                 230                 235                 240

Arg Thr Gly Pro Asp Ile Val Cys Ser Met Asp Glu Gln Ala Thr Arg
                245                 250                 255

Glu Leu Ile Val Asn Ser Ala Glu Ile Ala Leu Met Arg Gly Gly Thr
            260                 265                 270

Lys Lys Pro Ala Ala Glu Glu Gln Val Thr Ile Asp Phe Ala Phe Ala
        275                 280                 285

Thr Val Cys Ser Ile Ala Pro Ile Lys Lys Gly Glu Val Phe Thr Lys
    290                 295                 300

Glu Asn Ile Trp Val Lys Arg Pro Gly Thr Gly Lys Ile Leu Ala Glu
305                 310                 315                 320

His Phe Glu Arg Leu Leu Gly Lys Thr Ala Thr Arg Asp Ile Glu Asn
                325                 330                 335

Asp Glu Gln Leu Asp Phe Ser Asp Val Glu
            340                 345

<210> SEQ ID NO 59
<211> LENGTH: 372
<212> TYPE: PRT
<213> ORGANISM: Campylobacter jejuni
<220> FEATURE:
<221> NAME/KEY: MISC_FEATURE
<222> LOCATION: (1)..(372)
<223> OTHER INFORMATION: NeuC, UDP-GlcNAc 2-epimerase, GenBank
      AAK91727.1

<400> SEQUENCE: 59

Met Lys Lys Ile Leu Phe Ile Thr Gly Ser Arg Ala Asp Tyr Ser Lys
1               5                   10                  15

Ile Lys Ser Leu Met Tyr Arg Val Gln Asn Ser Ser Glu Phe Glu Leu
            20                  25                  30

Tyr Ile Phe Ala Thr Gly Met His Leu Ser Lys Asn Phe Gly Tyr Thr
        35                  40                  45

Val Lys Glu Leu Tyr Lys Asn Gly Phe Lys Asn Ile Tyr Glu Phe Ile
    50                  55                  60

Asn Tyr Asp Lys Tyr Tyr Gln Thr Asp Lys Ala Leu Ala Thr Thr Ile
65                  70                  75                  80

Asp Gly Phe Ser Arg Tyr Ala Asn Glu Leu Lys Pro Asp Leu Ile Val
                85                  90                  95

Val His Gly Asp Arg Ile Glu Pro Leu Ala Ala Ala Ile Val Gly Ala
            100                 105                 110

Leu Asn Asn Ile Leu Val Ala His Ile Glu Gly Gly Glu Ile Ser Gly
```

```
              115                 120                 125
Thr Ile Asp Asp Ser Leu Arg His Ala Ile Ser Lys Leu Ala His Ile
    130                 135                 140

His Leu Val Asn Asp Glu Phe Ala Lys Arg Arg Leu Met Gln Leu Gly
145                 150                 155                 160

Glu Asp Glu Lys Ser Ile Phe Ile Ile Gly Ser Pro Asp Leu Glu Leu
                165                 170                 175

Leu Asn Asp Asn Lys Ile Ser Leu Ser Glu Ala Lys Lys Tyr Tyr Asp
            180                 185                 190

Ile Asn Tyr Glu Asn Tyr Ala Leu Leu Met Phe His Pro Val Thr Thr
        195                 200                 205

Glu Ile Thr Ser Ile Lys Asn Gln Ala Asp Asn Leu Val Lys Ala Leu
    210                 215                 220

Ile Gln Ser Asn Lys Asn Tyr Ile Val Ile Tyr Pro Asn Asn Asp Leu
225                 230                 235                 240

Gly Phe Glu Leu Ile Leu Gln Ser Tyr Glu Glu Phe Lys Asn Asn Pro
                245                 250                 255

Arg Phe Lys Leu Phe Pro Ser Leu Arg Phe Glu Tyr Phe Ile Thr Leu
            260                 265                 270

Leu Lys Asn Ala Asp Phe Ile Ile Gly Asn Ser Ser Cys Ile Leu Lys
        275                 280                 285

Glu Ala Leu Tyr Leu Lys Thr Ala Gly Ile Leu Val Gly Ser Arg Gln
    290                 295                 300

Asn Gly Arg Leu Gly Asn Glu Asn Thr Leu Lys Val Asn Ala Asn Ser
305                 310                 315                 320

Asp Glu Ile Leu Lys Ala Ile Asn Thr Ile His Lys Lys Gln Asp Leu
                325                 330                 335

Phe Ser Ala Lys Leu Glu Ile Leu Asp Ser Ser Lys Leu Phe Phe Glu
            340                 345                 350

Tyr Leu Gln Ser Gly Asp Phe Phe Lys Leu Ser Thr Gln Lys Val Phe
        355                 360                 365

Lys Asp Ile Lys
    370

<210> SEQ ID NO 60
<211> LENGTH: 391
<212> TYPE: PRT
<213> ORGANISM: Enterobacteriaceae
<220> FEATURE:
<221> NAME/KEY: MISC_FEATURE
<222> LOCATION: (1)..(391)
<223> OTHER INFORMATION: NeuC, UDP-GlcNAc 2-epimerase, GenBank ID:
      WP_000723250.1

<400> SEQUENCE: 60

Met Lys Lys Ile Leu Tyr Val Thr Gly Ser Arg Ala Glu Tyr Gly Ile
1               5                   10                  15

Val Arg Arg Leu Leu Thr Met Leu Arg Glu Thr Pro Glu Ile Gln Leu
                20                  25                  30

Asp Leu Ala Val Thr Gly Met His Cys Asp Asn Ala Tyr Gly Asn Thr
            35                  40                  45

Ile His Ile Ile Glu Gln Asp Asn Phe Asn Ile Lys Val Val Asp
        50                  55                  60

Ile Asn Ile Asn Thr Thr Ser His Thr His Ile Leu His Ser Met Ser
65                  70                  75                  80

Val Cys Leu Asn Ser Phe Gly Asp Phe Phe Ser Asn Asn Thr Tyr Asp
```

```
                            85                  90                  95
Ala Val Met Val Leu Gly Asp Arg Tyr Glu Ile Phe Ser Val Ala Ile
                100                 105                 110

Ala Ala Ser Met His Asn Ile Pro Leu Ile His Ile His Gly Gly Glu
            115                 120                 125

Lys Thr Leu Ala Asn Tyr Asp Glu Phe Ile Arg His Ser Ile Thr Lys
        130                 135                 140

Met Ser Lys Leu His Leu Thr Ser Thr Glu Glu Tyr Lys Lys Arg Val
145                 150                 155                 160

Ile Gln Leu Gly Glu Lys Pro Gly Ser Val Phe Asn Ile Gly Ser Leu
                165                 170                 175

Gly Ala Glu Asn Ala Leu Ser Leu His Leu Pro Asn Lys Gln Glu Leu
            180                 185                 190

Glu Leu Lys Tyr Gly Ser Leu Leu Lys Arg Tyr Phe Val Val Phe
        195                 200                 205

His Pro Glu Thr Leu Ser Thr Gln Ser Val Asn Asp Gln Ile Asp Glu
    210                 215                 220

Leu Leu Ser Ala Ile Ser Phe Phe Lys Asn Thr His Asp Phe Ile Phe
225                 230                 235                 240

Ile Gly Ser Asn Ala Asp Thr Gly Ser Asp Ile Ile Gln Arg Lys Val
                245                 250                 255

Lys Tyr Phe Cys Lys Glu Tyr Lys Phe Arg Tyr Leu Ile Ser Ile Arg
            260                 265                 270

Ser Glu Asp Tyr Leu Ala Met Ile Lys Tyr Ser Cys Gly Leu Ile Gly
        275                 280                 285

Asn Ser Ser Ser Gly Leu Ile Glu Val Pro Ser Leu Lys Val Ala Thr
    290                 295                 300

Ile Asn Ile Gly Asp Arg Gln Lys Gly Arg Val Arg Gly Ala Ser Val
305                 310                 315                 320

Ile Asp Val Pro Val Glu Lys Asn Ala Ile Val Arg Gly Ile Asn Ile
                325                 330                 335

Ser Gln Asp Glu Lys Phe Ile Ser Val Val Gln Ser Ser Asn Pro
            340                 345                 350

Tyr Phe Lys Glu Asn Ala Leu Ile Asn Ala Val Arg Ile Ile Lys Asp
        355                 360                 365

Phe Ile Lys Ser Lys Asn Lys Asp Tyr Lys Asp Phe Tyr Asp Ile Pro
    370                 375                 380

Glu Cys Thr Thr Ser Tyr Asp
385                 390

<210> SEQ ID NO 61
<211> LENGTH: 391
<212> TYPE: PRT
<213> ORGANISM: Escherichia coli S88
<220> FEATURE:
<221> NAME/KEY: MISC_FEATURE
<222> LOCATION: (1)..(391)
<223> OTHER INFORMATION: NeuC, UDP-GlcNAc 2-epimerase, GenBank ID:
      CAR04561.1

<400> SEQUENCE: 61

Met Lys Lys Ile Leu Tyr Val Thr Gly Ser Arg Ala Glu Tyr Gly Ile
1               5                   10                  15

Val Arg Arg Leu Leu Thr Met Leu Arg Glu Thr Pro Glu Ile Gln Leu
            20                  25                  30

Asp Leu Ala Val Thr Gly Met His Cys Asp Asn Ala Tyr Gly Asn Thr
```

```
                35                  40                  45
Ile His Ile Ile Glu Gln Asp Asn Phe Asn Ile Ile Lys Val Val Asp
 50                  55                  60

Ile Asn Ile Asn Thr Thr Ser His Thr His Ile Leu His Ser Met Ser
 65                  70                  75                  80

Val Cys Leu Asn Ser Phe Gly Asp Phe Phe Ser Asn Asn Thr Tyr Asp
                 85                  90                  95

Ala Val Met Val Leu Gly Asp Arg Tyr Glu Ile Phe Ser Val Ala Ile
                100                 105                 110

Ala Ala Ser Met His Asn Ile Pro Leu Ile His Ile His Gly Gly Glu
                115                 120                 125

Lys Thr Leu Ala Asn Tyr Asp Glu Phe Ile Arg His Ser Ile Thr Lys
130                 135                 140

Met Ser Lys Leu His Leu Thr Ser Thr Glu Glu Tyr Lys Lys Arg Val
145                 150                 155                 160

Ile Gln Leu Gly Glu Lys Pro Gly Ser Val Phe Asn Ile Gly Ser Leu
                165                 170                 175

Gly Ala Glu Asn Ala Leu Ser Leu His Leu Pro Asn Lys Gln Glu Leu
                180                 185                 190

Glu Leu Lys Tyr Gly Ser Leu Leu Lys Arg Tyr Phe Val Val Val Phe
                195                 200                 205

His Pro Glu Thr Leu Ser Thr Gln Ser Val Asn Asp Gln Ile Asp Glu
210                 215                 220

Leu Leu Ser Ala Ile Ser Phe Phe Lys Asn Thr His Asp Phe Ile Phe
225                 230                 235                 240

Ile Gly Ser Asn Ala Asp Thr Gly Ser Asp Ile Ile Gln Arg Lys Val
                245                 250                 255

Lys Tyr Phe Cys Lys Glu Tyr Lys Phe Arg Tyr Leu Ile Ser Ile Arg
                260                 265                 270

Ser Glu Asp Tyr Leu Ala Met Ile Lys Tyr Ser Cys Gly Leu Ile Gly
                275                 280                 285

Asn Ser Ser Ser Gly Leu Ile Glu Val Pro Ser Leu Lys Val Ala Thr
290                 295                 300

Ile Asn Ile Gly Asp Arg Gln Lys Gly Arg Val Arg Gly Ala Ser Val
305                 310                 315                 320

Ile Asp Val Pro Val Glu Lys Asn Ala Ile Val Arg Gly Ile Asn Ile
                325                 330                 335

Ser Gln Asp Glu Lys Phe Ile Ser Val Val Gln Ser Ser Ser Asn Pro
                340                 345                 350

Tyr Phe Lys Glu Asn Ala Leu Ile Asn Ala Val Arg Ile Ile Lys Asp
                355                 360                 365

Phe Ile Lys Ser Lys Asn Lys Asp Tyr Lys Asp Phe Tyr Asp Ile Pro
370                 375                 380

Glu Cys Thr Thr Ser Tyr Asp
385                 390

<210> SEQ ID NO 62
<211> LENGTH: 392
<212> TYPE: PRT
<213> ORGANISM: Pantoea vagans
<220> FEATURE:
<221> NAME/KEY: MISC_FEATURE
<222> LOCATION: (1)..(392)
<223> OTHER INFORMATION: Vag MFS transporter, WP_048785139.1

<400> SEQUENCE: 62
```

```
Met Lys Ser Leu Leu Thr Arg Lys Arg Arg Ile Asn Pro Val Phe Leu
1               5                   10                  15

Ala Phe Met Ala Ala Ser Phe Met Ile Gly Val Ala Gly Ala Leu Gln
            20                  25                  30

Ala Pro Thr Leu Ser Leu Phe Leu Thr Arg Glu Val Gln Ala Arg Pro
                35                  40                  45

Leu Trp Val Gly Leu Phe Phe Thr Val Asn Ala Ile Ala Gly Ile Val
50                          55                  60

Val Ser Met Leu Val Ala Lys Arg Ser Asp Ser Arg Gly Asp Arg Arg
65                      70                  75                  80

Thr Leu Ile Leu Phe Cys Cys Ala Met Ala Phe Cys Asn Ala Leu Leu
                    85                  90                  95

Phe Ala Phe Thr Arg His Tyr Leu Thr Leu Ile Thr Leu Gly Val Leu
                100                 105                 110

Leu Ser Ala Leu Ala Ser Val Ser Met Pro Gln Ile Phe Ala Leu Ala
            115                 120                 125

Arg Glu Tyr Ala Asp Gln Ser Ala Arg Glu Ala Val Met Phe Ser Ser
    130                 135                 140

Val Met Arg Ala Gln Leu Ser Leu Ala Trp Val Ile Gly Pro Pro Leu
145                 150                 155                 160

Ser Phe Ala Leu Ala Leu Asn Phe Gly Phe Val Thr Leu Phe Leu Val
                165                 170                 175

Ala Ala Ala Leu Phe Leu Val Cys Ile Leu Leu Ile Lys Phe Thr Leu
            180                 185                 190

Pro Ser Val Pro Arg Ala Glu Pro Leu Met Arg Ser Gly Gly Met Pro
        195                 200                 205

Leu Ser Gly Trp Arg Asp Arg Asp Val Arg Leu Leu Phe Ile Ala Ser
    210                 215                 220

Val Thr Met Trp Thr Cys Asn Thr Met Tyr Ile Ile Asp Met Pro Leu
225                 230                 235                 240

Tyr Ile Ser Val Thr Leu Gly Leu Pro Glu Lys Leu Ala Gly Leu Leu
                245                 250                 255

Met Gly Thr Ala Ala Gly Leu Glu Ile Pro Val Met Leu Leu Ala Gly
            260                 265                 270

His Tyr Ala Lys Arg Val Gly Lys Arg Asn Leu Met Leu Ile Ala Val
    275                 280                 285

Ala Ala Gly Val Leu Phe Tyr Ala Gly Leu Ala Met Phe Ala Ser Gln
290                 295                 300

Thr Ala Leu Met Ala Leu Gln Leu Phe Asn Ala Val Phe Ile Gly Ile
305                 310                 315                 320

Ile Ala Gly Ile Gly Met Leu Trp Phe Gln Asp Leu Met Pro Gly Arg
                325                 330                 335

Pro Gly Ala Ala Thr Met Phe Thr Asn Ser Ile Ser Thr Gly Met
        340                 345                 350

Ile Leu Ala Gly Val Ile Gln Gly Thr Leu Ser Glu Arg Phe Gly His
            355                 360                 365

Ile Ala Val Tyr Trp Leu Ala Leu Gly Leu Ala Val Ala Ala Phe Ala
    370                 375                 380

Met Ser Ala Arg Val Lys Asn Val
385                 390

<210> SEQ ID NO 63
<211> LENGTH: 393
```

```
<212> TYPE: PRT
<213> ORGANISM: Yersinia frederiksenii
<220> FEATURE:
<221> NAME/KEY: MISC_FEATURE
<222> LOCATION: (1)..(393)
<223> OTHER INFORMATION: Fred MFS transporter, WP_087817556.1

<400> SEQUENCE: 63
```

Met Lys Ser Ala Leu Thr Phe Ser Arg Arg Ile Asn Pro Val Phe Leu
1               5                   10                  15

Ala Phe Phe Val Ala Phe Leu Ser Gly Ile Ala Gly Ala Leu Gln
            20                  25                  30

Ala Pro Thr Leu Ser Leu Phe Leu Ser Thr Glu Val Lys Val Arg Pro
            35                  40                  45

Leu Trp Val Gly Leu Phe Tyr Thr Val Asn Ala Ile Ala Gly Ile Thr
        50                  55                  60

Val Ser Phe Val Leu Ala Lys Arg Ser Asp Leu Arg Gly Asp Arg Arg
65                  70                  75                  80

Lys Leu Ile Leu Val Cys Tyr Leu Met Ala Val Gly Asn Cys Leu Leu
                85                  90                  95

Phe Ala Phe Asn Arg Asp Tyr Leu Thr Leu Ile Thr Ala Gly Val Leu
            100                 105                 110

Leu Ala Ala Val Ala Asn Thr Ala Met Pro Gln Ile Phe Ala Leu Ala
        115                 120                 125

Arg Glu Tyr Ala Asp Asn Ser Ala Arg Glu Val Val Met Phe Ser Ser
    130                 135                 140

Ile Met Arg Ala Gln Leu Ser Leu Ala Trp Val Ile Gly Pro Pro Leu
145                 150                 155                 160

Ser Phe Met Leu Ala Leu Asn Tyr Gly Phe Thr Leu Met Phe Cys Ile
                165                 170                 175

Ala Ala Gly Ile Phe Val Leu Ser Ala Leu Val Val Trp Phe Ile Leu
            180                 185                 190

Pro Ser Val Gln Arg Ala Glu Pro Val Met Asp Ala Pro Thr Val Ala
        195                 200                 205

Gln Gly Ser Leu Phe Ala Asp Lys Asp Val Leu Leu Leu Phe Ile Ala
    210                 215                 220

Ser Met Leu Met Trp Thr Cys Asn Thr Met Tyr Ile Ile Asp Met Pro
225                 230                 235                 240

Leu Tyr Ile Thr Ala Ser Leu Gly Leu Pro Glu Arg Leu Ala Gly Leu
                245                 250                 255

Leu Met Gly Thr Ala Ala Gly Leu Glu Ile Pro Ile Met Leu Leu Ala
            260                 265                 270

Gly Tyr Ser Val Arg Arg Phe Gly Lys Arg Lys Ile Met Leu Phe Ala
        275                 280                 285

Val Leu Ala Gly Val Leu Phe Tyr Thr Gly Leu Val Leu Phe Lys Phe
    290                 295                 300

Lys Ser Ala Leu Met Leu Leu Gln Ile Phe Asn Ala Ile Phe Ile Gly
305                 310                 315                 320

Ile Val Ala Gly Ile Gly Met Leu Tyr Phe Gln Asp Leu Met Pro Gly
                325                 330                 335

Arg Ala Gly Ala Ala Thr Thr Leu Phe Thr Asn Ser Ile Ser Thr Gly
            340                 345                 350

Val Ile Leu Ala Gly Val Leu Gln Gly Val Leu Thr Glu Thr Trp Gly
        355                 360                 365

His Asn Ser Val Tyr Val Met Ala Met Ile Leu Ala Ile Leu Ser Leu

```
                370             375             380
Ile Ile Cys Ala Arg Val Arg Glu Ala
385                 390

<210> SEQ ID NO 64
<211> LENGTH: 398
<212> TYPE: PRT
<213> ORGANISM: Serratia marcescens
<220> FEATURE:
<221> NAME/KEY: MISC_FEATURE
<222> LOCATION: (1)..(398)
<223> OTHER INFORMATION: Marc MFS transporter, WP_060448169.1

<400> SEQUENCE: 64

Met Gln Arg Leu Ser Arg Leu Ser Leu Arg Ile Asn Pro Ile Phe Ala
1               5                   10                  15

Ala Phe Leu Leu Ile Ala Phe Leu Ser Gly Ile Ala Gly Ala Leu Leu
                20                  25                  30

Thr Pro Thr Leu Ser Leu Phe Leu Thr Thr Glu Val Lys Val Arg Pro
            35                  40                  45

Leu Trp Val Gly Leu Phe Tyr Thr Ala Asn Ala Val Ala Gly Ile Val
        50                  55                  60

Val Ser Phe Leu Leu Ala Lys Arg Ser Asp Thr Arg Gly Asp Arg Arg
65                  70                  75                  80

Arg Leu Ile Leu Leu Cys Cys Leu Met Ala Val Gly Asn Cys Leu Leu
                85                  90                  95

Phe Ala Phe Asn Arg Asp Tyr Leu Thr Leu Ile Thr Ala Gly Val Leu
                100                 105                 110

Met Ser Ala Val Ala Asn Thr Ala Met Pro Gln Ile Phe Ala Leu Ala
            115                 120                 125

Arg Glu Tyr Ala Asp Ser Glu Ala Arg Glu Val Val Met Phe Ser Ser
130                 135                 140

Val Met Arg Ala Gln Leu Ser Leu Ala Trp Val Ile Gly Pro Pro Leu
145                 150                 155                 160

Ser Phe Ala Leu Ala Leu Asn Tyr Gly Phe Thr Val Met Phe Leu Ile
                165                 170                 175

Ala Ala Val Thr Phe Ala Val Cys Val Leu Val Gly Phe Met Leu
                180                 185                 190

Pro Ser Val Pro Arg Ala Ala Glu Asn Glu Gly Leu Gln Gly Gly Val
            195                 200                 205

Ser Ala Pro Ile Ala Pro Ala Ser Ala Trp Arg Asn Arg Asp Val Arg
        210                 215                 220

Leu Leu Phe Ile Ala Ser Met Leu Met Trp Thr Cys Asn Thr Leu Tyr
225                 230                 235                 240

Ile Ile Asp Met Pro Leu Tyr Ile Thr Ala Asp Leu Gly Leu Pro Glu
                245                 250                 255

Gly Leu Ala Gly Val Leu Met Gly Thr Ala Ala Gly Leu Glu Ile Pro
                260                 265                 270

Ala Met Leu Leu Ala Gly Tyr Tyr Val Lys Arg Phe Gly Lys Arg Asn
            275                 280                 285

Met Met Leu Leu Ala Val Val Ala Gly Val Leu Phe Tyr Leu Gly Leu
290                 295                 300

Thr Val Leu Glu Ser Lys Pro Ala Leu Ile Ala Leu Gln Leu Leu Asn
305                 310                 315                 320

Ala Val Phe Ile Gly Ile Val Ala Gly Ile Gly Met Leu Tyr Phe Gln
                325                 330                 335
```

-continued

Asp Leu Met Pro Gly Arg Pro Gly Ala Ala Thr Thr Leu Phe Thr Asn
            340                 345                 350

Ser Ile Ser Thr Gly Val Ile Leu Ala Gly Val Leu Gln Gly Ala Leu
        355                 360                 365

Val Glu Asn Leu Gly His Gly Ser Val Tyr Trp Met Ala Ala Leu Leu
370                 375                 380

Ala Leu Ala Ala Leu Gly Met Ser Ala Lys Val Arg Glu Val
385                 390                 395

<210> SEQ ID NO 65
<211> LENGTH: 387
<212> TYPE: PRT
<213> ORGANISM: Rouxiella badensis
<220> FEATURE:
<221> NAME/KEY: MISC_FEATURE
<222> LOCATION: (1)..(387)
<223> OTHER INFORMATION: Bad MFS transporter, WP_017489914.1

<400> SEQUENCE: 65

Met Ser Ser Arg Arg Leu Ser Ile Ile Phe Ala Thr Phe Leu Leu Val
1               5                   10                  15

Ser Phe Leu Thr Gly Ile Ala Gly Ala Leu Gln Ala Pro Thr Leu Ser
            20                  25                  30

Leu Phe Leu Thr Asn Glu Val Lys Val Arg Pro Leu Trp Val Gly Leu
        35                  40                  45

Phe Tyr Thr Val Asn Ala Leu Gly Gly Ile Val Ile Ser Phe Leu Leu
    50                  55                  60

Ala Asn Tyr Ser Asp Lys Lys Gly Asp Arg Arg Lys Leu Leu Phe Phe
65                  70                  75                  80

Cys Thr Leu Met Ala Ile Gly Asn Ser Leu Ile Phe Ala Tyr Ser Arg
                85                  90                  95

Asp Tyr Leu Val Leu Ile Ser Val Gly Val Leu Leu Ala Ala Ile Gly
            100                 105                 110

Asn Ala Ser Met Pro Gln Leu Phe Ala Leu Ala Arg Glu Tyr Ala Asp
        115                 120                 125

Arg Ser Ala His Glu Val Val Met Phe Ser Ser Met Met Arg Ala Thr
    130                 135                 140

Leu Ser Leu Ala Trp Val Leu Gly Pro Pro Ile Ser Phe Thr Leu Ala
145                 150                 155                 160

Leu Asn Tyr Gly Phe Thr Leu Met Tyr Leu Cys Ala Ala Gly Val Phe
                165                 170                 175

Ile Phe Ser Ala Leu Met Val Trp Phe Leu Pro Ser Val Gly Arg
            180                 185                 190

Ile Glu Gln Pro Val Asp Lys Val Val His Val Ser Ala Trp Lys
        195                 200                 205

Asn Arg Asp Val Arg Leu Leu Phe Phe Ala Ser Leu Leu Met Trp Thr
    210                 215                 220

Cys Asn Ile Met Tyr Ile Ile Asp Met Pro Leu Tyr Ile Thr Ser Asp
225                 230                 235                 240

Leu Gly Leu Pro Glu Gly Leu Ala Gly Leu Met Gly Ala Ala Ala
                245                 250                 255

Gly Leu Glu Ile Pro Val Met Leu Ile Ala Gly Tyr Leu Val Lys Arg
            260                 265                 270

Thr Gly Lys Arg Arg Leu Met Leu Cys Ala Ala Val Phe Gly Ile Leu
        275                 280                 285

```
Phe Tyr Leu Gly Leu Val Leu Phe Gln Phe Lys Ala Ala Leu Met Ile
            290                 295                 300

Leu Gln Leu Phe Asn Ala Ile Phe Ile Gly Ile Ile Ala Gly Ile Gly
305                 310                 315                 320

Met Leu Tyr Phe Gln Asp Leu Met Pro Gly Arg Ala Gly Ser Ala Thr
            325                 330                 335

Thr Leu Phe Thr Asn Ser Ile Ser Thr Gly Ala Ile Leu Ala Gly Val
            340                 345                 350

Ile Gln Gly Thr Ile Val Gln Asn Phe Gly His Tyr Gln Val Tyr Trp
            355                 360                 365

Met Ala Leu Ala Leu Ala Val Gly Ala Leu Val Leu Met Thr Arg Val
370                 375                 380

Lys Asn Val
385

<210> SEQ ID NO 66
<211> LENGTH: 394
<212> TYPE: PRT
<213> ORGANISM: Rosenbergiella nectarea
<220> FEATURE:
<221> NAME/KEY: MISC_FEATURE
<222> LOCATION: (1)..(394)
<223> OTHER INFORMATION: Nec MFS transporter, WP_092672081.1

<400> SEQUENCE: 66

Met Gln Ser Phe Thr Pro Ala Pro Lys Gly Gly Asn Pro Val Phe
1               5                   10                  15

Met Met Phe Met Leu Val Thr Phe Phe Val Ser Ile Ala Gly Ala Leu
                20                  25                  30

Gln Ala Pro Thr Leu Ser Leu Tyr Leu Ser Gln Glu Leu Ala Ala Lys
            35                  40                  45

Pro Phe Met Val Gly Leu Phe Phe Thr Ile Asn Ala Val Thr Gly Ile
50                  55                  60

Ile Ile Ser Phe Ile Leu Ala Lys Arg Ser Asp Arg Lys Gly Asp Arg
65                  70                  75                  80

Arg Arg Leu Leu Met Phe Cys Cys Ala Met Ala Ile Ala Asn Ala Leu
                85                  90                  95

Met Phe Ala Phe Val Arg Gln Tyr Val Val Leu Ile Thr Leu Gly Leu
            100                 105                 110

Ile Leu Ser Ala Leu Thr Ser Val Val Met Pro Gln Leu Phe Ala Leu
            115                 120                 125

Ala Arg Glu Tyr Ala Asp Arg Thr Gly Arg Glu Val Val Met Phe Ser
130                 135                 140

Ser Val Met Arg Thr Gln Met Ser Leu Ala Trp Val Ile Gly Pro Pro
145                 150                 155                 160

Ile Ser Phe Ala Leu Ala Leu Asn Tyr Gly Phe Ile Thr Leu Tyr Leu
                165                 170                 175

Val Ala Ala Ala Leu Phe Leu Leu Ser Leu Ile Leu Ile Lys Thr Thr
            180                 185                 190

Leu Pro Ser Val Pro Arg Leu Tyr Pro Ala Glu Asp Leu Ala Lys Ser
            195                 200                 205

Ala Ala Ser Gly Trp Lys Arg Thr Asp Val Arg Phe Leu Phe Ala Ala
210                 215                 220

Ser Val Leu Met Trp Val Cys Asn Leu Met Tyr Ile Ile Asp Met Pro
225                 230                 235                 240

Leu Tyr Ile Ser Lys Ser Leu Gly Met Pro Glu Ser Phe Ala Gly Val
```

-continued

```
                    245                 250                 255
Leu Met Gly Thr Ala Ala Gly Leu Glu Ile Pro Val Met Leu Leu Ala
                260                 265                 270
Gly Tyr Leu Ala Lys Arg Val Gly Lys Arg Pro Leu Val Ile Val Ala
                275                 280                 285
Ala Val Cys Gly Leu Ala Phe Tyr Pro Ala Met Leu Val Phe His Gln
                290                 295                 300
Gln Thr Gly Leu Leu Ile Ile Gln Leu Leu Asn Ala Val Phe Ile Gly
305                 310                 315                 320
Ile Val Ala Gly Leu Val Met Leu Trp Phe Gln Asp Leu Met Pro Gly
                325                 330                 335
Lys Ala Gly Ala Ala Thr Thr Leu Phe Thr Asn Ser Val Ser Thr Gly
                340                 345                 350
Met Ile Phe Ala Gly Leu Cys Gln Gly Leu Leu Ser Asp Leu Leu Gly
                355                 360                 365
His Gln Ala Ile Tyr Val Leu Ala Thr Val Leu Met Val Ile Ala Leu
                370                 375                 380
Leu Leu Leu Leu Arg Val Lys Glu Gln Ala
385                 390

<210> SEQ ID NO 67
<211> LENGTH: 393
<212> TYPE: PRT
<213> ORGANISM: Yersinia bercovieri
<220> FEATURE:
<221> NAME/KEY: MISC_FEATURE
<222> LOCATION: (1)..(393)
<223

Gln Gly Ser Leu Phe Ala Asp Lys Asn Val Leu Leu Leu Phe Ile Ala
    210                 215                 220

Ser Met Leu Met Trp Thr Cys Asn Thr Met Tyr Ile Ile Asp Met Pro
225                 230                 235                 240

Leu Tyr Ile Thr Ala Ser Leu Gly Leu Pro Glu Arg Leu Ala Gly Leu
                245                 250                 255

Leu Met Gly Thr Ala Ala Gly Leu Glu Ile Pro Ile Met Leu Leu Ala
            260                 265                 270

Gly Tyr Ser Val Arg Tyr Phe Gly Lys Arg Lys Ile Met Leu Phe Ala
        275                 280                 285

Val Leu Ala Gly Val Leu Phe Tyr Thr Gly Leu Val Leu Phe Lys Phe
    290                 295                 300

Lys Thr Ala Leu Met Leu Leu Gln Ile Phe Asn Ala Ile Phe Ile Gly
305                 310                 315                 320

Ile Val Ala Gly Ile Gly Met Leu Tyr Phe Gln Asp Leu Met Pro Gly
                325                 330                 335

Arg Ala Gly Ala Ala Thr Thr Leu Phe Thr Asn Ser Ile Ser Thr Gly
            340                 345                 350

Val Ile Leu Ala Gly Val Leu Gln Gly Gly Leu Thr Glu Thr Trp Gly
        355                 360                 365

His Asp Ser Val Tyr Val Met Ala Met Val Leu Ser Ile Leu Ala Leu
    370                 375                 380

Ile Ile Cys Ala Arg Val Arg Glu Ala
385                 390

<210> SEQ ID NO 68
<211> LENGTH: 107
<212> TYPE: DNA
<213> ORGANISM: Escherichia coli
<220> FEATURE:
<221> NAME/KEY: misc_feature
<222> LOCATION: (1)..(107)
<223> OTHER INFORMATION: Plac, lac operon promoter

<400> SEQUENCE: 68
tgtgagttag ctcactcatt aggcacccca ggctttacac tttatgcttc cggctcgtat    60
gttgtgtgga attgtgagcg ataacaatt tcacacagga aacagct                  107

<210> SEQ ID NO 69
<211> LENGTH: 291
<212> TYPE: DNA
<213> ORGANISM: Artificial Sequence
<220> FEATURE:
<223> OTHER INFORMATION: PgatY_70UTR, variant of E. coli promoter for
      gatYZABCD; tagatose-1,6-bisP aldolase

<400> SEQUENCE: 69
cggcaaccta tgcctgatgc gacgctgaag cgtcttatca tgcctacata gcactgccac    60
gtatgtttac accgcatccg gcataaaaac acgcgcactt tgctacggct tccctatcgg   120
gaggccgttt ttttgccttt cactcctcga ataattttca tattgtcgtt tttgtgatcg   180
ttatctcgat atttaaaaac aaataatttc attatatttt gtgcctacaa gcatcgtgga   240
ggtccgtgac tttcacgcat acaacaaaca ttaaccaagg aggaaacagc t            291

<210> SEQ ID NO 70
<211> LENGTH: 300
<212> TYPE: DNA
<213> ORGANISM: Artificial Sequence

```
<220> FEATURE:
<223> OTHER INFORMATION: PglpF, E. Coli promoter sequence of glpFKX
      operon

<400> SEQUENCE: 70
gcggcacgcc ttgcagatta cggttttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg tttttgctcg ttaacgataa gtttacagca tgcctacaag   240
catcgtggag gtccgtgact ttcacgcata caacaaacat taaccaagga ggaaacagct   300

<210> SEQ ID NO 71
<211> LENGTH: 300
<212> TYPE: DNA
<213> ORGANISM: Artificial Sequence
<220> FEATURE:
<223> OTHER INFORMATION: PglpF_SD1, variant of PglpF E. Coli promoter
      sequence of glpFKX operon

<400> SEQUENCE: 71
gcggcacgcc ttgcagatta cggttttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg tttttgctcg ttaacgataa gtttacagca tgcctacaag   240
catcgtggag gtccgtgact ttcacgcata caacaaacat taaccaaatt cgaaacagct   300

<210> SEQ ID NO 72
<211> LENGTH: 300
<212> TYPE: DNA
<213> ORGANISM: Artificial Sequence
<220> FEATURE:
<223> OTHER INFORMATION: PglpF_SD10, variant of PglpF E. Coli promoter
      sequence of glpFKX operon

<400> SEQUENCE: 72
gcggcacgcc ttgcagatta cggttttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg tttttgctcg ttaacgataa gtttacagca tgcctacaag   240
catcgtggag gtccgtgact ttcacgcata caacaaacat taaccaactg agaaacagct   300

<210> SEQ ID NO 73
<211> LENGTH: 300
<212> TYPE: DNA
<213> ORGANISM: Artificial Sequence
<220> FEATURE:
<223> OTHER INFORMATION: PglpF_SD2, variant of PglpF E. Coli promoter
      sequence of glpFKX operon

<400> SEQUENCE: 73
gcggcacgcc ttgcagatta cggttttgcca cacttttcat ccttctcctg gtgacataat    60
ccacatcaat cgaaaatgtt aataaatttg ttgcgcgaat gatctaacaa acatgcatca   120
tgtacaatca gatggaataa atggcgcgat aacgctcatt ttatgacgag gcacacacat   180
tttaagttcg atatttctcg tttttgctcg ttaacgataa gtttacagca tgcctacaag   240
catcgtggag gtccgtgact ttcacgcata caacaaacat taaccaagcg caaaacagct   300
```

<210> SEQ ID NO 74
<211> LENGTH: 300
<212> TYPE: DNA
<213> ORGANISM: Artificial Sequence
<220> FEATURE:
<223> OTHER INFORMATION: PglpF_SD3 variant of PglpF E. Coli promoter
      sequence of glpFKX operon

<400> SEQUENCE: 74

```
gcggcacgcc ttgcagatta cggtttgcca cactttcat ccttctcctg gtgacataat      60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
catcgtggag gtccgtgact ttcacgcata caacaaacat taaccaagaa caaaacagct    300
```

<210> SEQ ID NO 75
<211> LENGTH: 300
<212> TYPE: DNA
<213> ORGANISM: Artificial Sequence
<220> FEATURE:
<223> OTHER INFORMATION: PglpF_SD4, variant of PglpF E. Coli promoter
      sequence of glpFKX operon

<400> SEQUENCE: 75

```
gcggcacgcc ttgcagatta cggtttgcca cactttcat ccttctcctg gtgacataat      60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
catcgtggag gtccgtgact ttcacgcata caacaaacat taaccaacta ggaaacagct    300
```

<210> SEQ ID NO 76
<211> LENGTH: 300
<212> TYPE: DNA
<213> ORGANISM: Artificial Sequence
<220> FEATURE:
<223> OTHER INFORMATION: PglpF_SD5, variant of PglpF E. Coli promoter
      sequence of glpFKX operon

<400> SEQUENCE: 76

```
gcggcacgcc ttgcagatta cggtttgcca cactttcat ccttctcctg gtgacataat      60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
catcgtggag gtccgtgact ttcacgcata caacaaacat taaccaaccg agaaacagct    300
```

<210> SEQ ID NO 77
<211> LENGTH: 300
<212> TYPE: DNA
<213> ORGANISM: Artificial Sequence
<220> FEATURE:
<223> OTHER INFORMATION: PglpF_SD6, variant of PglpF E. Coli promoter
      sequence of glpFKX operon

<400> SEQUENCE: 77

```
gcggcacgcc ttgcagatta cggtttgcca cactttcat ccttctcctg gtgacataat      60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
```

```
tttaagttcg atatttctcg tttttgctcg ttaacgataa gtttacagca tgcctacaag    240
catcgtggag gtccgtgact ttcacgcata caacaaacat taaccaagag ctaaacagct    300

<210> SEQ ID NO 78
<211> LENGTH: 300
<212> TYPE: DNA
<213> ORGANISM: Artificial Sequence
<220> FEATURE:
<223> OTHER INFORMATION: PglpF_SD7, variant of PglpF E. Coli promoter
      sequence of glpFKX operon

<400> SEQUENCE: 78
gcggcacgcc ttgcagatta cggtttgcca cacttttcat ccttctcctg gtgacataat    60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
catcgtggag gtccgtgact ttcacgcata caacaaacat taaccaagag caaaacagct    300

<210> SEQ ID NO 79
<211> LENGTH: 300
<212> TYPE: DNA
<213> ORGANISM: Artificial Sequence
<220> FEATURE:
<223> OTHER INFORMATION: PglpF_SD8, variant of PglpF E. Coli promoter
      sequence of glpFKX operon

<400> SEQUENCE: 79
gcggcacgcc ttgcagatta cggtttgcca cacttttcat ccttctcctg gtgacataat    60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
catcgtggag gtccgtgact ttcacgcata caacaaacat taaccaagag aaaaacagct    300

<210> SEQ ID NO 80
<211> LENGTH: 300
<212> TYPE: DNA
<213> ORGANISM: Artificial Sequence
<220> FEATURE:
<223> OTHER INFORMATION: PglpF_SD9, variant of PglpF E. Coli promoter
      sequence of glpFKX operon

<400> SEQUENCE: 80
gcggcacgcc ttgcagatta cggtttgcca cacttttcat ccttctcctg gtgacataat    60
ccacatcaat cgaaaatgtt aataaatttg ttgcgcgaat gatctaacaa acatgcatca    120
tgtacaatca gatggaataa atggcgcgat aacgctcatt ttatgacgag gcacacacat    180
tttaagttcg atatttctcg tttttgctcg ttaacgataa gtttacagca tgcctacaag    240
catcgtggag gtccgtgact ttcacgcata caacaaacat taaccaagg aaaaacagct     300

<210> SEQ ID NO 81
<211> LENGTH: 107
<212> TYPE: DNA
<213> ORGANISM: Artificial Sequence
<220> FEATURE:
<223> OTHER INFORMATION: Plac_16UTR, variant of E. coli lac operon
      promoter

<400> SEQUENCE: 81
```

```
tgtgagttag ctcactcatt aggcacccca ggctttacac tttatgcttc cggctcgtat    60
gttgtgtgga attgtgagcg ataacaatt tcaaggagga aacagct                  107
```

<210> SEQ ID NO 82
<211> LENGTH: 203
<212> TYPE: DNA
<213> ORGANISM: Artificial Sequence
<220> FEATURE:
<223> OTHER INFORMATION: PmglB_70UTR, variant of E. coli promoter for
      mglBAC galactose/methyl-galactosidade transporter

<400> SEQUENCE: 82

```
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa ggaggaaaca gct                                           203
```

<210> SEQ ID NO 83
<211> LENGTH: 203
<212> TYPE: DNA
<213> ORGANISM: Artificial Sequence
<220> FEATURE:
<223> OTHER INFORMATION: PmglB_70UTR_SD4, variant of E. coli promoter
      for mglBAC; galactose/methyl-galactosidade transporter

<400> SEQUENCE: 83

```
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa ctaggaaaca gct                                           203
```

<210> SEQ ID NO 84
<211> LENGTH: 76
<212> TYPE: DNA
<213> ORGANISM: Artificial Sequence
<220> FEATURE:
<223> OTHER INFORMATION: CP6 promotor sequence

<400> SEQUENCE: 84

```
catgtgggag tttattcttg acacagatat ttccggatga tataataact gagtactgtt    60
cacacaggaa acagct                                                    76
```

<210> SEQ ID NO 85
<211> LENGTH: 269
<212> TYPE: DNA
<213> ORGANISM: Escherichia coli
<220> FEATURE:
<221> NAME/KEY: misc_feature
<222> LOCATION: (1)..(269)
<223> OTHER INFORMATION: PosmY, promotor for osmY-ytjA; perplasmic
      chaperone

<400> SEQUENCE: 85

```
caaaattgtg atctatattt aacaaagtga tgacatttct gacggcgtta ataccgttc     60 aatgcgtaga tatcagtatc taaagccgtc gattgtcatt ctaccgatat taataactga   120
ttcagaggct gtaatggtcg ttattcatca ctcatcgctt ttgtgatggc gaccattgac   180
ttctgtagag ggtgaagtct ctccctattc agcaatgcaa cctcgtgttg ccaggctcaa   240
attacgagca aaccaaggag gaaacagct                                     269
```

<210> SEQ ID NO 86
<211> LENGTH: 483
<212> TYPE: PRT
<213> ORGANISM: Avibacterium gallinarum
<220> FEATURE:
<221> NAME/KEY: MISC_FEATURE
<222> LOCATION: (1)..(483)
<223> OTHER INFORMATION: SacC_AgaI, glycoside hydrolase family 32 protein, WP_103853210.1

<400> SEQUENCE: 86

Met Ile Ile Phe Asn Glu Gly Lys Tyr Lys Ser Leu Tyr Ala Ala Glu
1               5                   10                  15

Gln Gly Glu Leu Glu Lys Ile Ala Gln Thr Val Ala Gln Asp Gln Asp
            20                  25                  30

Phe Arg Pro Val Tyr His Leu Ala Pro Pro Thr Gly Leu Leu Asn Asp
        35                  40                  45

Pro Asn Gly Leu Ile Phe Asp Gly Lys Tyr His Leu Phe Tyr Gln
    50                  55                  60

Trp Tyr Pro Phe Asp Ala Leu His Gly Met Lys His Trp Gln His Phe
65                  70                  75                  80

Ile Thr Gln Asp Phe Lys Gln Phe Ser Gln Ala Asp Leu Leu Val Pro
                85                  90                  95

Cys Glu Leu Tyr Glu Ser His Gly Cys Tyr Ser Gly Ala Val Lys
            100                 105                 110

Ile Gly Asp Gln Ile Ala Val Phe Tyr Thr Gly Asn Thr Arg Arg Pro
        115                 120                 125

Ser Asp Asn Gln Arg Val Pro Tyr Gln Asn Leu Ala Ile Phe Ser Lys
130                 135                 140

Asp Gly Lys Leu Leu Ser Lys Arg Pro Leu Ile Glu Gln Ala Pro Gln
145                 150                 155                 160

Gly Tyr Thr Glu His Val Arg Asp Pro Lys Pro Phe Leu Thr Lys Asp
                165                 170                 175

Gly Lys Ile Arg Phe Ile Cys Gly Ala Gln Arg Glu Asn Leu Thr Gly
            180                 185                 190

Thr Ala Leu Val Phe Glu Met Asp Asn Leu Ala Asp Thr Pro Arg Leu
        195                 200                 205

Leu Gly Glu Leu Ala Leu Pro Ala Phe Asp Asn Gln Gly Val Phe Met
    210                 215                 220

Trp Glu Cys Pro Asp Leu Ser Gln Met Gly Asp Lys Ser Leu Phe Ile
225                 230                 235                 240

Trp Ser Pro Gln Gly Lys Ala Arg Glu Leu Glu Gln Tyr Gln Asn Asn
                245                 250                 255

Tyr His Ala Val Tyr Ala Leu Gly Glu Leu Ala Asp Arg Gln Phe His
            260                 265                 270

Ala Glu Gln Ile Ala Glu Leu Asp Gln Gly Phe Asp Phe Tyr Ala Pro
        275                 280                 285

Gln Thr Phe Ser Gly Thr Gln Thr Met Leu Leu Gly Trp Val Gly Leu
    290                 295                 300

Pro Asp Leu Ser Tyr Pro Thr Asp Leu Tyr Lys Trp His Ser Met Leu
305                 310                 315                 320

Ser Met Pro Arg Gln Leu Arg Leu Gln Asp Gly Lys Ile Tyr Gln Gln
                325                 330                 335

Pro Ile Glu Asn Ile Tyr Lys Asn Leu Thr Ala Leu Gly Ser Ile Thr
            340                 345                 350

```
Val Glu Lys Glu Ala Glu Ile Ala Asp Leu Asp Arg Ala Tyr Leu Lys
            355                 360                 365

Phe Asp Ala Asn Ala Gln Pro Phe Ser Leu Lys Phe Asn Asn Ala
370                 375                 380

Gln Asn Gln Arg Leu Ile Leu Ser Tyr Asp Gly Glu Met Leu Cys Leu
385                 390                 395                 400

Asp Arg Ser Gln Thr Glu Gln Thr Asp Ser Met Lys Ser Phe Gly Asp
            405                 410                 415

Lys Arg Tyr Cys Arg Ile Glu Asp Leu Arg Gln Val Glu Ile Phe Phe
                420                 425                 430

Asp Arg Ser Val Ala Glu Ile Phe Leu Asn Gln Gly Glu Lys Ala Met
            435                 440                 445

Thr Ser Arg Phe Phe Ile Cys Ala Arg Glu Asn Gln Leu Cys Thr Asp
            450                 455                 460

Lys Pro Leu Thr Leu Gln Val Gly Tyr Pro Lys Lys Ile Glu Val Asp
465                 470                 475                 480

Tyr Thr Lys

<210> SEQ ID NO 87
<211> LENGTH: 548
<212> TYPE: PRT
<213> ORGANISM: Arthrobacter globiformis
<220> FEATURE:
<221> NAME/KEY: MISC_FEATURE
<222> LOCATION: (1)..(548)
<223> OTHER INFORMATION: Bff, beta-fructofuranosidase protein,
      BAD18121.1

<400> SEQUENCE: 87

Met Glu Arg Thr Cys Ile Thr Val Arg Ala Ile Val Arg Phe His Ile
1               5                   10                  15

Glu Gln Arg Gln Thr Ile Val Asn Lys Gln Arg Thr Lys Arg Gly Ile
                20                  25                  30

Leu Thr Ala Ala Leu Ser Ile Gly Ala Leu Gly Ala Thr Leu Ile Ser
            35                  40                  45

Gly Pro Ala Val Ala Ala Thr Asp Ala Ala Pro Gly Phe Pro Gln Pro
50                  55                  60

Thr Glu His Thr Gln Lys Ala Tyr Ser Pro Thr Asp Asn Phe Thr Ser
65                  70                  75                  80

Arg Trp Thr Arg Ala Asp Ala Lys Gln Leu Lys Ala Met Ser Asp Pro
                85                  90                  95

Asp Ala Gly Ser Arg Glu Asn Ser Met Pro Thr Glu Tyr Thr Met Pro
            100                 105                 110

Thr Val Ser Gln Asp Phe Pro Asp Met Ser Asn Glu Lys Val Trp Val
        115                 120                 125

Trp Asp Thr Trp Pro Leu Ile Asp Glu Asn Ala Asn Gln Tyr Ser Val
130                 135                 140

Asn Gly Gln Glu Ile Ile Phe Ser Leu Val Ala Asp Arg Lys Leu Gly
145                 150                 155                 160

Phe Asp Glu Arg His Gln Tyr Ala Arg Ile Gly Tyr Phe Tyr Arg Pro
                165                 170                 175

Ala Gly Ile Pro Ala Asp Glu Arg Pro Glu Asp Gly Trp Thr Tyr
            180                 185                 190

Gly Gly Gln Val Phe Asp Glu Gly Val Thr Gly Lys Ile Phe Glu Asp
        195                 200                 205

Gln Ser Phe Thr His Gln Thr Gln Trp Ser Gly Ser Ala Arg Val Ser
```

```
            210                 215                 220
Lys Asn Gly Glu Ile Lys Leu Phe Phe Thr Asp Val Ala Phe Tyr Arg
225                 230                 235                 240

Asp Lys Asp Gly Gln Asp Val Lys Pro Tyr Asp Ser Arg Ile Ala Leu
                245                 250                 255

Ser Val Gly His Val His Ser Asn Lys Gly Val Lys Leu Thr Gly
                260                 265                 270

Phe Asn Lys Val Lys Glu Leu Leu Gln Ala Asp Gly Lys Asn Tyr Gln
                275                 280                 285

Asn Ala Ala Gln Asn Ser Tyr Tyr Asn Phe Arg Asp Pro Phe Thr Phe
290                 295                 300

Val Asp Pro Ala His Pro Gly Glu Thr Tyr Met Val Phe Glu Gly Asn
305                 310                 315                 320

Ser Ala Met Asp Arg Asp Glu Ala Lys Cys Thr Ala Glu Asp Leu Gly
                325                 330                 335

Tyr Arg Glu Gly Glu Thr Asn Gly Thr Val Glu Gln Val Asn Asn
                340                 345                 350

Ser Gly Ala Thr Tyr Gln Ile Gly Asn Val Gly Leu Ala Arg Ala Lys
                355                 360                 365

Asn Lys Ala Leu Thr Glu Trp Glu Phe Leu Pro Ile Leu Ser Ala
                370                 375                 380

Asn Cys Val Thr Asp Gln Thr Glu Arg Pro Gln Ile Tyr Met Gln Asp
385                 390                 395                 400

Gly Lys Tyr Tyr Leu Phe Thr Ile Ser His Arg Ser Thr Phe Ala Thr
                405                 410                 415

Gly Ile Asp Gly Pro Glu Gly Val Tyr Gly Phe Val Gly Asn Gly Ile
                420                 425                 430

Arg Ser Asp Tyr Gln Pro Leu Asn Arg Gly Ser Gly Leu Ala Leu Gly
                435                 440                 445

Ser Pro Thr Asn Leu Asn Phe Ala Ala Gly Thr Pro Phe Ala Pro Asp
                450                 455                 460

Tyr Asn Gln His Pro Gly Gln Phe Gln Ala Tyr Ser His Tyr Val Met
465                 470                 475                 480

Pro Gly Gly Leu Val Gln Ser Phe Ile Asp Thr Ile Gly Thr Lys Asp
                485                 490                 495

Asn Phe Val Arg Gly Thr Leu Gly Pro Thr Val Lys Leu Asn Ile
                500                 505                 510

Lys Gly Asp Ser Ala Thr Val Asp Tyr Asn Tyr Gly Asp Asn Gly Leu
                515                 520                 525

Gly Gly Trp Ala Asp Ile Pro Ala Asn Arg Glu Leu Lys Asn Ser Lys
530                 535                 540

Ala Val Ala Lys
545

<210> SEQ ID NO 88
<211> LENGTH: 505
<212> TYPE: PRT
<213> ORGANISM: Klebsiella pneumoniae
<220> FEATURE:
<221> NAME/KEY: MISC_FEATURE
<222> LOCATION: (1)..(505)
<223> OTHER INFORMATION: ScrY, sucrose porin, GeneBank ID CAA40657.1

<400> SEQUENCE: 88

Met Tyr Lys Lys Arg Lys Leu Ala Ile Leu Ile Ala Leu Leu Thr Gly
1               5                   10                  15
```

```
Thr Ala Ala Ala His Gly Gln Thr Asp Leu Asn Ser Ile Glu Ala Arg
            20                  25                  30

Leu Ala Ala Leu Glu Lys Arg Leu Gln Asp Ala Glu Thr Arg Ala Ser
        35                  40                  45

Thr Ala Glu Ser Arg Ala Ala Ser Ala Glu Gln Lys Val Gln Gln Leu
 50                  55                  60

Thr Gln Gln Gln Gln Thr Gln Ala Thr Thr Gln Gln Val Ala Arg
 65                  70                  75                  80

Arg Thr Thr Gln Leu Glu Glu Lys Ala Glu Arg Pro Gly Gly Phe Glu
                85                  90                  95

Phe His Gly Tyr Ala Arg Ser Gly Val Ile Met Asn Asp Ser Ala Ala
            100                 105                 110

Ser Thr Lys Ser Gly Ala Tyr Met Thr Pro Ala Gly Glu Thr Gly Gly
        115                 120                 125

Ala Ile Gly Arg Leu Gly Asn Gln Ala Asp Thr Tyr Val Glu Met Asn
130                 135                 140

Leu Glu His Lys Gln Thr Leu Asp Asn Gly Ala Thr Thr Arg Phe Lys
145                 150                 155                 160

Val Met Val Ala Asp Gly Gln Thr Thr Tyr Asn Asp Trp Thr Ala Ser
            165                 170                 175

Ser Ser Asp Leu Asn Val Arg Gln Ala Phe Val Glu Leu Gly Asn Leu
        180                 185                 190

Pro Thr Phe Glu Gly Pro Phe Lys Gly Ser Thr Leu Trp Ala Gly Lys
    195                 200                 205

Arg Phe Asp Arg Asp Asn Phe Asp Ile His Trp Ile Asp Ser Asp Val
210                 215                 220

Val Phe Leu Ala Gly Thr Gly Gly Ile Tyr Asp Val Lys Trp Asn
225                 230                 235                 240

Asp Ser Leu Arg Ser Asn Phe Ser Leu Tyr Gly Arg Asn Phe Gly Asp
            245                 250                 255

Ile Ala Asp Ser Ser Asn Ser Val Gln Asn Tyr Ile Val Ser Met Asn
        260                 265                 270

Asn Phe Ala Gly Pro Val Gln Met Met Val Ser Gly Met Arg Ala Lys
    275                 280                 285

Asp Asn Asp Asp Arg Gln Asp Ala Asn Gly Asn Leu Val Lys Gly Asp
290                 295                 300

Ala Ala Asn Thr Gly Val His Ala Leu Leu Gly Leu His Asn Glu Ser
305                 310                 315                 320

Phe Tyr Gly Leu Arg Asp Gly Thr Ser Lys Thr Ala Leu Leu Tyr Gly
            325                 330                 335

His Gly Leu Gly Ala Glu Val Lys Gly Ile Gly Ser Asp Gly Ala Leu
        340                 345                 350

Arg Pro Gly Ala Asn Thr Trp Arg Phe Ala Ser Tyr Gly Thr Thr Pro
    355                 360                 365

Leu Ser Asp Arg Trp Phe Ile Ala Pro Ala Val Leu Ala Gln Ser Ser
370                 375                 380

Lys Asp Arg Tyr Val Asp Gly Asp Ser Tyr Gln Trp Ala Thr Leu Asn
385                 390                 395                 400

Leu Arg Leu Ile Gln Glu Val Thr Gln Asn Phe Ala Leu Ala Trp Glu
            405                 410                 415

Gly Ser Tyr Gln Tyr Met Asp Leu Gln Pro Glu Gly Tyr Asn Asp Arg
        420                 425                 430
```

```
His Ala Val Asn Gly Ser Phe Tyr Lys Leu Thr Phe Ala Pro Thr Phe
                435                 440                 445

Lys Val Gly Ser Ile Gly Asp Phe Phe Ser Arg Pro Glu Ile Arg Phe
450                 455                 460

Tyr Thr Ser Trp Met Asp Trp Ser Lys Lys Leu Asp Asn Tyr Ala Asn
465                 470                 475                 480

Asp Asp Ala Leu Gly Ser Asn Gly Phe Lys Ser Gly Glu Trp Ser
                485                 490                 495

Phe Gly Met Gln Met Glu Thr Trp Phe
                500                 505

<210> SEQ ID NO 89
<211> LENGTH: 456
<212> TYPE: PRT
<213> ORGANISM: Klebsiella pneumoniae
<220> FEATURE:
<221> NAME/KEY: MISC_FEATURE
<222> LOCATION: (1)..(456)
<223> OTHER INFORMATION: ScrA, sucrose-specific enzyme II, GeneBank ID:
      CAA40658.1

<400> SEQUENCE: 89

Met Asp Phe Glu Gln Ile Ser Arg Ser Leu Leu Pro Leu Leu Gly Gly
1                   5                   10                  15

Lys Glu Asn Ile Ala Ser Ala Ala His Cys Ala Thr Arg Leu Arg Leu
                20                  25                  30

Val Leu Val Asp Asp Ala Leu Ala Asp Gln Gln Ala Ile Gly Lys Ile
            35                  40                  45

Asp Gly Val Lys Gly Cys Phe Arg Asn Ala Gly Gln Met Gln Ile Ile
    50                  55                  60

Phe Gly Thr Gly Val Val Asn Lys Val Tyr Ala Ala Phe Ile Gln Ala
65                  70                  75                  80

Ala Gly Ile Ser Glu Ser Ser Lys Ser Glu Ala Ala Asp Leu Ala Ala
                85                  90                  95

Lys Lys Leu Asn Pro Phe Gln Arg Ile Ala Arg Leu Leu Ser Asn Ile
                100                 105                 110

Phe Val Pro Ile Ile Pro Ala Ile Val Ala Ser Gly Leu Leu Met Gly
            115                 120                 125

Leu Leu Gly Met Val Lys Thr Tyr Gly Trp Val Asp Pro Ser Asn Ala
130                 135                 140

Leu Tyr Ile Met Leu Asp Met Cys Ser Ser Ala Ala Phe Ile Ile Leu
145                 150                 155                 160

Pro Ile Leu Ile Gly Phe Thr Ala Ala Arg Glu Phe Gly Gly Asn Pro
                165                 170                 175

Tyr Leu Gly Ala Thr Leu Gly Gly Ile Leu Thr His Pro Ala Leu Thr
            180                 185                 190

Asn Ala Trp Gly Val Ala Ala Gly Phe His Thr Met Asn Phe Phe Gly
    195                 200                 205

Ile Glu Val Ala Met Ile Gly Tyr Gln Gly Thr Val Phe Pro Val Leu
210                 215                 220

Leu Ala Val Trp Phe Met Ser Met Val Glu Lys Arg Leu Arg Arg Val
225                 230                 235                 240

Ile Pro Asp Ala Leu Asp Leu Ile Leu Thr Pro Phe Leu Thr Val Ile
                245                 250                 255

Ile Ser Gly Phe Ile Ala Leu Leu Leu Ile Gly Pro Ala Gly Arg Ala
            260                 265                 270
```

Leu Gly Asp Gly Ile Ser Phe Ile Leu Ser Thr Leu Ile Ser His Ala
            275                 280                 285

Gly Trp Leu Ala Gly Leu Leu Phe Gly Gly Leu Tyr Ser Val Ile Val
290                 295                 300

Ile Thr Gly Ile His His Ser Phe His Ala Ile Glu Ala Gly Leu Leu
305                 310                 315                 320

Gly Asn Pro Ser Ile Gly Val Asn Phe Leu Leu Pro Ile Trp Ala Met
                325                 330                 335

Ala Asn Val Ala Gln Gly Gly Ala Cys Phe Ala Val Trp Phe Lys Thr
            340                 345                 350

Lys Asp Ala Lys Ile Lys Ala Ile Thr Leu Pro Ser Ala Phe Ser Ala
        355                 360                 365

Met Leu Gly Ile Thr Glu Ala Ala Ile Phe Gly Ile Asn Leu Arg Phe
370                 375                 380

Val Lys Pro Phe Ile Ala Ala Leu Val Gly Gly Ala Ala Gly Gly Ala
385                 390                 395                 400

Trp Val Val Ser Met His Val Tyr Met Thr Ala Val Gly Leu Thr Ala
                405                 410                 415

Ile Pro Gly Met Ala Ile Val Gln Ala Ser Ser Leu Leu Asn Tyr Ile
            420                 425                 430

Ile Gly Met Ala Ile Ala Phe Ala Val Ala Phe Ala Leu Ser Leu Thr
        435                 440                 445

Leu Lys Tyr Lys Thr Asp Ala Glu
    450                 455

<210> SEQ ID NO 90
<211> LENGTH: 466
<212> TYPE: PRT
<213> ORGANISM: Salmonella enterica subsp. enterica serovar Typhimurium
<220> FEATURE:
<221> NAME/KEY: MISC_FEATURE
<222> LOCATION: (1)..(466)
<223> OTHER INFORMATION: ScrB, beta-fructofuranosidase, GeneBank ID:
      CAA47974.1

<400> SEQUENCE: 90

Met Ser Leu Pro Ser Arg Leu Pro Ala Ile Leu Gln Ala Val Met Gln
1                   5                   10                  15

Gly Gln Pro Arg Ala Leu Ala Asp Ser His Tyr Pro Arg Trp His His
                20                  25                  30

Ala Pro Val Thr Gly Leu Met Asn Asp Pro Asn Gly Phe Ile Glu Phe
            35                  40                  45

Ala Gly Arg Tyr His Leu Phe Tyr Gln Trp Asn Pro Leu Ala Cys Asp
        50                  55                  60

His Thr Phe Lys Cys Trp Ala His Trp Ser Ser Ile Asp Leu Leu His
65                  70                  75                  80

Trp Gln His Glu Pro Ile Ala Leu Met Pro Asp Glu Glu Tyr Asp Arg
                85                  90                  95

Asn Gly Cys Tyr Ser Gly Ser Ala Val Asp Asn Gly Thr Leu Thr
            100                 105                 110

Leu Cys Tyr Thr Gly Asn Val Lys Phe Ala Glu Gly Gly Arg Thr Ala
        115                 120                 125

Trp Gln Cys Leu Ala Thr Glu Asn Ala Asp Gly Thr Phe Arg Lys Ile
    130                 135                 140

Gly Pro Val Leu Pro Leu Pro Glu Gly Tyr Thr Gly His Val Arg Asp
145                 150                 155                 160

```
Pro Lys Val Trp Arg His Glu Asp Leu Trp Tyr Met Val Leu Gly Ala
            165                 170                 175

Gln Asp Arg Gln Lys Arg Gly Lys Val Leu Leu Phe Ser Ser Ala Asp
        180                 185                 190

Leu His Gln Trp Thr Ser Met Gly Glu Ile Ala Gly His Gly Ile Asn
            195                 200                 205

Gly Leu Asp Asp Val Gly Tyr Met Trp Glu Cys Pro Asp Leu Phe Pro
210                 215                 220

Leu Gly Asp Gln His Ile Leu Ile Cys Cys Pro Gln Gly Ile Ala Arg
225                 230                 235                 240

Glu Glu Glu Cys Tyr Leu Asn Thr Tyr Pro Ala Val Trp Met Ala Gly
                245                 250                 255

Glu Phe Asp Tyr Ala Ala Gly Ala Phe Arg His Gly Glu Leu His Glu
                260                 265                 270

Leu Asp Ala Gly Phe Glu Phe Tyr Ala Pro Gln Thr Met Leu Thr Ser
            275                 280                 285

Asp Gly Arg Arg Leu Leu Val Gly Trp Met Gly Val Pro Glu Gly Glu
        290                 295                 300

Glu Met Leu Gln Pro Thr Leu Asn Asn Gly Trp Ile His Gln Met Thr
305                 310                 315                 320

Cys Leu Arg Glu Leu Glu Phe Ile Asn Gly Gln Leu Tyr Gln Arg Pro
                325                 330                 335

Leu Arg Glu Leu Ser Ala Leu Arg Gly Glu Ala Asn Gly Trp Ser Gly
                340                 345                 350

Asn Ala Leu Pro Leu Ala Pro Met Glu Ile Asp Leu Gln Thr Arg Gly
            355                 360                 365

Gly Asp Met Leu Ser Leu Asp Phe Gly Gly Val Leu Thr Leu Glu Cys
370                 375                 380

Asp Ala Ser Gly Leu Arg Leu Ala Arg Arg Ser Leu Ala Ser Asp Glu
385                 390                 395                 400

Met His Tyr Arg Tyr Trp Arg Gly Asn Val Arg Ser Leu Arg Val Phe
                405                 410                 415

Ile Asp Gln Ser Ser Val Glu Ile Phe Ile Asn Gly Gly Glu Gly Val
            420                 425                 430

Met Ser Ser Arg Tyr Phe Pro Ala Cys Ser Gly Gln Leu Thr Phe Ser
        435                 440                 445

Gly Ile Thr Pro Asp Ala Phe Cys Tyr Trp Pro Leu Arg Thr Cys Met
450                 455                 460

Val Glu
465

<210> SEQ ID NO 91
<211> LENGTH: 334
<212> TYPE: PRT
<213> ORGANISM: Salmonella enterica subsp. enterica serovar Typhimurium
<220> FEATURE:
<221> NAME/KEY: MISC_FEATURE
<222> LOCATION: (1)..(334)
<223> OTHER INFORMATION: ScrR, sucrose repressor, GeneBank ID:
      CAA47975.1

<400> SEQUENCE: 91

Met Lys Thr Lys Arg Val Thr Ile Lys Asp Ile Ala Glu Gln Ala Gly
1               5                   10                  15

Val Ser Lys Ala Thr Ala Ser Leu Val Leu Asn Gly Arg Gly Lys Glu
            20                  25                  30
```

| | | | | | | | | | | | |
|---|---|---|---|---|---|---|---|---|---|---|---|
|Leu|Arg|Val|Ala|Gln|Glu|Thr|Arg|Glu|Arg|Val|Leu|Ser|Ile|Ala|Arg|
| |35| | | | |40| | | | |45| | | | |

Leu Arg Val Ala Gln Glu Thr Arg Glu Arg Val Leu Ser Ile Ala Arg
        35                  40                  45

Lys His His Tyr Gln Pro Ser Ile His Ala Arg Ser Leu Arg Asn Asn
 50                  55                  60

Arg Ser His Thr Ile Gly Leu Val Val Pro Glu Ile Thr Asn His Gly
 65                  70                  75                  80

Phe Ala Val Phe Ala His Glu Leu Glu Met Leu Cys Arg Glu Ala Gly
                85                  90                  95

Val Gln Leu Leu Ile Ser Cys Thr Asp Glu Asn Pro Gly Gln Glu Ser
            100                 105                 110

Val Val Val Asn Asn Met Ile Ala Arg Gln Val Asp Gly Met Ile Val
            115                 120                 125

Ala Ser Cys Met His Asn Asp Ala Asp Tyr Leu Lys Leu Ser Gln Gln
130                 135                 140

Leu Pro Val Val Leu Phe Asp Arg Cys Pro Asn Glu Ser Ala Leu Pro
145                 150                 155                 160

Leu Val Met Thr Asp Ser Ile Thr Pro Thr Ala Glu Leu Ile Ser Arg
                165                 170                 175

Ile Ala Pro Gln His Ser Asp Glu Phe Trp Phe Leu Gly Gly Gln Ala
            180                 185                 190

Arg Leu Ser Pro Ser Arg Asp Arg Leu Thr Gly Phe Thr Gln Gly Leu
            195                 200                 205

Ala Gln Ala Gly Ile Ala Leu Arg Pro Glu Trp Val Ile Asn Gly Asn
        210                 215                 220

Tyr His Pro Ser Ser Gly Tyr Glu Met Phe Ala Ala Leu Cys Ala Arg
225                 230                 235                 240

Leu Gly Arg Pro Pro Lys Ala Leu Phe Thr Ala Ala Cys Gly Leu Leu
                245                 250                 255

Glu Gly Val Leu Arg Tyr Met Ser Gln His His Leu Leu Asp Ser Asp
            260                 265                 270

Ile His Leu Thr Ser Phe Asp Asp His Tyr Leu Tyr Asp Ser Leu Ser
        275                 280                 285

Leu Arg Ile Asp Thr Val Gln Gln Asp Asn Arg Gln Leu Ala Trp His
    290                 295                 300

Cys Tyr Asp Leu Ile Ser Gln Leu Ile Glu Gly Asp Thr Pro Glu Thr
305                 310                 315                 320

Leu Gln Arg Tyr Leu Pro Ala Thr Leu Gln Phe Arg His Gln
                325                 330

<210> SEQ ID NO 92
<211> LENGTH: 730
<212> TYPE: DNA
<213> ORGANISM: Escherichia coli
<220> FEATURE:
<221> NAME/KEY: misc_feature
<222> LOCATION: (1)..(730)
<223> OTHER INFORMATION: glpR coding sequence

<400> SEQUENCE: 92
atgaaacaaa cacaacgtca caacggtatt atcgaactgg ttaaacagca gggttatgtc     60
agtaccgaag agctggtaga gcatttctcc gtcagcccgc agactattcg ccgcgacctc    120
aatgagctgg cggagcaaaa cctgatcctg gccatcatgg cggtgcggcg ctgccttcca    180
gttcggttaa cacgccgtgg cacgatcgca aggccaccca gaccgaagaa aaagagcgca    240
tcgcccgcaa agtggcggag caaatcccca atggctcgac gctgtttatc gatatcggca    300

```
ccacgccgga agcggtagcg cacgcactgc tcaatcacag caatttgcgc attgtcacca    360
acaatctcaa cgttgctaac acgttgatgg taaaagaaga ttttcgcatc attctcgccg    420
gtggcgaatt acgcagccgc gatggcggga tcattggcga agcgacgctc gattttatct    480
cccagttccg ccttgatttc ggcattctgg ggataagcgg catcgatagc gacggctcgc    540
tgctggagtt cgattaccac gaagttcgca ccaaacgcgc cattattgag aactcgcgcc    600
acgttatgct ggttgtcgat cactcgaaat ttggccgtaa cgcgatggtc aatatgggca    660
gcatcagcat ggtagatgcc gtctacaccg acgccccgcc gccagtaagc gtgatgcagg    720
tgctgacgga                                                           730

<210> SEQ ID NO 93
<211> LENGTH: 203
<212> TYPE: DNA
<213> ORGANISM: Artificial Sequence
<220> FEATURE:
<223> OTHER INFORMATION: PmglB_70UTR_SD8 promoter sequence

<400> SEQUENCE: 93
tgcgtcgcca ttctgtcgca acacgccaga atgcggcggc gatcactaac tcaacaaatc     60
aggcgatgta accgctttca atctgtgagt gatttcacag tatcttaaca atgtgatagc    120
tatgattgca ccgtgcctac aagcatcgtg gaggtccgtg actttcacgc atacaacaaa    180
cattaaccaa gagaaaaaca gct                                            203

<210> SEQ ID NO 94
<211> LENGTH: 203
<212> TYPE: DNA
<213> ORGANISM: Artificial Sequence
<220> FEATURE:
<223> OTHER INFORMATION: PmglB_70UTR_SD10 promoter sequence

<400> SEQUENCE: 94
tgcgtcgcca ttctgtcgca acacgccaga atgcggcggc gatcactaac tcaacaaatc     60
aggcgatgta accgctttca atctgtgagt gatttcacag tatcttaaca atgtgatagc    120
tatgattgca ccgtgcctac aagcatcgtg gaggtccgtg actttcacgc atacaacaaa    180
cattaaccaa ctgagaaaca gct                                            203

<210> SEQ ID NO 95
<211> LENGTH: 203
<212> TYPE: DNA
<213> ORGANISM: Artificial Sequence
<220> FEATURE:
<223> OTHER INFORMATION: PmglB-54UTR promoter sequence

<400> SEQUENCE: 95
tgcgtcgcca ttctgtcgca acacgccaga atgcggcggc gatcactaac tcaacaaatc     60
aggcgatgta accgctttca atctgtgagt gatttcacag tatcttaaca atgtgatagc    120
tatgattgca ccgtgcctac aagcatcgtg gaggtccgtg actttcacgc atacaacaaa    180
cattaacaaa aaccggagat acc                                            203

<210> SEQ ID NO 96
<211> LENGTH: 141
<212> TYPE: DNA
<213> ORGANISM: Artificial Sequence
<220> FEATURE:
<223> OTHER INFORMATION: Plac 70_UTR promoter sequence

<400> SEQUENCE: 96
```

```
tgtgagttag ctcactcatt aggcacccca ggctttacac tttatgcttc cggctcgtat    60
gttgtgtgga atgcctacaa gcatcgtgga ggtccgtgac tttcacgcat acaacaaaca   120
ttaaccaagg aggaaacagc t                                              141
```

<210> SEQ ID NO 97
<211> LENGTH: 203
<212> TYPE: DNA
<213> ORGANISM: Artificial Sequence
<220> FEATURE:
<223> OTHER INFORMATION: PmglB_70UTR_SD9 promoter sequence

<400> SEQUENCE: 97

```
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa aggaaaaaca gct                                           203
```

<210> SEQ ID NO 98
<211> LENGTH: 203
<212> TYPE: DNA
<213> ORGANISM: Artificial Sequence
<220> FEATURE:
<223> OTHER INFORMATION: PmglB_70UTR_SD5 promoter sequence

<400> SEQUENCE: 98

```
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa ccgagaaaca gct                                           203
```

<210> SEQ ID NO 99
<211> LENGTH: 203
<212> TYPE: DNA
<213> ORGANISM: Artificial Sequence
<220> FEATURE:
<223> OTHER INFORMATION: PmglB_70UTR_SD7 promoter sequence

<400> SEQUENCE: 99

```
tgcgtcgcca ttctgtcgca acacgccaga atgcggcggc gatcactaac tcaacaaatc    60
aggcgatgta accgctttca atctgtgagt gatttcacag tatcttaaca atgtgatagc   120
tatgattgca ccgtgcctac aagcatcgtg gaggtccgtg actttcacgc atacaacaaa   180
cattaaccaa gagcaaaaca gct                                           203
```

<210> SEQ ID NO 100
<211> LENGTH: 189
<212> TYPE: DNA
<213> ORGANISM: Artificial Sequence
<220> FEATURE:
<223> OTHER INFORMATION: PglpA_70UTR promoter sequence

<400> SEQUENCE: 100

```
gaaaacattc ataaattaaa tgtgaattgc cgcacacatt attaaataag atttacaaaa    60
tgttcaaaat gacgcatgaa atcacgtttc actttcgaat tatgagcgaa tatgcgcgat   120
gcctacaagc atcgtggagg tccgtgactt tcacgcatac aacaaacatt aaccaggag   180 gaaacagct                                                           189
```

<210> SEQ ID NO 101
<211> LENGTH: 239
<212> TYPE: DNA
<213> ORGANISM: Artificial Sequence
<220> FEATURE:
<223> OTHER INFORMATION: PglpT_70UTR promoter sequence

<400> SEQUENCE: 101

```
ccatttagcc atagtaaaaa catgaattgt ttgatttcgc gcatattcgc tcataattcg      60
aaagtgaaac gtgatttcat gcgtcatttt gaacattttg taaatcttat ttaataatgt     120
gtgcggcaat tcacatttaa tttatgaatg ttttcttaac atcgcggcat gcctacaagc     180
atcgtggagg tccgtgactt tcacgcatac aacaaacatt aaccaaggag gaaacagct     239
```

<210> SEQ ID NO 102
<211> LENGTH: 350
<212> TYPE: DNA
<213> ORGANISM: Artificial Sequence
<220> FEATURE:
<223> OTHER INFORMATION: PmglB_16UTR promoter sequence

<400> SEQUENCE: 102

```
tgcgtcgcca ttctgtcgca acacgccaga atgcggcggc gatcactaac tcaacaaatc      60
aggcgatgta accgctttca atctgtgagt gatttcacag tatcttaaca atgtgatagc     120
tatgattgca ccgttttaac gttgtaaccc gtatgtaaca gtgataatc acttttgccg     180 aggtaacagc gtcataacaa caattaaagc cgttttctgg agcgttaccg ggcatggaag     240
aacgaatttt aaaagtgag cttcggcgtt cagtaacact tcattaactc tactgccccg     300
ccgagcattt atctcaagca ctaccctgca taagcaagga ggaaacagct                350
```

<210> SEQ ID NO 103
<211> LENGTH: 189
<212> TYPE: DNA
<213> ORGANISM: Artificial Sequence
<220> FEATURE:
<223> OTHER INFORMATION: PglpA_16UTR promoter sequence

<400> SEQUENCE: 103

```
gaaaacattc ataaattaaa tgtgaattgc cgcacacatt attaaataag atttacaaaa      60
tgttcaaaat gacgcatgaa atcacgtttc actttcgaat tatgagcgaa tatgcgcgat     120
gcctacaagc atcgtggagg tccgtgactt tcacgcatac aacaaacatt aaccaaggag     180
gaaacagct                                                             189
```

ENHANCING FORMATION OF MILK OLIGOSACCHARIDES (HMOS) BY MODIFYING LACTOSE IMPORT IN THE CELL

CROSS-REFERENCE TO RELATED APPLICATIONS

This application is a national stage entry pursuant to 35 U.S.C. § 371 of International Application No. PCT/EP2022/063311, filed on May 17, 2022, which claims priority to Denmark Application No. PA202170249, filed on May 17, 2021, the entire contents of all of which are hereby incorporated by reference in their entirety.

SEQUENCE LISTING

This instant application contains a Sequence Listing which has been submitted in a ASCII text file via Patent Center and is hereby incorporated by reference in its entirety. Said text file, created on Nov. 15, 2023, is named 032991-8011 Sequence Listing.txt, and is 277,123 bytes in size.

FIELD

This invention relates to a method of producing one or more human milk oligosaccharides (HMOs), in particular LNT and/or LNnT, in a genetically engineered cell comprising an enhanced oligosaccharide transport capability. The genetically modified cell comprises a series of genetic modification that enables the production of one or more HMOs, and a series of genetic modification that enhances the transport of lactose and produced HMO(s).

BACKGROUND

Human milk oligosaccharides (HMO(s)) have become of great interest in the last decade, due to the discovery of their important functionality in human development. Besides their prebiotic properties, HMO(s) have been linked to additional positive effects, expanding their field of application. The health benefits of HMO(s) have enabled their approval for use in food, such as infant formulas and food, and for consumer health products.

To date, the structures of at least 115 HMO(s) have been determined, and considerably more are probably present in human milk.

Due to the limited availability of HMO(s), an effective commercial, i.e., large scale production, is highly desirable. The manufacturing of large-scale quantities, as well as qualities, required for food and medical applications, through chemical synthesis, has yet to be provided. Furthermore, chemical synthetic routes to HMO(s) involve several noxious chemicals, which impose a contamination risk to the final product.

To bypass the drawbacks associated with chemical synthesis of HMO(s), several enzymatic methods and fermentative approaches have been developed. Fermentation based processes have been developed for several HMO(s), such as 2'-fucosyllactose, 3-fucosyllactose, lacto-N-tetraose, lacto-N-neotetraose, 3'-sialyllactose and 6'-sialyllactose. Fermentation based processes typically utilize genetically engineered bacterial strains, such as recombinant *Escherichia coli* (*E. coli*), or yeast, such as *Saccharomyces cerevisiae* (*S. cerevisiae*).

Biosynthetic production of HMO(s) in engineered bacterial strains is a valuable, cost-efficient and large-scale applicable solution for HMO manufacturing. It relies on genetically engineered bacteria with modified metabolic engineering, such as modified sugar nucleotide synthesis pathway(s) and are constructed so as to express the glycosyltransferases needed for the synthesis of the desired oligosaccharides and often take advantage of the bacteria's pool of nucleotide sugars as HMO precursors.

Recent developments in biotechnological production of HMO(s) have made it possible to overcome certain inherent limitations of bacterial expression systems. For example, HMO-producing bacterial cells may be genetically engineered to increase the limited intracellular pool of nucleotide sugars in the bacteria (WO2012112777), to improve activity of enzymes involved in the HMO production (WO2016040531), or to facilitate the import of HMO precursors and secretion of synthesized HMO(s) into the extracellular media (WO2010142305, WO2017042382). Further, expression of genes of interest in recombinant cells may be regulated by using particular promoter sequences or other gene expression regulators, e.g., as recently described in WO2019123324.

One way to optimize the production of HMOs is to modify sugar transport, where especially the import of the HMO precursor lactose could have a favorable effect on the HMO production, due to its role as a starting point for HMO biosynthesis. This has been done by overexpression of the *E. coli*, lactose permease LacY, which represents one of the most intensively characterized solute transporters (Guan and Kaback, Annu Rev Biophys Biomol Struct. 2006; 35:67-91).

WO2014018596 suggests enhancing the production of 2'-FL, LDFT, LNFP-1 or LNDFH-1 through a modified lactose catabolism and overexpression of the *E. coli* lactose permease, LacY, wherein the expression of LacY is driven by a lac/q promoter, an inducible synthetic promoter with much higher levels of transcription than the wild-type promoter (Penumetcha, et al., BIOS, 81(1):7-15 (2010)). This enhances the intracellular pool of lactose and phosphornucleotides, leading to an enhanced HMO production.

WO2017042382 combines inactivating the endogenous beta-galactosidase gene and overexpressing or deleting a native or heterologous sugar efflux transporter and having a functional lactose permease protein, in order to produce one or more HMOs. Specific examples show that deletion of oligosaccharide exporters can increase LNT formation.

EP2927316 discloses 2'FL production from a host with a native LacY gene under control of the Ptet promoter and the YberC transporter expressed from a plasmid. It also discloses that overexpression of LacY in the presence of lactose can cause lactose-induced stress of the cell and therefore the cell has been genetically modified to be able to totally ferment an oligosaccharide of interest without the exogenous addition of lactose.

Herein, a method is for the first time disclosed for producing one or more HMOs, that comprises a combination of enhancing the expression of a lactose permease gene, such as an endogenous lactose permease gene, with the expression of a heterologous non-LacY sugar transporter, which surprisingly facilitates an optimized transportation equilibrium leading to an effectively enhanced production of one or more HMOs, while also reducing the amount of side product formation.

SUMMARY

The present disclosure relates to a genetically engineered cell and a method for producing one or more HMO(s) in particular LNT and/or LNnT, wherein the method comprises a suitably genetically engineered cell in which the lactose uptake system is upregulated in combination with an expression of a second sugar transporter, thus promoting the import/export of lactose and/or oligosaccharides in the genetically engineered cell to advance the HMO production. The identification of key steps in the cellular pathways that regulate the biosynthesis of HMOs has enabled the modification of said pathways to enhance the cellular production of HMOs by regulating the cellular equilibrium between metabolites and products. In particular, maintenance of the favourable lactose/HMO equilibrium has been achieved, wherein overexpression of the lactose permease, LacY, in combination with another sugar transporter from the MFS transporter family, enhances the level of overall LNT and/or LNnT produced by the cell, as well as the transport of particular HMOs into the fermentation media. In general, the invention promotes a more sustainable manufacturing process, wherein the conversion from carbon source to HMO product in fermentation is done at a higher overall yield.

In its broadest sense, the present disclosure thus relates to a method for producing one or more HMO(s), in particular LNT and/or LNnT, which comprises providing a genetically engineered cell, wherein the cell overexpresses one or more lactose permease(s), expresses a heterologous MFS transporter selected from the group consisting of Vag, Nec, Fred, Marc, YberC, Bad and a functional homologue of any one of Vag, Nec, Fred, Marc, YberC or Bad, having an amino acid sequence which is 80% identical to the amino acid sequence of any one of Vag, Nec, Fred, Marc, YberC or Bad, and wherein the cell further expresses one or more glycosyltransferases selected from the group consisting of β-1,3-GlcNAc-transferase, β-1,3-Gal-transferase and β-1,4-gal-transferase and optionally a sucrose utilisation system. The method comprises culturing said cell in a suitable medium containing lactose and harvesting the one or more HMO(s) produced.

In a preferred embodiment, the genetically engineered cell of the present invention overexpresses one or more native lactose permease(s).

The amino acid sequence of the one or more lactose permease(s) is selected from the group consisting of SEQ ID NOs 1, 2, 3, 4, 5, 6, 7, 8, 9, 10, 11, 12, 13, 14, 15, 16 [LacY variants] and an amino acid sequence which is at least 70% identical to any one of the SEQ ID NOs 1, 2, 3, 4, 5, 6, 7, 8, 9, 10, 11, 12, 13, 14, 15, 16 [LacY variants] and which is a functional homologue.

In a presently preferred embodiment, the one or more overexpressed lactose permease(s) is identical to SEQ ID NO: 1 [LacY K-12] or at least 70% identical to SEQ ID NO: 1 [LacY K-12]. The genetically engineered cell may comprise at least one nucleic acid sequence encoding a lactose permease, or it may comprise more than one nucleic acid sequence encoding one or more lactose permeases(s). The nucleic acid sequence encoding the lactose permease is preferably a native gene to the genetically engineered cell, it may be encoded by a recombinant nucleic acid sequence.

The heterologous MFS transporter protein is selected from the group of SEQ ID NOs: 62 [Vag], 63 [Fred], 64 [Marc], 65 [Bad], 66 [Nec], 67 [YberC], and a functional homologue of any one of SEQ ID NOs: 62 [Vag], 63 [Fred], 64 [Marc], 65 [Bad], 66 [Nec], 67 [YberC], having an amino acid sequence which is at least 70% identical to any one of SEQ ID NOs: 62 [Vag], 63 [Fred], 64 [Marc], 65 [Bad], 66 [Nec], 67 [YberC]. In one or more exemplary embodiment(s), the MFS transporter is Nec, YberC and/or Vag. The genetically engineered cell may comprise at least one nucleic acid sequence encoding one or more heterologous MFS transporter(s), according to the invention. It may comprise more than one nucleic acid sequence encoding one or more heterologous MFS transporter(s). The nucleic acid sequence encoding the heterologous MFS transporter(s) may be encoded by a synthetic or recombinant nucleic acid sequence.

The genetically engineered cell may comprise one nucleic acid sequence encoding one or more glycosyltransferase(s) selected from β-1,3-GlcNAc-transferase, β-1,3-Gal-transferase and β-1,4-gal-transferase according to the invention. It may comprise more than one nucleic acid sequence encoding one or more glycosyltransferase(s). The nucleic acid sequence encoding the one or more glycosyltransferase(s) may be encoded by a synthetic or recombinant nucleic acid sequence.

In one or more exemplary embodiment(s) of the present disclosure, the β-1,3-Gal-transferase or β-1,4-gal-transferase is selected from the group consisting of CvB3galT and GalTK, or GalT, respectively and a functional homologue of any one of CvB3galT, GalTK or GalT, having an amino acid sequence which is at least 70% identical to any one of SEQ ID NOs: 17 [CvB3galT], 18 [GalTK] and 19 [GalT].

In one or more further exemplary embodiment(s) of the present disclosure, the β-1,3-GlcNAc-transferase is selected from the group consisting of LgtA, PmnagT, HD0466 and a functional homologue of any one of LgtA, PmnagT or HD0466, having an amino acid sequence which is at least 70% identical to any one of SEQ ID NO: 20 [LgtA], 21 [PmnagT] or 22 [HD0466].

In one or more exemplary embodiment(s), the genetically engineered cell comprises one or more heterologous nucleic acid sequence encoding one or more heterologous polypeptide(s) which when expressed constitute a sucrose utilisation system that enables utilization of sucrose as sole carbon and energy source of said genetically engineered cell. In one or more preferred exemplary embodiment(s), the genetically engineered cell comprises expresses a PTS-dependent sucrose utilization system, further comprising the scrYA and scrBR operons. In another preferred embodiment, the genetically engineered cell expresses a polypeptide capable of hydrolysing sucrose into glucose and fructose, preferably a single polypeptide.

One way to enhance the HMO production is also to modify the biosynthesis of the activated sugar nucleotides, which are used in the biosynthesis of the HMOs. Thus, the genetically engineered cell may comprise at least one nucleic acid sequence encoding one or more heterologous polypeptides involved in the biosynthesis of activated sugars according to the present disclosure. In one or more exemplary embodiment(s) the genetically engineered cell expresses one or more polypeptides involved in the biosynthesis of activated sugar nucleotides, such as one or more polypeptide(s) selected from the group consisting of Pgm [SEQ ID NO: 43 or 44], GalU [SEQ ID NO: 45 or 46], GalE [SEQ ID NO: 47 or 48], GlmM [SEQ ID NO: 49 or 50], GlmU [SEQ ID NO: 51 or 52], GlmS [SEQ ID NO: 33 or 54], and a functional homologue thereof having an amino acid sequence which is at least 70% identical to any one of SEQ ID NOs: 43, 44, 45, 46, 47, 48, 49, 50, 51, 52, 53 or 54.

Genetic expression of proteins in the genetically engineered cell according to the invention is regulated by regulatory elements. Thus, any one or more nucleic acid sequence(s) according to the invention may be regulated by one or more regulatory element(s). In one or more exemplary embodiment(s) the regulatory element comprises one or more promoter sequence(s with a nucleic acid sequence as identified in Table 8, preferably a promoter sequence selected from the group consisting of SEQ ID NO: 70 (PgIpF) or SEQ ID NO: 68 (Plac) or SEQ ID NO: 69 (PgatY_70UTR), SEQ ID NO: 82 (PmgIB_UTR70) or SEQ ID NO: 100 (PglpA_70UTR) or SEQ ID NO: 101 (PglpT_70UTR) or cp6 (SEQ ID NO: 84) or Posmy (SEQ ID NO: 85) or variants of these.

In a presently exemplified embodiment, in the genetically engineered cell of the present invention, the one or more lactose permease(s) is regulated by the promoter sequence PgipF.

In another presently exemplified embodiment, in the genetically engineered cell of the present invention, the one or more heterologous MFS transporter(s) is regulated by the promoter sequence Plac and/or PgIpF.

Thus, in a presently preferred embodiment, in the genetically engineered cell of the present invention, the one or more lactose permease(s) is native and is regulated by the promoter sequence PgIpF and the one or more heterologous MFS transporter(s) is selected from the group consisting of Nec, YberC and/or Vag and is regulated by the promoter sequence Plac and/or PgIpF.

The regulatory element may further comprise an endogenous, heterologous, synthetic and/or optimized Shine-Dalgarno sequence.

The nucleic acid sequence(s) comprising the elements of the present disclosure, may be integrated into the genome of the genetically engineered cell. Alternatively, the one or more nucleic acid sequence(s) may be expressed from a plasmid, such as a one or more low, medium and/or high copy number plasmid(s).

In one or more exemplary embodiment(s), the genetically engineered cell is a bacterial or yeast cell, such as an *Escherichia coli* cell, such as preferably a strain derived from *Escherichia coli* K-12.

The invention also relates to the use of the method and/or the genetically engineered cell in the production and/or manufacturing of one or more HMOs, such as LNT and/or LNnT.

DETAILED DESCRIPTION

The present disclosure relates to a genetically engineered cell and a method for producing one or more HMO(s), wherein the lactose uptake system of the cell is upregulated in combination with an expression of a second sugar transporter, thus promoting the import/export of oligosaccharides in the genetically engineered cell to advance the HMO production of in particular LNT and LNnT.

In the present disclosure, the cellular production of LNT and/or LNnT is enhanced by regulating the cellular equilibrium between metabolites and products. In particular, maintenance of the favourable lactose/HMO equilibrium has been achieved, wherein overexpression of the lactose permease, LacY, in combination with another sugar transporter from the MFS transporter family, in particular selected from the group consisting of Vag, Nec, Fred, Marc, YberC and Bad, enhances the level of over-all HMO produced by the cell, as well as the level of HMO transported into the fermentation media, resulting in a higher overall yield of HMO(s) produced by the engineered cell, in particular LNT and/or LNnT.

Regulation of the biosynthesis of HMOs has enabled the modification of cellular pathways that may enhance the cellular production of HMOs by regulating the cellular equilibrium between metabolites and products. By the term "biosynthesis" is meant a synthesis of one or more HMOs which is conducted by and/or in a genetically engineered cell. The cellular equilibrium between metabolites and products is an essential feature to maintain cellular viability, where accumulation of either the metabolites, such as phosphates and/or product precursors e.g., lactose, can lead to cellular stress which reduces the efficiency of the HMO production. On the other hand, cellular accumulation of product, such as one or more HMOs, may also lead to cellular stress responses, which may also hamper the efficiency of the HMO production. Thus, engineering of the cellular pathways, tailoring each point of the biosynthesis of HMOs in combination with a tailored import/export system, so that cellular accumulation of metabolites and/or HMOs is reduced, while enhancing the export of the produced HMO(s), is highly advantageous in large scale production of HMOs.

In the present disclosure, the maintenance of a favourable cellular equilibrium between metabolites and products has been achieved through overexpression of the lactose permease, LacY, in combination with another sugar transporter, such as but not limited to the MFS transporters YberC, Nec or Vag, which enhances the overall level of produced LNT or LNnT and in some cases affects biomass formation, as described in examples 1-3.

In specific, the present disclosure relates to a genetically engineered cell, which overexpresses one or more lactose permease(s) in combination with a heterologous MFS transporter protein, selected from the group consisting of Vag, Nec, Fred, Marc, YberC, Bad and a functional homologue of any one of Vag, Nec, Fred, Marc, YberC or Bad, having an amino acid sequence which is 70% identical to the amino acid sequence of any one of Vag, Nec, Fred, Marc, YberC or Bad, and which further expresses one or more glycosyltransferase(s). In a preferred embodiment the genetically engineered cell expresses two or more glycosyltransferase(s), wherein the glycosyltransferases are a β-1,3-GlcNAc-transferase and a β-1,3-Gal-transferase, or a β-1,3-GlcNAc-transferase and a β-1,4-gal-transferase, or a β-1,3-GlcNAc-transferase and a β-1,3-Gal-transferase and a β-1,4-Gal-transferase.

In a preferred embodiment, the present disclosure relates to a genetically engineered cell, which overexpresses one or more native lactose permease(s) in combination with a heterologous MFS transporter protein, selected from the group consisting of Vag, Nec, Fred, Marc, YberC, Bad and a functional homologue of any one of Vag, Nec, Fred, Marc, YberC or Bad, having an amino acid sequence which is 70% identical to the amino acid sequence of any one of Vag, Nec, Fred, Marc, YberC or Bad, and which further expresses one or more glycosyltransferase(s). In a preferred embodiment the genetically engineered cell expresses two or more glycosyltransferase(s), wherein the glycosyltransferases are a β-1,3-GlcNAc-transferase and a β-1,3-Gal-transferase, or a β-1,3-GlcNAc-transferase and a β-1,4-gal-transferase, or a β-1,3-GlcNAc-transferase and a β-1,3-Gal-transferase and a β-1,4-Gal-transferase.

A Method for Producing One or More Human Milk Oligosaccharide(s)

The present disclosure provides to a method for producing one more human milk oligosaccharides (HMOs), in particular LNT and/or LNnT, that comprises a combination of enhancing the expression of a lactose permease gene with the expression of a heterologous non-LacY sugar transporter, which surprisingly facilitates an enhanced production of the one or more HMOs, while also reducing the amount of side product formation. Preferably, said lactose permease gene is endogenous to the host cell.

This is illustrated in e.g., example 1 and 2, wherein an additional copy of LacY is inserted into a strain that already expresses the heterologous transporter YberC or Nec or Vag and which enhances the production of the LNT in example 1, and LNnT and pLNnH in example 2, and which at the same time reduces the by-product formation, such as a reduction in LNT-II and pLNH2 production. It is also evident from example 3 that the HMO titer in fermentation reaches a higher level, upon overexpression of LacY, compared to the normal expression level of LacY. The lower by-product formation and the higher titer are features that are essential in a large-scale production setting, where a lower by-product formation may result in a simpler post-fermentation purification and where the higher titer may result in a higher production yield, thus reducing the HMO production cost.

Human milk oligosaccharide (HMO) In the context of the disclosure, the term "oligosaccharide" means a saccharide polymer containing a number of monosaccharide units. In some embodiments, preferred oligosaccharides are saccharide polymers consisting of three, four, five or six monosaccharide units, i.e., trisaccharides, tetrasaccharides, penta saccharides or hexasaccharides. Preferable oligosaccharides of the disclosure are human milk oligosaccharides (HMOs).

The term "human milk oligosaccharide" or "HMO" in the present context means a complex carbohydrate found in human breast milk. The HMOs have a core structure comprising a lactose unit at the reducing end that can be elongated by one or more beta-N-acetyl-lactosaminyl and/or one or more beta-lacto-N-biosyl units, and this core structure can be substituted by an alpha-L-fucopyranosyl and/or an alpha-N-acetyl-neuraminyl (sialyl) moiety.

In the context of the present disclosure, lactose is not regarded as an HMO species.

The non-acidic (or neutral) HMOs are devoid of a sialyl residue, and the acidic HMOs have at least one sialyl residue in their structure. The method of the present disclosure is particularly designed to enhance the production and over-all yield of both neutral and acidic HMOs.

The non-acidic (or neutral) HMOs can be fucosylated or non-fucosylated. Examples of such neutral non-fucosylated HMOs include lacto-N-triose II (LNT-II) lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-1), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-1), fucosyl-para-lacto-N-hexaose I (FpLNH-1), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), 3'-O-sialyllacto-N-tetraose a (LST a), fucosyl-LST a (FLST a), 6'-O-sialyllacto-N-tetraose b (LST b), fucosyl-LST b (FLST b), 6'-O-sialyllacto-N-neotetraose (LST c), fucosyl-LST c (FLST c), 3'-O-sialyllacto-N-neotetraose (LST d), fucosyl-LST d (FLST d), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

In one or more preferred embodiment(s), the one or more produced HMO is selected from the group consisting of LNT-II, pLNnH, LNT and LNnT, LNFP-I, LNFP-II, LNFP-III, LNFP-V, LNFP-VI, LNDFH-1, LNDFH-II, LNDFH-III, 2'-FL, DFL, 3-FL, LST-a, 3'-SL, 6'-SL, LST-b, LST-c, FSL, FLST-a, DSLNT, LNnH and LNH.

Preferably, the HMO produced by the herein disclosed method and/or genetically engineered cell is an HMO that comprises an LNT-II core, such as LNT and/or LNnT, pLNnH and/or LNFP-l.

Even more preferably, the produced HMO is LNT and/or LNnT.

In one or more exemplary embodiment(s) the produced HMO is LNT. In one or more further exemplary embodiment(s) the produced HMO is LNnT.

LNT, LNnT and LNFP-1 comprise an LNT-II core and may be synthesized in a suitably genetically engineered cell by selecting a series of glycosyltransferases, that have the capability of attaching specific saccharides, such as galactose (Gal) or N-Acetylglucosamine (GlcNAc) to a lactose backbone.

A Genetically Engineered Cell

A genetically engineered cell of the present disclosure is a host cell that has been genetically engineered so that it is for HMO production.

In particular, the present disclosure relates to a engineered cell, which overexpresses one or more lactose permease(s) in combination with a heterologous MFS transporter protein, selected from the group consisting of Vag, Nec, Fred, Marc, YberC, Bad and a functional homologue of any one of Vag, Nec, Fred, Marc, YberC or Bad, having an amino acid sequence which is 70% identical to the amino acid sequence of any one of Vag, Nec, Fred, Marc, YberC or Bad, and which further expresses one or more glycosyltransferase(s). The one or more lactose permease(s) can be native to the host cell.

A genetically engineered cell can in general contain one or more genes that are not present in the native (not genetically engineered) form of the cell. Techniques for introducing exogenous nucleic acid molecules/sequences and/or inserting exogenous nucleic acid molecules/sequences (recombinant, heterologous) into a cell's hereditary information for inserting, deleting or altering the nucleic acid sequence of a cell's genetic information are known to the skilled artisan.

A genetically engineered cell according to the present disclosure can contain one or more genes that are present in the native form of the cell, wherein said genes are modified and re-introduced into the microbial cell by artificial means.

The term "genetically engineered cell" also encompasses a cell that contains a nucleic acid molecule being endogenous to the cell that has been modified without removing the nucleic acid molecule from the cell. Such modifications include those obtained by gene replacement, site-specific mutations, and related techniques.

A genetically engineered cell of the invention can be provided using standard methods of the art e.g., those described in the manuals by Sambrook et al., Wilson & Walker, "Maniatis et al., and Ausubel et al.

The genetically engineered cell may be any cell useful for HMO production including mammalian cell lines. Preferably, the host cell is a unicellular microorganism of eucaryotic or prokaryotic origin.

Appropriate microbial cells that may function as a host cell include yeast cells, bacterial cells, archaebacterial cells, algae cells, and fungal cells.

In one or more exemplary embodiment(s), the genetically engineered cell is a prokaryotic cell. In one or more preferred exemplary embodiment(s), the genetically engineered cell is a bacterial cell.

The genetically engineered cell of the present disclosure may be eubacteria (gram-positive or gram-negative) or archaebacteria, as long as they allow genetic manipulation for insertion of a gene of interest and can be cultivated on a manufacturing scale. Preferably, the host cell has the property to allow cultivation to high cell densities.

In embodiments of the invention the genetically engineered cell is a bacterial or yeast cell. In one preferred embodiment, the genetically engineered cell is preferably a prokaryotic cell, such as a bacterial cell.

Non-limiting examples of bacterial cells that are suitable for use in the present disclosure are selected from recipient organisms that do not naturally contain any of the mentioned MFS transporters Vag, Nec, Fred, Marc, YberC and Bad. These include, but are not limited to, *E. coli* K-12 strains (such as EMG2, MG1655, W3110, W3350, C600, and DH5a), which is the strain background for the majority of genetic engineering work done in *E. coli*, ATCC 8739 (*E. coli* C), ATCC 11303 (*E. coli* B), BL21 (see New England Biolabs catalog, 2007-2008) and derivatives of these strains.

In a presently preferred embodiment, the genetically engineered cell of the invention is an *Escherichia coli* cell. In a particularly preferred embodiment, the genetically engineered cell of the invention is an *E. coli* cell derived from the *E. coli* K-12 strain or DE3 strain.

In one or more exemplary embodiments, the genetically engineered cell is selected from the group consisting of *E. coli, C. glutamicum, L. lactis, B. subtilis, S. lividans*, In one or more exemplary embodiments, the genetically engineered cell is selected from the group consisting of *B. subtilis*, and *E. coli*.

In one or more exemplary embodiments, the genetically engineered cell is selected from the group consisting of *E. coli, C. glutamicum, L. lactis, B. subtilis, S. lividans*.

In one or more exemplary embodiments, the genetically engineered cell is *B. subtilis*.

In one or more exemplary embodiments, the genetically engineered cell is *Corynebacterium glutamicum*.

In one or more exemplary embodiments, the genetically engineered cell is *E. coli*.

Non-limiting examples of fungal host cells that are suitable for recombinant industrial production of a HMO product could be yeast cells, such as Komagataella phaffii, *Kluyveromyces lactis, Yarrowia lipolytica, Pichia pastoris*, and *Saccharomyces cerevisiae* or filamentous fungi such as *Aspargillus* sp, *Fusarium* sp or *Thricoderma* sp, exemplary species are *A. niger, A. nidulans, A. oryzae, F. solani, F. graminearum* and *T. reesei*.

In one or more exemplary embodiments, the genetically engineered cell is selected from the group consisting of *Yarrowia lipolytica, Pichia pastoris*, and *Saccharomyces cerevisiae*.

In one or more exemplary embodiments, the genetically engineered cell is *S. cerevisiae* or *P. pastoris*.

In one or more exemplary embodiments, the genetically engineered cell is *Pichia pastoris*.

Expression in the Genetically Engineered Cell

In relation to the invention, the term "expression" may refer to expression of a gene or a nucleic acid sequence which results in the production of a protein, or it may relate to expression of a protein i.e., it may relate directly to the production of a protein. In specific, the term "expression" may refer to the expression of a lactose permease gene, which results in the expression of a lactose permease protein, or to the expression of a lactose permease protein, as well as to the expression of an MFS transporter protein gene or an MFS transporter protein, respectively.

The use of the term "enhanced expression" is in the present context used interchangeably with the term "overexpression" e.g., of a lactose permease protein, and refers to an elevated level of a protein being expressed compared to the normal level of protein expression of a native protein in said cell. Enhanced expression of a protein or gene can be achieved in multiple ways, and may comprise, modification of the gene copy number, controlling the expression of any copy of a gene at the transcriptional or the translational level, e.g. by substituting the native promoter with a strong promoter, deleting of regulatory elements that repress the expression of a gene, or introduction of an episomal element, such as a plasmid, that bears and expresses the coding sequence of the gene of interest.

Increasing the gene copy number and/or the expression of one or more genes encoding the enzymes and/or transporter proteins that are directly or indirectly involved in the HMO biosynthetic pathways may be advantageous, as described herein and exemplified in examples 1-3.

In one or more exemplary embodiment(s), expression is controlled by increasing the copy number of the gene or nucleic acid sequence encoding a protein of interest.

In one or more exemplary embodiment(s), expression is controlled by using a strong promoter sequence to enhance expression of the gene or nucleic acid sequence encoding a protein of interest.

Overexpressing One or More Lactose Permease(s)

The present disclosure relates to a genetically engineered cell, as well as to a method comprising said genetically engineered cell, which overexpresses one or more lactose permease(s).

In a preferred embodiment, the present disclosure relates to a genetically engineered cell, as well as to a method comprising said genetically engineered cell, which overexpresses one or more native lactose permease(s).

The overexpression of one or more lactose permease(s) according to the present disclosure results in an enhanced production of one or more HMO(s), in particular LNT and/or LNnT, while in some cases also in a reduction of the amount of side products in the production, as described in examples 1-3.

By "overexpression" is in the present context meant that the expression level of protein is higher than what is obtained naturally by the cell of the invention. Thus, introduction of, and expression of a heterologous gene is not considered "overexpression" in relation to the invention. Overexpression may be determined by transcriptional or translational analysis, of for instance, quantitative determination of mRNA levels or protein levels in any of the methods known to the person skilled in the art, such as but not limited to, quantitative PCR or mass spectrometry. In the present disclosure, overexpression is preferably determined by experimental observation of an effect which may be related to an enhanced expression of one or more lactose permease(s), such as the experimental data provided in examples 1-3 and FIGS. 1-5.

A Lactose Permease Gene

In one or more embodiment(s) of the present invention, a genetically engineered cell comprises one or more lactose permease genes which is/are overexpressed. A lactose permease gene can be a lacY gene.

The genetically engineered cell according to the invention may comprise least one, such as at least two, three, four, five, six, seven, eight, nine or ten nucleic acid sequence(s) encoding a lactose permease.

In one or more preferred exemplary embodiment(s) the genetically engineered cell comprises more than one nucleic acid sequence encoding one or more lactose permeases(s).

In one or more exemplary embodiment(s), the genetically engineered cell comprises one or more additional lactose permease(s), such as one or more heterologous lactose permease.

In one or more further exemplary embodiment(s) the one or more lactose permease(s) is/are encoded by a heterologous and/or recombinant nucleic acid sequence.

In one or more preferred exemplary embodiment(s) the nucleic acid sequence(s) encoding the one or more lactose permease(s) is a native gene to the genetically engineered cell.

Native Lactose Permease Gene

In one or more exemplified embodiments, a genetically engineered cell of the present disclosure comprises a lactose permease gene native to the host cell which is overexpressed.

A native lactose permease of the present disclosure is a gene which is found endogenously in the host cell of the invention. E.g., a native lactose permease gene can be selected from the lacY gene of E. coli K-12 MG1655 of SEQ ID NO: 2, encoding the lactose permease LacY of SEQ ID NO: 1, in an E. coli K-12 MG1655 derived strain. Thus, the lacY gene native to E. coli BL-21(DE3) overexpressed in an E. coli K-12 MG1655 derived strain would not be native to the E. coli K-12 MG1655 derived strain, given that the gene encoding the E. coli BL-21(DE3) LacY is non-identical to the gene encoding the E. coli K-12 MG1655 LacY.

LacY

In on embodiment, the one or more lactose permease(s) may be any one or more of the amino acid sequences selected from the group consisting of SEQ ID NOs 1, 2, 3, 4, 5, 6, 7, 8, 9, 10, 11, 12, 13, 14, 15, 16 [LacY variants] and functional homologues thereof, having an amino acid sequence which is at least 70% identical, such as at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9% identical, to any one of the SEQ ID NOs 1, 2, 3, 4, 5, 6, 7, 8, 9, 10, 11, 12, 13, 14, 15 or 16 [LacY variants].

In one or more preferred exemplary embodiment(s), the one or more lactose permease(s) is/are identical to SEQ ID NO: 1.

In one or more embodiment(s), the lactose permease is a native lactose permease.

MFS Transporter Protein

The genetically engineered cell of the present disclosure comprises at least one nucleic acid sequence encoding one or more heterologous MFS transporter protein(s). The genetically engineered cell of the present disclosure thus expresses a heterologous MFS transporter protein.

The transporters of the Major Facilitator Superfamily (MFS) facilitate the transport of molecules, such as but not limited to oligosaccharides, across the cellular membranes.

By the term "Major Facilitator Superfamily (MFS)" is meant a large and exceptionally diverse family of the secondary active transporter class, which members are responsible for transporting a range of different substrates, including sugars, drugs, hydrophobic molecules, peptides, organic ions, etc.

The term "MFS transporter" in the present context means a protein that facilitates transport of an oligosaccharide, preferably, an HMO, through or across the cell membrane, preferably of an HMO/oligosaccharide synthesized by the genetically engineered cell as described herein from the cell cytosol to the cell medium. Additionally, or alternatively, the MFS transporter may also facilitate efflux of molecules that are not considered HMO or oligosaccharides, such as lactose, glucose, cell metabolites and/or toxins. In a preferred embodiment the MFS transporter is capable of exposing LNT and/or LNnT from the cell cytosol to the cell medium.

In the context of the present invention the lactose permease is not considered to be a heterologous MFS transporter.

In example 1-3, it is shown how introduction of selected heterologous genes encoding sugar efflux transporter proteins in the genetic background of LacY expressing strains, or LacY overexpressing strains, can inverse the order of abundance of the HMO precursors and/or side products of the cellular HMO production and thus facilitate an improved production of the HMO(s) by the genetically modified cell.

In one or more exemplary embodiment(s), the MFS transporter is selected from the group consisting of Bad, Nec, YberC, Fred, Vag and Marc.

The genetically engineered cell of the present disclosure thus in one or more exemplary embodiment(s) expresses a heterologous MFS transporter protein selected from the group consisting of Vag, Nec, Fred, Marc, YberC, Bad and a functional homologue of any one of Vag, Nec, Fred, Marc, YberC or Bad having an amino acid sequence which is 70% identical to the amino acid sequence of any one of SEQ ID NOs: 62 [Vag], 63 [Fred], 64 [Marc], 65 [Bad], 66 [Nec] or 67 [YberC].

Bad

The MFS transporter protein identified herein as "Bad protein" or "Bad transporter" or "Bad", interchangeably, has the amino acid sequence of SEQ ID NO: 65; The amino acid sequence identified herein as SEQ ID NO: 65 is an amino acid sequence that has 100% identity with the amino acid sequence having the GenBank accession ID WP_017489914.1.

In one or more exemplary embodiment(s), the MFS transporter, expressed according to the present disclosure is Bad. The genetically engineered cell of the present disclosure thus in one or more exemplary embodiment(s) expresses a heterologous MFS transporter protein that is Bad.

In one or more embodiment(s) of the invention, the genetically engineered cell expresses the heterologous MFS transporter protein bad or a functional homologue thereof, having an amino acid sequence which is at least 80%, such as at least 90%, such as at least 95%, such as at least 99% identical to the amino acid sequence of bad [SEQ ID NO: 65].

In one or more embodiment(s) the expression of bad is regulated by a regulatory element comprising the Plac promoter element of SEQ ID NO: 68.

In one embodiment of the invention, the genetically engineered cell, which overexpresses one or more native lactose permease(s) in combination with the heterologous MFS transporter protein, Bad of SEQ ID NO: 65, or a functional homologue thereof, having an amino acid sequence which is 70% identical to the amino acid sequence of SEQ ID NO: 65, and which further expresses one or more glycosyltransferase(s).

Nec

The MFS transporter protein identified herein as "Nec protein" or "Nec transporter" or "Nec", interchangeably, has the amino acid sequence of SEQ ID NO: 66; The amino acid sequence identified herein as SEQ ID NO: 66 is an amino acid sequence that has 100% identity with the amino acid sequence having the GenBank accession ID WP_092672081.1.

In one or more exemplary embodiment(s), the MFS transporter, expressed according to the present disclosure is Nec. The genetically engineered cell of the present disclosure thus in one or more exemplary embodiment(s) expresses a heterologous MFS transporter protein that is Nec.

In one or more embodiment(s) of the invention, the genetically engineered cell expresses the heterologous MFS transporter protein Nec or a functional homologue thereof, having an amino acid sequence which is at least 80%, such as at least 90%, such as at least 95%, such as at least 99% identical to the amino acid sequence of Nec [SEQ ID NO: 66].

In one or more embodiment(s) the expression of Nec is regulated by a regulatory element comprising the Plac promoter element of SEQ ID NO: 68.

In one embodiment of the invention, the genetically engineered cell, which overexpresses one or more native lactose permease(s) in combination with the heterologous MFS transporter protein, nec of SEQ ID NO: 66, or a functional homologue thereof, having an amino acid sequence which is 70% identical to the amino acid sequence of SEQ ID NO: 66, and which further expresses one or more glycosyltransferase(s).

YberC

The MFS transporter protein identified herein as "YberC protein" or "YberC transporter" or "YberC", interchangeably, has the amino acid sequence of SEQ ID NO: 67; The amino acid sequence identified herein as SEQ ID NO: 67 is an amino acid sequence that has 100% identity with the amino acid sequence having the GenBank accession ID EEQ08298.1.

In one or more exemplary embodiment(s), the MFS transporter, expressed according to the present disclosure is YberC. The genetically engineered cell of the present disclosure thus in one or more exemplary embodiment(s) expresses a heterologous MFS transporter protein that is YberC.

In one or more embodiment(s) of the invention, the genetically engineered cell expresses the heterologous MFS transporter protein YberC or a functional homologue thereof, having an amino acid sequence which is at least 80%, such as at least 90%, such as at least 95%, such as at least 99% identical to the amino acid sequence of YberC [SEQ ID NO: 67].

In one or more embodiment(s) the expression of YberC is regulated by a regulatory element comprising the Plac promoter element of SEQ ID NO: 68.

In one embodiment of the invention, the genetically engineered cell, which overexpresses one or more native lactose permease(s) in combination with the heterologous MFS transporter protein, YberC of SEQ ID NO: 67, or a functional homologue thereof, having an amino acid sequence which is 70% identical to the amino acid sequence of SEQ ID NO: 67, and which further expresses one or more glycosyltransferase(s).

Fred

The MFS transporter protein identified herein as "Fred protein" or "Fred transporter" or "Fred", interchangeably, has the amino acid sequence of SEQ ID NO: 63; The amino acid sequence identified herein as SEQ ID NO: 63 is an amino acid sequence that has 100% identity with the amino acid sequence having the GenBank accession ID WP_087817556.1.

In one or more exemplary embodiment(s), the MFS transporter, expressed according to the present disclosure is Fred. The genetically engineered cell of the present disclosure thus in one or more exemplary embodiment(s) expresses a heterologous MFS transporter protein that is Fred.

In one or more embodiment(s) of the invention, the genetically engineered cell expresses the heterologous MFS transporter protein fred or a functional homologue thereof, having an amino acid sequence which is at least 80%, such as at least 90%, such as at least 95%, such as at least 99% identical to the amino acid sequence of fred [SEQ ID NO: 63].

In one or more embodiment(s) the expression of fred is regulated by a regulatory element comprising the Plac promoter element of SEQ ID NO: 68.

In one embodiment of the invention, the genetically engineered cell, which overexpresses one or more native lactose permease(s) in combination with the heterologous MFS transporter protein, Fred of SEQ ID NO: 63, or a functional homologue thereof, having an amino acid sequence which is 70% identical to the amino acid sequence of SEQ ID NO: 63, and which further expresses one or more glycosyltransferase(s).

Vag

The MFS transporter protein identified herein as "Vag protein" or "Vag transporter" or "Vag", interchangeably, has the amino acid sequence of SEQ ID NO: 62; The amino acid sequence identified herein as SEQ ID NO: 62 is an amino acid sequence that has 100% identity with the amino acid sequence having the GenBank accession ID WP_048785139.1.

In one or more exemplary embodiment(s), the MFS transporter, expressed according to the present disclosure is Vag. The genetically engineered cell of the present disclosure thus in one or more exemplary embodiment(s) expresses a heterologous MFS transporter protein that is Vag.

In one or more embodiment(s) of the invention, the genetically engineered cell expresses the heterologous MFS transporter protein vag or a functional homologue thereof, having an amino acid sequence which is at least 80%, such as at least 90%, such as at least 95%, such as at least 99% identical to the amino acid sequence of vag [SEQ ID NO: 62].

In one or more embodiment(s) the expression of vag is regulated by a regulatory element comprising the Plac promoter element of SEQ ID NO: 68.

In one embodiment of the invention, the genetically engineered cell, which overexpresses one or more native lactose permease(s) in combination with the heterologous MFS transporter protein, vag of SEQ ID NO: 62, or a functional homologue thereof, having an amino acid sequence which is 70% identical to the amino acid sequence of SEQ ID NO: 62, and which further expresses one or more glycosyltransferase(s).

Marc

The MFS transporter protein identified herein as "Marc protein" or "Marc transporter" or "Marc", interchangeably, has the amino acid sequence of SEQ ID NO: 64; The amino acid sequence identified herein as SEQ ID NO: 64 is an amino acid sequence that has 100% identity with the amino acid sequence having the GenBank accession WP_060448169.1.

In one or more exemplary embodiment(s), the MFS transporter, expressed according to the present disclosure is Marc. The genetically engineered cell of the present disclosure thus in one or more exemplary embodiment(s) expresses a heterologous MFS transporter protein that is Marc.

In one or more embodiment(s) of the invention, the genetically engineered cell expresses the heterologous MFS transporter protein marc or a functional homologue thereof, having an amino acid sequence which is at least 80%, such as at least 90%, such as at least 95%, such as at least 99% identical to the amino acid sequence of marc [SEQ ID NO: 64].

In one or more embodiment(s) the expression of marc is regulated by a regulatory element comprising the Plac promoter element of SEQ ID NO: 68.

In one embodiment of the invention, the genetically engineered cell, which overexpresses one or more native lactose permease(s) in combination with the heterologous MFS transporter protein, marc of SEQ ID NO: 64, or a functional homologue thereof, having an amino acid sequence which is 70% identical to the amino acid sequence of SEQ ID NO: 64, and which further expresses one or more glycosyltransferase(s).

The genetically engineered cell of the present disclosure thus in one or more exemplary embodiment(s) expresses a heterologous MFS transporter protein which is either Vag, Nec, Fred, Marc, YberC or Bad. In one or more further exemplary embodiment(s), the genetically engineered cell of the present disclosure expresses more than one heterologous MFS transporter protein selected from the group consisting of SEQ ID NOs: 62 [Vag], 63 [Fred], 64 [Marc], 65 [Bad], 66 [Nec], and 67 [YberC].

In one or more exemplary embodiment(s), the genetically engineered cell of the present disclosure expresses a functional homologue of Vag, Nec, Fred, Marc, YberC and/or Bad having an amino acid sequence which is at least 70%, 80%, 85%, 90%, 95% or at least 99% identical to any one of SEQ ID NOs: 62, 63, 64, 65, 66 or 67.

In a presently preferred embodiment, the MFS transporter expressed is Nec, Vag and/or YberC.

In an especially preferred embodiment, the MFS transporter expressed is YberC.

In an especially preferred embodiment, the MFS transporter expressed is Nec.

In an especially preferred embodiment, the MFS transporter expressed is Vag.

Heterologous Expression

In the present disclosure, the term heterologous means that a protein is experimentally put into a cell that does not normally make (i.e., express) that protein. Thus, heterologous refers to the fact that often the transferred protein was initially cloned from or derived from a different cell type or a different species from the recipient. The protein itself may not necessarily be transferred, but instead the 'correctly edited' genetic material coding for the protein (the complementary DNA or cDNA) can be added to the recipient cell. The genetic material that is transferred typically must be within a format that encourages the recipient cell to express the cDNA as a protein (i.e., it is put in an expression vector). Methods for transferring foreign genetic material into a recipient cell include transfection and transduction. The choice of recipient cell type is often based on an experimental need to examine the protein's function in detail, and the most prevalent recipients, known as heterologous expression systems, are chosen usually because they are easy to transfer DNA into or because they allow for a simpler assessment of the protein's function.

Glycosyltransferase

The genetically engineered cell of the present disclosure for use according to the present disclosure further expresses one or more glycosyltransferase(s). The nucleic acid sequence encoding the one or more expressed glycosyltransferase(s) may be integrated into the genome (by chromosomal integration) of the genetically engineered cell, or alternatively, it may be comprised in a plasmid and expressed as plasmid-borne, as described in the present disclosure.

If two or more glycosyltransferases are needed for the genetically engineered cell to be suitable of producing an HMO, e.g., LNT or LNnT, two or more heterologous nucleic acids encoding different enzymes with glycosyltransferase activity may be integrated into a nucleic acid construct or they may be provided as individual nucleic acid sequences, which may be integrated in the genome and/or expressed from a plasmid.

In one exemplary embodiment, a β-1,3-N-acetylglucosaminyltransferase (a first heterologous nucleic acid sequence encoding a first glycosyltransferase) is introduced into the host cell in combination with a β-1,3-galactosyltransferase (a second heterologous nucleic acid sequence encoding a second glycosyltransferase) for the production of LNT, where the first and second heterologous nucleic acid can independently from each other be integrated chromosomally or be expressed from a plasmid or they can be combined into a nucleic acid construct, optionally comprised in a nucleic acid construct also comprising the additional features of the present disclosure. Thus, in one or more exemplary embodiment(s), the genetically engineered cell of the invention comprises at least one nucleic acid sequence encoding one or more heterologous glycosyltransferase(s).

In another exemplary embodiment, a β-1,3-N-acetylglucosaminyltransferase (a first heterologous nucleic acid sequence encoding a first glycosyltransferase) is introduced into the host cell in combination with a β-1,4-Galactosyltransferase (a second heterologous nucleic acid sequence encoding a second glycosyltransferase) for the production of LNnT, where the first and second heterologous nucleic acid can independently from each other be integrated chromosomally or be expressed from a plasmid or they can be combined into a nucleic acid construct, optionally comprised in a nucleic acid construct also comprising the additional features of the present disclosure. Thus, in one or more exemplary embodiment(s), the genetically engineered cell of the invention comprises at least one nucleic acid sequence encoding one or more heterologous glycosyltransferase(s).

In one or more exemplary embodiment(s), both the first and second heterologous nucleic acid encoding one or more glycosyltransferase(s) is/are stably integrated into the chromosome of the genetically engineered cell; in another preferred embodiment, the first and second heterologous nucleic acid encoding one or more glycosyltransferases are integrated independently of the nucleic acid sequence encoding the native lactose permease and/or the MFS transporter, according to the invention. In one or more further exemplary embodiment(s), the first and second heterologous nucleic acids encoding one or more glycosyltransferases are integrated into a nucleic acid construct. In one or more further exemplary embodiment(s), at least one of the heterologous nucleic acid sequence(s) encoding the glycosyltransferase(s) are plasmid-borne.

A glycosyltransferase of the present disclosure is selected from the group of enzymes having the activity of an α-1,2-fucosyltransferase, α-1,3-fucosyltransferase, α-1,3/4-fucosyltransferase, α-1,4-fucosyltransferase α-2,3-sialyltransferase, α-2,6-sialyltransferase, β-1,3-N-acetylglucosaminyltransferase, β-1,6-N-acetylglucosaminyltransferase, β-1,3-galactosyltransferase and β-1,4-galactosyltransferase.

In a preferred embodiment the glycosyl transferase(s) are selected from the group consisting of β-1,3-GlcNAc-transferase, β-1,3-Gal-transferase and β-1,4-gal-transferase.

Table 1 shows some non-limiting embodiments of proteins having glycosyltransferase activity which can be encoded by the heterologous genes comprised in the production cell.

TABLE 1

| Gene | GenBank or NCBI Reference Sequence ID | Description | HMO example |
| --- | --- | --- | --- |
| lgtA_Nm | WP_002248149.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| lgtA_Nm_MC58 | AAF42258.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| lgtA_Hd | AAN05638.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| lgtA_Ng_PID2 | AAK70338.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| lgtA_Ng_NCCP 11945 | ACF31229.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| lgtA_Past | AAK02595.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| lgtA_Nc | EEZ72046.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| lgtA_Nm_87255 | ELK60643.1 | β-1,3-N-acetylglucosaminyl-transferase | LNT-II, LNT, LNnT, LNFP-I, LNFP-II, LNFP-III, LNFP-V, LNFP-VI, LNDFH-I, LNDFH-II, LNDFH-III, pLNH, F-pLNH I, pLNnH |
| galT_Hp/ HP0826 | NP_207619.1 | β-1,4-galactosyltransferase | LNnT, LNFP-III, LNFP-VI, pLNH I, F-pLNH I, pLNnH |
| galT_Nm/ lgtB | AAF42257.1 | β-1,4-galactosyltransferase | LNnT, LNFP-III, LNFP-VI, pLNH I, F-pLNH I, pLNnH |
| wbgO | WP_000582563.1 | β-1,3-galactosyltransferase | LNT, LNFP-I, LNFP-II, LNFP-V, LNDFH-I, LNDFH-II, pLNH, F-pLNH I |
| cpsIBJ | AB050723.1 | β-1,3-galactosyltransferase | LNT, LNFP-I, LNFP-II, LNFP-V, LNDFH-I, LNDFH-II, pLNH, F-pLNH I |
| jhp0563 | AEZ55696.1 | β-1,3-galactosyltransferase | LNT, LNFP-I, LNFP-II, LNFP-V, LNDFH-I, LNDFH-II, pLNH, F-pLNH I |
| galTK | SEQ ID NO: 18 | β-1,3-galactosyltransferase | LNT, LNFP-I, LNFP-II, LNFP-V, LNDFH-I, LNDFH-II, pLNH, F-pLNH I |
| futC | SEQ ID NO: 23 | α-1,2-fucosyl-transferase | 2'-FL, DFL, LNFP-I, LNDFH-I |
| FucT2_HpUA802 | AAC99764.1 | α-1,2-fucosyl-transferase | 2'-FL, DFL, LNFP-I, LNDFH-I |
| FucT2_EcO126t | ABE98421.1 | α-1,2-fucosyl-transferase | 2'-FL, DFL, LNFP-I, LNDFH-I |
| FucT2_Hm12198 | CBG40460.1 | α-1,2-fucosyl-transferase | 2'-FL, DFL, LNFP-I, LNDFH-I |

TABLE 1-continued

| Gene | GenBank or NCBI Reference Sequence ID | Description | HMO example |
|---|---|---|---|
| FucT2_Pm9515 | ABM71599.1 | α-1,2-fucosyltransferase | 2'-FL, DFL, LNFP-I, LNDFH-I |
| FucT2_HpF57 | BAJ59215.1 | α-1,2-fucosyltransferase | 2'-FL, DFL, LNFP-I, LNDFH-I |
| FucT6_3_Bf | CAH09151.1 | α-1,3-fucosyltransferase | 2'-FL, 3-FL, DFL, LNFP-I, LNFP-III, LNFP-V, LNFP-VI, LNDFH-II, F-pLNH I |
| FucT7_3_Bf | CAH09495.1 | α-1,3-fucosyltransferase | 2'-FL, 3-FL, DFL, LNFP-I, LNFP-III, LNFP-V, LNFP-VI, LNDFH-II, F-pLNH I |
| FucT_3_Am | ACD04596.1 | α-1,3-fucosyltransferase | 2'-FL, 3-FL, DFL, LNFP-I, LNFP-III, LNFP-V, LNFP-VI, LNDFH-II, F-pLNH I |
| MAMA_R764 | AGC02224.1 | α-1,3-fucosyltransferase | 2'-FL, 3-FL, DFL, LNFP-I, LNFP-III, LNFP-V, LNFP-VI, LNDFH-II, F-pLNH I |
| Mg791 | AEQ33441.1 | α-1,3-fucosyltransferase | 2'-FL, 3-FL, DFL, LNFP-I, LNFP-III, LNFP-V, LNFP-VI, LNDFH-II, F-pLNH I |
| Moumou_00703 | YP_007354660 | α-1,3-fucosyltransferase | 2'-FL, 3-FL, DFL, LNFP-I, LNFP-III, LNFP-V, LNFP-VI, LNDFH-II, F-pLNH I |
| futA | WP_000487428, SEQ ID NO: 26 | α-1,3-fucosyltransferase | 2'-FL, 3-FL, DFL, LNFP-I, LNFP-III, LNFP-V, LNFP-VI, LNDFH-II, LNDFH-III, F-pLNH I |
| fucT | AAB81031.1, SEQ ID NO: 27 | α-1,3-fucosyltransferase | 2'-FL, 3-FL, DFL, LNFP-I, LNFP-III, LNFP-V, LNFP-VI, LNDFH-II, LNDFH-III, F-pLNH I |
| fucTIII | AAR88243.1 | α-1,4-fucosyltransferase | LNDFH-I, LNDFH-II |
| fucTa | AF194963.1 | α-1,3/4-fucosyltransferase | LNFP-II, LNDFH-I, LNDFH-II |
| Pd2, 6ST | SEQ ID NO: 29 | α-2,6-sialyltransferase | 6'-SL |
| PspST6 | BAF92026.1 | α-2,6-sialyltransferase | 6'-SL |
| PiST6_145 | BAF91416.1 | α-2,6-sialyltransferase | 6'-SL |
| PiST6_119 | BAI49484.1 | α-2,6-sialyltransferase | 6'-SL |
| NST | SEQ ID NO: 30 | α-2,3-sialyltransferase | 3'-SL |
| Smob | WP_126455392.1, SEQ ID NO: 24 | α-1,2-fucosyltransferase | 2'-FL, LNFP-I |
| HD0466 | WP_010944479.1, SEQ ID NO: 22 | β-1,3-N-acetylglucosaminyltransferase | LNT-II, LNT, LNnT, LNFP-I, LNFP-II, LNFP-III, LNFP-V, LNFP-VI, LNDFH-I, LNDFH-II, pLNH, F-pLNH I, pLNnH |
| PmnagT | WP_014390683.1, SEQ ID NO: 21 | β-1,3-N-acetylglucosaminyltransferase | LNT-II, LNT, LNnT, LNFP-I, LNFP-II, LNFP-III, LNFP-V, LNFP-VI, LNDFH-I, LNDFH-II, pLNH, F-pLNH I, pLNnH |
| Cvb3galT | WP_080969100.1, SEQ ID NO: 17 | β-1,3-galactosyltransferase | LNT, LNFP-I, LNFP-II, LNFP-V, LNDFH-I, LNDFH-II, pLNH, F-PLNH I |
| Mtun | WP_031437198.1, SEQ ID NO: 25 | α-1,2-fucosyltransferase | 2'-FL, LNFP-I, LNDFH-I |

The above-mentioned enzymes enable the biosynthetic production of HMO core structures as well as fucosylated and/or sialylated HMO(s) and their glycosidic derivatives.

Production of neutral N-acetylglucosamine-containing HMOs in modified bacteria is known in the art (see e.g., Gebus C et al. (2012) Carbohydrate Research 363 83-90).

In one or more exemplary embodiment(s), the β-1,3-Gal-transferase(s) or β-1,4-gal-transferase(s) is/are selected from the group consisting of CvB3galT and GalTK, or GalT, respectively, and a functional homologue thereof, having an amino acid sequence which is at least 70% identical, such as at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9% identical, to any one of SEQ ID NOs: 17, 18 or 19.

In one or more preferred exemplary embodiment(s), the β-1,3-Gal-transferase is CvB3galT with the amino acid sequence of SEQ ID NO: 17.

In one or more preferred exemplary embodiment(s) the β-1,3-Gal-transferase is GalTK with the amino acid sequence of SEQ ID NO: 18.

In another presently preferred embodiment, the β-1,4-gal-transferase is GalT with the amino acid sequence of SEQ ID NO: 19.

In one or more further exemplary embodiment(s), the β-1,3-GlcNAc-transferase(s) is/are selected from the group consisting of LgtA, PmnagT, HD0466 and a functional homologue thereof having an amino acid sequence which is at least 70% identical, such as at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9% identical, to any one of SEQ ID NOs: 20, 21 or 22.

In one or more yet further exemplary embodiment(s), the β-1,3-GlcNAc-transferase is LgtA with the amino acid sequence of of SEQ ID NO: 20.

In another one or more further exemplary disclosure(s), the α-1,2-fucosyl-transferase(s) is/are selected from the group consisting of FutC, Smob, Mtun and a functional homologue thereof having an amino acid sequence which is at least 70% identical, such as at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9% identical, to any one of SEQ ID NOs: 23, 24 or 25.

In one or more further exemplary disclosure, the α-1,3-fucosyl-transferase(s) is/are selected from the group consisting of FutA, FucT, FucTIII and a functional homologue thereof having an amino acid sequence which is at least 70% identical, such as such as at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9% identical, to any one of SEQ ID NO: 26, 27 or 28.

In a one or more yet further exemplary disclosure (s), the α-2,3-sialyl-transferase(s) is/are Pd2 and/or Nst and/or a functional homologue thereof having an amino acid sequence which is at least 70% identical, such as at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9% identical to any one of SEQ ID NO: 29 or 30.

Sucrose Fermentation

In the production of one or more HMOs, the starting material can have a great influence on the produced product, in terms of quality, purity and amount of product. The utilization of glucose as a carbon and energy source can in some cases be problematic due to difficulties in the handling and sterilization of glucose, which often leads to glucose degradation, formation of derivates and caramelization. Thus, the ability to utilize another sugar, such as but not limited to sucrose, with simpler handling parameters, is highly advantageous in the production of one or more HMOs.

In large scale manufacturing, the cost price and purity of starting materials is of vast importance for the viability of the production. Therefore, the utilization of the more resilient sugar sucrose, which comprises a glucose and a fructose moiety, is largely beneficial in large scale manufacturing. However, many manufacturing and/or production strains are incapable of utilizing sucrose as a carbon source due to lack of an enzyme capable of hydrolysing the sucrose. This has in some cases been overcome by addition of sucrose and a sucrose hydrolysing enzyme, such as an invertase, to the fermentation media, thus allowing the hydrolysis of sucrose into glucose and fructose.

In one or more preferred exemplary embodiment(s), the genetically engineered cell expresses a sucrose utilization system. Such a system can be endogenous to the cell, but it may also be heterologous if the cell is not capable of utilizing sucrose.

In one or more preferred exemplary embodiment(s), the genetically engineered cell comprises one or more heterologous nucleic acid sequence encoding one or more heterologous polypeptide(s), which enables utilization of sucrose as sole carbon and energy source of said genetically engineered cell.

In one or more preferred exemplary embodiment(s), the genetically engineered cell expresses a polypeptide capable of hydrolysing sucrose into glucose and fructose. Preferably, polypeptide capable of hydrolysing sucrose into glucose and fructose is a single heterologous enzyme.

Accordingly, in one or more exemplary embodiment(s), the heterologous polypeptide capable of hydrolysing sucrose into fructose and glucose expressed by the genetically modified cell of the present disclosure is selected from the group consisting of SEQ ID NO: 86 [SacC_Agal, glycoside hydrolase family 32 protein, WP_103853210.1] and SEQ ID NO: 87 [Bff, beta-fructofuranosidase protein, BAD18121.1], and a functional homologue of any one of SEQ ID NOs: 86 or 87, having an amino acid sequence which is at least 70% identical, such as at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9% identical, to any one of SEQ ID NOs: 86 or 87.

Another approach is to express a heterologous sucrose utilization system, such as but not limited to expression of a PTS-dependent system or to express an invertase, enabling the cell to utilize sucrose as a carbon and energy source, which is described in examples 2 and 3 of the present disclosure.

A heterologous PTS-dependent sucrose utilization transport system containing a sucrose specific porin, a sucrose transport protein and a sucrose-6-phosphate hydrolase is e.g., described in WO2015197082. The oxidation of glucose-6-phosphate and fructose therein provides a biological energy source by the organism's own metabolic system. Also, glucose-6-phosphate and fructose serve as carbon source for producing sugar nucleotides in the cell's natural biosynthetic pathway. The so-produced sugar nucleotides are donors for glycosylating carbohydrate acceptors (e.g., lactose), internalized through a specific permease by the cell, and thereby manufacturing oligosaccharides of interest. The glycosylation is mediated by one or more glycosyl transferases which are directly produced by expressing heterologous genes. The organism lacks any enzyme degrading either the acceptor or the oligosaccharide product in the cell.

Thus, in one or more exemplary embodiment(s), the genetically engineered cell of the present disclosure comprises one or more heterologous nucleic acid sequence encoding one or more heterologous polypeptide(s) which enables utilization of sucrose as sole carbon and energy source of said genetically engineered cell. In one or more preferred exemplary embodiment(s), the genetically engineered cell comprises a PTS-dependent sucrose utilization system, further comprising the scrYA and scrBR operons.

Thus, in one or more exemplary embodiment(s), the genetically engineered cell according to the present disclosure comprises a PTS-dependent sucrose utilization transport system and/or a recombinant nucleic acid sequence encoding a heterologous polypeptide capable of hydrolysing sucrose into fructose and glucose.

In one or more exemplary embodiment(s), the polypeptide encoded by the scrYA operon are polypeptides with an amino acid sequence according to SEQ ID NOs: 88 and 89 [scrY and scrA] or a functional homologue of any one of SEQ ID NOs: 88 and 89 [scrY and scrA], having an amino acid sequence which is at least 80% identical, such as at least 90% identical such as at least 95% identical to any one of SEQ ID NO: 88 and 89 [scrY and scrA].

In one or more exemplary embodiment(s) the polypeptide encoded by the scrBR operon are polypeptides with an amino acid sequence according to SEQ ID NOs: 90 and 91 [scrB and scrR] or a functional homologue of any one of SEQ ID NOs: 90 and 91 [scrB and scrR], having an amino acid sequence which is at least 80% identical such as at least 90% identical such as at least 95% identical to any one of SEQ ID NOs: 90 and 91 [scrB and scrR].

Such cells as described above are capable of utilizing sucrose as carbon and energy source.

Further, the culturing step of the method(s) disclosed herein may comprise a two-step sucrose feeding, with a second feeding phase by continuously adding to the culture an amount of sucrose that is less than that added continuously in a first feeding phase, so as to slow the cell growth and increase the content of product produced in a high cell density culture.

The feeding rate of sucrose added continuously to the cell culture during the second feeding phase may be around 30-40% less than that of sucrose added continuously during the first feeding phase.

During both feeding phases, lactose can be added continuously, preferably with sucrose in the same feeding solution, or sequentially.

Optionally, the culturing further comprises a third feeding phase when considerable amount of unused acceptor remained after the second phase in the extracellular fraction.

Then the addition of sucrose is continued without adding the acceptor, preferably with around the same feeding rate set for the second feeding phase until consumption of the acceptor.

Sugar Nucleotide Synthesis

The biosynthesis of activated sugar nucleotides can influence the production of one or more HMOs in several ways, firstly an enhanced production of specific sugar nucleotides that act as substrates in the HMO synthesis may enhance the overall HMO production or reduce the side product formation, secondly a reduction in specific sugar nucleotides may reduce the amount of side products produced while maintaining the level of produced target HMO. Thus, in one or more exemplary embodiment(s) of the present disclosure, the genetically engineered cell comprises at least one nucleic acid sequence encoding one or more heterologous polypeptides involved in the biosynthesis of activated sugars.

The term "activated sugars" or "activated sugar nucleotide" or "sugar nucleotide" are used interchangeably, and in the present context relates to modified sugars that act as precursors in the HMO synthesis, such as nucleotide sugars (e.g., UDP-galactose). In general monosaccharides are activated through conjugation to a nucleotide or phosphorylation, to be utilized in the glycosyltransferase mediated reactions, synthesizing the HMOs. Thus, modification of the sugar nucleotide synthesis is highly advantageous in the production of one or more HMOs.

An activated sugar nucleotide generally has a phosphorylated glycosyl residue attached to a nucleoside. A specific glycosyl transferase enzyme accepts only a specific activated sugar nucleotide. Thus, preferably the following activated sugar nucleotides are involved in the glycosyl transfer: glucose-UDP-GlcNAc, UDP-galactose, UDP-glucose, UDP-N-acetylglucosamine, UDP-N-acetylgalactosamine (GlcNAc) and CMP-N-acetylneuraminic acid. The genetically modified cell according to the present disclosure can comprise one or more pathways to produce a nucleotide-activated sugar selected from the group consisting of glucose-UDP-GlcNAc, GDP-fucose, UDP-galactose, UDP-glucose, UDP-N-acetylglucosamine, UDP-N-acetylgalactosamine and CMP-N-acetylneuraminic acid (CMP-Neu5Ac). In table 7 below are non-limiting examples of glycosyl-doners and the HMO products they can be used to produce, the list may not be exhaustive.

TABLE 7 glycosyl-donor HMO product list

| Glycosyl-donor | HMO product |
|---|---|
| UDP-GlcNAc | LNT, LNnT, LNFP-I, LNFP-II, LNFP-III, LNFP-V, LNFP-VI, LNDFH-I, LNDFH-II, LNDFH-III, LNH, LNnH, pLNH, pLNnH, F-pLNH-I, F-pLNH-II, F-pLNH-I, F-pLNnH-II, FLSTa, FLSTb, FLSTc, FLSTd, LSTa, LSTb, LSTc, LSTd, DSLNT, SLNH, SLNH-II |
| UDP-Gal | LNT, LNnT, LNFP-I, LNFP-II, LNFP-III, LNFP-V, LNFP-VI, LNDFH-I, LNDFH-II, LNDFH-III, LNH, LNnH, pLNH, pLNnH, F-pLNH-I, F-pLNH-II, F-pLNH-I, F-pLNnH-II, FLSTa, FLSTb, FLSTc, FLSTd, LSTa, LSTb, LSTc, LSTd, DSLNT, SLNH-I, SLNH-II |
| GDP-fucose | 2'FL, 3FL, DFL, LNFP-I, LNFP-II, LNFP-III, LNFP-V, LNFP-VI, LNDFH-I, LNDFH-II, LNDFH-III, F-LNH, F-LNnH, F-pLNH-I, F-pLNH-II, F-pLNH-I, F-pLNnH-II, FSL, FLSTa, FLSTb, FLSTc, FLSTd |
| CMP-Neu5Ac | 3'SL, 6'SL, FSL, FLSTa, FLSTb, FLSTc, FLSTd, LSTa, LSTb, LSTc, LSTd, DSLNT, SLNH-I, SLNH-II |

The present disclosure one or more exemplary embodiment(s) relates to a genetically modified cell which has a modified sugar nucleotide synthesis. In particular, an increased synthesis of the sugar nucleotide synthesis of UDP-GlcNAc and/or UDP-Gal may be advantageous in the production of LNT and/or LNnT.

In one or more exemplary disclosures(s), the genetically engineered cell expresses one or more polypeptides involved in the biosynthesis of activated sugar nucleotides. The one or more polypeptide involved in the biosynthesis of activated sugar nucleotides can be selected from the group consisting of Gmd, WcaG, WcaH, Wcal, ManC, ManB, Pgm, GalU, GalE, GlmM, GlmU, GlmS, NeuA, NeuB, NeuC and a functional homologue thereof having an amino acid sequence which is at least 70% identical to any one of SEQ ID NOs: 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 and 45.

In one or more exemplary embodiment(s) of the present disclosure, the genetically engineered cell expresses one or more polypeptides involved in the biosynthesis of activated sugar nucleotides wherein the one or more polypeptide involved in the biosynthesis of activated sugar nucleotides is selected from the group consisting of Pgm [SEQ ID NO: 43 or 44], GalU [SEQ ID NO: 45 or 46], GalE [SEQ ID NO: 47 or 48], GlmM [SEQ ID NO: 49 or 50], GlmU [SEQ ID NO: 51 or 52], GlmS [SEQ ID NO: 33 or 54], and a functional homologue thereof having an amino acid sequence which is at least 70% identical to any one of SEQ ID NOs: 43, 44, 45, 46, 47, 48, 49, 50, 51, 52, 53, or 54.

Colanic Acid Gene Cluster

The colanic acid gene cluster of *Escherichia coli* K-12 is responsible for the production of the extracellular polysaccharide colanic acid, a major oligosaccharide of the bacterial cell wall.

Since the colanic acid gene cluster is typically introduced in the genetically engineered cells as described in the examples, in the form of PglpF-driven expression cassettes, the deletion of the glpR gene (which codes the DNA-binding transcriptional repressor GlpR) eliminates the GlpR-imposed repression of transcription from all PglpF promoters in the cell and in this manner enhances gene expression from all PglpF-based cassettes, including the colanic acid gene cluster.

In one or more exemplary disclosure(s), the colanic acid gene cluster may be expressed from its native genomic locus. The expression may be actively modulated. The expression can be modulated by swapping the native promoter with a promoter of interest, and/or increasing the copy number of the colanic acid genes coding said protein(s) by expressing the gene cluster from another genomic locus than the native, or episomally expressing the colanic acid gene cluster or specific genes thereof.

Thus, in one or more exemplary disclosure (s), the expression of the colanic acid gene cluster is modulated by swapping the native promoter with a promoter of interest, and/or increasing the copy number of the colanic acid genes coding said protein(s) by expressing the gene cluster from another genomic locus than the native, or episomally expressing the colanic acid gene cluster.

In relation to the present disclosure, the term "native genomic locus", in relation to the colanic acid gene cluster, relates to the original and natural position of the gene cluster in the genome of the genetically engineered cell.

Gmd

The gmd gene encodes the protein GDP-mannose-4,6-dehydratase, which catalyzes the conversion of GDP-D-mannose to GDP-4-dehydro-6-deoxy-D-mannose. The protein is involved in the reaction that synthesizes GDP-L-fucose from GDP-alpha-D-mannose. In one or more exemplary disclosure (s), the gmd gene is over-expressed.

wcaG

The wcaG gene, also known as fcI, encodes the protein GDP-L-fucose synthase (EC 1.1.1.271), which catalyses the two-step NADP-dependent conversion of GDP-4-dehydro-6-deoxy-D-mannose to GDP-fucose, involving an epimerase and a reductase reaction. In one or more exemplary disclosure (s), the wcaG gene is over-expressed.

wcaH

The wcaH gene encodes the protein GDP-mannose mannosyl hydrolase (EC 3.6.1.-), that hydrolyzes both GDP-mannose and GDP-glucose. In one or more exemplary disclosure (s), the wcaH gene is over-expressed.

wcaI

The wcaI gene encodes the colanic acid biosynthesis glycosyltransferase WcaI, and it catalyses the transfer of unmodified fucose to UPP-Glc (α-D-glucopyranosyl-di-phosphoundecaprenol-glucose). In one or more exemplary disclosure (s), the wcaI gene is over-expressed.

manB

The manB gene encodes the protein phosphomannomutase (EC 5.4.2.8), which is involved in the biosynthesis of GDP-mannose by catalysing conversion α-D-mannose-1-phosphate into D-mannose-6-phosphate. Thus, the expression level of manB regulates the formation of GDP-mannose. In one or more exemplary disclosure (s), the manB gene is over-expressed.

manC

The manC gene encodes the protein mannose-1-phosphate guanylyltransferase (EC 2.7.7.13), that is involved in the biosynthesis of GDP-mannose through synthesis of GDP-mannose from GTP and α-D-mannose-1-phosphate. In one or more exemplary disclosure (s), the manC gene is over-expressed.

Sialic Acid Catabolic Pathway

Furthermore, the genetically engineered cell may also comprise a sialic acid synthetic capability. For example, the cell comprises a sialic acid synthetic capability through provision of an exogenous UDP-GlcNAc 2-epimerase (e.g., neuC of *Campylobacter jejuni* (GenBank AAK91727.1) or equivalent (e.g., (GenBank CAR04561.1), a Neu5Ac synthase (e.g., neuB of *C. jejuni* (GenBank AAK91726.1) or equivalent, (e.g., *Flavobacterium limnosediminis* sialic acid synthase, NCBI reference sequence WP_023580510.1), and/or a CMP-Neu5Ac synthetase (e.g., neuA of *C. jejuni* (GenBank AAK91728.1) or equivalent, (e.g., *Vibrio brasiliensis* CMP-sialic acid synthase, NCBI reference sequence WP_006881452.1).

In one or more exemplary disclosure (s), the genetically engineered cell, contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway described herein is the *E. coli* pathway. In this pathway, sialic acid (Neu5Ac; N-acetylneuraminic acid) is degraded by the enzymes NanA (N-acetylneuraminic acid lyase) and NanK (N-acetylmannosamine kinase) and NanE (N-acetylmannosamine-6-phosphate epimerase), all encoded from the nanATEK-yhcH operon, and repressed by NanR (http://ecocyc.org/ECOLI). A deficient sialic acid catabolic pathway is rendered in the *E. coli* host by introducing a mutation in the endogenous nanA (N-acetylneuraminate lyase) (e.g., GenBank Accession Number D00067.1(GL216588)) and/or nanK (N-acetylmannosamine kinase) genes (e.g., GenBank reference (amino acid) BAE77265.1 (GL85676015)), and/or nanE (N-acetylmannosamine-6-phosphate epimerase, GeneID: 947745, incorporated herein by reference). Optionally, the nanT (N-acetylneuraminate transporter) gene is also inactivated or mutated. Other intermediates of sialic acid metabolism include: (ManNAc-6-P) N-acetylmannosamine-6-phosphate; (GlcNAc-6-P) N-acetylglucosamine-6-phosphate; (GlcN-6-P) Glucosamine-6-phosphate, and (Fruc-6-P) Fructose-6-phosphate.

In one or more preferred exemplary disclosure (s), nanA is mutated. In other preferred embodiment(s), nanA and nanK are mutated, while nanE remains functional. In another preferred embodiment, nanA and nanE are mutated, while nanK has not been mutated, inactivated or deleted. A mutation in the present context refers to one or more changes in the nucleic acid sequence coding the gene product of nanA, nanK, nanE, and/or nanT. For example, the mutation may be 1, 2, up to 5, up to 10, up to 25, up to 50 or up to 100 changes in the nucleic acid sequence. For example, the nanA, nanK, nanE, and/or nanT genes are mutated by a null mutation. Null mutations as described herein encompass amino acid substitutions, additions, deletions, or insertions, which either cause a loss of function of the enzyme (i.e., reduced or no activity) or loss of the enzyme (i.e., no gene product). By "deleted" is meant that the coding region is removed completely or in part such that no (functional) gene product is produced. By inactivated is meant that the coding sequence has been altered such that the resulting gene product is functionally inactive or encodes for a gene product with less than 100%, e.g., 90%, 80%, 70%, 60%, 50%, 40%, 30% or 20% of the activity of the native, naturally occurring, endogenous gene product. A "not mutated" gene or protein does not differ from a native, naturally occurring, or endogenous coding sequence by 1, 2, up to 5, up to 10, up to 20, up to 50, up to 100, up to 200 or up to 500 or more codons, or to the corresponding encoded amino acid sequence.

Repressors

In one or more exemplary embodiment(s), the genetically engineered cell disclosed herein comprises a non-functional or absent gene product that normally binds to a regulatory element and represses the expression of any of the proteins of the present disclosure regulated by said regulatory element.

The term a non-functional (or absent) gene product that normally binds to and represses the expression driven by the regulatory element in the present context relates to DNA binding sites upstream of the coding sequence of a gene of interest and specifically at the promoter region of said gene.

In one or more exemplary embodiments, the cell may have a non-functional (or absent) gene product(s) that would normally bind to and repress the expression of the lacY gene and/or any of the proteins having an amino acid sequence of SEQ ID NOs: 1, 2, 3, 4, 5, 6, 7, 8, 9, 10, 11, 12, 13, 14, 15 or 16, or regions upstream of the regulatory element for controlling the expression of the lacY gene and/or any of the proteins having an amino acid sequence of SEQ ID NOs: 1, 2, 3, 4, 5, 6, 7, 8, 9, 10, 11, 12, 13, 14, 15 or 16.

In one or more exemplary embodiments, said gene product is the DNA-binding transcriptional repressor GlpR.

GlpR

GlpR belongs to the DeoR family of transcriptional regulators and acts as the repressor of the glycerol-3-phosphate regulon, which is organized in different operons. This regulator is part of the glpEGR operon, yet it can also be constitutively expressed as an independent (glpR) transcription unit. In addition, the operons regulated are induced when *Escherichia coli* is grown in the presence of inducer, glycerol, or glycerol-3-phosphate (G3P), and the absence of glucose. In the absence of inducer, this repressor binds in tandem to inverted repeat sequences that consist of 20-nucleic acid-long DNA target sites.

The term "non-functional or absent" in relation to the glpR gene refers to the inactivation of the glpR gene by complete or partial deletion of the corresponding nucleic acid sequence from the bacterial genome (e.g. SEQ ID NO: 92 or variants thereof encoding glpR capable of downregulating glpF derived promoters). The glpR gene encodes the DNA-binding transcriptional repressor GlpR. In this way promoter sequences of the PglpF family are upregulated in the genetically engineered cell, due to deletion of the repressor gene that would otherwise downregulate the PglpF promoters.

In one or more exemplary embodiment(s), the glpR gene is deleted.

Activators

In one or more exemplary embodiment(s), the genetically engineered cell disclosed herein comprises an over-expressed gene product that enhances the expression of any of the genes and/or proteins of the present disclosure regulated by said regulatory element.

In one or more exemplary embodiments, the cell of the present disclosure may comprise an over-expressed gene product that enhances the expression of the gene(s) encoding the lactose permease LacY and/or any of the proteins having an amino acid sequence of SEQ ID NOs: 1-16.

In one or more exemplary embodiments, said gene product is the cAMP DNA-binding transcriptional dual regulator CRP.

CRP

CRP belongs to the CRP-FNR superfamily of transcription factors. CRP regulates the expression of several of the *E. coli* genes, many of which are involved in catabolism of secondary carbon sources. Upon activation by cyclic-AMP, (cAMP) CRP binds directly to specific promoter sequences, the binding recruits the RNA polymerase through direct interaction, which in turn activates the transcription of the nucleic acid sequence following the promoter sequence leading to expression of the gene of interest.

Thus, over-expression of CRP may lead to an enhanced expression of a gene/nucleic acid sequence of interest. Amongst other functions, CRP exerts its function on the PglpF promoters, where it contrary to the repressor GlpR, activates promoter sequences of the PglpF family. In this way, over-expression of CRP in the genetically engineered cell of the present disclosure, promotes expression of genes that are regulated by promoters of the PglpF family.

Thus, in one or more exemplary embodiments, the crp gene is over-expressed.

Genetic engineering of GlpR and/or CRP, as suggested in the present disclosure, in 2'-FL producing strains is beneficial for the overall production of 2'-FL by these strains.

Regulator Element

The genetically engineered cell according to present disclosure may comprise regulatory elements enabling the controlled overexpression of endogenous, heterologous and/or synthetic nucleic acid sequences.

The term "regulatory element", comprises promoter sequences, signal sequence, and/or arrays of transcription factor binding sites, which sequences affect transcription and/or translation of a nucleic acid sequence operably linked to the regulatory element.

Regulatory elements are found at transcriptional and post-transcriptional levels and further enable molecular networks at those levels. For example, at the post-transcriptional level, the biochemical signals controlling mRNA stability, translation and subcellular localization are processed by regulatory elements.

RNA binding proteins are another class of post-transcriptional regulatory elements and are further classified as sequence elements or structural elements. Specific sequence motifs that may serve as regulatory elements are also associated with mRNA modifications. A variety of DNA regulatory elements are involved in the regulation of gene expression and rely on the biochemical interactions involving DNA, the cellular proteins that make up chromatin, and transcription factors.

In general, the transcriptional and translational regulatory sequences include, but are not limited to, promoter sequences, ribosomal binding sites, transcriptional start and stop sequences, translational start and stop sequences, and enhancer or activator sequences.

Promoters and enhancers are the primary genomic regulatory components of gene expression. Promoters are DNA regions within 1-2 kilobases (kb) of a gene's transcription start site (TSS); they contain short regulatory elements (DNA motifs) necessary to assemble RNA polymerase transcriptional machinery. However, transcription is often minimal without the contribution of DNA regulatory elements located more distal to the TSS. Such regions, often termed enhancers, are position-independent DNA regulatory elements that interact with site-specific transcription factors to establish cell type identity and regulate gene expression. Enhancers may act independently of their sequence context and at distances of several to many hundreds of kb from their target genes through a process known as looping. As a consequence of these features, it is difficult to identify suitable enhancers and link them to their target genes on the basis of DNA sequence alone.

The promoter, together with other transcriptional and translational regulatory nucleic acid sequences (also termed "control sequences") is necessary to express a given gene or group of genes (an operon).

Identification of suitable promoter sequences that promotes expression of the specific gene of interest is a tedious task, which in many cases require laborious efforts. In relation to the present disclosure regulator elements may or may not be post-translational regulators or it may or may not be translational regulators.

In one or more exemplary embodiment(s) of the invention, the expression of any one or more nucleic acid sequence(s) and/or genes is/are regulated by one or more regulatory element(s).

In one or more exemplary embodiment(s), the regulatory element comprises one or more elements capable of enhancing the expression, i.e., overexpression of any one or more nucleic acid sequence(s) according to the present disclosure.

In that regard, the regulatory element may be endogenous or heterologous, and/or recombinant and/or synthetic nucleic acid sequences. In the present context, the term "heterologous regulatory element" is to be understood as a regulatory element that is not endogenous to the original, genetically engineered cell described herein. The heterologous regulatory element may also be a recombinant regulatory element, wherein two or more non-operably linked native regulatory element(s) are recombined into a heterologous and/or synthetic regulatory element. The heterologous regulatory element, may be introduced into the genetically engineered cell using methods known to the person skilled in the art.

The regulatory element may be a native regulatory element, such as e.g., the Plac promoter, promoting the expression of the lac operon native to E. coli.

Promoter Sequences

The present disclosure relates to a genetically engineered cell and/or a method comprising providing said genetically engineered cell, wherein the expression of any one or more of said nucleic acid sequence(s) is/are regulated by one or more regulatory element(s). Said regulatory element can comprise one or more promoter sequence(s).

The regulatory element or elements regulating the expression of the genes and/or nucleic acid sequence(s), may comprise one or more promoter sequence(s), wherein the promoter sequence, is operably linked to the nucleic acid sequence of the gene of interest in that sense regulating the expression of the nucleic acid sequence of the gene of interest.

In general, a promoter may comprise native, heterologous and/or synthetic nucleic acid sequences, and may be a recombinant nucleic acid sequence, recombining two or more nucleic acid sequences or same or different origin as described above, thereby generating a homologous, heterologous, or synthetic nucleic promoter sequence, and/or a homologous, heterologous, or synthetic nucleic regulatory element.

A wide selection of promoter sequences derived from the PglpF, PigpA, PlgpT, PgatY, PmgIB and Plac promoter systems are described in detail WO2019123324A1 and WO2020255054A1.

In one or more exemplary embodiment(s), the regulatory element of the genes and/or heterologous nucleic acid sequences of the genetically engineered cell comprises more than one native or heterologous promoter sequence.

In one or more exemplary embodiment(s), the regulatory element of the genes and/or heterologous nucleic acid sequences of the genetically engineered cell comprises two or more regulatory elements with identical promoter sequences.

In one or more exemplary embodiment(s), the regulatory element of the genes and/or heterologous nucleic acid sequences of the genetically engineered cell comprises two or more regulatory elements with non-identical promoter sequences.

The regulatory architectures i.e., gene-by-gene distributions of transcription-factor-binding sites and identities of the transcription factors that bind those sites can be used in multiple different growth conditions and there are more than 100 genes from across the E. coli genome, which act as regulatory elements. Thus, any promoter sequence enabling transcription and/or regulation of the level of transcription, of one or more heterologous or native nucleic acid sequences that encode one or more proteins as described herein may be suitable.

One way to increase the production of a product may be to regulate the production of the desired enzyme activity used to produce the product or precursor/substrate import, such as the glycosyltransferases or the MFS transporter or the lactose permease.

Increasing the promoter strength driving the expression of the desired enzyme may be one way of doing this. The strength of a promoter can be assed using a lacZ enzyme assay where β-galactosidase activity is assayed as described previously (see e.g. Miller J. H. Experiments in molecular genetics, Cold spring Harbor Laboratory Press, N Y, 1972). Briefly the cells are diluted in Z-buffer and permeabilized with sodium dodecyl sulfate (0.1%) and chloroform. The LacZ assay is performed at 30° C. Samples are preheated, the assay initiated by addition of 200 µl ortho-nitro-phenyl-β-galactosidase (4 mg/ml) and stopped by addition of 500 µl of 1 M $Na_2CO_3$ when the sample had turned slightly yellow. The release of ortho-nitrophenol is subsequently determined as the change in optical density at 420 nm. The specific activities are reported in Miller Units (MU) [A420/(min*ml*A600)]. A regulatory element with an activity above 10,000 MU is considered strong and a regulatory element with an activity below 3,000 MU is considered weak, what is in between has intermediate strength. An example of a strong regulatory element is the PglpF promoter with an activity of approximately 14.000 MU and an example of a weak promoter is Plac which when induced with IPTG has an activity of approximately 2300 MU.

Alternatively, if there is a need for balancing the expression level of one or more proteins to optimize the production it may be beneficial to use a promoter with the desired strength, e.g., middle or low strength. Table 8 below lists a series of wildtype and recombinant promoters according to their strength relative to the PglpF promoter.

TABLE 8

Promoter sequences according to strength

| Promoter name | % activity relative to PglpF* | Strength | Seq ID in appl. |
|---|---|---|---|
| PmglB_70UTR_SD8 | 291% | high | 93 |
| PmglB_70UTR_SD10 | 233-281% | high | 94 |
| PmglB_54UTR | 197% | high | 95 |
| Plac_70UTR | 182-220% | high | 96 |
| PmglB_70UTR_SD9 | 180-226% | high | 97 |
| PmglB_70UTR_SD4 | 153%-353% | high | 83 |
| PmglB_70UTR_SD5 | 146-152% | high | 98 |
| PglpF_SD4 | 140-161% | high | 75 |
| PmglB_70UTR_SD7 | 127-173% | high | 99 |
| PmglB_70UTR | 124-234% | high | 82 |
| PglpA_70UTR | 102-179% | high | 100 |
| PglpT_70UTR | 102-240% | high | 101 |
| pgatY_70UTR | 112% | high | 69 |
| PglpF | 100% | high | 70 |

TABLE 8-continued

Promoter sequences according to strength

| Promoter name | % activity relative to PglpF* | Strength | Seq ID in appl. |
|---|---|---|---|
| PglpF_SD10 | 88-96% | high | 72 |
| PglpF_SD5 | 82-91% | high | 76 |
| PglpF_SD8 | 81-82% | high | 79 |
| PmglB_16UTR | 78-171% | high | 102 |
| PglpF_SD9 | 73-93% | middle | 80 |
| PglpF_SD7 | 47-57% | middle | 78 |
| PglpF_SD6 | 46-47% | middle | 77 |
| PglpA_16UTR | 38-64% | middle | 103 |
| Plac | 15-28% | low | 68 |
| PglpF_SD3 | 9% | low | 74 |
| PglpF_SD1 | 5% | low | 71 |
| PglpF_SD2 | na |  | 73 |
| Plac_16UTR |  |  | 81 |
| Cp6 | na |  | 84 |
| PosmY | na |  | 85 | na = not accessed
*The promoter activity is assessed in the LacZ assay described below with the PglpF promoter run as positive reference in the same assay. To compare across assays the activity is calculated relative to the PglpF promoter, a range indicates results from multiple assays The promoter may be of heterologous origin, native to the genetically modified cell or it may be a recombinant promoter, combining heterologous and/or native elements.

In one or more exemplary embodiment(s), the regulatory element comprises a promoter sequence selected from the group consisting of PBAD, PxyI, Plac, PsacB, PxyIA, PrpR, PnitA, PT7, Ptac, PL, PR, PnisA, Pb, PgatY_70UTR, PglpF, PglpF_SDI, PglpF_SD10, PglpF_SD2, PglpF_SD3, PglpF_SD4, PglpF_SD5, PglpF_SD6, PglpF_SD7, PglpF_SD8, PglpF_SD9, Plac_16UTR, PmglB_70UTR, PmglB_70UTR_SD4, CP6, PosmY, Pspc, Pbla, Prrn1 and Prrn2.

In a currently preferred embodiment, the promoter sequence is selected from the group consisting of PgatY_70UTR, PglpF, PglpF_SD1, PglpF_SD10, PglpF_SD2, PglpF_SD3, PglpF_SD4, PglpF_SD5, PglpF_SD6, PglpF_SD7, PglpF_SD8, PglpF_SD9, Plac_16UTR, and Plac.

In one or more exemplary embodiments, the regulatory element is a promoter selected from the group consisting of PglpF (SEQ ID NO: 70), PglpT 70UTR (SEQ ID NO: 101), SEQ ID NO: 69 (PgatY_70UTR), Plac (SEQ ID NO: 68), Pmglf 70UTR (SEQ ID NO: 82), PglpA_70UTR (SEQ ID NO: 100), Cp6 (SEQ ID NO: 84), Posmy (SEQ ID NO: 85) or variants of these, and variants thereof. Specifically, the variants disclosed in table 8 are preferred.

In one or more exemplary embodiments, the regulatory element is a promoter with high or middle strength, such as a promoter sequence selected from the group consisting of PmglB_70UTR_SD8, PmglB_70UTR_SD10, PmglB_54UTR, Plac_70UTR, PmglB_70UTR_SD9, PmglB_70UTR_SD4, PmglB_70UTR_SD5, PglpF_SD4, PmglB_70UTR_SD7, PmglB_70UTR, PglpA_70UTR, PglpT_70UTR, pgatY_70UTR, PglpF, PglpF_SD10, PglpF_SD5, PglpF_SD8, PglpF_B28, PglpF_B29, PmglB_16UTR, PglpF_SD9, PglpF_SD7, PglpF_SD6 and PglpA_16UTR.

In one preferred embodiment the promoter is a strong promoter selected from the group consisting of PmglB_70UTR_SD8, PmglB_70UTR_SD10, PmglB_54UTR, Plac_70UTR, PmglB_70UTR_SD9, PmglB_70UTR_SD4, PmglB_70UTR_SD5, PglpF_SD4, PmglB_70UTR_SD7, PmglB_70UTR, PglpA_70UTR, PglpT_70UTR, pgatY_70UTR, PglpF, PglpF_SD10, PglpF_SD5, PglpF_SD8, and PmglB_16UTR. This may in particular be advantageous for the expression the heterologous glycosyltransferase and or MFS transporter.

In another embodiment the promoter is selected from the group consisting of promoters with middle strength, such as PglpF_SD9, PglpF_SD7, PglpF_SD6 and PglpA_16UTR, This may in particular be advantageous for the expression the heterologous MFS transporter, if there is a need to balance the expression towards the expression of the lactose permease.

In another embodiment the promoter is selected from the group consisting of promoters with low strength, such as Plac, PglpF_SD3 and PglpF_SD1. This may in particular be advantageous for the expression the heterologous MFS transporter, if there is a need to balance the expression towards the expression of the lactose permease.

In a currently preferred embodiment, the promoter sequence is PglpF as shown in SEQ ID NO: 70. In a preferred embodiment of the invention, a promoter element of middle or low strength, such as the Plac promoter (SEQ ID NO: 68) is comprised in the regulatory element regulating the heterologous MFS transporter and a promoter of high strength, such as the PglpF (SEQ ID NO: 70) is comprised in the regulatory element regulating LacY.

In a currently preferred embodiment, the Plac promoter element of SEQ ID NO: 68 is comprised in the regulatory element regulating YberC and PglpF as shown in SEQ ID NO: 70 is comprised in the regulatory element regulating LacY An example of another type of regulatory elements is a Shine-Dalgarno sequence, which is a ribosomal binding site in bacterial and archaeal messenger RNA, generally located around 8 bases upstream of the start codon AUG, which helps recruiting the ribosome to the mRNA and initiate protein synthesis. Thus, modification of the Shine-Dalgarno sequence upstream of the coding nucleic acid sequence may modify the expression level of the any one or more of the genes and/or nucleic acid sequences and/or polypeptides of the invention.

Accordingly, in one or more exemplary embodiment(s), the genetically engineered cell according to the present disclosure comprises one or more endogenous, heterologous, synthetic and/or optimized Shine-Dalgarno sequence(s).

Sequence Identity

The term "sequence identity of [a certain] %" in the context of two or more nucleic acid or amino acid sequences means that the two or more sequences have nucleic acids or amino acid residues in common in the given percent, when compared and aligned for maximum correspondence over a comparison window or designated sequences of nucleic acids or amino acids (i.e., the sequences have at least 90 percent (%) identity). Percent identity of nucleic acid or amino acid sequences can be measured using a BLAST 2.0 sequence comparison algorithm with default parameters, or by manual alignment and visual inspection (see e.g., http://www.ncbi.nlm.nih.gov/BLAST/). This definition also applies to the complement of a test sequence and to sequences that have deletions and/or additions, as well as those that have substitutions. An example of an algorithm that is suitable for determining percent identity, sequence similarity and for alignment is the BLAST 2.2.20+ algorithm, which is described in Altschul et al. *Nucl. Acids Res.* 25, 3389 (1997). BLAST 2.2.20+ is used to determine percent sequence identity for the nucleic acids and proteins of the disclosure. Software for performing BLAST analyses is publicly available through the National Center for Biotechnology Information (http://www.ncbi.nlm.nih.gov/). Examples of commonly used sequence alignment algorithms are
- CLUSTAL Omega (http://www.ebi.ac.uk/Tools/msa/clustaio/),
- EMBOSS Needle (http://www.ebi.ac.uk/Tools/psa/emboss_needle/),
- MAFFT (http://mafft.cbrc.jp/alkinment/server/), or
- MUSCLE (http://www.ebi.ac.uk/Tools/msa/muscle/).

For purposes of the present invention, the sequence identity between two amino acid sequences is preferably determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later (available at https://www.ebi.ac.uk/Tools/psa/emboss needle/). The parameters used are gap open penalty of 10, gap extension penalty of 0.5, and the EBLOSUM62 (EMBOSS version of 30 BLOSUM62) substitution matrix. The output of Needle labeled "longest identity" (obtained using the -nobrief option) is used as the percent identity and is calculated as follows: (Identical Residues×100)/(Length of Alignment−Total Number of Gaps in Alignment).

For purposes of the present invention, the sequence identity between two nucleotide sequences is preferably determined using the Needleman-Wunsch algorithm (Needleman and Wunsch, 1 970, supra) as implemented in the Needle program of the EMBOSS package (EMBOSS: The European Molecular Biology Open Software Suite, Rice et al., 2000, Trends Genet. 16: 276-277), 10 preferably version 5.0.0 or later. The parameters used are gap open penalty of 10, gap extension penalty of 0.5, and the DNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides× 100)/(Length of Alignment−Total Number of Gaps in Alignment).

Functional Homologues

A functional homologue of a protein/nucleotide as described herein is a protein/nucleotide with alterations in the genetic code, which retains its original functionality. A functional homologue may be obtained by mutagenesis. The functional homologue should have a remaining functionality of at least 50%, such as 60%, 70%, 80%, 90% or 100% compared to the functionality of the protein/nucleotide.

A functional homologue of any one of the disclosed amino acid sequences can also have a higher functionality. A functional homologue of any one of the herein disclosed polypeptides, should ideally be able to participate in the HMO production, in terms of HMO yield, purity, reduction in biomass formation, viability of the genetically engineered cell, robustness of the genetically engineered cell according to the disclosure, or reduction in consumables.

Integrated into the Genome

The nucleic acid sequence(s) expressed in the genetically engineered cell according to the present disclosure may be integrated into the genome of the genetically engineered cell.

Integration of the heterologous nucleic acid of interest, potentially comprised in a construct (expression cassette), into the genome can be achieved by conventional methods, e.g., by using linear cartridges that contain flanking sequences homologous to a specific site on the chromosome, as described for the attTn7-site (Waddell C. S. and Craig N. L., Genes Dev. (1988) February; 2(2):137-49); methods for genomic integration of nucleic acid sequences in which recombination is mediated by the Red recombinase function of the phage λ or the RecE/RecT recombinase function of the Rac prophage (Murphy, J Bacteriol. (1998); 180(8): 2063-7; Zhang et al., Nature Genetics (1998) 20: 123-128; Muyrers et al., EMBO Rep. (2000) 1(3): 239-243); methods based on Red/ET recombination (Wenzel et al., Chem Biol. (2005), 12(3):349-56; Vetcher et al., Appl Environ Microbiol. (2005); 71(4):1829-35); or positive clones, i.e., clones that carry the expression cassette, can be selected e.g., by means of a marker gene, or loss or gain of gene function.

Expression and/or overexpression of the native or heterologous genes may one or more exemplary embodiment(s) be obtained from episomal integration of said genes, i.e., the nucleic acid encoding the heterologous polypeptide may be inserted into a nucleic acid construct, which is then subsequently comprised in a plasmid or in another chromosomal independent expression vector, wherein the expression vector at some instances is capable of integrating into the chromosome, however not be required to do so in order to obtain expression of the heterologous nucleic acid encoding a heterologous polypeptide of the invention. Examples of episomes are for instance transposons and insertion sequences.

In the scope of the invention as disclosed, the term "genomically integrated" refers to the integration of one or more native or heterologous nucleic acid sequences into the chromosome or into an endogenous plasmid, thus being integrated into the genome of the genetically engineered cell of the invention.

Thus, in one or more exemplary preferred embodiment, the invention relates to a genetically engineered cell as described above, which comprises one or more heterologous nucleic acid sequence(s) encoding one or more episomal and/or genomically integrated copies of e.g., one or more lactose permease(s) and/or a heterologous MFS transporter gene and/or one or more glycosyltransferases as described above.

In one or more exemplary embodiment(s), the one or more native and/or heterologous nucleic acid sequence(s) encoding e.g., one or more lactose permease(s) and/or a heterologous MFS transporter and/or one or more glycosyltransferases according to the invention, is/are integrated into the genome of the genetically engineered cell in a stable manner.

In one or more further exemplary embodiment(s), the one or more native and/or heterologous nucleic acid sequence(s) encoding e.g., one or more lactose permease(s) and/or a heterologous MFS transporter and/or one or more glycosyltransferases according to the invention, is/are integrated into the genome of the genetically engineered cell in a transiently manner.

Expressed from a Plasmid

In one or more further exemplary embodiment(s), the one or more nucleic acid sequence(s) is/are expressed from a plasmid.

In the present disclosure, one or more nucleic acid sequences encoding e.g., one or more lactose permease(s) and/or a heterologous MFS transporter and/or one or more glycosyltransferases, according to the invention, can be introduced to the genetically engineered cell in a transient manner.

Thus, in one or more exemplary embodiment(s) one or more heterologous nucleic acid sequence(s) which e.g., encodes one or one or more lactose permease(s) and/or a heterologous MFS transporter gene and/or one or more glycosyltransferases is/are plasmid-borne, such as but not limited to a low, medium, or high copy number plasmid.

In the present disclosure, low/medium/high copy number plasmid relates to the number of plasmid copies per bacterial cell. In one or more exemplary embodiment(s) of the present disclosure, a low copy number plasmid is a plasmid wherein the cell comprises on average 1-20 copies of said plasmid, such as on average 1, 2, 3, 4, 5, 6, 7, 8, 9, 10, 11, 12, 13, 14, 15, 16, 17, 18, 19 or 20 copies per cell. Accordingly, in one or more exemplary embodiment(s) of the present disclosure, a medium copy number plasmid is a plasmid wherein the cell comprises on average 21-100 copies of said plasmid, such as on average 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 copies per cell.

Further, in one or more exemplary embodiment(s) of the present disclosure, a high copy number plasmid is a plasmid wherein the cell comprises at least on average 101 copies of said plasmid, such as on average at least 200, 300, 400, 500, 600, 700, 800, 900 or 1000 copies per cell.

Cell Culture Medium

In the present context, a growth medium or culture medium is a liquid or gel designed to support the growth of microorganisms, cells, or small plants. The medium comprises an appropriate source of energy and may comprise compounds which regulate the cell cycle. The culture medium may be semi-defined, i.e., containing complex media compounds (e.g., yeast extract, soy peptone, casamino acids, etc.), or it may be chemically defined, without any complex compounds. Exemplary suitable media are provided in the experimental examples.

In one or more exemplary embodiment(s), the culturing media is minimal media.

In one or more exemplary embodiment(s), the culturing media is supplemented with one or more energy and carbon sources selected form the group containing glycerol, sucrose, glucose, and fructose.

In one or more exemplary embodiment(s), the culturing media is supplemented with one or more energy and carbon sources selected form the group containing glycerol, sucrose, and glucose.

In one or more exemplary embodiment(s), the culturing media is supplemented with glycerol, sucrose and/or glucose.

In one or more exemplary embodiment(s), the culturing media is supplemented with glycerol and/or glucose.

In one or more exemplary embodiment(s), the culturing media is supplemented with sucrose and/or glucose.

In one or more exemplary embodiment(s), the culturing media is supplemented with glycerol and/or sucrose.

In one or more exemplary embodiment(s), the culturing media is supplemented only with sucrose.

In one or more exemplary embodiment(s), the culturing media contains sucrose as the sole carbon and energy source.

In one or more exemplary embodiment(s), the culturing media is supplemented with lactose as a suitable acceptor for the glycosyl transferases of the invention.

Culturing of Said Cell

The present disclosure relates to a method for producing HMO in a bio-synthetic process, comprising culturing a genetically engineered cell according to the present disclosure in a suitable media and harvesting the one or more HMO(s). Preferably the medium contains lactose.

According to the invention, the term "culturing" (or "cultivating" or "cultivation", also termed "fermentation") relates to the propagation of bacterial expression cells in a controlled bioreactor according to methods known in the industry.

According to said method the genetically engineered cell, preferably a bacterium, more preferably an $E.\ coli$, is a strain that is optimized for an industrially profitable transformation like HMO production. Such an optimization may comprise the steps described in the present disclosure.

To produce one or more HMO(s), the HMO-producing microorganism as described herein are cultivated according to the procedures known in the art and the produced HMO is harvested from the cultivation media and the biomass formed during the cultivation process. Thereafter, the HMO (s) are purified according to the procedures known in the art, e.g., such as described in WO2015188834, WO2017182965 or WO2017152918, and the purified HMO(s) are used as nutraceuticals, pharmaceuticals, or for any other purpose, e.g., for research.

During culturing of the genetically engineered cell, disclosed herein, the oligosaccharide-producing cell is fed with a carbon and energy source, such as but not limited to sucrose, that provides energy via glycolysis for growing, reproducing, and maintaining its structure. In addition, the energy and carbon source taken up by the cell provides or acts as precursors for the synthesis of the activated sugar nucleotide(s) necessary for the glycosylation process that takes place in the cell, as described above. Additionally, a lactose solution is added to the media.

As is demonstrated in example 1, lactose can be provided as a bolus injection of 20% lactose solution (0.1 ml) to a basal minimal medium supplemented with magnesium sulphate and thiamine. Alternatively, or in addition, lactose can be added continuously, preferably with sucrose in the same feeding solution, or sequentially.

Level of Lactose During Culturing

In one or more exemplary embodiment(s), the level of lactose in the culturing media is modulated.

In one or more exemplary embodiment(s), the level of lactose during the culturing of the genetically engineered cell is modulated from low to high. In the present context this results in the following lactose concentration ranges: high lactose process 30-80 g/L, low lactose process 0-15 g/L, such as 0.5-15 g/L.

In one or more exemplary embodiment(s), a high level of lactose level relates to 30-80 g/L, such as but not limited to 30-40 g/L, 30-50 g/L, 30-60 g/L, 30-70 g/L, 40-50 g/L, 40-60 g/L, 40-70 g/L, 40-80 g/L, 50-60 g/L, 50-70 g/L, 50-80 g/L, 60-70 g/L, 60-80 g/L, 35-50 g/L, 35-60 g/L, 35-70 g/L, 35-75 g/L, 35-80 g/L, 45-55 g/L, 45-75 g/L, 55-65 g/L, 55-75 g/L, 55-80 g/L, 65-75 g/L, or 65-80 g/L.

In one or more exemplary embodiment(s), a low level of lactose level relates to 0-15 g/L, such as but not limited to 0-5 g/L, 0-7.5 g/L, 0-10 g/L, 0-12.5 g/L, 0.5-5 g/L, 0.5-7.5 g/L, 0.5-10 g/L, 0.5-12.5, 0.5-15 g/L g/L, 2.5-5 g/L, 2.5-7.5 g/L, 2.5-10 g/L, 2.5-12.5 g/L, 2.5-15 g/L, 5-7.5 g/L, 5-10 g/L, 5-12.5 g/L, 5-15 g/L, 7.5-10 g/L, 7.5-12.5 g/L, 7.5-15 g/L, 10-12.5 g/L, 10-15 g/L, or 12.5-15 g/L.

The internalized HMO backbone precursor, such as lactose, participates in the glycosyltransferase induced glycosylation reaction, in which a glycosyl residue of an activated nucleotide donor produced by the cell is transferred so that the acceptor is glycosylated. Optionally, when more than one glycosyltransferase is/are expressed by the cell, additional glycosylation reactions can occur resulting in the formation of the target oligosaccharide and/or side-products.

The cell preferably lacks any enzyme activity which would degrade the oligosaccharide derivatives produced in the cell.

Harvesting

The term "harvesting" in the context in the invention relates to collecting the produced HMO(s) following the termination of fermentation. In different embodiment(s) it may include collecting the HMO(s) included in both the biomass (i.e., the genetically engineered cell) and cultivation media, i.e., before/without separation of the fermentation broth from the biomass. In other embodiment(s) the produced HMO(s) may be collected separately from the biomass and fermentation broth, i.e., after/following the separation of biomass from cultivation media (i.e., fermentation broth).

The separation of cells from the medium can be carried out with any of the methods well known to the skilled person in the art, such as any suitable type of centrifugation or filtration. The separation of cells from the medium can follow immediately after harvesting the fermentation broth or be carried out at a later stage after storing the fermentation broth at appropriate conditions. Recovery of the produced HMO(s) from the remaining biomass (or total fermentation) include extraction thereof from the biomass (the production cells).

It can be done by any suitable methods of the art, e.g., by sonication, boiling, homogenization, enzymatic lysis using lysozyme, or freezing and grinding.

After recovery from fermentation, HMO(s) are available for further processing and purification.

Use of the Method or the Genetically Engineered Cell for the Production and/or Manufacturing The disclosure also relates to any commercial use of the method, or the genetically engineered cell described herein.

Thus, in one or more exemplary disclosures(s), the method or genetically engineered cell according to the invention is used in the manufacturing of one or more HMOs. The one or more HMOs can be selected from the group consisting of LNT-II, pLNnH, LNT, LNnT, LNFP-I, LNFP-II, LNFP-III, LNFP-V, LNFP-VI, LNDFH-I, LNDFH-II, LNDFH-III, 2'-FL, DFL, 3-FL, LST-a, 3'-SL, 6'-SL, LST-b, LST-c, FSL, FLST-a, DSLNT, LNnH and LNH. In a presently preferred embodiment, the one or more HMOs has an LNT-II core such as one or more HMO(s) is selected from the group consisting of LNT, LNnT and LNFP-1.

In one or more exemplary embodiment(s), the method and/or the genetically engineered cell is used in the manufacturing of more than one HMO(s), wherein the one or more HMOs is/are selected from the group consisting of LNT, LNnT and LNFP-1.

In one or more further exemplary embodiment(s), the method and/or the genetically engineered cell according to the present disclosure, is used in the manufacturing of more than one HMO(s), wherein the HMOs are LNT and/or LNnT.

Manufacturing of HMOs

To produce one or more HMOs, the genetically engineered cells as described herein are cultivated according to the procedures known in the art in the presence of a suitable carbon and energy source, e.g., glucose, glycerol or sucrose, and a suitable acceptor, e.g., lactose or any HMO, and the produced HMO blend is harvested from the cultivation media and the microbial biomass formed during the cultivation process. Thereafter, the HMOs are purified according to the procedures known in the art, e.g., such as described in WO2016095924, WO2015188834, WO2017152918, WO2017182965, US20190119314, and the purified HMOs are used as nutraceuticals, pharmaceuticals, or for any other purpose, e.g., for research.

Manufacturing of HMOs is typically accomplished by performing cultivation in larger volumes. The term "manufacturing" and "manufacturing scale" in the meaning of the invention defines a fermentation with a minimum volume of 5 L culture broth. Usually, a "manufacturing scale" process is defined by being capable of processing large volumes of a preparation containing the product of interest and yielding amounts of the HMO product of interest that meet, e.g., in the case of a therapeutic compound or composition, the demands for clinical trials as well as for market supply. In addition to the large volume, a manufacturing scale method, as opposed to simple lab scale methods like shake flask cultivation, is characterized by the use of the technical system of a bioreactor (fermenter) which is equipped with devices for agitation, aeration, nutrient feeding, monitoring and control of process parameters (pH, temperature, dissolved oxygen tension, back pressure, etc.). To a large extent, the behavior of an expression system in a lab scale method, such as shake flasks, benchtop bioreactors or the deep well format described in the examples of the disclosure, does allow to predict the behavior of that system in the complex environment of a bioreactor.

Manufactured Product

The term "manufactured product" according to the use of the genetically engineered cell or the nucleic acid construct refer to the one or more HMOs indented as the one or more product HMO. The various products are described above.

Advantageously, the methods disclosed herein provides both a decreased ratio of by-product to product and an increased overall yield of the product (and/or HMOs in total). This, less by-product formation in relation to product formation facilitates an elevated product production and increases efficiency of both the production and product recovery process, providing superior manufacturing procedure of HMOs.

The manufactured product may be a powder, a composition, a suspension, or a gel comprising one or more HMOs.

General

The terms Lacto-N-triose, LNT-II, LNT II, LNT2 and LNT 2, are used interchangeably.

Figure 1:
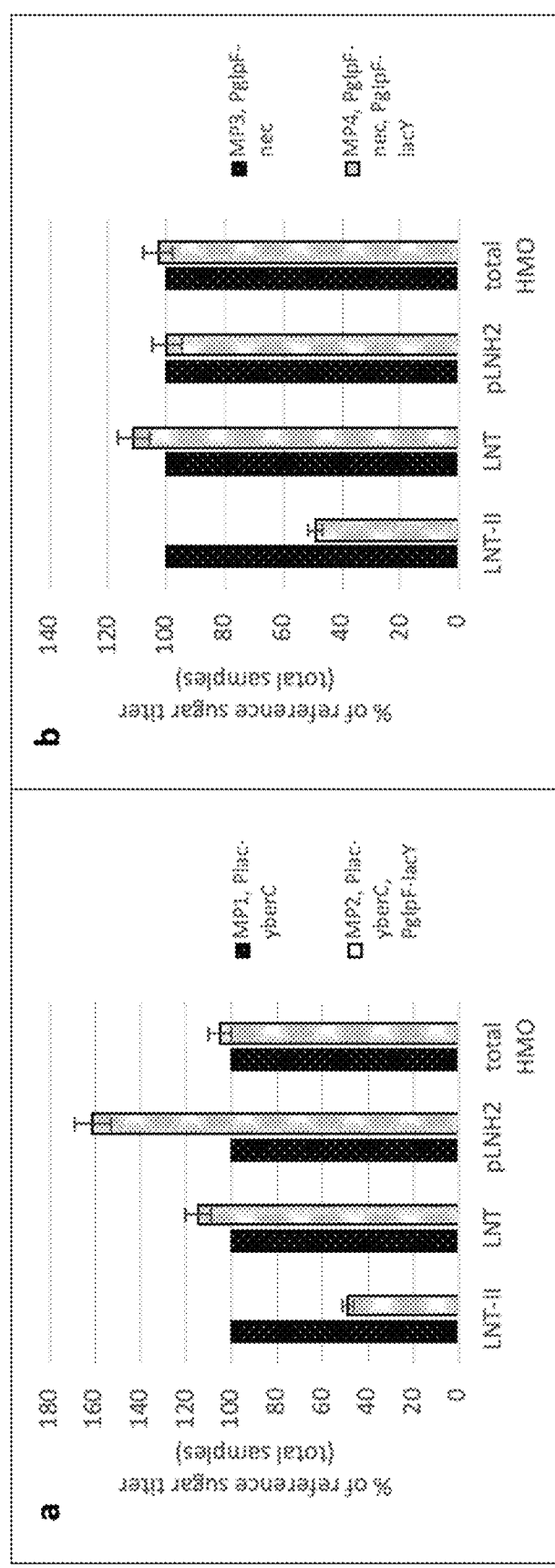
FIG. 1

The effect of lacY over-expression on the relative titers of LNT-II, LNT, pLNH2 and the total HMO content for (a) the yberC-expressing strains MP1 and MP2 and (b) the nec-expressing strains MP3 and MP4, as revealed by the analysis of total samples.

FIG. 2

The effect of lacY over-expression on (a) the LNT fraction in % of the final HMO blend and (b) the final optical density reached by the yberC-expressing strains MP1 and MP2 and the nec-expressing strains MP3 and MP4.

FIG. 3

The effect of lacY over-expression on the fraction of LNT-II, LNT and pLNH2 detected in the supernatant of cultures of (a) the yberC-expressing strains MP1 and MP2 and (b) the nec-expressing strains MP3 and MP4, as revealed by the analysis of supernatant and cell pellet samples.

FIG. 4

The effect of lacY over-expression on the relative titers of LNT-II, LNT, pLNnH and the total HMO content for the vag-expressing strains MP5 and MP6, as revealed by the analysis of total samples.

FIG. 5

The effect of lacY over-expression on (a) the LNnT fraction in % of the final HMO blend and (b) the final optical density reached by the vag-expressing strains MP5 and MP6.

FIG. 6

Performance of LNT producing strains MP7 and MP8 in fermentation runs using a high lactose process. Time course profiles shown for: (a) lactose concentration, (b) biomass concentration, (c) relative accumulated LNT yields on sucrose, (d) ratio of LNT-11 to LNT, and (e) ratio of pLNH2 to LNT.

FIG. 7

Performance of LNnT producing strains MP5 and MP6 in fermentation runs using a high lactose process. Time course profiles shown for: (a) lactose concentration, (b) biomass concentration, (c) relative accumulated LNnT yields on sucrose, (d) ratio of LNT-II to LNnT, and (e) ratio of pLNnH to LNnT.

FIG. 8

3'SL production as % of the respective MFS transporter strain set to 100%. Strains containing the MFS transporter nec are presented as the dotted bars, yberC strains are cross stiped and fred strains are horizontally striped

FIG. 9

2'FL production as % of the control nec transporter strain (MP18) set to 100%. The 2'FL titers of strains containing the MFS transporter nec in combination with an additional copy of lacY expressed from either PgIpF_SD7 (MP19) or PgIpF (MP20) are shown relative to the nec transporter strain.

SEQUENCE ID'S

The current application contains a sequence listing in text format and electronical format which is hereby incorporated by reference. Table 9 provides a summary of the sequences in the present application.

TABLE 9 sequences

| Protein/gene/promoter Abbreviation | Function | Public reference | SEQ ID NO: |
| --- | --- | --- | --- |
| LacY | Lactose permease | NP_414877.1 | 1 |
|  |  | WP_042094275.1 | 3 |
|  |  | WP_000291549.1 | 4 |
|  |  | WP_089607162.1 | 5 |
|  |  | WP_152280604.1 | 6 |
|  |  | EGT4952364.1 | 7 |
|  |  | WP_134216118.1 | 8 |
|  |  | EDI1749185.1 | 9 |
|  |  | WP_084912833.1 | 10 |
|  |  | WP_103826752.1 | 11 |
|  |  | WP_021804673.1 | 12 |
|  |  | WP_084984472.1 | 13 |
|  |  | WP_199428647.1 | 14 |
|  |  | WP_046596210.1 | 15 |
|  |  | XP_452193.1 | 16 |
| lacY | E. Coli K-12 lactose permease gene | NC_000913.3 | 2 |
| CvB3galT | β-1,3-Gal-transferase | WP_080969100.1 | 17 |
| GalTK | β-1,3-Gal-transferase | homologous to BD182026.1 | 18 |
| GalT | β-1,4-gal-transferase | WP_001262061.1 | 19 |
| LgtA | β-1,3-GlcNAc-transferase | WP_033911473.1 | 20 |
| PmnagT | β-1,3-GlcNAc-transferase | WP_014390683.1 | 21 |
| HD0466 | β-1,3-GlcNAc-transferase | WP_010944479.1 | 22 |
| FutC | α-1,2-fucosyl-transferase | WP_080473865.1 (with two additional amino acids (LG) at the C-terminus) | 23 |
| Smob | α-1,2-fucosyl-transferase | WP_126455392.1 | 24 |
| Mtun | α-1,2-fucosyl-transferase | WP_031437198.1 | 25 |
| FutA | α-1,3-fucosyl-transferase | NP_207177.1 | 26 |
| FucT | α-1,3-fucosyl-transferase | AAB81031.1 | 27 |
| FucTIII | α-1,3-fucosyl-transferase | AAR88243.1 | 28 |
| Pd2 | α-2,3-sialyl-transferase | — | 29 |
| Nst | α-2,3-sialyl-transferase | — | 30 |
| Gmd | GDP-mannose 4,6-dehydratas | NP_416557.1 | 31 |
|  |  | WP_000048190.1 | 32 |
| WcaG | GDP-L-fucose synthase | NP_416556.1 | 33 |
|  |  | WP_000043654.1 | 34 |
| WcaH | GDP-mannose mannosyl hydrolase | NP_416555.2 | 35 |
|  |  | WP_001393539.1 | 36 |
| WcaI | colanic acid biosynthesis fucosyltransferase WcaI | NP_416554.1 | 37 |
|  |  | WP_000699693.1 | 38 |
| ManC | mannose-1-phosphate guanylyltransferase | NP_416553.1 | 39 |
|  |  | WP_000079274.1 | 40 |
| ManB | Phosphomannomutase | NP_416552.1 | 41 |
|  |  | WP_001350528.1 | 42 |

TABLE 9-continued sequences

| Protein/gene/promoter Abbreviation | Function | Public reference | SEQ ID NO: |
|---|---|---|---|
| Pgm | Phosphoglucomutase | NP_415214.1 | 43 |
| | | WP_001396326.1 | 44 |
| GalU | UTP-glucose-1-phosphate uridylyltransferase | NP_415752.1 | 45 |
| | | WP_000718995.1 | 46 |
| GalE | UDP-glucose 4-epimerase | NP_415280.3 | 47 |
| | | WP_001265438.1 | 48 |
| GlmM | Phosphoglucosamine mutase | NP_417643.1 | 49 |
| | | WP_000071134.1 | 50 |
| GlmU | N-acetylglucosamine-1-phosphate uridyltransferase and glucosamine-1-phosphate acetyltransferase | NP_418186.1 | 51 |
| | | WP_000933736.1 | 52 |
| GlmS | L-glutamine-D-fructose-6-phosphate aminotransferase | NP_418185.1 | 53 |
| | | WP_000334099.1 | 54 |
| NeuA | CMP-Neu5Ac synthetase | AAK91728.1 | 55 |
| | | WP_006881452.1 | 56 |
| NeuB | Neu5Ac synthase | AAK91726.1 | 57 |
| | | WP_023580510.1 | 58 |
| NeuC | UDP-GlcNAc 2-epimerase | AAK91727.1 | 59 |
| | | WP_000723250.1 | 60 |
| | | CAR04561.1 | 61 |
| Vag | MFS transporter | WP_048785139.1 | 62 |
| Fred | MFS transporter | WP_087817556.1 | 63 |
| Marc | MFS transporter | WP_060448169.1 | 64 |
| Bad | MFS transporter | WP_017489914.1 | 65 |
| Nec | MFS transporter | WP_092672081.1 | 66 |
| YberC | MFS transporter | EEQ08298.1 | 67 |
| Plac | promoter | — | 68 |
| PgatY_70UTR | promoter | WO2020255054A1 | 69 |
| PglpF | promoter | WO2019123324A1 | 70 |
| PglpF_SD1 | promoter | WO2019123324A1 | 71 |
| PglpF_SD10 | promoter | WO2019123324A1 | 72 |
| PglpF_SD2 | promoter | WO2019123324A1 | 73 |
| PglpF_SD3 | promoter | WO2019123324A1 | 74 |
| PglpF_SD4 | promoter | WO2019123324A1 | 75 |
| PglpF_SD5 | promoter | WO2019123324A1 | 76 |
| PglpF_SD6 | promoter | WO2019123324A1 | 77 |
| PglpF_SD7 | promoter | WO2019123324A1 | 78 |
| PglpF_SD8 | promoter | WO2019123324A1 | 79 |
| PglpF_SD9 | promoter | WO2019123324A1 | 80 |
| Plac_16UTR | promoter | WO2020255054A1 | 81 |
| PmglB_70UTR | promoter | WO2020255054A1 | 82 |
| PmglB_70UTR_SD4 | promoter | WO2020255054A1 | 83 |
| CP6 | promoter | — | 84 |
| PosmY | promoter | — | 85 |
| SacC_Agal | glycoside hydrolase family 32 protein | WP_103853210.1 | 86 |
| Bff | beta-fructofuranosidase protein | BAD18121.1 | 87 |
| scrY | Sucrose porin | WO2015197082 | 88 |
| scrA | PTS system sucrose-specific EIIBC component | WO2015197082 | 89 |
| scrB | Sucrose-6-phosphate hydrolase | WO2015197082 | 90 |
| scrR | Sucrose operon repressor | WO2015197082 | 91 |
| glpR | Regulator of the Glp Operon | | 92 |
| PmglB_70UTR_SD8 | promoter | WO2020255054 | 93 |
| PmglB_70UTR_SD10 | promoter | WO2020255054 | 94 |
| PmglB_54UTR | promoter | WO2020255054 | 95 |
| Plac_70UTR | promoter | WO2019123324 | 96 |
| PmglB_70UTR_SD9 | promoter | WO2020255054 | 97 |
| PmglB_70UTR_SD5 | promoter | WO2020255054 | 98 |
| PmglB_70UTR_SD7 | promoter | WO2020255054 | 99 |
| PglpA_70UTR | promoter | WO2019123324 | 100 |
| PglpT_70UTR | promoter | WO2019123324 | 101 |
| PmglB_16UTR | promoter | WO2020255054 | 102 |
| PglpA_16UTR | promoter | WO2019123324 | 103 |

EXAMPLES

Example 1—Improvement of LNT Production Systems by Increasing the Expression of the lacY Gene Encoding Lactose Permease in Cells Expressing a Heterologous MFS Transporter Genotype of Strains MP1, MP2, MP3 and MP4

The strains (genetically engineered cells) constructed in the present application were based on *Escherichia coli* K-12 DH1 with the genotype: F−, λ−, gyrA96, recA1, relA1, endA1, thi-1, hsdR17, supE44. Additional modifications were made to the *E. coli* K-12 DH1 strain to generate the platform strain "MDO" with the following modifications: lacZ: deletion of 1.5 kbp, lacA: deletion of 0.5 kbp, nanKETA: deletion of 3.3 kbp, melA: deletion of 0.9 kbp, wcaJ: deletion of 0.5 kbp, mdoH: deletion of 0.5 kbp, and insertion of Plac promoter upstream of the gmd gene.

Methods of inserting or deleting gene(s) of interest into the genome of *E. coli* are well known to the person skilled in the art. Insertion of genetic cassettes into the *E. coli* chromosome can be done using gene gorging (see e.g., Herring and Blattner 2004 J. Bacteriol. 186: 2673-81 and Warming et al 2005 Nucleic Acids Res. 33(4): e36) with specific selection marker genes and screening methods.

Based on the platform strain "MDO" (e.g., also reported in WO2020255054A1 or WO2019123324A1), the modifications summarised in the table below, were made to obtain the fully chromosomal strains MP1, MP2, MP3 and MP4. The strains can produce the tetrasaccharide HMO LNT. The glycosyltransferase enzymes LgtA (a beta-1,3-N-acetyloglucosamine transferase) from *N. meningitidis* and GalTK (a beta-1,3-galactosyltransferase) from H. pylon are present in all four strains. Moreover, MP1 and MP2 express the heterologous transporter YberC from *Yersinia bercovieri*, while the strains MP3 and MP4 express the heterologous transporter Nec from *Rosenbergiella nectarea*. Moreover, the strains MP2 and MP4 over-express the lacY gene from an additional PglpF-driven genomic copy, while the strains MP1 and MP3 do not.

In the present example, it is demonstrated how the overexpression of the lacY gene coding lactose permease is used as a genetic tool to enhance LNT production in strains that already express the heterologous transporter YberC or Nec. This invention also demonstrates how the over-expression of the lacY gene can be advantageously used to increase the total HMO content of the broth, and simultaneously reduce the formation of other HMOs, such as LNT-II, and increase the LNT content in the final HMO blend. As shown in table 2, the only difference among each strain of the two strain pairs, namely MP1-MP2 and MP3-MP4, is the presence of an additional lacY expression cassette at a genomic locus that is different from the native lacY locus.

TABLE 2

Genotypes of the strains MP1, MP2, MP3 and MP4

| Strain ID | Genotype | Plasmid-free |
|---|---|---|
| MP1 | MDO x3 GlcNACT* x2 GalTK**, Plac-yberC | LNT |
| MP2 | MDO x3 GlcNACT* x2 GalTK**, Plac-yberC, PglpF-lacY | LNT |
| MP3 | MDO x3 GlcNACT* x2 GalTK**, PglpF-nec | LNT |
| MP4 | MDO x3 GlcNACT* x2 GalTK**, PglpF-nec, PglpF-lacY | LNT |

*GlcNAcT: beta-1,3-N-acetyloglucosamine transferase
**GalTK: beta-1,3-galactosyltransferase Deep Well Assay The strains disclosed in the present example were screened in 96 deep well plates using a 4-day protocol. During the first 24 hours, precultures were grown to high densities and subsequently transferred to a medium that allowed induction of gene expression and product formation. More specifically, during day 1, fresh precultures were prepared using a basal minimal medium (BMM) supplemented with magnesium sulphate, thiamine and glucose. The precultures were incubated for 24 hours at 34° C. and 1000 rpm shaking and then further transferred to a new BMM (pH 7.5) in order to start the main culture. The new BMM was supplemented with magnesium sulphate, thiamine, a bolus of 20% glucose solution (0.5 μL per mL) and a bolus of 20% lactose solution (0.1 μL per μL).

Moreover, a 20% stock solution of a specific polysaccharide was provided as carbon source, accompanied by the addition of a specific hydrolytic enzyme, so that glucose was released at a rate suitable for carbon-limited growth and similar to that of a typical fed-batch fermentation process. The main cultures were incubated for 72 hours at 28° C. and 1000 rpm shaking. For the analysis of total broth, the 96 well plates were boiled at 100° C., subsequently centrifuged, and finally the supernatants were analyzed by HPLC.

Results

Strains were characterized in deep well assays and samples were collected from the total broth, the supernatant, and the cell pellet. All samples were analysed for HMO content by HPLC following the 72-hour protocol described above.

The concentration of the detected HMOs (in g/L) in each sample was used to calculate the % quantitative differences in the HMO content of the strains tested, i.e., the % differences in the HMO concentrations of lacY-expressing cells relative to the ones expressing lacY at physiological levels. Moreover, the absolute fraction (%) of LNT in the final HMO blend was calculated by considering the HMO concentrations detected by HPLC, i.e., LNT-II and LNT concentrations. The final optical density at 600 nm was also measured for all strains at the end of the experiment, i.e., after 72 hours in the production phase. Finally, the HPLC measurements for the supernatant and pellet samples were used to calculate the absolute sugar ratio (%) of the supernatant (S) fraction to the sum of the supernatant and pellet fractions (total, T).

As revealed by the analysis of total samples in deep-well cultures, some gains in LNT and total HMO titers can be obtained by over-expressing the lacY gene both in nec- and yberC-expressing cells. Specifically, the strain expressing the Nec transporter and over-expressing the lacY gene, MP2, produced approximately 15% more LNT and provided approximately 10% more total HMO content than the nec-expressing strain MP1 that has wild-type expression levels of the lacY gene (FIG. 1a). Similarly, gains up to 15% both in LNT titers and the total HMO content can be obtained by over-expressing the lacY gene in the yberC-expressing strain MP3 to generate the strain MP4748 (FIG. 1b). Moreover, the increase in the intracellular lactose concentration mediated by lacY over-expression in both nec- and yberC-expressing cells (strains MP2 and MP4) results in markedly lower by-product (LNT-II) formation compared to cells that express lacY at physiological levels (strains MP1 and MP3) (FIG. 1a-1b).

Figure 2:
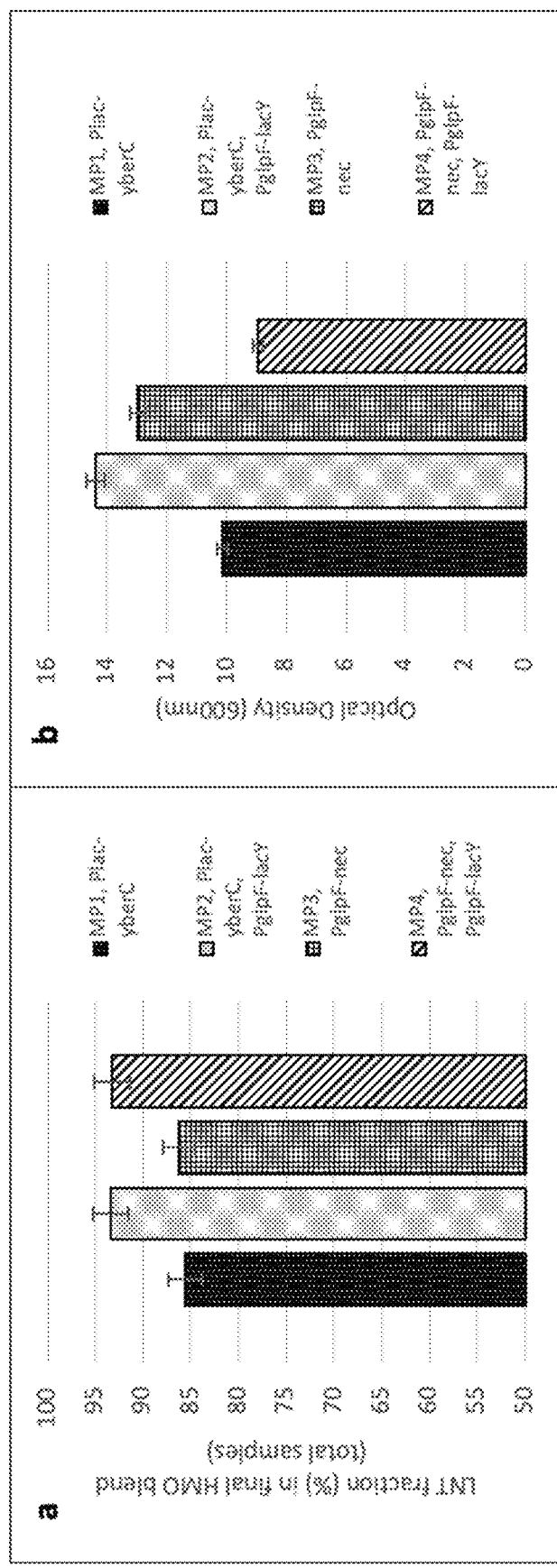

The facts mentioned above are directly reflected to the LNT content (%) in the final HMO blend of both nec- and yberC-expressing cells that over-express the lacY gene. Specifically, the LNT fraction of the final HMO blend generated by cells over-expressing the lacY and nec genes (strain MP3) or the lacY and yberC genes (strain MP2) is approximately 10% higher than for cells that express the nec (strain MP4) or yberC (strain MP1) gene alone (FIG. 2a). Interestingly, the effect of lacY over-expression on biomass formation for heterologous MFS-expressing strains can vary depending on the heterologous MFS being expressed. In detail, the strain MP4 that over-expresses both the lacY and nec genes reaches significantly lower optical density values after 72 hours of cultivation compared to the similar strain MP3 that does not over-express the lacY gene (FIG. 2b). The opposite is true for the strain MP2 that over-expresses both the lacY and yberC genes, i.e., MP2 forms higher biomass than the strain MP1 that expresses the yberC gene alone (FIG. 2b) In conclusion, the over-expression of the lacY gene in transporter expressing LNT production strains seems to change the sugar transport dynamics across the cell membrane in such a manner that the final LNT and total HMO titer in these strains is much higher when the lacY gene is over-expressed (strains MP2 and MP4) than when it is expressed at physiological levels (strains MP1 and MP3).

Figure 3:
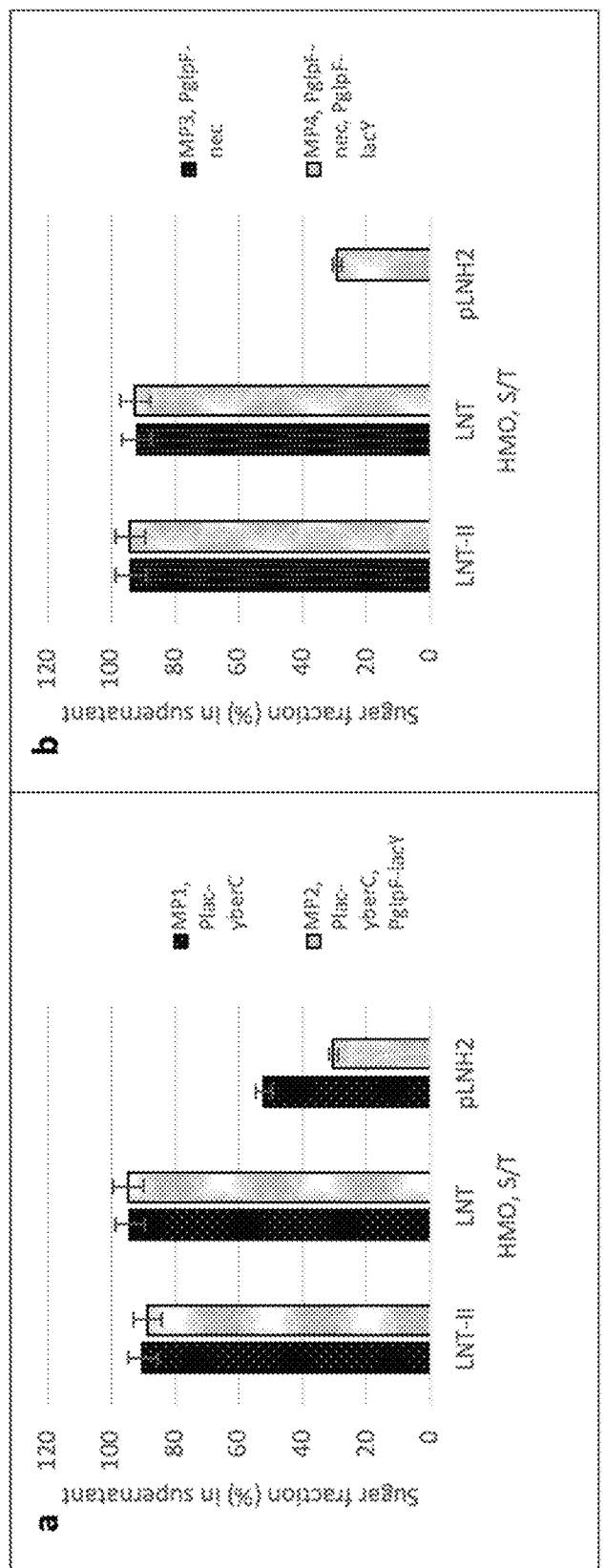

As it is apparent from the analysis of the supernatant and pellet fractions of the broth, the % fraction of LNT and LNT-II in the supernatant is not affected by the over-expression of the lacY gene in yberC-expressing cells (FIG. 3a). Approximately 25% less pLNH2 is, however, detected in the culture medium when yberC-expressing cells over-express lacY (strain MP2) rather than when lacY is solely expressed from the Plac promoter of the lac operon of E. coli (strain MP1) (FIG. 3a).

As for yberC-expressing cells, the fraction of LNT and LNT-II detected in the supernatant is not affected by the over-expression of the lacY gene in nec-expressing cells (FIG. 3b). Contrary to yberC-expressing cells (strain MP3), however, the over-expression of the lacY gene in nec-expressing cells (strain MP4) results in higher pLNH2 in the culture medium (FIG. 3b).

Example 2—Improvement of LNnT Production Systems by Increasing the Expression of the lacY Gene Encoding Lactose Permease in Cells Expressing a Heterologous MFS Transporter Genotype of Strains MP5 and MP6

Based on the platform strain "MDO" (e.g., see example 1 and also reported in WO2020255054A1 or WO2019123324A1), the modifications summarised in the table below, were made to obtain the fully chromosomal strains MP5 and MP6. The strains can produce the tetrasaccharide HMO LNnT. The glycosyltransferase enzymes LgtA (a beta-1,3-N-acetyloglucosamine transferase) from N. meningitidis and GalT (a beta-1,4-galactosyltransferase) from H. pylon are present in both strains. Moreover, MP5 and MP6 express the heterologous transporter Vag from Pantoea vagans, and the strain MP6, but not MP5, over-expresses the lacY gene from an additional genomic copy under the control of the PgIpF promoter.

In the present Example, it is demonstrated how the over-expression of the lacY gene coding lactose permease is used as a genetic tool to enhance LNnT production in strains that already express the heterologous transporter Vag. This invention also demonstrates how the over-expression of the lacY gene can be advantageously used to increase the pLNnH and total HMO content of the broth. As shown in table 3 below, the only difference between the two vag-expressing strains, MP5 and MP6, is the presence of an additional lacY expression cassette at a genomic locus that is different from the native lacY locus.

TABLE 3

Genotypes of the strains MP5 and MP6

| Strain ID | Genotype | Product |
|---|---|---|
| MP5 | MDO x2 GlcNACT* x1 GalT**, PglpF-vag, scrBRYA*** | LNnT |
| MP6 | MDO x2 GlcNACT* x1 GalT**, PglpF-vag, PglpF-lacY, scrBRYA*** | LNnT |

*GlcNACT: beta-1,3-N-acetyloglucosamine transferase
**GalT: beta-1,4-galactosyltransferase
***scrBRYA: sucrose utilization genes Deep Well Assay The strains disclosed in the present example were screened in 96 deep well plates using a 4-day protocol. During the first 24 hours, precultures were grown to high densities and subsequently transferred to a medium that allowed induction of gene expression and product formation. More specifically, during day 1, fresh precultures were prepared using a basal minimal medium (BMM) supplemented with magnesium sulphate, thiamine and glucose. The precultures were incubated for 24 hours at 34° C. and 1000 rpm shaking and then further transferred to a new BMM (pH 7.5) in order to start the main culture. The new BMM was supplemented with magnesium sulphate, thiamine, a bolus of 20% glucose solution (0.5 μL per mL) and a bolus of 20% lactose solution (0.1 μL per μL).

Moreover, a 20% stock solution of a specific polysaccharide was provided as carbon source, accompanied by the addition of a specific hydrolytic enzyme, so that glucose was released at a rate suitable for carbon-limited growth and similar to that of a typical fed-batch fermentation process. The main cultures were incubated for 72 hours at 28° C. and 1000 rpm shaking. For the analysis of total broth, the 96 well plates were boiled at 100° C., subsequently centrifuged, and finally the supernatants were analysed by HPLC.

Results

Strains were characterized in deep well assays and samples were collected from the total broth and analysed for HMO content by HPLC following the 72-hour protocol described above. The concentration of the detected HMOs (in g/L) in each sample was used to calculate the % quantitative differences in the HMO content of the strains tested, i.e., the % differences in the HMO concentrations of lacY-expressing cells (strain MP6) relative to the ones expressing lacY at physiological levels (strain MP5). Moreover, the absolute fraction (%) of LNnT in the final HMO blend was calculated by considering the HMO concentrations detected by HPLC, i.e., LNT-II, LNnT and pLNnH concentrations. The final optical density at 600 nm was also measured for all strains at the end of the experiment, i.e., after 72 hours in the production phase.

Figure 4:
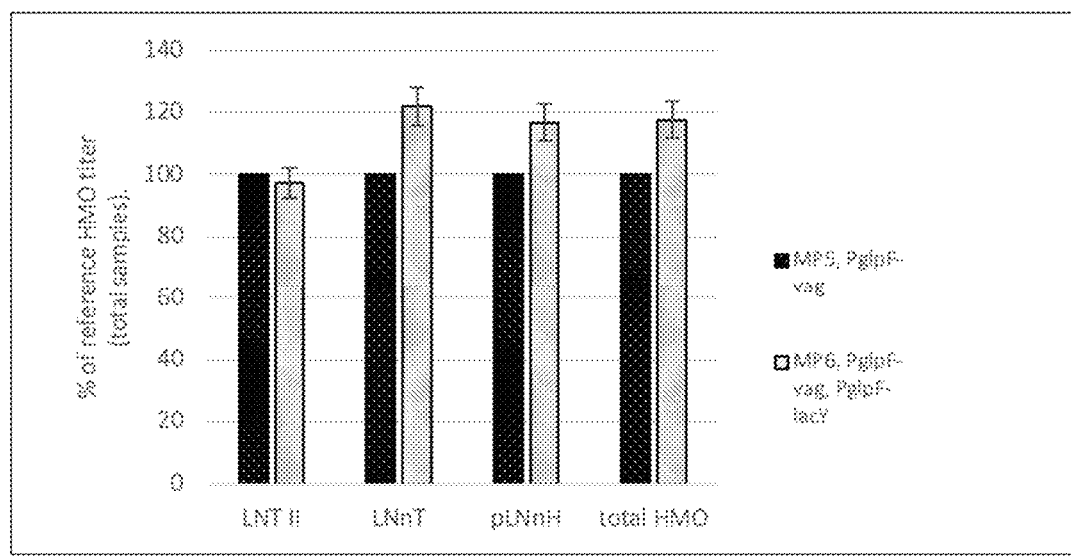

As revealed by the analysis of total samples in deep-well cultures, marked gains in LNnT, pLNnH and total HMO titers can be obtained by over-expressing the lacY gene in vag-expressing cells. Specifically, the strain expressing the Vag transporter and over-expressing the lacY gene, MP6, produced approximately 20% more LNnT, 20% more pLNnH and had 20% more total HMO content than the vag-expressing strain MP5 that expresses the lacY gene at wild-type levels (FIG. 4). No significant differences in the LNT-II content among the two strains could be detected (FIG. 4).

Figure 5:
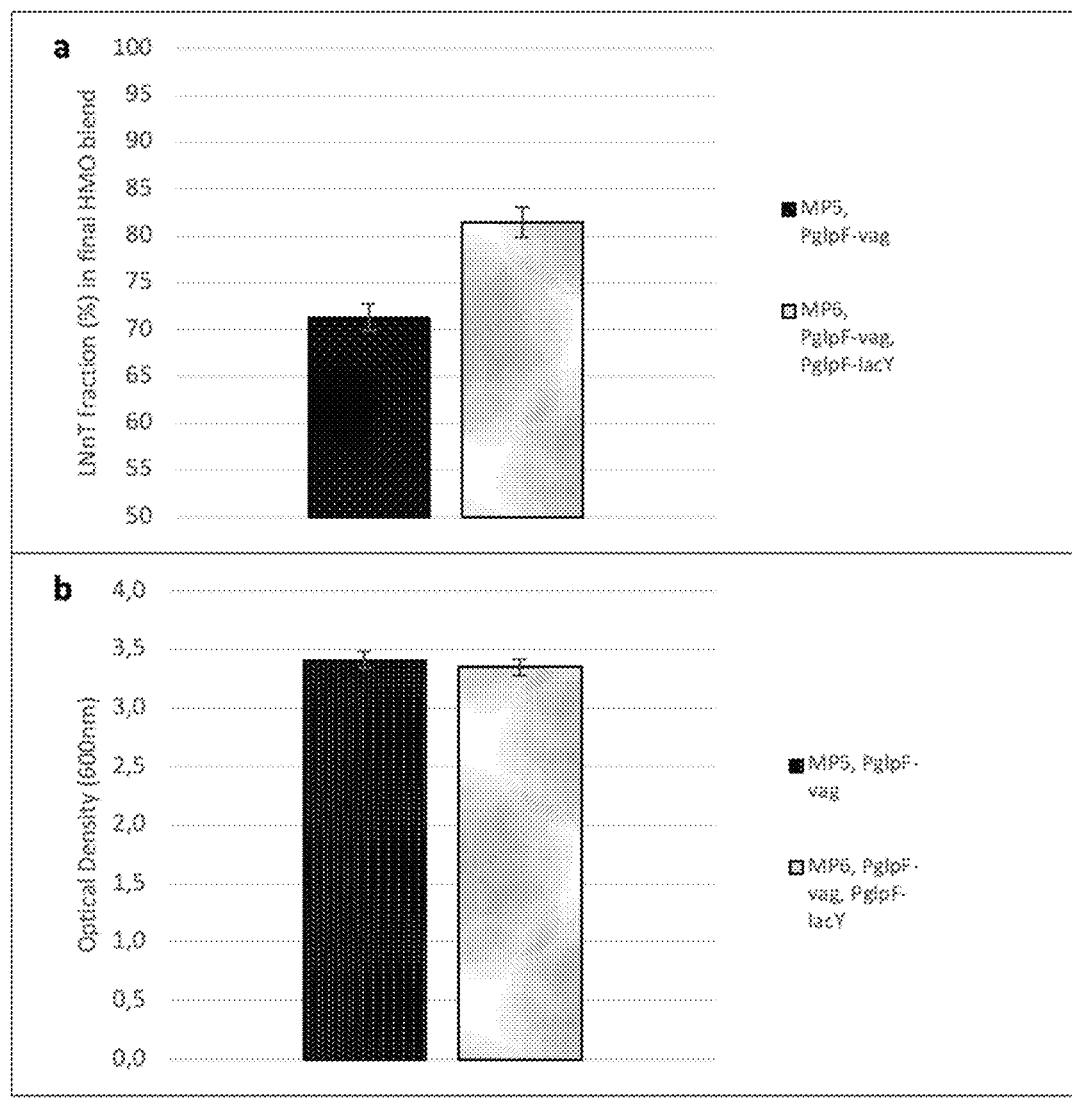

The facts mentioned above are directly reflected to the LNnT content (%) in the final HMO blend of vag-expressing cells that over-express the lacY gene. Specifically, the LNnT fraction of the final HMO blend generated by the strain MP6 that over-expresses the lacY gene and the vag gene is approximately 10% higher than for the strain MP5 that expresses the vag gene alone (FIG. 5a). Contrary to the marked impact of lacY over-expression on biomass formation for the LNT production strains presented in example 1, the impact of lacY over-expression on biomass formation for the heterologous MFS-expressing LNnT strain MP6 is negligible. In detail, the final optical density of cells over-expressing both the lacY and vag genes (strain MP6) is very similar to the one of cells expressing the vag gene alone (strain MP5) (FIG. 5b).

Example 3—Fermentation Performance of LNT and LNnT Strains Over-Expressing the lacY Gene and Expressing a Gene Encoding a Heterologous Sugar Exporter Genotype of Strains MP7, MP8, MP5 and MP6

Based platform strain "MDO" (e.g., see Example 1 and also reported in WO2020255054A1 or WO2019123324A1), the modifications summarised in table 4, were made to obtain the fully chromosomal strains MP7, MP8, MP5 and MP6. The strains can produce the tetrasaccharide HMO LNT (MP7 and MP8) or LNnT (MP5 and MP6). All four strains can grow on sucrose. The glycosyltransferase enzymes LgtA (a beta-1,3-N-acetyloglucosamine transferase) from *N. meningitidis* is present in all four strains, while the GalTK (a beta-1,3-galactosyltransferase) or the GalT (a beta-1,4-galactosyltransferase) from H. pylon is introduced in strains MP7-MP8 and MP5-MP6, respectively. Moreover, the strains MP7 and MP8 express the heterologous transporter YberC from *Yersinia bercovieri*, while the strains MP5 and MP6 express the heterologous transporter Vag from *Pantoea vagans*. Moreover, the strains MP8 and MP6 over-express the lacY gene from an additional PglpF-driven genomic copy, while the strains MP7 and MP5 do not.

In the present Example, it is demonstrated how the over-expression of the lacY gene coding lactose permease is used as a strain engineering tool to enhance LNT or LNnT production in fed-batch fermentations using strains that already express the heterologous transporter YberC or Vag, respectively. This invention also demonstrates how the over-expression of the lacY gene can be advantageously used to obtain higher total HMO content in the fermentation broth, and simultaneously modulate the formation of HMOs other than LNT and LNnT, e.g., LNT-II, pLNnH and pLNH2. As shown in table 4, the only difference between the two pairs of strains, MP7-MP8 and MP5-MP6, is the presence of an additional lacY expression cassette at a genomic locus that is different from the native lacY locus.

TABLE 4

Genotypes of the strains MP7, MP8, MP5 and MP6

| Strain ID | Genotype | Product |
|---|---|---|
| MP7 | MDO x3 GlcNACT* x2 GalTK**, Plac-yberC, scrBRYA**** | LNT |
| MP8 | MDO x3 GlcNACT* x2 GalTK**, Plac-yberC, PglpF-lacY, scrBRYA**** | LNT |
| MP5 | MDO x2 GlcNACT* x1 GalT***, PglpF-vag, scrBRYA**** | LNnT |
| MP6 | MDO x2 GlcNAcT* x1 GalT***, PglpF-vag, PglpF-lacY, scrBRYA**** | LNnT |

*GlcNAcT: beta-1,3-N-acetyloglucosamine transferase
**GalTK: beta-1,3-galactosyltransferase
***GalT: beta-1,4-galactosyltransferase
****scrBRYA: sucrose utilization genes Fermentation Processes The fermentations were carried out in 200 mL DasBox bioreactors (Eppendorf, Germany), starting with 100 mL of defined mineral culture medium, consisting of a suitable concentration of a carbon source (sucrose or glucose), $MgSO_4 \times 7H_2O$, KOH, NaOH, $NH_4H_2PO_4$, $KH_2PO_4$, trace metal solution, citric acid, antifoam and thiamine. The trace metal solution (TMS) contained Mn, Cu, Fe, Zn as sulfate salts and citric acid. Fermentations were started by inoculation with 2% (v/v) of pre-cultures grown in a defined minimal medium. After depletion of the carbon source present in the batch medium, a sterile feed solution containing sucrose (or glucose), $NH_4SO_4$, and TMS was fed continuously in a carbon-limited manner using a predetermined, linear profile.

Lactose addition was done by a "high" lactose process ("LNT98" and "LNT108" for LNT fermentations, and "L232" for LNnT fermentations), where lactose monohydrate solution was added by two bolus additions, the first one at approx. 10 hours after feed start, the second one at approx. 70 hours EFT. For LNT fermentations, the processes "LNT98" and "LNT108" differ only in the fact that the second lactose pulse was performed approx. 20 h earlier for LNT108 than for LNT98. In this manner, lactose was ensured not to be the limiting factor for HMO formation at least until 90 hours EFT, as shown in FIGS. 6a and 7a. The process L232 is identical with LNT98.

The pH throughout fermentation was controlled at 6.8 by titration with 14% NH4OH solution. Aeration was controlled at 1 vvm using air, and dissolved oxygen was kept above 23% of air saturation, controlled by the stirrer rate. At 15 min after sucrose feed start, the fermentation temperature setpoint was lowered from 33° C. to 28° C. This temperature drop was conducted without a ramp. The total duration of the fermentations was 4-5 days.

Throughout the fermentations, samples were taken to determine the concentration of LNT or LNnT, LNT-II, lactose, pLNnH or pLNH2 and other minor by-products using HPLC. Total broth samples were diluted three-fold in deionized water and boiled for 20 minutes. This was followed by centrifugation at 17000g for 3 minutes, where after the resulting supernatant was analysed by HPLC. The above measurements were used along with data on carbon source utilization to accurately calculate product yields on sucrose as well as the ratios of LNT-II and hexasaccharide (pLNnH or pLNH2) relative to the main product (respectively, LNnT or LNT).

Results

Figure 6:
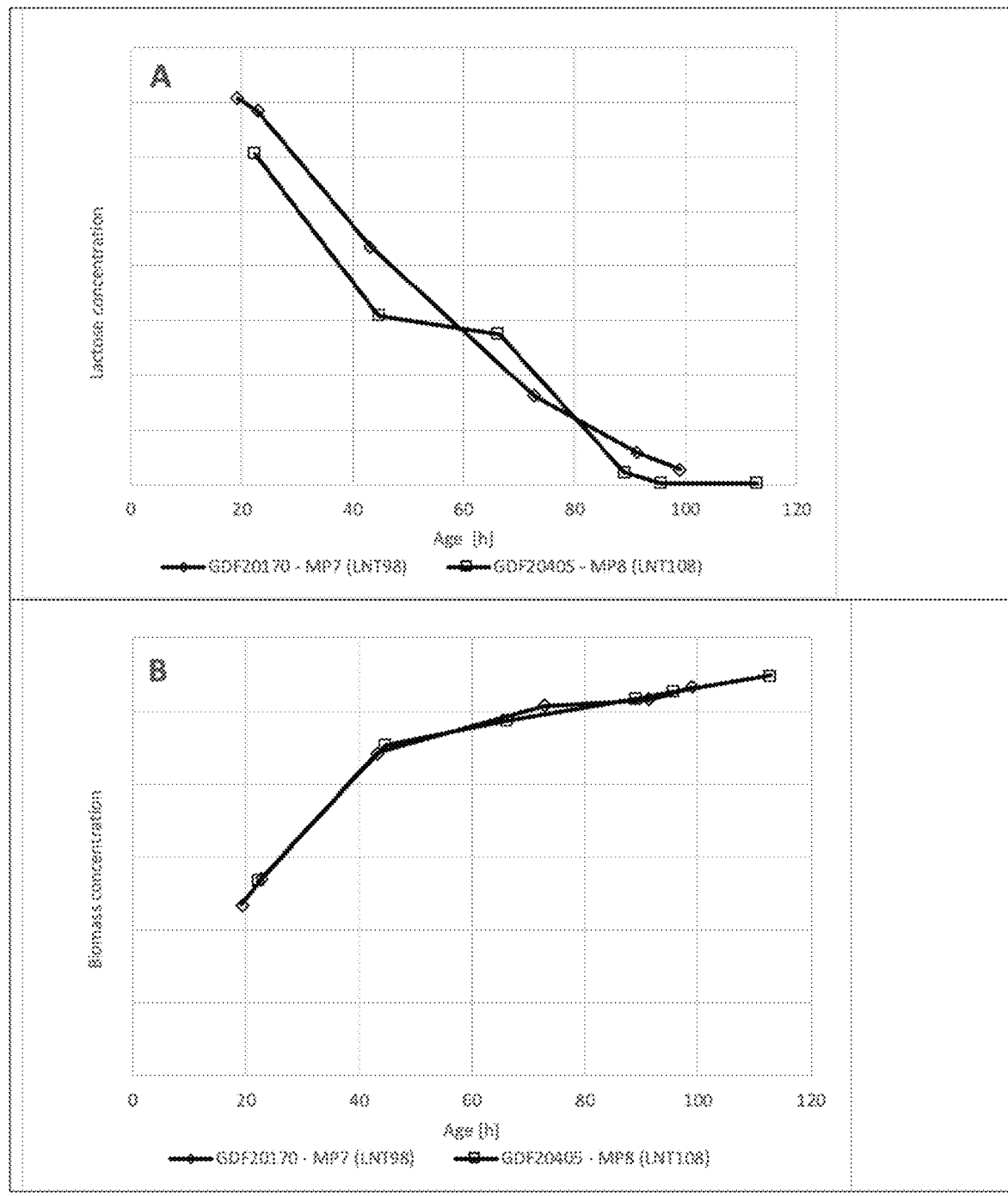
Figure 6:
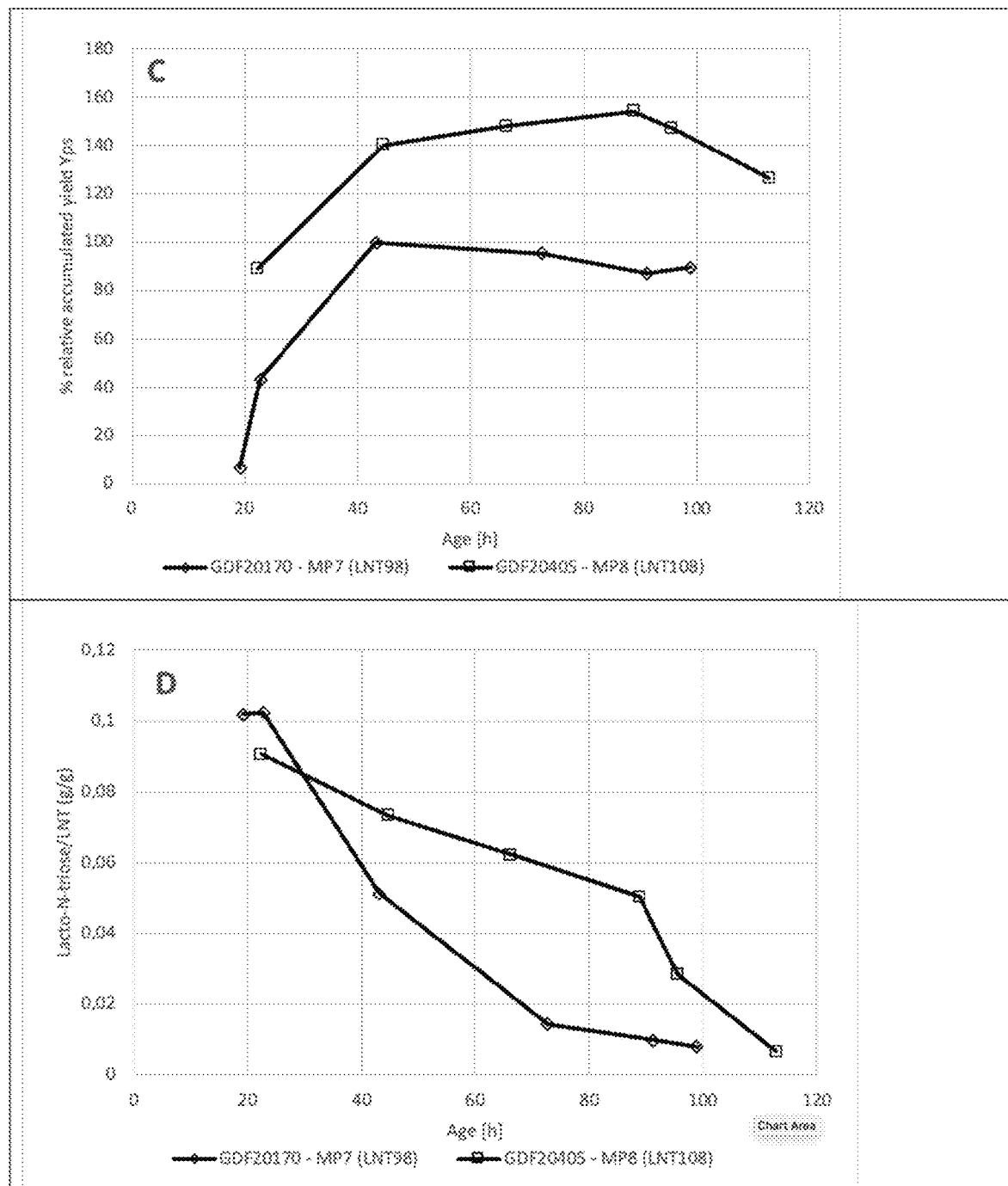
Figure 6:
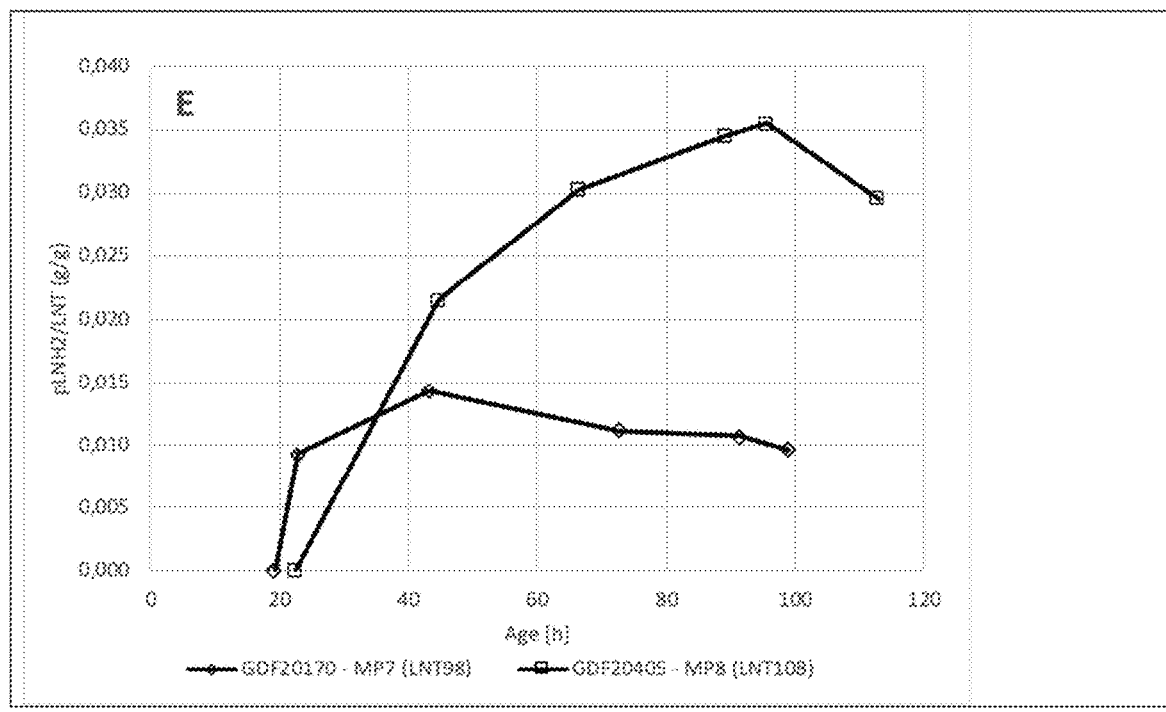
Figure 7:
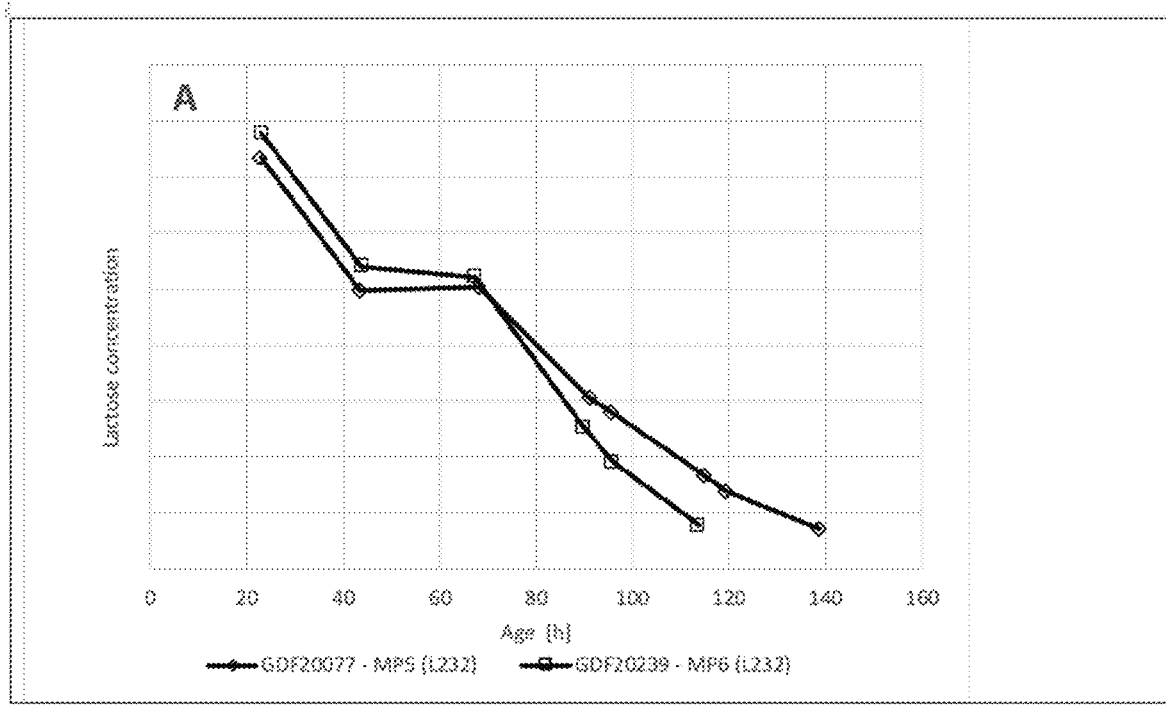
Figure 7:
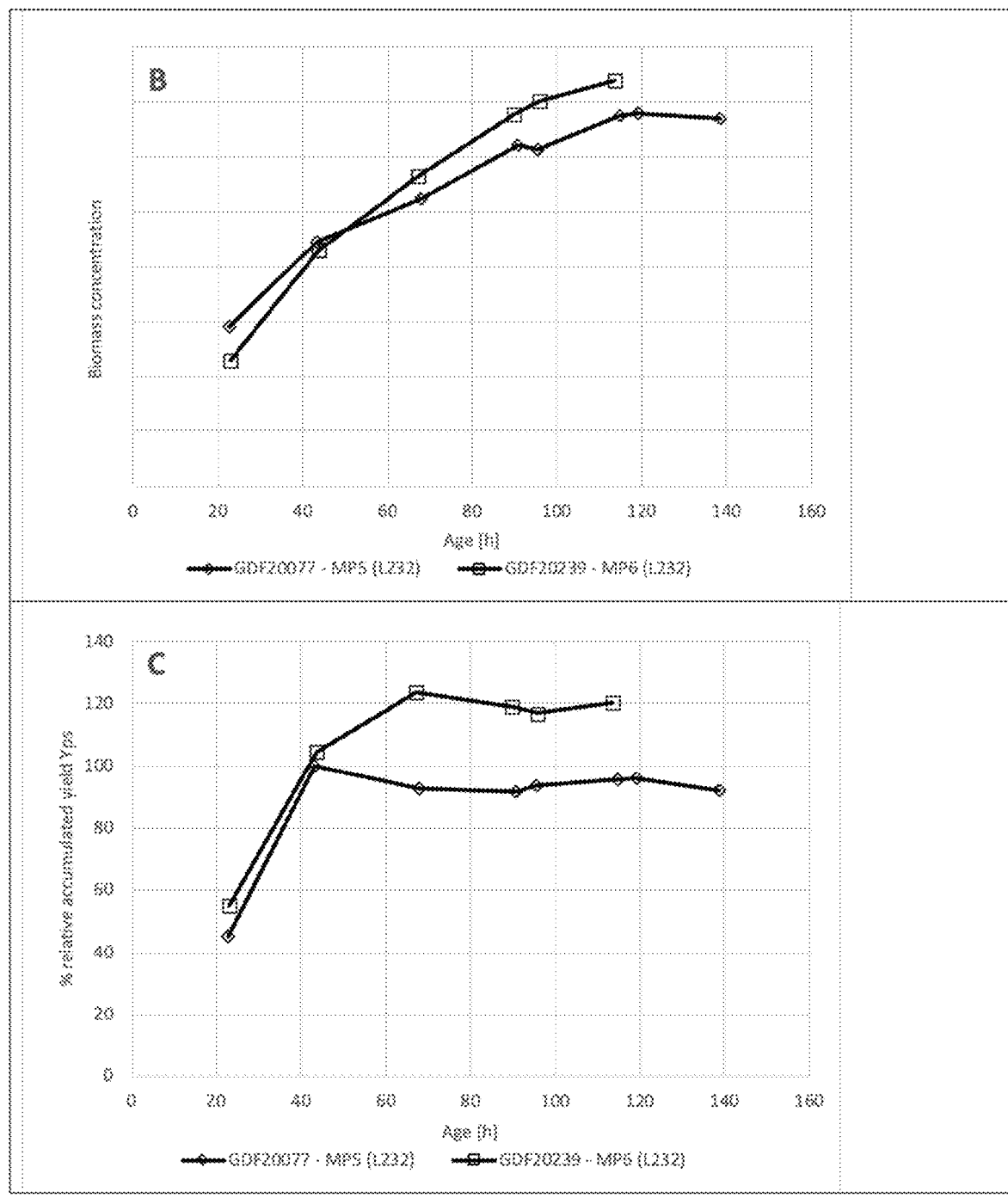
Figure 7:
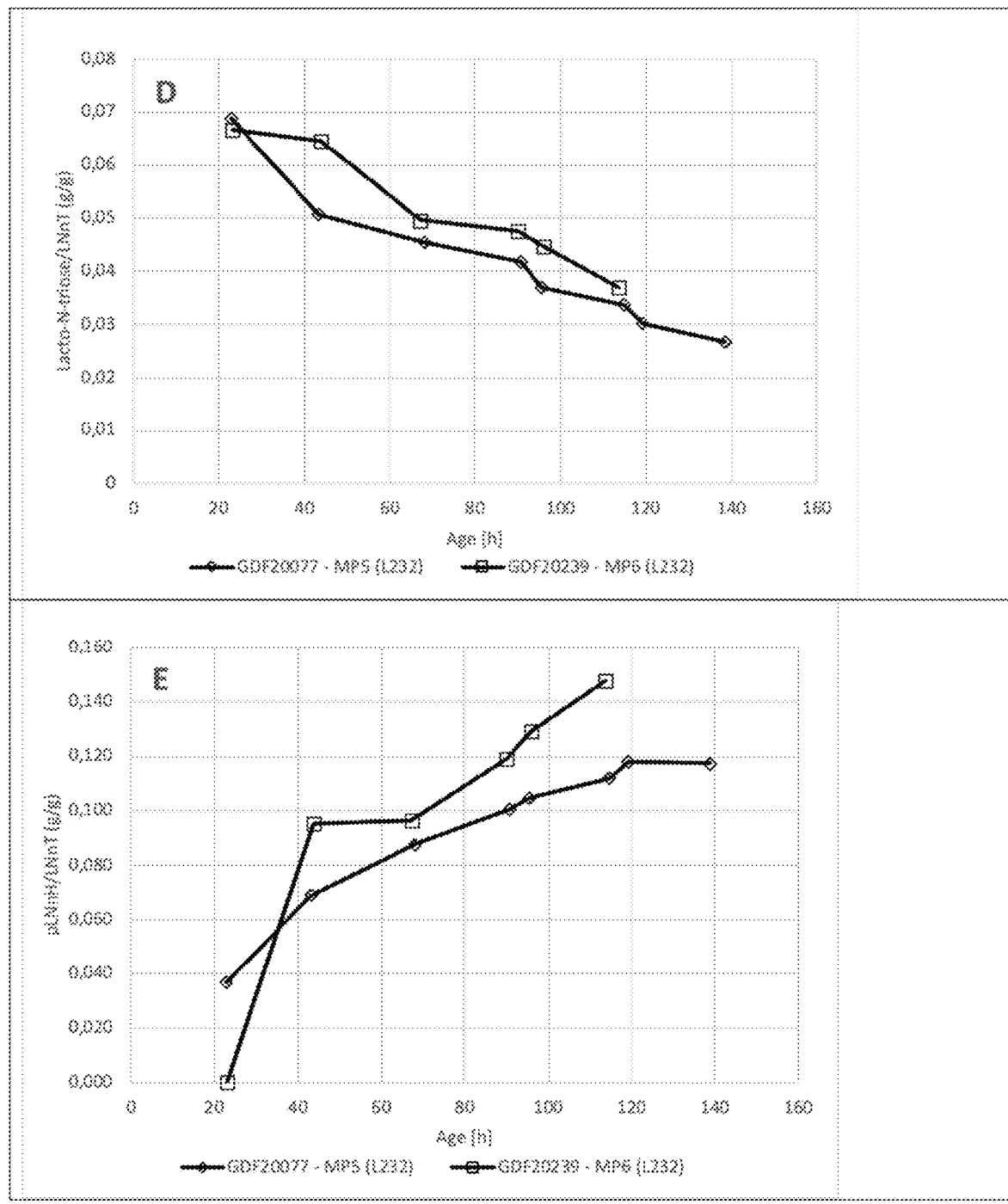

All four fermentations ran in a stable manner for at least 4 days (FIGS. 6 and 7).

As shown in FIG. 6c, the performance of the LNT strain that bears an extra copy of the lacY gene (strain MP8) is superior to the one observed by the strain that expresses lacY at physiological levels (strain MP7), with the former showing an approximately 50% higher LNT yield on sucrose (FIG. 6c), while retaining the biomass formation at a comparable level (FIG. 6B). Moreover, as revealed by the calculations of ratios of by-products to LNT, the strains MP8 and MP7 show similar LNT-II levels (FIG. 6d), while the over-expression of the lacY gene in strain MP8 results in increased pLNH2 formation (FIG. 6e).

As shown in FIG. 7c, the performance of the LNnT strain that bears an extra copy of the lacY gene (strain MP6) is superior to the one observed by the strain that expresses lacY at physiological levels (strain MP5), with the former showing an approximately 25% higher LNnT yield on sucrose (FIG. 7c), while retaining the biomass formation at a comparable level (FIG. 7b). As mentioned above for the LNT strains, the strains MP8 and MP7 show similar LNT-II levels (FIG. 7d), and the over-expression of the lacY gene in strain MP6 results in higher pLNnH formation than in strain MP5 (FIG. 7e).

Example 4—Increased Expression of lacY in Combination with an MFS Transporter does not Improve 3'SL Expression In Examples 1 to 3 it has been illustrated that LacY overexpression in combination with certain MFS transporters has a positive effect on LNT and LNnT production.

In the following example the MFS transporters nec, yberC or fred (1 copy genomically integrated) have been tested in a 3'-SL producing strain without (MP9, MP12 and MP15) or with overexpression of LacY, either as an extra copy from the chromosome (MP10, MP13 and MP16) or from a medium copy nr plasmid (pSU2719-lacY-chr) (MP11, MP14 and MP17).

All strains were based on the platform strain "MDO" (e.g., see example 1 and also reported in WO2020255054A1 or WO2019123324A1) and contained a truncated version (29 aa n-terminal deletion) of the α-2,3-sialyltransferase from Neisseria meningitidis, nst (GenBank assession nr. AAC44541.1), heterologous CMP-Neu5Ac synthetase, neuA (GenBank assession nr. AAK91728.1), heterologous sialic acid synthase, neuB (GenBank assession nr. AAK91726.1) and heterologous GlcNAc-6-phosphate 2 epimerase, neuC (GenBank assession nr. AAK91727.1) incorporated with a single copy at different loci in the genome of the MDO strain. The genotypes of the tested strains are given in table 5.

TABLE 5

Genotypes of the strains 3'-SL producing strains with different MFS transporters

| Strain ID | Genotype | Transporter |
| --- | --- | --- |
| MP9 | MDO x1 PglpF-nst, PglpF-nec, 1xPglpF-neuB, 1xPglpF-neuC, 1xPglpF-neuA | nec |
| MP10 | MDO x1 PglpF-nst, PglpF-nec, 1xPglpF-neuB, 1xPglpF-neuC, 1xPglpF-neuA, x1 PglpF-LacY | nec |
| MP11 | MDO x1 PglpF-nst, PglpF-nec, 1xPglpF-neuB, 1xPglpF-neuC, 1xPglpF-neuA, pSU2719-lacY-chr | nec |
| MP12 | MDO x1 PglpF-nst, PglpF-yberC, 1xPglpF-neuB, 1xPglpF-neuC, 1xPglpF-neuA | yberC |
| MP13 | MDO x1 PglpF-nst, PglpF-yberC, 1xPglpF-neuB, 1xPglpF-neuC, 1xPglpF-neuA, x1 PglpF-LacY | yberC |
| MP14 | MDO x1 PglpF-nst, PglpF-yberC, 1xPglpF-neuB, 1xPglpF-neuC, 1xPglpF-neuA, pSU2719-lacY-chr | yberC |
| MP15 | MDO x1 PglpF-nst, PglpF-fred, 1xPglpF-neuB, 1xPglpF-neuC, 1xPglpF-neuA, x1 PglpF-LacY | fred |
| MP16 | MDO x1 PglpF-nst, PglpF-fred, 1xPglpF-neuB, 1xPglpF-neuC, 1xPglpF-neuA, | fred |
| MP17 | MDO x1 PglpF-nst, PglpF-fred, 1xPglpF-neuB, 1xPglpF-neuC, 1xPglpF-neuA, pSU2719-lacY-chr | fred |

Deep-Well Assay

The strains disclosed in the present example were screened for 3'SL production in a 96-deep well plate assay. Three replicates per strain were tested. More specifically, during day 1, fresh precultures were prepared using a basal minimal medium (BMM) supplemented with magnesium sulphate, thiamine and glucose. The precultures were incubated at 34° C. with 1000 rpm for 24 h and then transferred to a new BMM (pH 7.5) in order to start the main culture. The new BMM was supplemented with magnesium sulphate, thiamine, a bolus of 20% glucose solution (0.5 μL/mL) and a bolus of 20% lactose solution (0.1 μL/μL).

To the main culture 50% sucrose solution as carbon source (52.5 μl/ml) was provided to the cells accompanied by the addition of sucrose hydrolase (invertase 0.1 g/L) and 50 mg/ml IPTG, so that glucose was released at a rate suitable for C-limited growth allowing for gene expression and 3'SL production.

Antibiotic (chloramphenicol 20 mg/ml) was added in wells when required for plasmid maintenance. The main cultures were incubated at 34° C. with 1000 rpm for 96 h. For the analysis of total broth, the 96 well plates were boiled at 100° C., subsequently centrifuged, and finally the supernatants were analysed by HPLC.

Results

Figure 8:
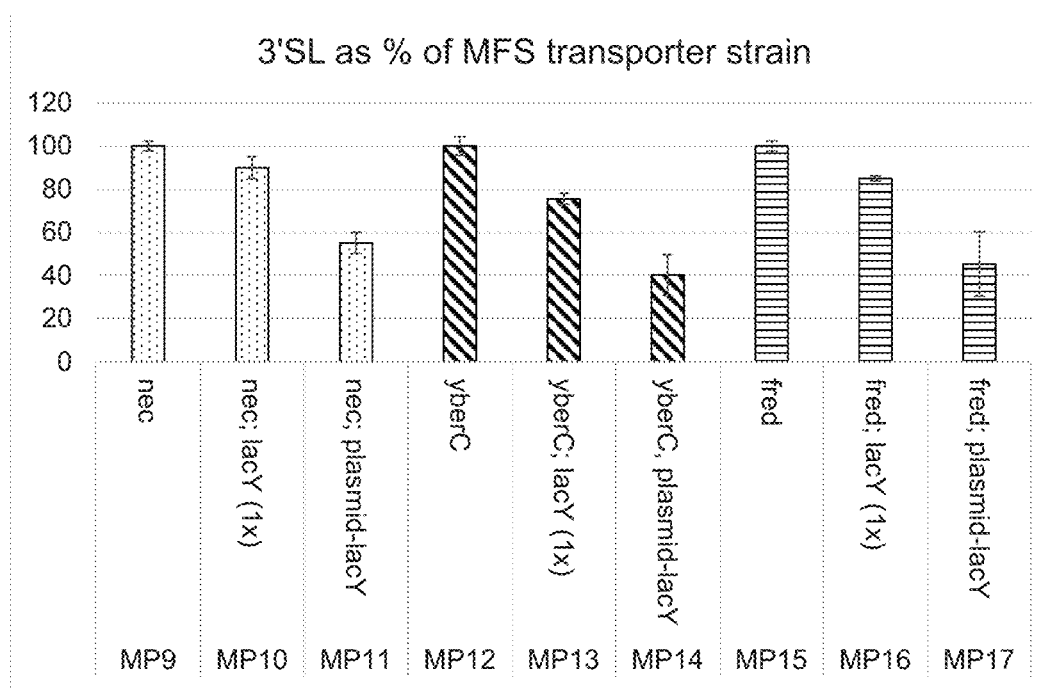

The strains of the present example only produce 3'SL. The results from deep-well assays are shown in FIG. 8. The 3'SL production for the strain expressing the MFS transporter was set to 100 and the corresponding strains with either one extra copy of LacY on the chromosome or LacY expressed from a multicopy plasmid was normalized to the respective MFS transporter strain.

From FIG. 8 it can be seen that in a 3'SL producing strain, overexpression of LacY does not increase the total 3'SL production. In fact, the production seems to be reduced with increased overexpression of lacY as indicated by the strains expressing lacY from a medium copy nr plasmid (MP11, MP14 and MP17, respectively) which have further reduced 3'SL levels compared to strain with a single additional copy of LacY (MP10, MP13 and MP16, respectively).

Example 5—Increased Expression of lacY in Combination with an MFS Transporter does not Improve 2'FL Expression In Examples 1 to 3 it has been illustrated that lacY overexpression in combination with certain MFS transports has a positive effect on LNT and LNnT production.

In the following example the MFS transporter Nec (1 copy genomically integrated) was tested in 2'FL producing strains with (MP19 and MP20) or without (MP18) overexpression of lacY. In the strains overexpressing lacy the additional genomic copy was placed under control of a weak promoter (MP19) or a strong promoter (MP20) to assess if the lacy expression level affected the 2'FL production.

All strains were based on the platform strain "MDO" (e.g., see example 1 and also reported in WO2020255054A1 or WO2019123324A1) and contained the α-1,2-fucolyltransferase from *Helicobacter pylori*, futC (GenBank assession nr. CP003904), incorporated in a single copy at two different loci in the genome of the MDO strain. The genotypes of the tested strains are given in table 6.

TABLE 6

Genotypes of the 2'FL producing strains with different expression levels of lacY

| Strain ID | Genotype | Transporter |
|---|---|---|
| MP18 | MDO x2 PglpF-futC, PglpF-nec, 1xCA* | nec |
| MP19 | MDO x2 PglpF-futC, PglpF-nec, PglpF_SD7-lacY, 1xCA* | nec |
| MP20 | MDO x2 PglpF-futC, PglpF-nec, PglpF-lacY, 1xCA* | nec |

*CA: extra colanic acid gene cluster (gmd-wcaG-wcaH-wcal-manC-manB) under the control of a PglpF promoter at a locus that is different than the native locus.

Deep-Well Assay

The strains disclosed in the present example were screened for 2'FL production in a 96-deep well plate assay. Three replicates per strain were tested. More specifically, during day 1, fresh precultures were prepared using a basal minimal medium (BMM) supplemented with magnesium sulphate, thiamine and glucose. The precultures were incubated at 34° C. with 700 rpm for 24 h and then transferred to a new BMM (pH 7.5) in order to start the main culture. The new BMM was supplemented with magnesium sulphate, thiamine, a bolus of 20% glucose solution (0.5 µL/mL) and a bolus of 10% lactose solution (0.1 µL/µL).

To the main culture 50% (52.5 µl/ml) was provided to the cells accompanied by the addition of sucrose hydrolase (invertase 0.1 g/L), so that glucose was released at a rate suitable for C-limited growth allowing for gene expression and 2'FL production. The main cultures were incubated at 28° C. with 700 rpm for 48 h. For the analysis of total broth, the 96 well plates were boiled at 100° C., subsequently centrifuged, and finally the supernatants were analysed by HPLC.

Results

Figure 9:
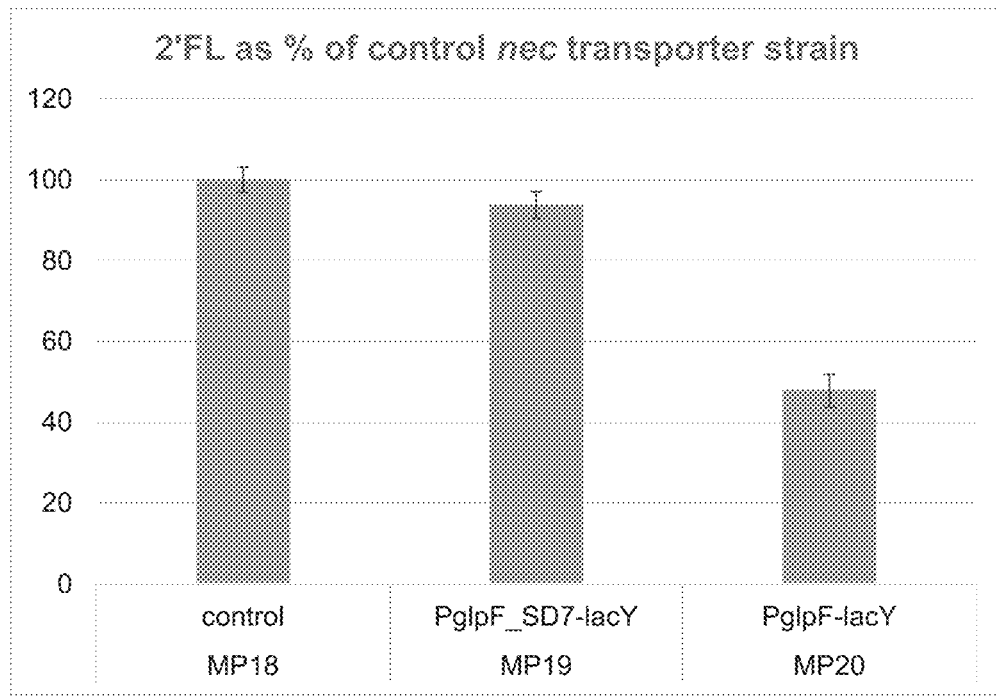

The strains of the present example produce 2'FL and very low levels of DFL. The results from deep-well assays are shown in FIG. 9. The 2'FL production for the strain expressing the MFS transporter nec was set to 100 and the corresponding strains with one additional copy of lacY on the chromosome expressed from either PgIpF or PgIpF SD7 promoter was normalized to the respective nec transporter strain.

From FIG. 9 it can be seen that in a 2'FL producing strain, overexpression of lacY does not increase the total 2'FL production. In fact, the production seems to be reduced with increased overexpression of lacY as indicated by the strains expressing lacY from a weak promoter (PgIpF_SD7 in strain MP19) and from a strong promoter, (PgIpF in strain MP20).

The invention claimed is:

1. A genetically engineered cell capable of producing lactose-N-tetrasaccharide (LNT), lactose-N-neotetrasaccharide (LNnT), or LNT and LNnT and wherein the cell
   a) overexpresses one or more lactose permease genes,
   b) expresses a heterologous MFS transporter protein selected from the group consisting of:
      i. Vag with the amino acid sequence according to SEQ ID NO: 62, or a functional homologue thereof having an amino acid sequence which is at least 95% identical to the amino acid sequence of SEQ ID NO: 62,
      ii. Nec with the amino acid sequence according to SEQ ID NO: 66, or a functional homologue thereof having an amino acid sequence which is at least 95% identical to the amino acid sequence of SEQ ID NO 66:
      iii. Fred, with the amino acid sequence according to SEQ ID NO: 63, or a functional homologue thereof having an amino acid sequence which is at least 95% identical to the amino acid sequence of SEQ ID NO: 63,
      iv. Marc with the amino acid sequence according to SEQ ID NO: 64, or a functional homologue thereof having an amino acid sequence which is at least 95% identical to the amino acid sequence of SEQ ID NO: 64 and
      v. Bad with the amino acid sequence according to SEQ ID NO: 65, or a functional homologue thereof having an amino acid sequence which is at least 95% identical to the amino acid sequence of SEQ ID NO: 65, and c) expresses two or more glycosyltransferases selected from the group consisting of β-1,3-GlcNAc-transferases, β-1,3-Gal-transferases and β-1,4-gal-transferases, and d) expresses one or more polypeptides involved in the biosynthesis of activated sugars.

2. A method for producing one or more human milk oligosaccharides (HMOs) comprising:
a) providing a genetically engineered cell of claim 1,
b) culturing the cell in a suitable media with added lactose, and
c) harvesting the one or more HMOs,
wherein the one or more HMOs are lactose-N-tetrasaccharide (LNT), lactose-N-neotetrasaccharide (LNnT), or both.

3. The method for producing the one or more HMOs according to claim 2, wherein the genetically engineered cell further expresses a sucrose utilisation system.

4. The method for producing the one or more HMOs according to claim 3, the sucrose utilization system comprising a polypeptide capable of hydrolysing sucrose into glucose and fructose, selected from the group consisting of SEQ ID NOs: 86 and 87, or a functional homologue of any one of SEQ ID NOs: 86 and 87, having an amino acid sequence which is at least 95% identical to any one of SEQ ID NOs: 86 or 87.

5. The method according to claim 2, wherein the amino acid sequence of the one or more lactose permeases is selected from the group consisting of SEQ ID NO: 1, 2, 3, 4, 5, 6, 7, 8, 9, 10, 11, 12, 13, 14, 15, and 16, or an amino acid sequence which is at least 95% identical to SEQ ID NO: 1, 2, 3, 4, 5, 6, 7, 8, 9, 10, 11, 12, 13, 14, 15, and 16 and which encodes a functional homologue.

6. The method according to claim 2, wherein the MFS transporter is the Nec or the Vag.

7. The method according to claim 2, wherein
d) the β-1,3-Gal-transferase is selected from the group consisting of CvB3galT and GalTK, or a functional homologue of CvB3galT or GalTK, having an amino acid sequence which is at least 95% identical to any one of the amino acid sequences of SEQ ID NO: 17 (CvB3galT), SEQ ID NO: 18 (GalTK), or
e) the β-1,4-gal-transferase is GalT, or a functional homologue of GalT, having an amino acid sequence which is at least 95% identical to SEQ ID NO: 19 (GalT).

8. The method according to claim 2, wherein the β-1,3-GlcNAc-transferase is selected from the group consisting of LgtA, PmnagT, HD0466 and a functional homologue of any one of LgtA, PmnagT or HD0466, having an amino acid sequence which is at least 95% identical to any one of SEQ ID NO: 20 (LgtA), SEQ ID NO: 21 (PmnagT), or SEQ ID NO: 22 (HD0466).

9. The method according to claim 2, wherein the genetically engineered cell further comprises one or more heterologous nucleic acid sequence encoding one or more heterologous polypeptides, which enables utilization of sucrose as sole carbon and energy source of said genetically engineered cell.

10. The method according to claim 2, wherein the genetically engineered cell expresses one or more polypeptides involved in the biosynthesis of activated sugar nucleotides selected from the group consisting of Pgm, GalU, GalE, GlmM, GlmU and GlmS, or a functional homologue thereof having an amino acid sequence which is at least 95% identical to any one of SEQ ID NO: 43 or 44 (Pgm), SEQ ID NO: 45 or 46 (GalU), SEQ ID NO: 47 or 48 (GalE), SEQ ID NO: 49 or 50 (GlmM), SEQ ID NO: 51 or 52 (GlmU), SEQ ID NO: 53 or 54.

11. The method according to claim 5, wherein the genetically engineered cell comprises more than one nucleic acid sequence encoding one or more of the lactose permeases.

12. The method according to claim 2, wherein the genetically engineered cell comprises at least one nucleic acid sequence encoding one or more heterologous polypeptides involved in the biosynthesis of activated sugars according to claim 11.

13. The method according to claim 11, wherein at least one of the nucleic acid sequences encoding lactose permease is regulated by one or more promoter sequences selected from the group consisting of Plac, PgatY_70UTR, PglpF, PglpF_SD1, PglpF_SD10, PglpF_SD2, PglpF_SD3, PglpF_SD4, PglpF_SD5, PglpF_SD6, PglpF_SD7, PglpF_SD8, PglpF_SD9, Plac_16UTR, PmglB_70UTR, PmglB_70UTR_SD4, CP6 and PosmY.

14. The method according to claim 2, wherein at least one nucleic acid sequence encoding the one or more lactose permeases is integrated into the genome of the genetically engineered cell.

15. The method according to claim 2, wherein at least one nucleic acid sequence encoding the heterologous MFS transporter is integrated into the genome of the genetically engineered cell.

16. The method according to claim 2, wherein at least one nucleic acid sequence encoding the two or more glycosyltransferases is integrated into the genome of the genetically engineered cell.

17. The method according to claim 11, wherein the at least one nucleic acid sequence encoding one or more heterologous polypeptides involved in the biosynthesis of activated sugars is integrated into the genome of the genetically engineered cell.

18. The method according to claim 2, wherein the genetically engineered cell is *Escherichia coli*.

19. The method according to claim 2, wherein the genetically engineered cell is *Escherichia coli* K-12.

20. The genetically engineered cell according to claim 1, wherein the cell comprises,
i. one or more lactose permeases selected from the group consisting of SEQ ID NO: 1, 2, 3, 4, 5, 6, 7, 8, 9, 10, 11, 12, 13, 14, 15, and 16; or a functional homologue thereof, having an amino acid sequence which is at least 95% identical to any one of SEQ ID NO: 1, 2, 3, 4, 5, 6, 7, 8, 9, 10, 11, 12, 13, 14, 15, or 16,
ii. two or more glycosyltransferases selected from the group consisting of CvB3galT, GalTK, GalT, LgtA, PmnagT, HD0466, and a functional homologue thereof, having an amino acid sequence which is at least 95% identical to any one of SEQ ID NO: 17 (CvB3galT), SEQ ID NO: 19 (GalTK), SEQ ID NO: 19 (GalT), SEQ ID NO: 20 (LgtA), SEQ ID NO: 21 (PmnagT), or SEQ ID NO: 22 (HD0466), and
iii. one or more polypeptides involved in the biosynthesis of activated sugars selected from the group consisting of SEQ ID NO: 43 or 44 (Pgm), SEQ ID NO: 45 or 46 (GalU), SEQ ID NO: 47 or 48 (GalE), SEQ ID NO: 49 or 50 (GlmM), SEQ ID NO: 51 or 52 (GlmU), and SEQ ID NO: 53 or 541 (GlmS).

* * * * *